United States Patent
Takeuchi et al.

(10) Patent No.: US 6,727,053 B2
(45) Date of Patent: Apr. 27, 2004

(54) DYE-FORMING COUPLER, SILVER HALIDE PHOTOGRAPHIC LIGHT-SENSITIVE MATERIAL AND AZOMETHINE DYE COMPOUND

(75) Inventors: Kiyoshi Takeuchi, Minami-ashigara (JP); Shigeki Uehira, Minami-ashigara (JP); Mario Aoki, Minami-ashigara (JP); Jun Ogasawara, Minami-ashigara (JP); Yasuhiro Shimada, Minami-ashigara (JP); Seiji Ichijima, Minami-ashigara (JP); Yasuaki Deguchi, Minami-ashigara (JP); Naoto Matsuda, Minami-ashigara (JP); Akira Ikeda, Minami-ashigara (JP); Hisashi Mikoshiba, Minami-ashigara (JP); Masaharu Sugai, Minami-ashigara (JP); Taiji Katsumata, Minami-ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/106,373

(22) Filed: Mar. 27, 2002

(65) Prior Publication Data

US 2003/0073047 A1 Apr. 17, 2003

(30) Foreign Application Priority Data

Mar. 29, 2001 (JP) .......................... 2001-97656
Mar. 29, 2001 (JP) .......................... 2001-298521
Mar. 29, 2001 (JP) .......................... 2001-298660
Mar. 29, 2001 (JP) .......................... 2001-299685

(51) Int. Cl.$^7$ .................... G03C 1/08; G03C 7/26; G03C 7/32
(52) U.S. Cl. .................... 430/558; 430/543; 430/557
(58) Field of Search .................... 430/543, 558, 430/557

(56) References Cited

U.S. PATENT DOCUMENTS

| | | | |
|---|---|---|---|
| 3,841,880 A | | 10/1974 | Kertel |
| 5,021,330 A | * | 6/1991 | Bergthaller et al. .......... 430/558 |
| 5,024,930 A | * | 6/1991 | Kita et al. .................... 430/558 |
| 5,213,958 A | | 5/1993 | Motoki et al. |
| 5,427,902 A | | 6/1995 | Shimura et al. |
| 5,455,149 A | | 10/1995 | Bergthaller |
| 6,043,017 A | * | 3/2000 | Bergthaller .................. 430/558 |

FOREIGN PATENT DOCUMENTS

| | | |
|---|---|---|
| EP | 0 336 411 | 4/1989 |
| EP | 0 953 870 A | 11/1999 |
| JP | 52-82423 | 7/1977 |
| JP | 58-111943 | 7/1983 |
| JP | 4-78582 | 3/1992 |

* cited by examiner

Primary Examiner—Geraldine Letscher
(74) Attorney, Agent, or Firm—Birch, Stewart, Kolasch & Birch, LLP

(57) ABSTRACT

A dye-forming coupler of formula (I), a silver halide photographic light-sensitive material containing the coupler, and an azomethine dye that can be derived from the dye-forming coupler:

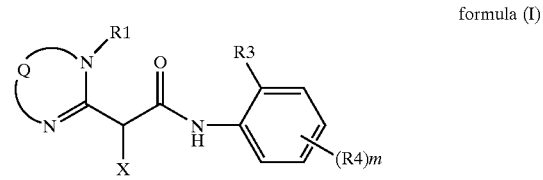

formula (I)

wherein Q is a group $-C(-R_{11})=C(-R_{12})-SO_2-$; $R_{11}$ and $R_{12}$ bond with each other to form, together with the $-C=C-$ moiety, a 5- to 7-membered ring, or they each represent a hydrogen atom or a substituent; R1, R3 and R4 each represent a substituent; m is an integer of 0 to 4; and X represents a hydrogen atom or a group that splits off upon a coupling reaction with an oxidized product of a developing agent; with the proviso that the following compound (I-A) is excluded from the dye-forming coupler of formula (I).

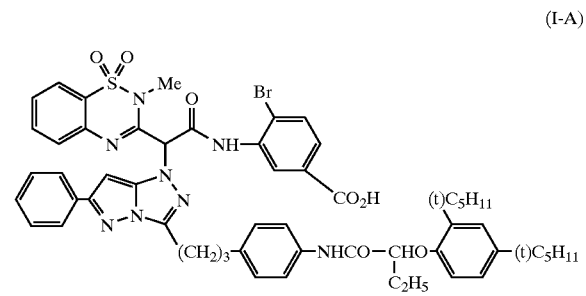

(I-A)

4 Claims, No Drawings

DYE-FORMING COUPLER, SILVER HALIDE PHOTOGRAPHIC LIGHT-SENSITIVE MATERIAL AND AZOMETHINE DYE COMPOUND

FIELD OF THE INVENTION

The present invention relates to a dye-forming coupler that forms an azomethine dye upon a coupling reaction with an oxidized product of a developing agent. The present invention also relates to a silver halide photographic light-sensitive material containing the dye-forming coupler. Further, the present invention relates to an azomethine dye compound that can be produced by the above-described coupling reaction.

BACKGROUND OF THE INVENTION

In a silver halide photographic light-sensitive material (hereinafter sometimes referred to simply as "light-sensitive material") for subtractive color photography, a color image is formed by dyes of three primary colors of yellow, magenta and cyan. In the color photography that uses a current p-phenylenediamine color-developing agent, an acylacetoanilide-type compound is used as a yellow coupler. However, the hue of the yellow dye obtained from these yellow couplers is tinted with red, due to inferior sharpness at the foot portion of a peak in interest of the absorption curve at the longer wavelength side (that is, on the absorption curve, the peak in interest has subsidiary absorption at its foot portion at the longer wavelength side), which renders it difficult to obtain a yellow hue of high purity. Further, there is the problem that, due to the low molecular extinction coefficient of said yellow dyes, large amounts of both the coupler and silver halide are needed to obtain a desired colored density. Therefore, sometimes it results in increasing film thickness of the light-sensitive material, and this consequently reduces the sharpness of the obtained color image. Further, the above-mentioned yellow dyes, which are easily decomposed under the conditions of high temperature and high humidity, or the condition of light irradiation, have insufficient image stability after development processing. Consequently, improvement of these problems is desired.

In order to solve such the problems, the acyl group and the anilido group were improved. Recently, as improved couplers of the conventional acylacetoanilide-series, there are proposed, for example, 1-alkylcyclopropanecarbonyl acetoanilide-series compounds, described in JP-A-4-218042 ("JP-A" means unexamined published Japanese patent application); cyclomalonic acid diamide-type couplers, described in JP-A-5-11416; pyrrole-2- or 3-yl- or indole-2- or 3-yl-carbonylacetoanilide-series couplers, described in, for example, European Patent Nos. 953870A1, 953871A1, 953872A1, 953873A1, 953874A1 and 953875A1. The dyes formed from these couplers were improved in terms of both hue and molecular extinction coefficient, compared with the conventional ones. However, they are still deficient in image stability. Further, owing to their complicated chemical structure, the synthesis route became longer, and consequently cost of the couplers became higher, causing a practical problem.

In addition, U.S. Pat. No. 3,841,880, JP-A-52-82423 and JP-A-2-28645 propose acetate ester-series and acetoanilide-series couplers to which 1,2,4-benzothiadiazine-1,1-dioxide is bonded. However, these couplers are low in color-forming property, they are insufficient in molecular extinction coefficient of a resultant dye, and they are inferior in sharpness at the foot portion of a peak in interest of the absorption curve at the longer wavelength side. Therefore, improvement of these problems is desired.

Further, JP-A-58-111943 discloses a blocked magenta-dye-forming coupler. In JP-A-58-11943, there is described the magenta-dye-forming coupler which has a partial structure of acetanilide in which 1,2,4-benzothiadiazine-1,1-dioxide bonds to the blocking group of the coupler. However, said partial structure is just a blocking group. Since the blocking group moiety flows out from a light-sensitive material during development processing, the coupler having the partial structure is not used as an image dye.

Further, JP-A-4-78582 discloses a particular acetanilide-series azomethine dye, to which 1,2,4-benzothiadiazine-1,1-dioxide bonds, and which dye is used as a dye for a thermal transfer recording material. However, the dye is not satisfactory because of such problems that the image obtained from the dye is apt to be ambiguity and it is low in sharpness. In addition, neither fastness nor hue in view of sharpness at the foot portion of a peak in interest of the absorption curve at the longer wavelength side are sufficient.

SUMMARY OF THE INVENTION

The present invention is a dye-forming coupler represented by formula (I):

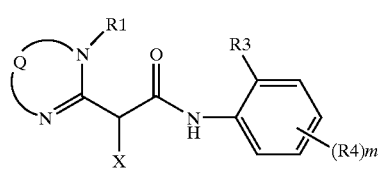

formula (I)

wherein Q represents a group represented by —C(—$R_{11}$)=C(—$R_{12}$)—$SO_2$—; $R_{11}$ and $R_{12}$ bond with each other to form, together with the —C=C— moiety, a 5- to 7-membered ring, or $R_{11}$ and $R_{12}$ each independently represent a hydrogen atom or a substituent; R1 represents a substituent; R3 represents a substituent; R4 represents a substituent; m represents an integer of 0 to 4; when m is 2 or more, R4s may be the same or different, or R4s may bond each other to form a ring; and X represents a hydrogen atom, or a group capable of being split-off upon a coupling reaction with an oxidized product of a developing agent; with the proviso that the following compound (I-A) is excluded from the dye-forming coupler represented by formula (I).

(I-A)

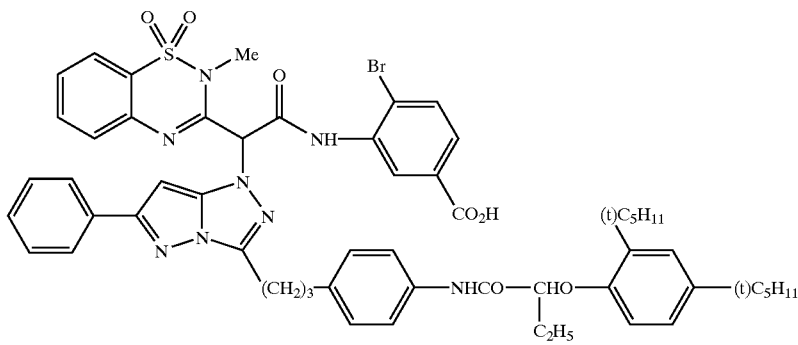

Further, the present invention is a dye-forming coupler represented by formula (II):

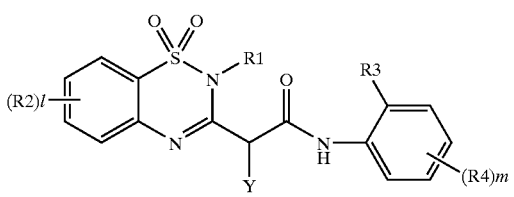

formula (II)

wherein R1 represents a substituent; R2 represents a substituent; l represents an integer of 0 to 4; when l is 2 or more, R2s may be the same or different, or R2s may bond with each other to form a ring; R3 represents a substituent; R4 represents a substituent; m represents an integer of 0 to 4; when m is 2 or more, R4s may be the same or different, or R4s may bond with each other to form a ring; and Y represents a group capable of being split-off upon a coupling reaction with an oxidized product of a developing agent; with the proviso that the following compound (I-A) is excluded from the dye-forming coupler represented by formula (I).

Further, the present invention is a dye-forming coupler represented by formula (I-2):

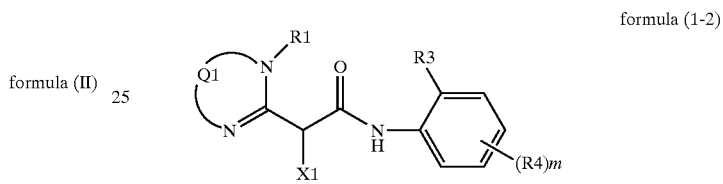

formula (1-2)

wherein Q1 represents a group represented by —C(—R$_{11}$)=C(—R$_{12}$)—Z—; Z represents —SO$_2$— or —CO—; R$_{11}$ and R$_{12}$ bond with each other to form, together with the —C=C— moiety, a 5- to 7-membered ring, or R$_{11}$ and R$_{12}$ each independently represent a hydrogen atom or a substituent; R1 represents a substituent; R3 represents a substituent; R4 represents a substituent; m represents an integer of 0 to 4; when m is 2 or more, R4s may be the same or different, or R4s may bond with each other to form a ring; and X1 represents a group that has thereon a dissociation group whose pKa is 1 to 12 and that is capable of being split-off upon a coupling reaction with an oxidized product of a developing agent.

Further, the present invention is a silver halide photographic light-sensitive material, which comprises at least one dye-forming coupler represented by the above formula (I), (II) or (I-2).-

(I-A)

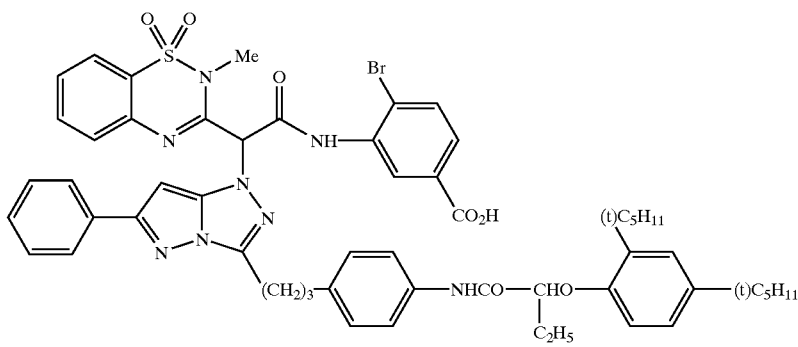

Further, the present invention is an azomethine dye compound represented by formula (D):

formula (D)

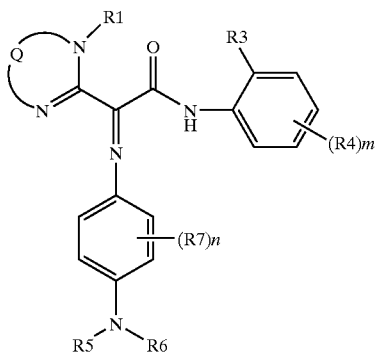

wherein Q represents a group represented by —C(—$R_{11}$)=C(—$R_{12}$)—$SO_2$—; $R_{11}$ and $R_{12}$ bond with each other to form, together with the —C=C— moiety, a 5- to 7-membered ring, or $R_{11}$ and $R_{12}$ each independently represent a hydrogen atom or a substituent; R1 represents a substituent; R3 represents a substituent; R4 represents a substituent; m represents an integer of 0 to 4; when m is 2 or more, R4s may be the same or different, or R4s may bond with each other to form a ring; R5 and R6 each independently represent a hydrogen atom or a substituent, or R5 and R6 may bond with each other to form a ring; R7 represents a substituent; n represents an integer of 0 to 4; when n is 2 or more, R7s may be the same or different, or R7s may bond with each other to form a fused ring; or when n is 1 or more, R7 may bond with R5 or R6 to form a fused ring; with the proviso that at least one group selected from the group consisting of R1, R3, R4, the substituent represented by $R_{11}$, the substituent represented by $R_{12}$, and at least one substituent on the ring that is formed by a combination of $R_{11}$ and $R_{12}$, is a group having 10 or more carbon atoms in total.

Further, the present invention is an azomethine dye compound represented by formula (IV), wherein an angle that is defined by a dihedral angle C*1 N*2 C*3 C*4 and that is the most stabilized stereochemical structure in terms of energy, which is measured by quantum chemistry calculations, is within the range between −28° and 28°:

formula (IV)

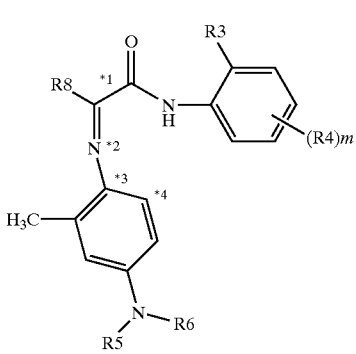

wherein, in formula (IV), *1, 2, *3 and 4 each express a number labeled on the atom and define the angle represented by the dihedral angle C*1 N*2 C*3 C*4; R3 and R4 each independently represent a substituent; m represents an integer of 0 to 4; when m is 2 or more, R4s may be the same or different, or R4s may bond with each other to form a ring; R5 and R6 each independently represent a hydrogen atom or a substituent, or R5 and R6 may bond with each other to form a ring; R8 represents an aryl group or a heterocyclic group, with the proviso that at least one group selected from the group consisting of R3, R4, and at least one substituent on the aryl ring or heterocycle represented by R8, is a group having 10 or more carbon atoms in total; and that the calculation based on quantum chemistry, which is used to measure the dihedral angle C*1 N*2 C*3 C*4 be carried out using the basis function of 6–31 G** or more according to the widely used B3LYP method (density-functional method).

Further, the present invention is a silver halide photographic light-sensitive material, which comprises a coupler capable of forming a dye upon a coupling reaction with an oxidized product of an aromatic primary amine, wherein at least one dye to be formed is a dye selected from the azomethine dye compounds described above.

Other and further features and advantages of the invention will appear more fully from the following description.

DETAILED DESCRIPTION OF THE INVENTION

According to the present invention, there is provided the following means:

(1) A dye-forming coupler represented by the following formula (I):

formula (I)

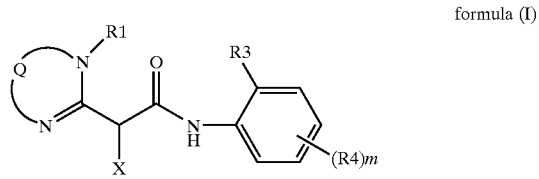

wherein Q represents a group represented by —C(—$R_{11}$)=C(—$R_{12}$)—$SO_2$— (in the present invention, this expression of the foregoing group should not be construed as limited to the direction of the bonds belonging to the group as represented by this expression); $R_{11}$ and $R_{12}$ bond with each other to form, together with the —C=C— moiety, a 5- to 7-membered ring, or $R_{11}$ and $R_{12}$ each independently represent a hydrogen atom or a substituent; R1 represents a substituent; R3 represents a substituent; R4 represents a substituent; m represents an integer of 0 to 4; when m is 2 or more, R4s may be the same or different, or R4s may bond with each other to form a ring; and X represents a hydrogen atom, or a group capable of being split-off upon a coupling reaction with an oxidized product of a developing agent;

with proviso that the following compound (I-A) is excluded from the dye-forming coupler represented by formula (I).

(I-A)

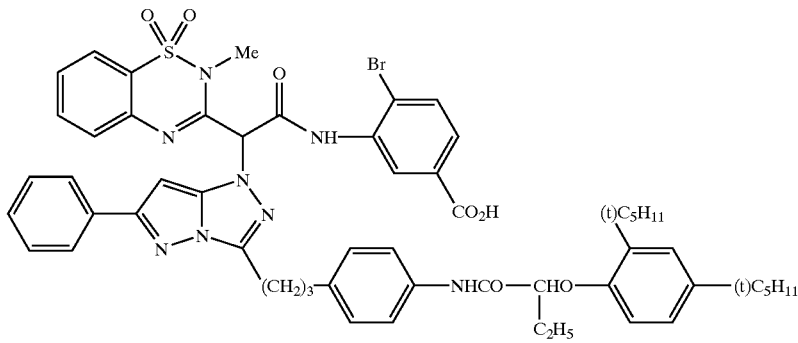

(2) A dye-forming coupler represented by the following formula (II):

formula (II)

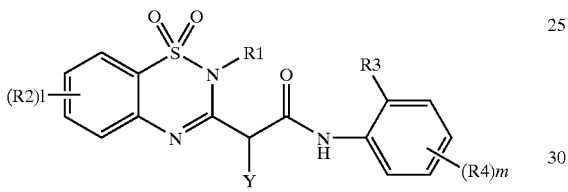

wherein R1 represents a substituent; R2 represets a substituent; l represents an integer of 0 to 4; when l is 2 or more, R2s may be the same or different, or R2s may bond with each other to form a ring; R3 represents a substituent; R4 represents a substituent; m represents an integer of 0 to 4; when m is 2 or more, R4s may be the same or different, or R4s may bond with each other to form a ring; and Y represents a group capable of being split-off upon a coupling reaction with an oxidized product of a developing agent;

with the proviso that the following compound (I-A) is excluded from the dye-forming coupler represented by formula (II).

(3) A dye-forming coupler represented by the following formula (I-2):

formula (I-2)

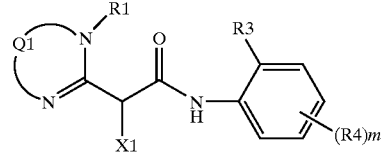

wherein Q1 represents a group represented by —C(—$R_{11}$)=C(—$R_{12}$)—Z— (in the present invention, this expression of the foregoing group should not be construed as limited to the direction of the bonds belonging to the group as represented by this expression); Z represents —$SO_2$— or —CO—; $R_{11}$ and $R_{12}$ bond with each other to form, together with the —C=C— moiety, a 5- to 7-membered ring, or $R_{11}$ and $R_{12}$ each independently represent a hydrogen atom or a substituent; R1 represents a substituent; R3 represents a substituent; R4 represents a substituent; m represents an integer of 0 to 4; when m is 2 or more, R4s may be the same or different, or R4s may bond with each other to form a ring; and X1 represents a group that has thereon a dissociation group whose pKa is 1 to 12 and that is capable of being spilt-off upon a coupling reaction with an oxidized product of a developing agent.

(I-A)

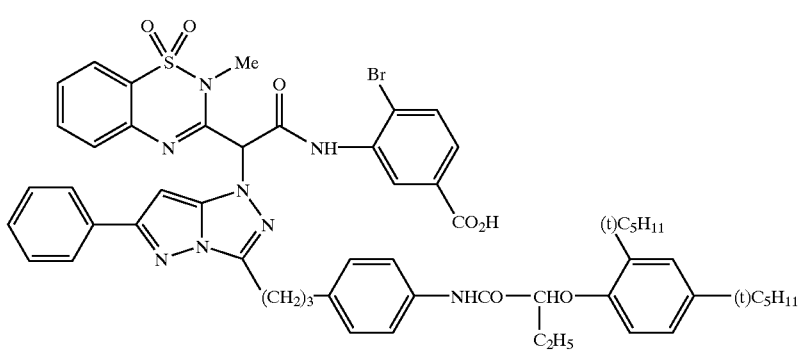

(4) A dye-forming coupler represented by the following formula (II-2):

formula (II-2)

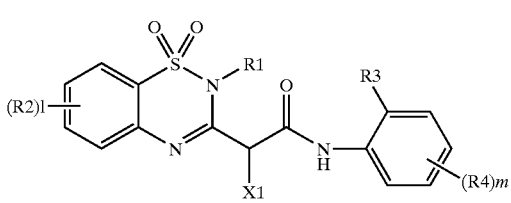

wherein R1 represents a substituent; R2 represents a substituent; l represents an integer of 0 to 4; when l is 2 or more, R2s may be the same or different, or R2s may bond with each other to form a ring; R3 represents a substituent; R4 represents a substituent; m represents an integer of 0 to 4; when m is 2 or more, R4s may be the same or different, or R4s may bond with each other to form a ring; and X1 represents a group that has thereon a dissociation group whose pKa is 1 to 12, and that is capable of being spilt-off upon a coupling reaction with an oxidized product of a developing agent.

(5) The dye-forming coupler according to any one of items (1) to (4), wherein R1 in said formula (I), (II), (I-2), or (II-2) is a substituted or unsubstituted alkyl group.

(6) The dye-forming coupler according to any one of items (1) to (5), wherein R3 in said formula (I), (II), (I-2), or (II-2) is a halogen atom, an alkoxy group, an aryloxy group, an alkyl group, an alkylthio group, or an arylthio group.

(7) The dye-forming coupler according to any one of items (1) to (6), wherein the substituent represented by R1 in said formula (I), (II), (I-2), or (II-2) has 11 or more carbon atoms in total.

(8) The dye-forming coupler according to any one of items (1) to (4), (6), and (7), wherein, in the above-mentioned formula (I), (II), (I-2) or (II-2), R1 represents a nondiffusible aliphatic group or aromatic group, and R3 represents a nondiffusible aliphatic oxy group or aromatic oxy group.

(9) The dye-forming coupler according to any one of items (1) to (8), wherein R1 in said formula (I), (II), (I-2), or (II-2) is a 3-(2,4-di-t-amylphenoxy)propyl group.

(10) The dye-forming coupler according to any one of items (1) to (8), wherein R1 in said formula (I), (II), (I-2), or (II-2) is a —$C_{16}H_{33}$ group or —$C_{18}H_{37}$ group.

(11) The dye-forming coupler according to any one of items (1) to (10), wherein X, X1 or Y in said formula (I), (II), (I-2), or (II-2) is a coupling-split-off group that substantially provides neither development inhibitor nor a precursor thereof, when the group splits off.

(12) The dye-forming coupler according to any one of items (1) to (11), wherein X, X1 or Y in the above-mentioned formula (I), (II), (I-2) or (II-2) is an imidazole-1-yl group which may have a substituent, a pyrazole-1-yl group which may have a substituent, or a pyrrole-1-yl group which may have a substituent.

(13) The dye-forming coupler according to any one of items (1) to (12), wherein R4 in the above-mentioned formula (I), (II), (I-2) or (II-2) is an alkoxy group or a t-alkyl group.

(14) The dye-forming coupler according to any one of items (1) to (7) and (9) to (13), wherein, in the above-mentioned formula (I), (II), (I-2) or (II-2), R3 represents an alkoxy group or alkylthio group, each of which has an alkyl moiety branched at the β-position.

(15) The dye-forming coupler according to any one of items (1) to (14), wherein at least one of R1, R2, R3, R4, Q, Q1, X, X1 and Y in the above-mentioned formula (I), (II), (I-2) or (II-2) is a group containing therein a hydroxyl group.

(16) The dye-forming coupler according to any one of items (3) to (15), wherein the dissociation group that X1 of the above-mentioned formula (I-2) or (II-2) has is a group selected from the group consisting of a —COOH group, a —$NHSO_2$— group, a phenolic hydroxyl group, a —CONHCO— group, a —$CONHSO_2$— group, a —$CONHSO_2NH_2$ group, and a —$SO_2NHSO_2$— group, each of which has a pKa of 3 to 12.

(17) The dye-forming coupler according to any one of items (3) to (15), wherein the dissociation group that X1 of the above-mentioned formula (I-2) or (II-2) has is a —COOH group.

(18) A silver halide photographic light-sensitive material, comprising at least one dye-forming coupler according to any one of items (1) to (17).

(19) An azomethine dye compound represented by formula (D):

formula (D)

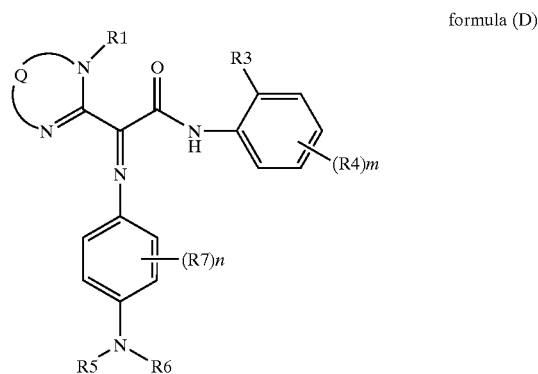

wherein Q represents a group represented by —C(—$R_{11}$)=C(—$R_{12}$)—$SO_2$— (in the present invention, this expression of the foregoing group should not be construed as limited to the direction of the bonds belonging to the group as represented by this expression); $R_{11}$ and $R_{12}$ bond with each other to form, together with the —C=C— moiety, a 5- to 7-membered ring, or $R_{11}$ and $R_{12}$ each independently represent a hydrogen atom or a substituent; R1 represents a substituent; R3 represents a substituent; R4 represents a substituent; m represents an integer of 0 to 4; when m is 2 or more, R4s may be the same or different, or R4s may bond with each other to form a ring; R5 and R6 each independently represent a hydrogen atom or a substituent, or R5 and R6 may bond with each other to form a ring; R7 represents a substituent; n represents an integer of 0 to 4; when n is 2 or more, R7s may be the same or different, or R7s may bond with each other to form a fused ring; or when n is 1 or more, R7 may bond with R5 or R6 to form a fused ring;

with the proviso that at least one group selected from the group consisting of R1, R3, R4, the substituent represented by $R_{11}$ the substituent represented by $R_{12}$, and at least one substituent on the ring that is formed by a combination of $R_{11}$ and $R_{12}$, is a group having 10 or more carbon atoms in total.

(20) An azomethine dye compound represented by the following formula (III):

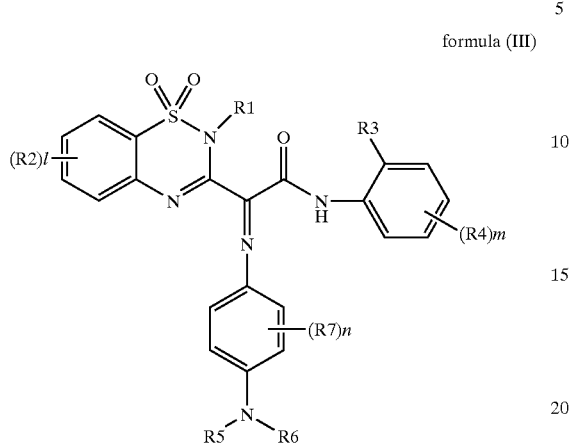

formula (III)

wherein R1 represents a substituent; R2 represents a substituent; l represents an integer of 0 to 4; when l is 2 or more, R2s may be the same or different, or R2s may bond with each other to form a ring; R3 represents a substituent; R4 represents a substituent; m represents an integer of 0 to 4; when m is 2 or more, R4s may be the same or different, or R4s may bond with each other to form a ring; R5 and R6 each independently represent a hydrogen atom or a substituent, or R5 and R6 may bond with each other to form a ring; R7 represents a substituent; n represents an integer of 0 to 4; when n is the integer of 2 or more, R7s may be the same or different, or R7s may bond with each other to form a condensed ring; or when n is 1 or more, R7 may bond with R5 or R6 to form a condensed ring;

with the proviso that at least one of the R1, R2, R3, or R4 is a group having 10 or more carbon atoms in total.

(21) The azomethine dye compound according to (19) or (20), wherein R1 in said formula (D) or (III) is a substituted or unsubstituted alkyl group.

(22) The azomethine dye compound according to any one of items (19) to (21), wherein R3 in said formula (D) or (III) is a halogen atom, an alkoxy group, an aryloxy group, an alkyl group, an alkylthio group, or an arylthio group.

(23) The azomethine dye compound according to any one of items (19) to (22), wherein the substituent represented by R1 in said formula (D) or (III) has 11 or more carbon atoms in total.

(24) The azomethine dye compound according to any one of items (19), (20), (22) or (23), wherein in the formula (D) or (III), R1 is a nondiffusible aliphatic group or aromatic group, and R3 is a nondiffusible aliphatic oxy group or aromatic oxy group.

(25) The azomethine dye compound according to any one of items (19) to (24), wherein R1 in said formula (D) or (III) is a 3-(2,4-di-t-amylphenoxy)propyl group.

(26) The azomethine dye compound according to any one of items (19) to (24), wherein R1 in said formula (D) or (III) is a —$C_{16}H_{33}$ group or —$C_{18}H_{37}$ group.

(27) An azomethine dye compound represented by the following formula (IV), wherein an angle that is defined by a dihedral angle C*1 N*2 C*3 C*4 and that is the most stabilized stereochemical structure in terms of energy, which is measured by quantum chemistry calculations, is within the range between −28° and 28°:

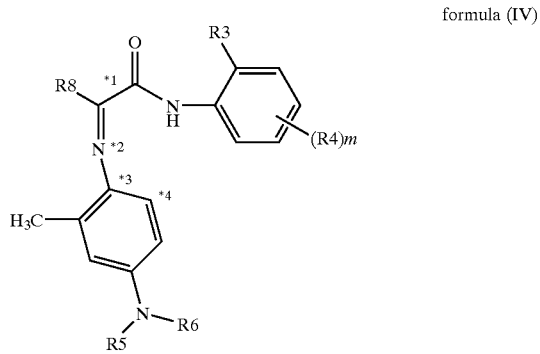

formula (IV)

wherein, in formula (IV), 1, 2, 3 and 4 each express a number labeled on the atom and define the angle represented by the dihedral angle C*1 N*2 C*3 C*4; R3 and R4 each independently represent a substituent; m represents an integer of 0 to 4; when m is 2 or more, R4s may be the same or different, or R4s may bond with each other to form a ring; R5 and R6 each independently represent a hydrogen atom or a substituent, or R5 and R6 may bond with each other to form a ring; R8 represents an aryl group or a heterocyclic group;

with the proviso that at least one group selected from the group consisting of R3, R4, and at least one substituent on the aryl ring or heterocycle represented by R8, is a group having 10 or more carbon atoms in total; and that the quantum chemistry calculations, which is used to measure the dihedral angle C*1 N*2 C*3 C*4, be carried out using the basis function of 6–31 G** or more according to a widely used B3LYP method (density-functional method).

(28) The azomethine dye compound according to (27), wherein the angle defined by the dihedral angle C*1 N*2 C*3 C*4 of the most stabilized stereochemical structure in terms of energy, which is measured by quantum chemistry calculations, is within the range between −24° and 24°.

(29) The azomethine dye compound according to (27) or (28), wherein R8 in said formula (IV) is a 6- or 7-membered heterocyclic group.

(30) The azomethine dye compound according to (27) or (28), wherein R8 in said formula (IV) is a group represented by the following formula (V):

formula (V)

wherein, in the formula (V), Q represents a group represented by —C(—$R_{11}$)=C(—$R_{12}$)—$SO_2$— (in the present invention, this expression of the foregoing group should not be construed as limited to the direction of the bonds belonging to the group as represented by this expression); $R_{11}$ and $R_{12}$ bond with each other to form, together with the —C=C— moiety, a 5- to 7-membered ring, or $R_{11}$ and $R_{12}$ each independently represent a hydrogen atom or a substituent; and R1 represents a substituent.

(31) The azomethine dye compound according to (27) or (28), wherein R8 in said formula (IV) is a group represented by the following formula (VI):

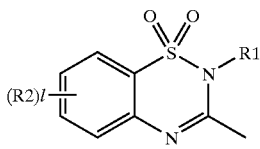

formula (VI)

wherein, in the formula (VI), R1 represents a substituent; R2 represents a substituent; and l represents an integer of 0 to 4; when l is 2 or more, R2s may be the same or different, or R2s may bond with each other to form a ring.

(32) The azomethine dye compound according to any one of items (27) to (31), wherein R3 in said formula (IV) is a halogen atom, an alkoxy group, an aryloxy group, an alkyl group, an alkylthio group, or an arylthio group.

(33) A silver halide photographic light-sensitive material, comprising a coupler capable of forming a dye upon coupling with an oxidized product of an aromatic primary amine, wherein at least one of said dyes is the azomethine dye compound according to any one of items (19) to (32).

(34) A silver halide photographic light-sensitive material, comprising a coupler capable of forming a dye upon coupling with an oxidized product of an aromatic primary amine, wherein at least one coupler is capable of giving the azomethine dye according to any one of items (19) or (32).

The present invention is explained in detail below.

(Dye-Forming Coupler)

The compound (herein also referred to as a dye-forming coupler) represented by the following formula (I) of the present invention is explained in detail.

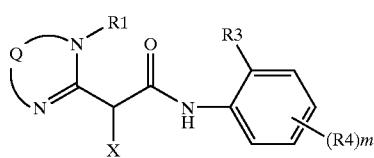

formula (I)

In formula (I), R1 represents a substituent excepting a hydrogen atom. Examples of the substituent include halogen atoms, alkyl (including cycloalkyl and bicycloalkyl), alkenyl (including cycloalkenyl and bicycloalkenyl), alkynyl, aryl, heterocyclic, cyano, hydroxyl, nitro, carboxyl, alkoxy, aryloxy, silyloxy, heterocyclic oxy, acyloxy, carbamoyloxy, alkoxycarbonyloxy, aryloxycarbonyloxy, amino (including alkylamino and anilino), acylamino, aminocarbonylamino, alkoxycarbonylamino, aryloxycarbonylamino, sulfamoylamino, alkyl- or aryl-sulfonylamino, mercapto, alkylthio, arylthio, heterocyclic thio, sulfamoyl, sulfo, alkyl- or aryl-sulfinyl, alkyl- or aryl-sulfonyl, acyl, aryloxycarbonyl, alkoxycarbonyl, carbamoyl, arylazo or heterocyclicazo, imido, phosphio, phosphinyl, phosphinyloxy, phosphinylamino, and silyl groups.

The above-mentioned substituent may be further substituted with another substituent. Examples of this another substituent are the same as described as the examples of the above-mentioned substituent.

Examples of the substituent represented by R1 are further explained below.

Examples of these substituents include a halogen atom (e.g., chlorine, bromine, iodine); an alkyl group (preferably a straight- or branched-chain, substituted or unsubstituted alkyl group having 1 to 30 carbon atoms, e.g., methyl, ethyl, n-propyl, isopropyl, t-butyl, n-octyl, eicosyl, 2-chloroethyl, 2-cyanoethyl, 2-ethylhexyl, and 3-(2,4-di-t-amylphenoxy) propyl); a cycloalkyl group (preferably a substituted or unsubstituted monocyclic cycloalkyl group having 3 to 30 carbon atoms, e.g., cyclohexyl, cyclopentyl, 4-n-dodecyl cyclohexyl; and polycyclic cycloalkyl groups including groups composed of a polycyclic structure, such as a bicycloalkyl group (preferably a substituted or unsubstituted bicycloalkyl group having 5 to 30 carbon atoms, e.g. bicyclo [1,2,2]heptane-2-yl and bicyclo[2,2,2]octane-3-yl), and a tricycloalkyl group; more preferably a monocyclic cycloalkyl group and a bicycloalkyl group, and particularly preferably a monocyclic cycloalkyl group); an alkenyl group (preferably a straight- or branched-chain, substituted or unsubstituted alkenyl group having 2 to 30 carbon atoms, e.g., vinyl, allyl, prenyl, geranyl, oleyl); a cycloalkenyl group (preferably a substituted or unsubstituted monocyclic cycloalkenyl group having 3 to 30 carbon atoms, e.g., 2-cyclopentene-1-yl, 2-cyclohexene-1-yl; and a polycyclic cycloalkenyl group, such as a bicycloalkenyl group (preferably a substituted or unsubstituted bicycloalkenyl group having 5 to 30 carbon atoms, e.g., bicyclo[2,2,1] hepto-2-ene-1-yl and bicyclo[2,2,2]octo-2-ene-4-yl) and a tricycloalkenyl group, with a monocyclic cycloalkenyl group being particularly preferred); an alkynyl group (preferably a substituted or unsubstituted alkynyl group having 2 to 30 carbon atoms, e.g., ethynyl, propargyl, trimethylsilylethynyl); an aryl group (preferably a substituted or unsubstituted aryl group having 6 to 30 carbon atoms, e.g., phenyl, p-tolyl, naphthyl, m-chlorophenyl, o-hexadecanoylaminophenyl); a heterocyclic group (preferably a 5- to 7-membered, substituted or unsubstituted, saturated or unsaturated, aromatic or non-aromatic, monocyclic or condensed heterocyclic group, more preferably a heterocyclic group having ring-constituting atoms selected from carbon, nitrogen and sulfur atoms, and containing at least one hetero atom selected from the group consisting of nitrogen, oxygen and sulfur atoms, further preferably a 5- or 6-membered aromatic heterocyclic group having 3 to 30 carbon atoms, e.g., 2-furyl, 2-thienyl, 2-pyridyl, 4-pyridyl, 2-pyrimidinyl, 2-bemzothiazolyl); a cyano group; a hydroxyl group; a nitro group; a carbxyl group; an alkoxy group (preferably a substituted or unsubstituted alkoxyl group having 1 to 30 carbon atoms, e.g., methoxy, ethoxy, isopropoxy, t-butoxy, n-octyloxy, 2-methoxyethoxy); an aryloxy group (preferably a substituted or unsubstituted aryloxy group having 6 to 30 carbon atoms, e.g., phenoxy, 2-methylphenoxy, 2,4-di-t-amylphenoxy, 4-t-buthylphenoxy, 3-nitrophenoxy, 2-tetradecanoylaminophenoxy); a silyloxy group (preferably a silyloxy group having 3 to 20 carbon atoms, e.g., trimethylsilyloxy, t-butyldimethylsilyloxy); a herocyclic oxy group (preferably a substituted or unsubstituted heterocyclic oxy group having 2 to 30 carbon atoms, more preferably having the same heterocycle moiety as that of the heterocyclic group, e.g., 1-phenyltetrazole-5-oxy, 2-tetrahydropyranyloxy); an acyloxy group (preferably formyloxy, a substituted or unsubstituted alkylcarbonyloxy group having 2 to 30 carbon atoms, a substituted or unsubstituted arylcarbonyloxy group having 6 to 30 carbon atoms, e.g., formyloxy, acetyloxy, pivaloyloxy, stealoyloxy, benzoyloxy, p-methoxyphenylcarbonyloxy); a carbamoyloxy group (preferably a substituted or unsubstituted carbamoyloxy group having 1 to 30 carbon atoms, e.g., N,N-dimethylcarbamoyloxy, N,N-diethylcarbamoyloxy, morpholino carbonyloxy, N,N-di-n-octylaminocarbonyloxy, N-n-octylcarbamoyloxy); an alkoxycarbonyloxy group (preferably a substituted or unsubstituted alkoxycarbonyloxy group having 2 to 30 carbon atoms, e.g., methoxycarbonyloxy, ethoxycarbonyloxy, t-butoxy carbonyloxy, n-octylcarbonyloxy); an aryloxycarbonyloxy group (preferably a substituted or unsubstituted aryloxycarbonyloxy group having 7 to 30 carbon atoms, e.g., phenoxycarbonyloxy, p-methoxy phenoxycarbonyloxy, p-n-hexadecyloxyphenoxy carbonyloxy); an amino group (preferably an unsubstituted amino group, a substituted or unsubstituted alkylamino group having 1 to 30 carbon atoms, a substituted or unsubstituted arylamino group having 6 to 30 carbon atoms, and a heterocyclic amino group having 0 to 30 carbon atoms, e.g., amino, methylamino, dimethylamino, anilino, N-methylanilino, diphenylamino, N-1,3,5-triazine-2-il amino), an acylamino group (preferably formylamino group, a substituted or unsubstituted alkylcarbonylamino group having 1 to 30 carbon atoms, a substituted or unsubstituted arylcarbonylamino group having 6 to 30 carbon atoms, e.g., formylamino, acetylamino, pivaloylamino, lauroylamino, benzoylamino and 3,4,5-tri-n-octyloxyphenylcarbonylamino); an aminocarbonylamino group (preferably a substituted or unsubstituted aminocarbonylamino group having 1 to 30 carbon atoms, e.g., carbamoylamino, N,N-dimethylaminocarbonylamino, N,N-diethylamino carbonylamino, morpholinocarbonylamino), an alkoxycarbonylamino group (preferably a substituted or unsubstituted alkoxycarbonylamino group having 2 to 30 carbon atoms, e.g., methoxycarbonylamino, ethoxy carbonylamino, t-butoxycarbonylamino, n-octadecyloxycarbonylamino, N-methyl-methoxycarbonylamino); an aryloxycarbonylamino group (preferably a substituted or unsubstituted aryloxycarbonylamino group having 7 to 30 carbon atoms, e.g., phenoxycarbonylamino, p-chlorophenoxycarbonylamino, m-n-octyloxyphenoxycarbonyl amino); a sulfamoyl amino group (preferably a substituted or unsubstituted sulfamoylamino group having 0 to 30 carbon atoms, e.g., sulfamoylamino, N,N-dimethylaminosulfonylamino, N-n-octyl aminosulfonylamino); an alkyl- or arylsulfonylamino group (preferably a substituted or unsubstituted alkyl-sulfonylamino group having 1 to 30 carbon atoms, and a substituted or unsubstituted aryl-sulfonylamino group having 6 to 30 carbon atoms, e.g., methylsulfonylamino, butylsulfonylamino, phenylsulfonylamino, 2,3,5-trichlorophenylsulfonylamino, p-methylphenylsulfonylamino); a mercapto group; an alkylthio group (preferably a substituted or unsubstituted alkylthio group having 1 to 30 carbon atoms, e.g., methylthio, ethylthio, n-hexadecylthio), an arylthio group (preferably a substituted or unsubstituted arylthio group having 6 to 30 carbon atoms, e.g., phenylthio, p-chlorophenylthio, m-methoxyphenylthio); a heterocyclic thio group (preferably a substituted or unsubstituted heterocyclic thio group having 2 to 30 carbon atoms in which the heterocycle moiety is preferably the same as that of the above-described heterocyclic group, e.g., 2-benzothiazolylthio, 1-phenyltetrazol-5-ylthio); a sulfamoyl group (preferably a substituted or unsubstituted sulfamoyl group having 0 to 30 carbon atoms, e.g., N-ethylsulfamoyl, N-(3-dodecyloxypropyl)sulfamoyl, N,N-dimethyl sulfamoyl, N-acetylsulfamoyl, N-benzoylsulfamoyl, N—(N'-phenylcarbamoyl) sulfamoyl); a sulfo group; an alkyl- or aryl-sulfinyl group (preferably a substituted or unsubstituted akylsulfinyl group having 1 to 30 carbon atoms, and a substituted or unsubstituted arylsulfinyl group having 6 to 30 carbon atoms, e.g., methyl sulfinyl, ethyl sulfinyl, phenylsulfinyl, p-methylphenylsulfinyl); an alkyl- or arylsulfonyl group (preferably a substituted or unsubstituted akyl sulfonyl group having 1 to 30 carbon atoms, and a substituted or unsubstituted arylsulfinyl group having 6 to 30 carbon atoms, e.g., methylsulfonyl, ethylsulfonyl, phenyl sulfonyl, p-methylphenylsulfonyl); an acyl group (preferably a formyl group, a substituted or unsubstituted alkylcarbonyl group having 2 to 30 carbon atoms, and a substituted or unsubstituted arylcarbonyl group having 7 to 30 carbon atoms, e.g., acetyl, pivaloyl, 2-chloroacetyl, stearoyl, benzoyl, p-n-octyloxyphenylcarbonyl); an aryloxycarbonyl group (preferably a substituted or unsubstituted aryloxycarbonyl group having 7 to 30 carbon atoms, e.g., phenoxycarbonyl, o-chlorophenoxycarbonyl, m-nitrophenoxy carbonyl, p-t-butylphenoxycarbonyl); an alkoxycarbonyl group (preferably a substituted or unsubstituted alkoxycarbonyl group having 2 to 30 carbon atoms, e.g., methoxycarbonyl, ethoxycarbonyl, t-butoxycarbonyl, n-octadecyloxycarbonyl); a carbamoyl group (preferably a substituted or unsubstituted carbamoyl group having 1 to 30 carbon atoms, e.g., carbamoyl, N-methylcarbamoyl, N,N-dimethylcarbamoyl, N,N-di-n-octylcarbamoyl, N-(methylsulfonyl)carbamoyl); an aryl azo group or heterocyclic azo group (preferably a substituted or unsubstituted aryl azo group having 6 to 30 carbon atoms, and a substituted or unsubstituted heterocyclic azo group having 3 to 30 carbon atoms, in which the heterocyclic moiety is preferably the same as that of the above-described heterocyclic group, e.g., phenylazo, p-chlorophenylazo, 5-ethylthio-1,3,4-thiadiazole-2-yl azo); an imido group (preferably a substituted or unsubstituted imido group having 2 to 30 carbon atoms, e.g., N-succinimido, N-phthalimido); a phosphino group (preferably a substituted or unsubstituted phosphino group having 2 to 30 carbon atoms, e.g., dimethylphosphino, diphenylphosphino, methylphenoxyphosphino); a phosphinyl group (preferably a substituted or unsubstituted phosphinyl group having 2 to 30 carbon atoms, e.g., phosphinyl, dioctyloxyphosphinyl, diethoxyphosphinyl); a phosphinyloxy group (preferably a substituted or unsubstituted phosphinyloxy group having 2 to 30 carbon atoms, e.g., diphenoxyphosphinyloxy, dioctloxyphosphinyloxy); a phosphinylamino group (preferably a substituted or unsubstituted phosphinylamino group having 2 to 30 carbon atoms, e.g., dimethoxyphosphinylamino, dimethylamino phosphinylamino); and a silyl group (preferably a substituted or unsubstituted silyl group having 3 to 30 carbon atoms, e.g., trimethylsilyl, t-butyl dimethylsilyl, phenyldimethylsilyl).

Among the above-described functional groups, a hydrogen atom(s) possessed in the functional group may be removed to replace with any one of the above-described groups. Examples of these functional groups include an alkylcarbonylaminosulfonyl group, an arylcarbonylaminosulfonyl group, an alkylsulfonylaminocarbonyl group, and an arylsulfonyl aminocarbonyl group. As the specific examples, methylsulfonyl aminocarbonyl, p-methylphenylsulfonylaminocarbonyl, acetylaminosulfonyl, and benzoylaminosulfonyl groups are enumerated.

R1 is preferably a substituted or unsubstituted alkyl group, more preferably a substituted alkyl group. As the substituent of the substituted alkyl group, those enumerated as the substituent of R1 mentioned above are exemplified. A total carbon atoms of R1 is preferably 1 to 60, more preferably 6 to 50, still more preferably 11 to 45, further more preferably 12 to 40, and most preferably 16 to 30.

R1 is preferably an alkyl group substituted with an alkoxy group or aryloxy group at the 2-, 3- or 4-position, more preferably an alkyl group substituted with an alkoxy group or aryloxy group at the 3-position, most preferably 3-(2,4-di-t-amylphenoxy)propyl group. As the unsubstituted alkyl group, a —$C_{16}H_{33}$ or —$C_{18}H_{37}$ group is preferred. In case where R1 is a —$C_{16}H_{33}$ or —$C_{18}H_{37}$ group, there is a merit that a coupler can be economically produced because $C_{16}H_{33}NH_2$ and $C_{18}H_{37}NH_2$, each of which is a raw material, are inexpensive.

In formula (I), Q represents a group represented by —C(—$R_{11}$)=C(—$R_{12}$)—$SO_2$— (in the present invention, this expression of the foregoing group should not be construed as limited to the direction of the bonds belonging to the group as represented by this expression). $R_{11}$ and $R_{12}$ collectively represent a group which forms a 5- to 7-membered ring, together with the —C=C— moiety, when $R_{11}$ and $R_{12}$ bond with each other, or alternatively $R_{11}$ and $R_{12}$ each independently represent a hydrogen atom or a substituent. The 5- to 7-membered ring thus formed may be saturated or unsaturated, and the unsaturated ring may be an alicyclic, aromatic or heterocyclic ring. Examples of these rings include benzene, furan, thiophene, cyclopentene, and cyclohexane rings. Further, examples of the substituent represented by $R_{11}$ and $R_{12}$ are those enumerated as the substituent of the above-described R1.

Each of these substituents, or the ring which is formed by binding two or more kinds of substituents with each other, may be further substituted with a substituent as enumerated as the substituent of the above-described R1.

In formula (I), R3 represents a substituent except for a hydrogen atom. Examples of the substituent include those enumerated as the substituent of the above-described R1. R3 is preferably a halogen atom (e.g., fluorine, chlorine, bromine), an alkyl group (e.g., methyl, isopropyl), an alkoxy group (e.g., methoxy, isopropoxy), an aryloxy group (e.g., phenoxy, o-(2-ethylhexyloxy)phenoxy), an amino group (e.g., dimethylamino, morpholino), an acylamino group (e.g., acetoamido), and an sulfonamido group (e.g., methanesulfonamido, benzenesulfonamido), an alkylthio group (e.g. methylthio, isopropylthio, dodecylthio), an arylthio group (e.g. phenylthio, o-dodecyloxyphenylthio), more preferably a halogen atom, an alkoxy group, an aryloxy group, an alkyl group, an alkylthio group, and an arylthio group, and most preferably a fluorine atom, a chrorine atom, an alkoxy group, an aryloxy group, an alkylthio group, and an arylthio group.

As the alkoxy group and the alkylthio group, both branched alkoxy and alkylthio groups are preferred. The position of branch is preferably an α-position or a β-position, more preferably a β-position.

As the aryloxy group and the arylthio group, preferred are those having a substituent at the ortho-position. Examples of the substituent are those enumerated as the substituent of the above-mentioned R1.

An aryloxy group and an arylthio group each having an alkyl group, an alkoxy group, or an alkylthio group at the ortho-position, are more preferred.

In formula (I), it is preferable that R1 is a nondiffusible aliphatic group or aromatic group, and R3 is a nondiffusible aliphatic oxy group or aromatic oxy group. As the nondiffusible aliphatic group, preferred are straight chain or branched alkyl groups having 7 to 30 carbon atoms, such as benzyl, octyl, 2-ethylhexyl, isotridecyl, hexadecyl, octadecyl, tetradecyl and dodecyl groups. As the nondiffusion aliphatic oxy group, preferred are straight chain or branched alkoxy groups having 7 to 30 carbon atoms, such as benzyloxy, octyloxy, 2-ethylhexyloxy, isotridecyloxy, hexadecyloxy, octadecyloxy, tetradecyloxy and dodecyloxy groups. Further, the alkyl moiety of the nondiffusible alkyl group represented by R1 and the nondiffusible alkoxy group represented by R3, may have a structure containing therein such a functional group as represented by the following formula (A):

formula (A)

—J1—J2—R10

In formula (A), J1 represents a straight chain or branched alkylene group having 1 to 20 carbon atoms, such as methylene, 1,2-ethylene, 1,1-dimethylmethyle and 1-decylmethylene groups. R10 represents a straight chain or branched alkyl group having 1 to 20 carbon atoms, such as methyl, ethyl, propyl, isopropyl, butyl, 2-ethylhexyl and dodecyl groups. J2 represents a divalent linking group with preferred examples of —O—, —OCO—, —$OSO_2$—, —CO—, —COO—, —CON(R121)—, —CON(R121)$SO_2$—, —N(R121)—, —N(R121)CO—, —N(R121)$SO_2$—, —N(R121)CON(R122)—, —N(R121)COO—, —S(O)$_n$— and —S(O)$_n$N(R121)—, in which R121 and R122 each represent a hydrogen atom, or those having the same meanings as the alkyl group and the aryl group represented by R1 in formula (I), and n represents an integer of 0 to 2. R10 and J1 may bond with each other to form a ring.

As the nondiffusible aromatic group represented by R1, preferred are aryl groups having 7 to 30 carbon atoms. The aryl group may have a substituent, such as those enumerated as the substituent of the above-mentioned R1.

As the nondiffusible aromatic oxy group represented by R3, preferred are aryloxy groups having 7 to 30 carbon atoms. The aryloxy groups may have a substituent such as those enumerated as the substituent of the above-mentioned R1.

In formula (I), R4 represents a substituent. Examples of the substituent include those enumerated as the substituent of the above-described R1. R4 is preferably a halogen atom, an alkyl group, an alkoxy group, an aryloxy group, an alkoxycarbonyl group, an aryloxycarbonyl group, a cabamoyl group, a sulfamoyl group, an acylamino group, an alkyl- or aryl-sulfonylamino group, an alkylthio group, and an arylthio group. m represents an integer of 0 to 4. When m is an integer of 2 or more, R4s may be the same or different, or R4s may bond with each other to form a ring.

More preferably, R4 is an alkyl group, an alkoxy group, an aryloxy group, an alkylthio group, or an arylthio group. More preferably, R4 is an alkyl group, or an alkoxy group. Most preferably, R4 is a t-alkyl group.

A substituted position of R4 is preferably para-position against a —CONH— group, or para-position against R3, more preferably, R4 is para-position against R3.

In formula (I), X represents a hydrogen atom, or a group that can be split-off upon a coupling reaction with an oxidized product of a developing agent. Examples of the above-described group capable of being split-off upon a coupling reaction with an oxidized product of a developing agent include a group capable of being split-off with a nitrogen, oxygen, or sulfur atom (a splitting-off atom), and a halogen atom (e.g., chlorine, bromine).

Examples of the group that splits off with a nitrogen atom include a heterocyclic group (preferably 5-to 7-membered substituted or unsubstituted saturated or unsaturated aromatic (herein the term "aromatic" is used to embrace a substance that has (4n+2) cyclic conjugated electrons) or non-aromatic, monocyclic or condensed heterocyclic groups, more preferably 5- or 6-membered heterocyclic groups, in which the ring-forming atoms are selected from carbon, nitrogen and sulfur atoms and in addition at least one of hetero atoms selected from nitrogen, oxygen and sulfur atoms is incorporated, with specific examples of the heterocyclic ring including succinimide, maleinimide, phthalimide, diglycolimide, pyrrole, pyrazole, imidazole, 1,2,4-triazole, tetrazole, indole, benzopyrazole, benzimidazole, benzotriazole, imidazoline-2,4-dione, oxazolidine-2,4-dione, thiazolidine-2-one, benzimidazoline-2-one, benzoxazoline-2-one, benzothiazoline-2-one, 2-pyrroline-5-one, 2-imidazoline-5-one, indoline-2,3-dione, 2,6-dioxypurine, parabanic acid, 1,2,4-triazolidine-3,5-dione, 2-pyridone, 4-pyridone, 2-pyrimidone, 6-pyridazone, 2-pyrazone, 2-amino-1,3,4-thiazolidine-4-one), a carbonamido group (e.g., acetamido, trifluoroacetamido), a sulfonamido group (e.g., methanesulfonamido, benzenesulfonamido), an arylazo group (e.g., phenylazo, naphthylazo), and a carbamoylamino group (e.g., N-methyl carbamoylamino).

Preferred of the group that splits off with a nitrogen atom are heterocyclic groups, more preferably aromatic heterocyclic groups having 1, 2, 3 or 4 ring-forming nitrogen atoms, or heterocyclic groups represented by the following formula (L). The heterocyclic groups represented by the following formula (L) are further more preferred:

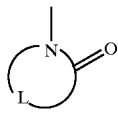

formula (L)

wherein L represents a moiety that forms a 5- to 6-membered nitrogen-containing heterocycle with —NC (=O)—.

Examples of the moieties are enumerated in the explanation of the above-mentioned heterocyclic group, and such moieties as enumerated above are more preferred. Particularly preferably L is a moiety that forms a 5-membered nitrogen-containing heterocyclic ring.

Examples of the group that splits off with an oxygen atom include an aryloxy group (e.g., phenoxy, 1-naphthoxy), a heterocyclic oxy group (e.g., pyridyloxy, pyrazolyloxy), an acyloxy group (e.g., acetoxy, benzoyloxy), an alkoxy group (e.g., methoxy, dodecyloxy), a carbamoyloxy group (e.g., N,N-diethylcarbamoyloxy, morpholinocarbamoyloxy), an aryloxycarbonyloxy group (e.g., phenoxycarbonyloxy), an alkoxycarbonyloxy group (e.g., methoxycarbonyloxy, ethoxycarbonyloxy), an alkylsulfonyloxy group (e.g., methanesulfonyloxy), and an aryl sulfonyloxy group (e.g., benzenesulfonyloxy, toluenesulfonyloxy).

Preferred of these groups capable of being spilt-off at the moiety of oxygen atom are an aryloxy group, an acyloxy group and a heterocyclic oxy group.

Examples of the group that splits off with a sulfur atom include an arylthio group (e.g., phenylthio, naphthylthio), a heterocyclic thio group (e.g., tetrazolylthio, 1,3,4-thiadiazolylthio, 1,3,4-oxazolylthio, benzimidazolyl thio), an alkylthio group (e.g., methylthio, octylthio, hexadecylthio), an alkylsulfinyl group (e.g., methane sulfinyl), an arylsulfinyl group (e.g., benzenesulfinyl), an arylsulfonyl group (e.g., benzenesulfonyl), and an alkylsulfonyl group (e.g., methansulfonyl).

Preferred of the group that splits off with a sulfur atom are an arylthio group and a heterocyclic thio group. A heterocyclic thio group is more preferred.

As X, a group that can be spilt-off upon a coupling reaction with an oxidized product of a developing agent is more preferred than a hydrogen atom. The above-said coupling spilt-off group may be substituted with a substituent such as those enumerated as the substituent of the above-mentioned R1.

X is preferably a group that can be spilt-off with a nitrogen or oxygen atom (a cleavable group), more preferably a group that can be spilt-off with a nitrogen atom. Further, those groups described as the preferable examples of the group that can be spilt-off with a nitrogen atom, are preferred in the same order as mentioned above.

X is more preferably a pyrazole-1-yl group, imidazole-1-yl group, pyrrole-1-yl group, each of which may have a substituent, or a heterocyclic group represented by the above-mentioned formula (L). X is more preferably a pyrazole-1-yl group, imidazole-1-yl group, pyrrole-1-yl group, each of which may have a substituent, most preferably an imidazole-1-yl group, or pyrrole-1-yl group, each of which may have a substituent.

X is preferably a group that gives substantially no development inhibitor, after X is spilt-off upon a coupling reaction with an oxidized product of a developing agent. The group X that releases a development inhibitor has a problem that the raw stock stability of an unexposed light-sensitive material is low due to the released development inhibitor. Examples of the group that releases a development inhibitor include a benzotriazole-1-yl, or -2-yl group, an arylthio group and a heterocyclic thio group.

Further, X is preferably a group that releases no magenta coupler, after X cleaved off upon a coupling reaction with an oxidized product of a developing agent. The group X that releases a magenta coupler, has a problem that a magenta dye and a yellow dye are present in a mixture after processing, resulting in a law color purity. Examples of the groups that release a magenta coupler after splitting, include a pyrazolo [5,1-b] [1,2,4] triazole-1-yl group a pyrazolo [1,5-b][1,2,4] triazole-1-yl group, an indazolone-1-yl group, and a pyrazolo [1,5-a] benzimidazole-4-yl group, each of which may have a substituent.

Further, in case where 1,2,4-benzothiadiazine-1,1-dioxide ring is formed by Q, and/or in case where R1 is a methyl group, R3 is a chlorine atom and m is 0, a group that is cleavable upon a coupling reaction with an oxidized product of a developing agent, is more preferred than a hydrogen atom from the viewpoint of the effects which is obtained by the present invention.

In order to render the coupler inmobile in a light-sensitive material, at least one of Q, R1, X, R3 and R4 has preferably 7 to 50 carbon atoms, more preferably 10 to 50 carbon atoms, further preferably 10 to 40 carbon atoms, most preferably 12 to 35 carbon atoms, in total respectively, including carbon atoms of a substituent(s) that they may have thereon.

From the viewpoint of color-forming property, at least one of Q, R1, X, R3 and R4 is preferably a group containing therein a hydroxyl group, or a dissociation group whose pKa is 3 to 12 (e.g., a —COOH group, a —NHSO$_2$-group, a phenolic hydroxyl group, a —CONHCO— group, a —CONHSO$_2$— group, a —CONHSO$_2$NH$_2$ group, and a —SO$_2$NHSO$_2$-group). More preferably X is a group carrying therein the above-mentioned group(s).

Next, the compound represented by formula (I-2) according to the present invention (herein also referred to as a dye-forming coupler) is explained in detail.

formula (I-2)

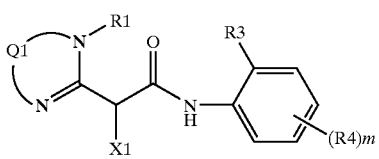

In formula (I-2), R1, R3, R4, and m each have the same meanings as those described in formula (I). Preferable examples of them are the same as described therein.

In formula (I-2), Q1 represents a group represented by —C(—$R_{11}$)=C(—$R_{12}$)—Z— (in the present invention, this expression of the foregoing group should not be construed as limited to the direction of the bonds belonging to the group as represented by this expression). z represents $SO_2$ or CO. $R_{11}$ and $R_{12}$, combined with each other, collectively represent a group that, together with the —C=C— moiety, forms a 5- to 7-membered ring, or $R_{11}$ and $R_{12}$ each independently represent a hydrogen atom or a substituent. The 5- to 7-membered ring that is formed by a combination of $R_{11}$ and $R_{12}$ may be a saturated or unsaturated alicyclic, aromatic or heterocyclic ring, such as benzene, furan, thiophene, cyclopentane and cyclohexane rings. In case where $R_{11}$ and $R_{12}$ represent a substituent, examples of the substituent are those enumerated as the substituent of the above-mentioned R1.

In formula (I-2), X1 is a group that has therein a dissociation group having pKa of 1 to 12, and that is capable of being spilt-off upon a coupling reaction with an oxidized product of a developing agent. Examples of the group that can be spilt-off upon a coupling reaction with an oxidized product of a developing agent, are the same as those of the coupling-spilt-off group of X in formula (I). Preferable examples of the group are also common to those of X. However, it is necessary in formula (I-2) that these coupling-cleavable groups further carry therein a dissociation group having pKa of 1 to 12. Said dissociation groups are explained below.

The pKa of the dissociation group carried in X1 preferably ranges from 1 to 12, more preferably from 3 to 12. Preferable examples of the dissociation group include a —COOH group, a —$NHSO_2$— group, a phenolic hydroxyl group, a —CONHCO— group, a —$CONHSO_2$— group, a —$CONHSO_2NH_2$— group and a —$SO_2NHSO_2$— group. It is more preferably a —COOH group, a —$NHSO_2$— group or a —$CONHSO_2$— group, and most preferably a —COOH group.

The number of dissociation groups is at least 1 as a necessity, preferably from 1 to 2, more preferably 1.

Next, the compound represented by formula (II) according to the present invention (herein also referred to as a dye-forming coupler) is explained in detail.

formula (II)

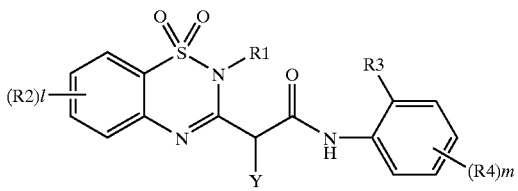

In formula (II), R1, R3, R4, and m each have the same meanings as those described in formula (I). Preferable examples of them are the same as described therein.

In formula (II), R2 represents a substituent. Examples of the substituent include those enumerated as the substituent of R1 described above. l represents an integer of 0 to 4. When l is 2 or more, R2s may be the same or different, or R2s may bond with each other to form a ring.

In formula (II), Y represents a group capable of being split-off upon a coupling reaction with an oxidized product of a developing agent. Examples of Y include those enumerated as the examples of X being a group capable of being split-off upon a coupling reaction with an oxidized product of a developing agent. Preferable examples of Y are the same as those of X.

Among the couplers represented by the formula (II), further preferable couplers include:

1) Couplers wherein R1 represents an alkyl group, Y represents an imidazole-1-yl group which may have a substituent or a pyrrole-1-yl group which may have a substituent (preferably an imidazole-1-yl group which may have a substituent), R3 represents an alkoxy group, m is 1 to 2 (preferably 1), and R4 represents a substituent, in which at least one of R4 is a group selected from an alkyl group, a cycloalkyl group or an alkoxy carbonyl group and substituted at a para-position relative to R3; or 2) Couplers wherein R1 represents an alkyl group, Y represents a group represented by the formula (L), R3 represents an alkoxy group, an aryloxy group, an alkyl thio group or an aryl thio group, m is 1 to 2 (preferably 1) and R4 represents a substituent, in which at least one of R4 is substituted at a para-position relative to R3.

Both 1) and 2) are those wherein R2 and l are as defined in the formula (II), and preferably both 1) and 2) are those wherein l is 0. Further, the respective groups described above are more preferable in the order of the description of the groups mentioned to be preferable.

Among the couplers in 1) above, further preferable couplers can be represented by the following formula (IIA). The couplers represented by the formula (IIA) are further preferable in respect of color-forming property and hue of the resultant dye.

formula (IIA)

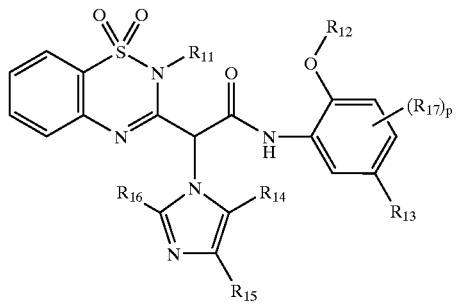

In the formula (IIA), $R_{11}$ and $R_{12}$ each independently represent a substituted or unsubstituted alkyl group. $R_{13}$ represents a substituted or unsubstituted alkyl group, a substituted or unsubstituted cycloalkyl group, or a substituted or unsubstituted alkoxy carbonyl group. $R_{14}$, $R_{15}$ and $R_{16}$ each independently represent a hydrogen atom or a substituent. $R_{17}$ represents a substituent. p represents an integer of 0 to 3. When p is 2 to 3, a plurality of $R_{17}$ groups may be the same or different.

Among the couplers represented by the formula (IIA), the couplers represented by the following formula (IIB) are preferable in respect of excellent color-forming property, even when the coupling reaction with an oxidized product of a developing agent is conducted under the condition of relatively high pH.

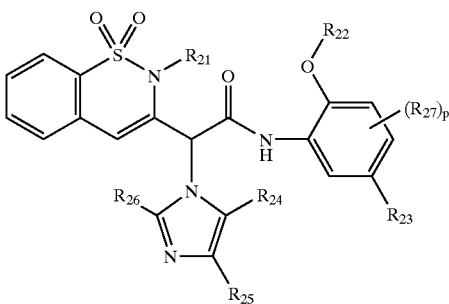

formula (IIB)

In the formula (IIB), $R_{21}$ and $R_{22}$ each independently represent a substituted or unsubstituted alkyl group. $R_{23}$ represents an unsubstituted alkyl group or an unsubstituted cycloalkyl group. $R_{24}$, $R_{25}$ and $R_{26}$ each independently represent a hydrogen atom, a chlorine atom, a substituted or unsubstituted alkyl group, or a substituted or unsubstituted alkoxy carbonyl group. $R_{27}$ represents a substituted or unsubstituted alkyl group, a halogen atom, a substituted or unsubstituted alkoxy group, or a substituted or unsubstituted alkylamino carbonyl group. p represents an integer of 0 to 3. When p is 2 or 3, a plurality of $R_{27}$ groups may be the same or different.

The couplers represented by the formula (IIB) are described in more detail.

$R_{21}$ is preferably a substituted or unsubstituted alkyl group having 1 to 30 carbon atoms (for example, methyl, ethyl, n-propyl, isopropyl, octadecyl). $R_{21}$ is more preferably an unsubstituted alkyl group having 1 to 30 carbon atoms, further preferably an unsubstituted alkyl group having 12 to 20 carbon atoms. $R_{21}$ is most preferably n-octadecyl.

$R_{22}$ is preferably a substituted or unsubstituted alkyl group having 1 to 30 carbon atoms (for example, methyl, ethyl, n-propyl, n-butyl). $R_{22}$ is more preferably an unsubstituted alkyl group having 1 to 6 carbon atoms. $R_{22}$ is most preferably methyl, ethyl or n-propyl.

$R_{23}$ is preferably an unsubstituted alkyl group having 1 to 20 carbon atoms (for example, methyl, ethyl, t-butyl, 1,1,3,3-tetramethylbutyl). $R_{23}$ is more preferably an alkyl group having 4 to 8 carbon atoms. $R_{23}$ is most preferably t-butyl.

Preferably, $R_{24}$ and $R_{25}$ each independently represent a hydrogen atom, an alkyl group having 1 to 3 carbon atoms, and an alkoxy carbonyl group having 2 to 20 carbon atoms which may have a substituent (preferably an unsubstituted alkoxy carbonyl group). More preferably, $R_{24}$ and $R_{25}$ each independently represent a hydrogen atom, methoxycarbonyl and ethoxycarbonyl.

$R_{26}$ is preferably a hydrogen atom or an alkyl group having 1 to 3 carbon atoms. $R_{26}$ is most preferably a hydrogen atom.

$R_{27}$ is preferably an unsubstituted alkyl group having 1 to 20 carbon atoms, a halogen atom, an unsubstituted alkoxy group having 1 to 20 carbon atoms.

p is preferably 0 or 1. p is more preferably 0.

The most preferable structure of the coupler represented by the formula (IIB) is a coupler wherein $R_{21}$ is an unsubstituted alkyl group having 12 to 20 carbon atoms, $R_{22}$ is an unsaturated alkyl group having 1 to 6 carbon atoms, $R_{23}$ is an unsubstituted alkyl group having 4 to 8 carbon atoms, $R_{24}$ and $R_{25}$ each independently represent a hydrogen atom, a methoxy carbonyl group or an ethoxy carbonyl group, $R_{26}$ is a hydrogen atom, and p is 0.

Next, the compound represented by formula (II-2) according to the present invention (herein also referred to as a dye-forming coupler) is explained in detail.

formula (II-2)

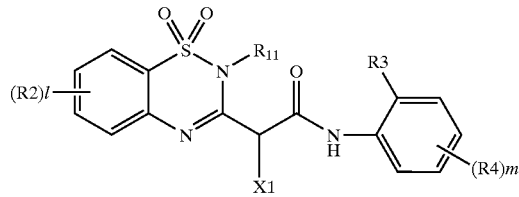

In formula (II-2), R1, R2, R3, R4, l, m, and X1 each have the same meanings as those described in formula (I), (II) or (I-2). Preferable examples of them are the same as described therein.

Preferable combinations of the groups (substituents) having bonded to the coupler represented by formula (I), (II), (I-2) or (II-2) according to the present invention are explained below. That is, R1 is a 3-(2,4-di-t-amylphenoxy)propyl group, a —$C_{16}H_{33}$ group, or a —$C_{18}H_{37}$ group; R3 is a halogen atom, an alkoxy group, an aryloxy group, an alkylthio group, or an arylthio group, and X, Y, and X1 are each independently a heterocyclic group represented by the above-mentioned formula (L), or a pyrazole-1-yl group, imidazole-1-yl group, or pyrrole-1-yl group, each of which may have a substituent.

In the present invention, the compound (I-A) described below is excluded from the couplers represented by formula (I) or (II). Said compound (I-A) is a blocked magenta coupler. The acetanilide moiety which bonds with 1,2,4-benzothiadiazine-1,1-dioxide, is just a blocking group, which flows out from a light-sensitive material after development processing, so that the acetanilide moiety is not used as an image dye. Even though this blocking group of the acetanilide moiety does not flow out from the light-sensitive material, a yellow dye and a magenta dye are present in a mixture, so that the intended effects of the present invention cannot be exhibited.

(I-A)

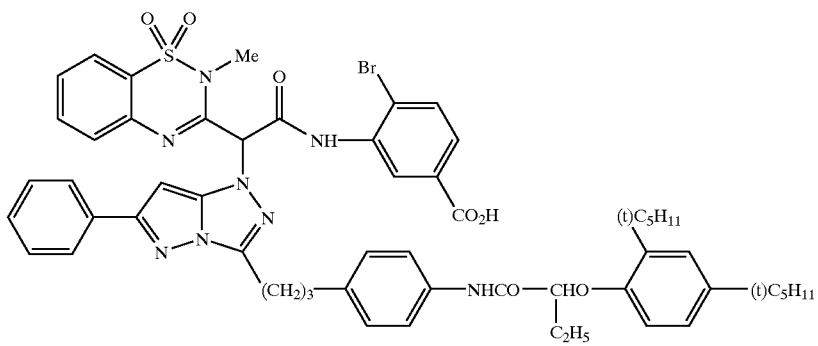

The coupler of the present invention is preferably useful as a yellow dye-forming coupler or a magenta dye-forming coupler, although according to a developing agent used in a coupling reaction. Especially, it is useful as a yellow dye-forming coupler. Additionally, a maximum absorption wavelength of the obtained dye is generally 400 to 500 nm, preferably 410 to 480 nm, and more preferably 420 to 460 nm.

Preferable specific examples of the couplers represented by formula (I), (II), (IIA), (IIB), (I-2), or (II-2) according to the present invention, are shown below, but the present invention should not be construed to be limited to them. Further, tautomers which have the hydrogen atom moved onto a nitrogen atom of the C=N moiety, which is bonded at the coupling site (in which the hydrogen atom at the coupling site is moved onto the nitrogen at the C=N moiety bonded to the coupling site), are also included in the present invention.

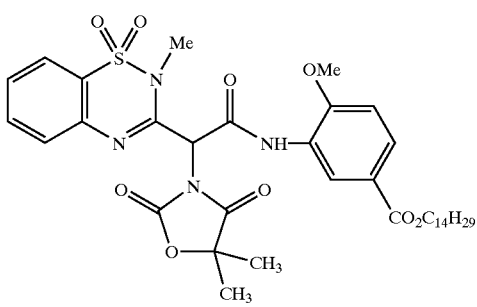

(1)

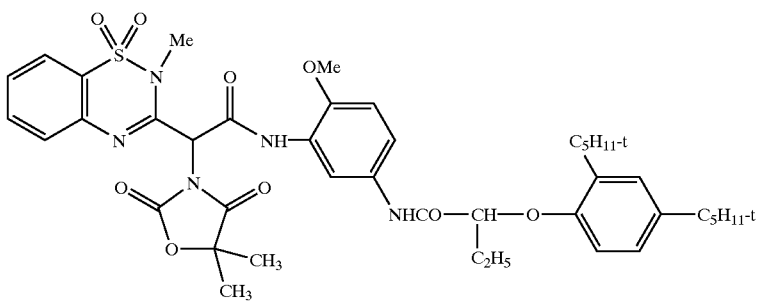

(2)

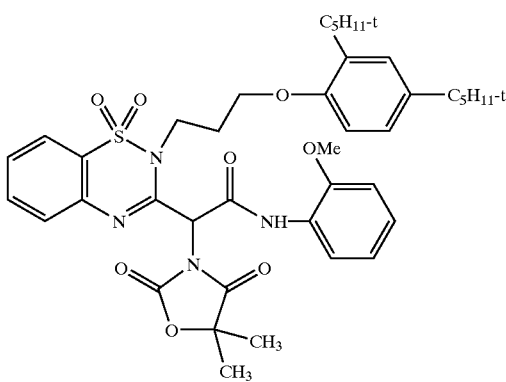

(3)

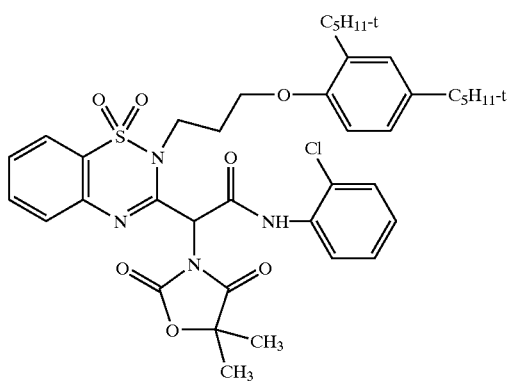

(4)

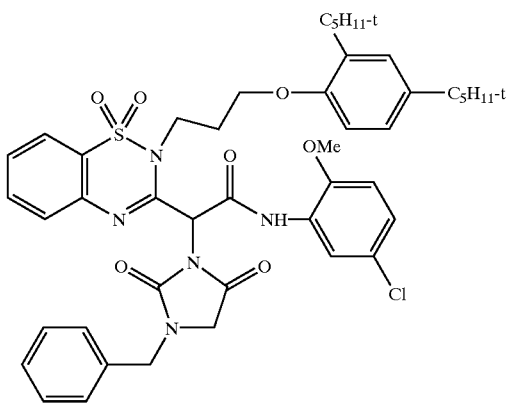

(5)

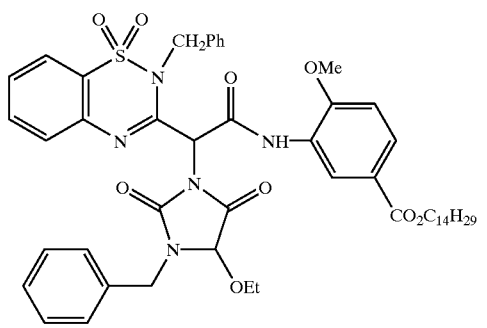

(6)

-continued
(7)
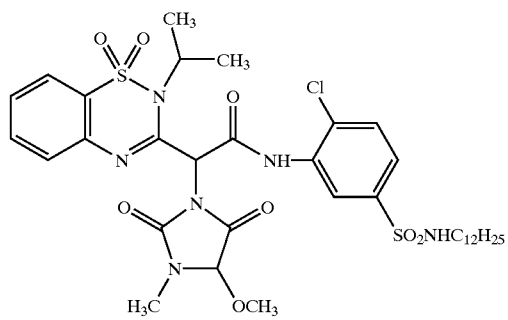
(8)
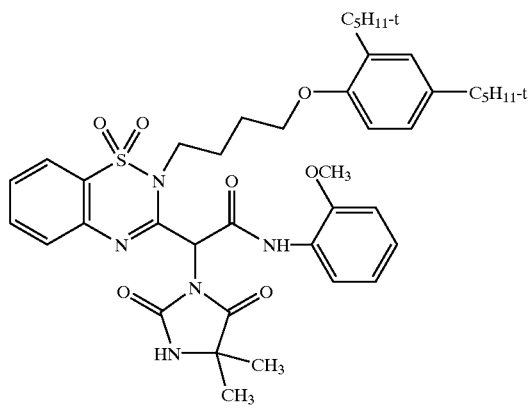
(9)
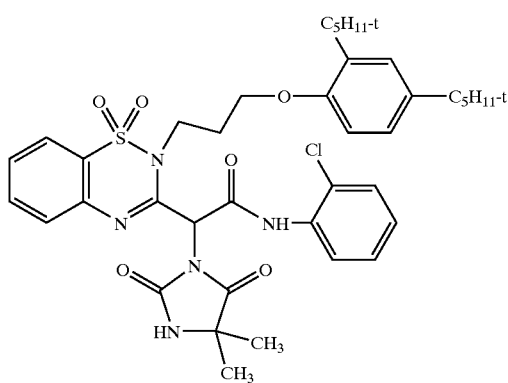
(10)
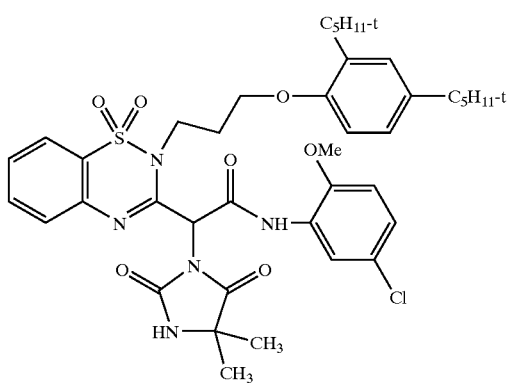
(11)
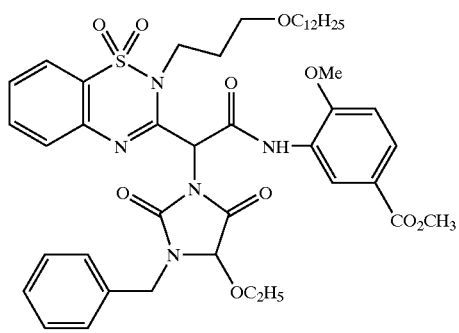
(12)
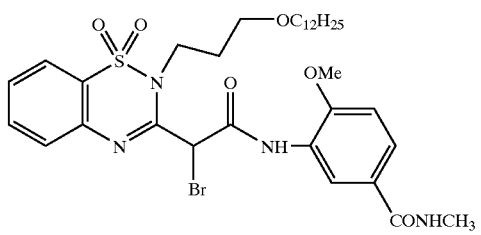
(13)
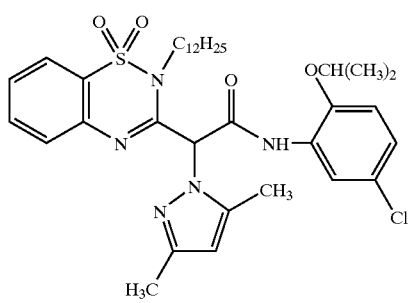
(14)
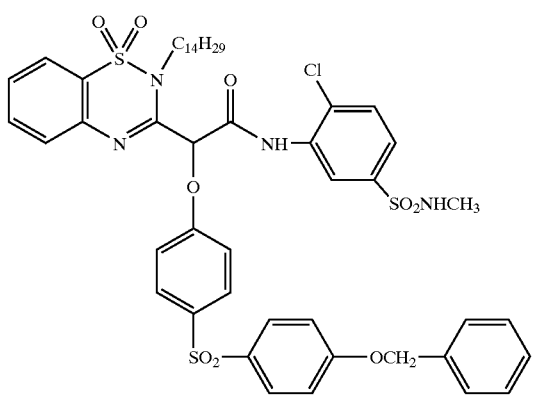

-continued
(15)
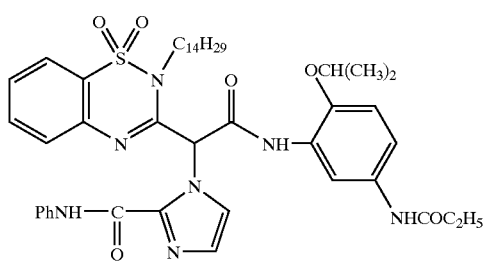
(16)
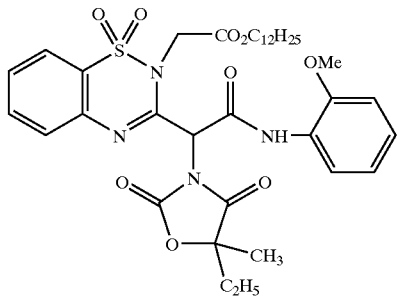
(17)
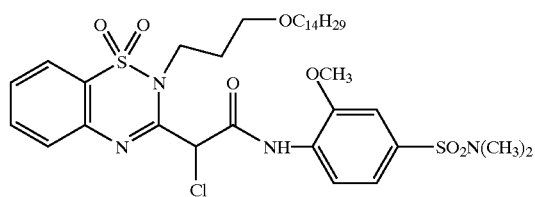
(18)
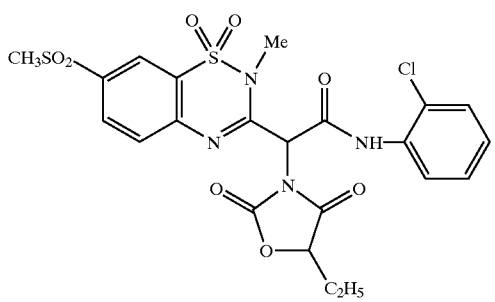
(19)
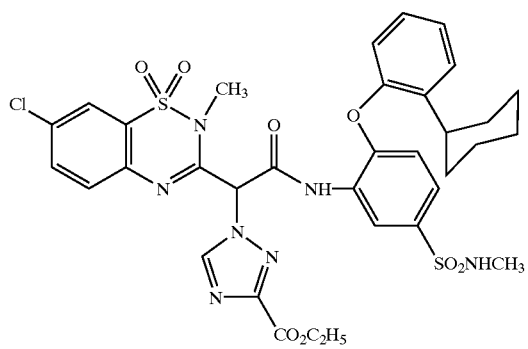
(20)
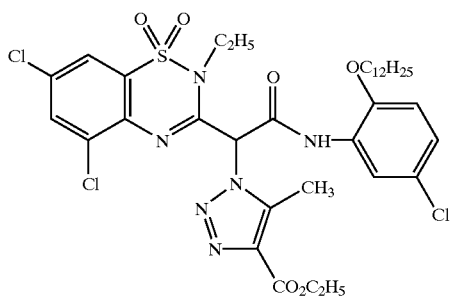
(21)
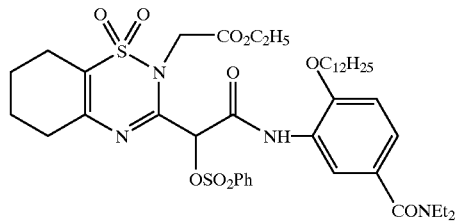
(22)
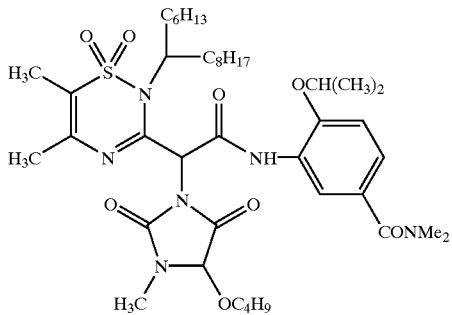
(23)
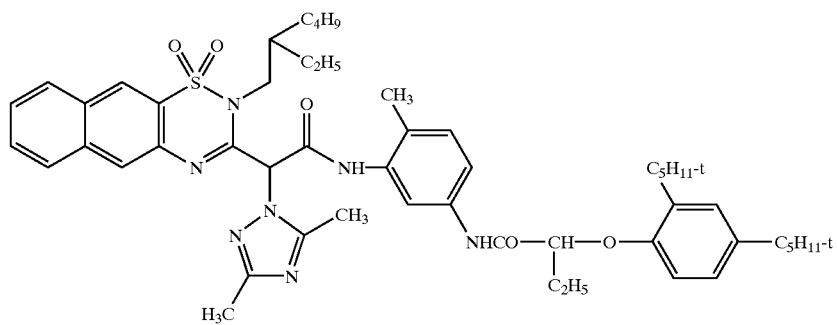

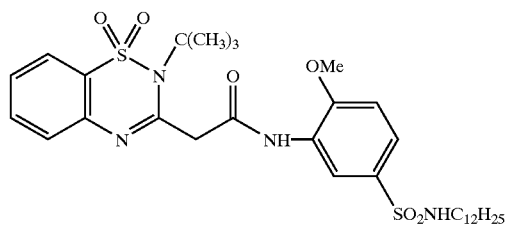
(24)
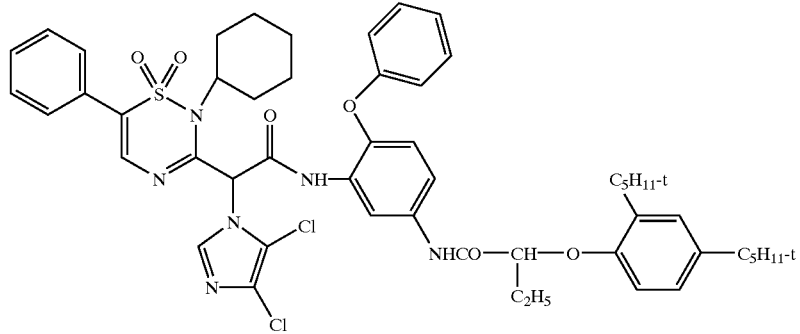
(25)
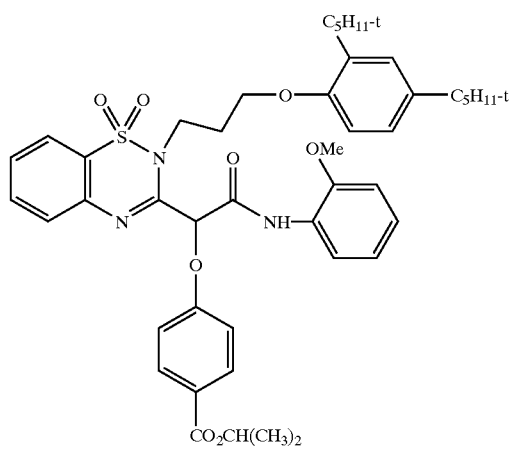
(26)
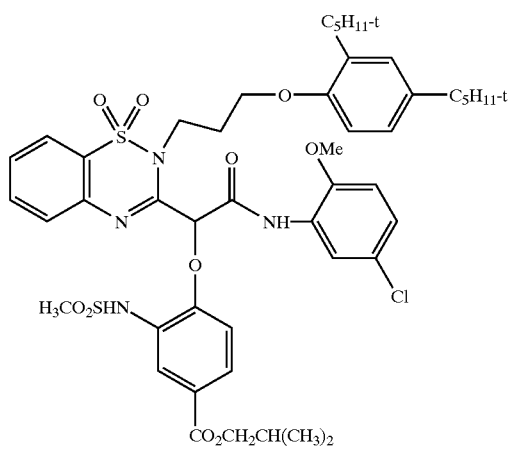
(27)
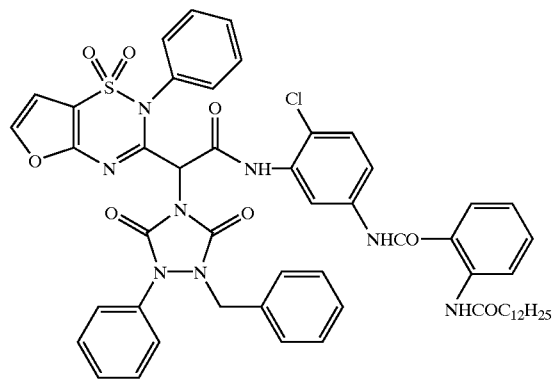
(28)
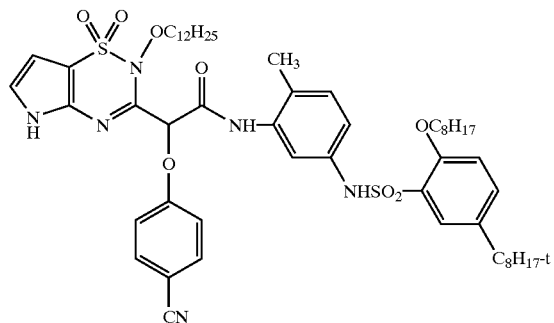
(29)

-continued
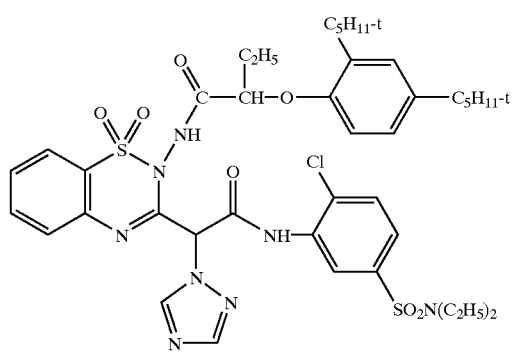
(30)
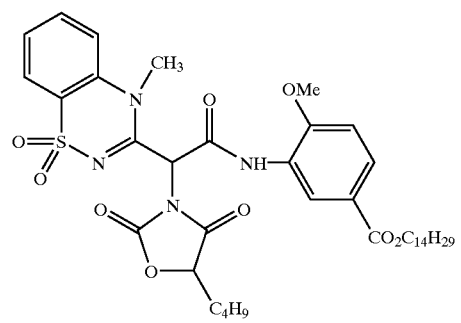
(31)
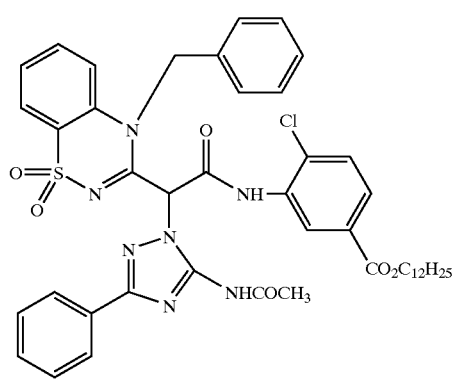
(32)
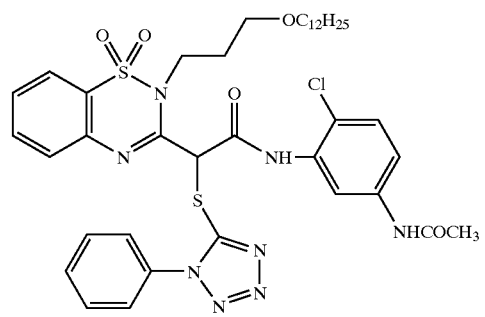
(33)
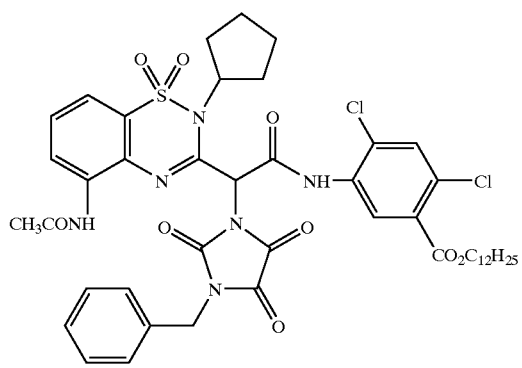
(34)
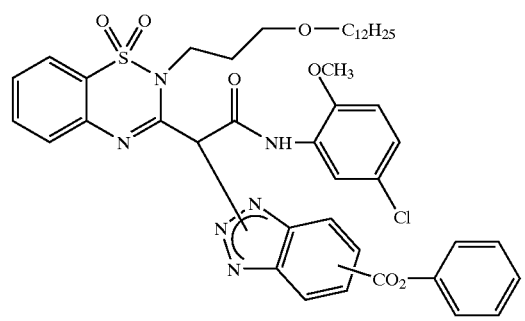
(35)
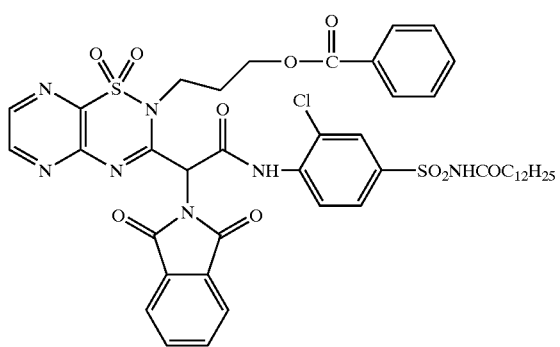
(36)
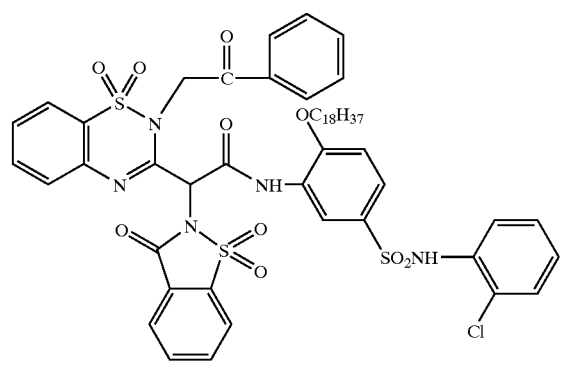
(37)

(38) 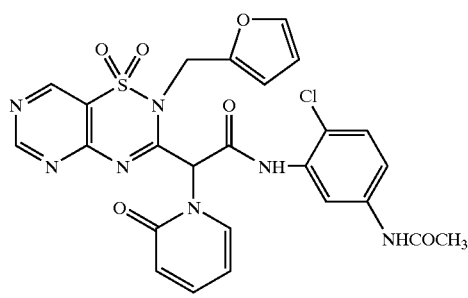
(39) 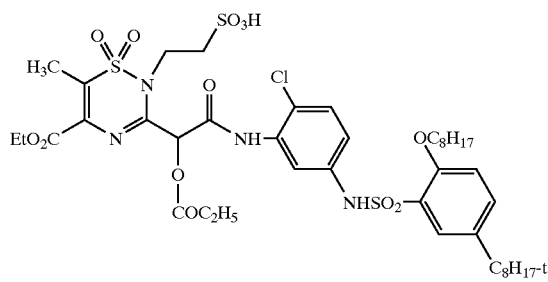
(40) 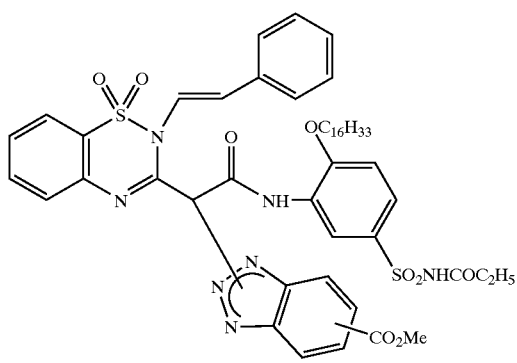
(41) 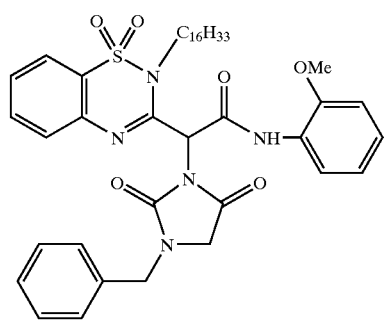
(42) 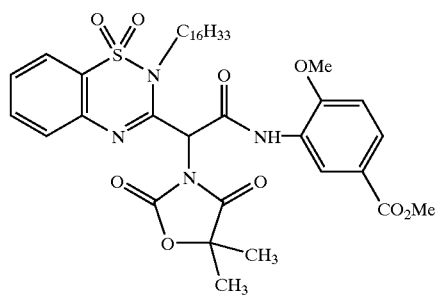
(43) 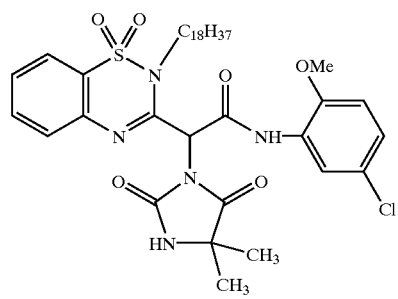
(44) 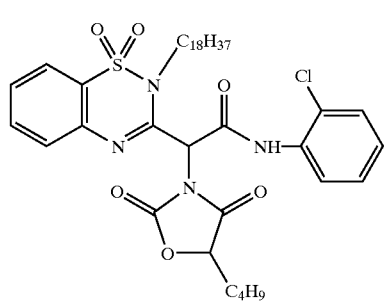
(45) 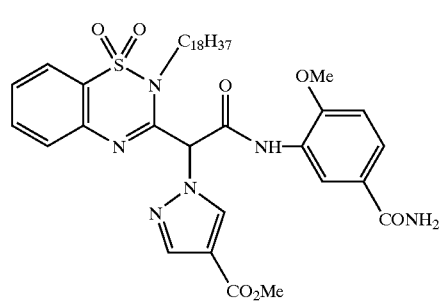
(46) 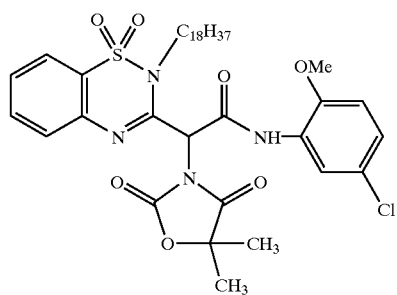
(47) 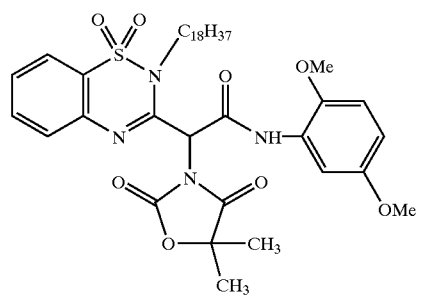

-continued
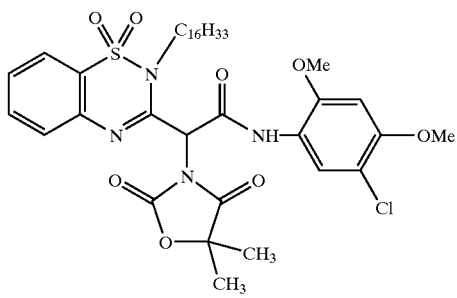
(48)
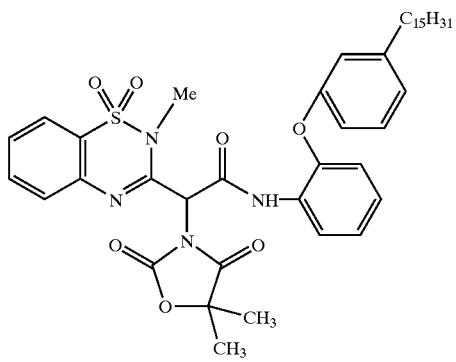
(49)
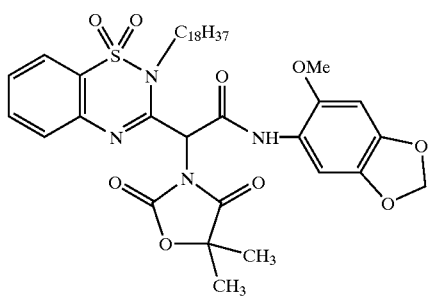
(50)
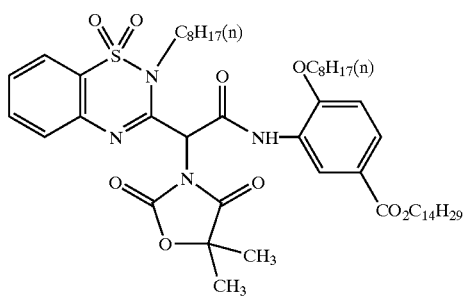
(51)
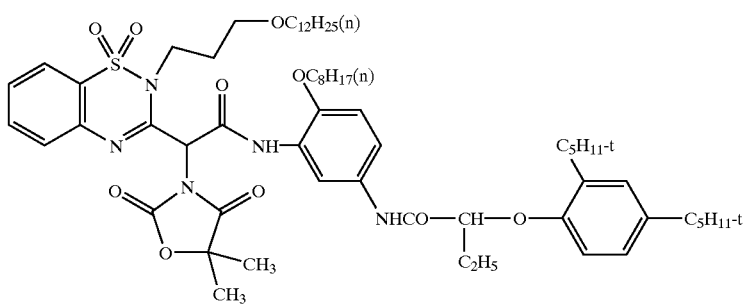
(52)
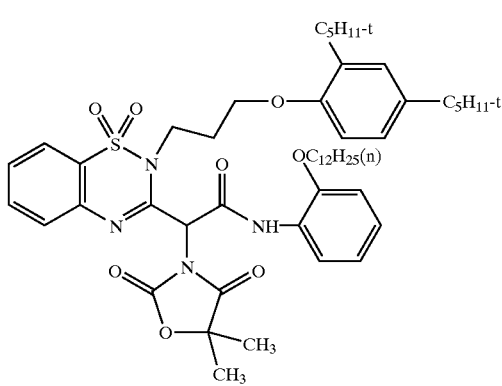
(53)
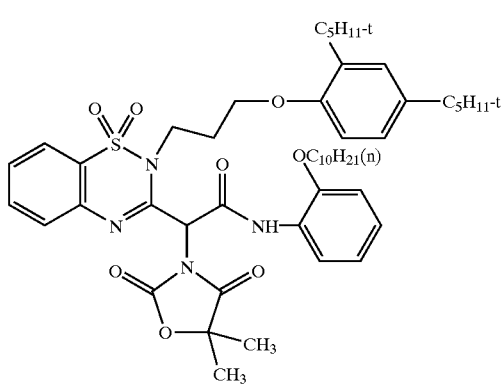
(54)

-continued
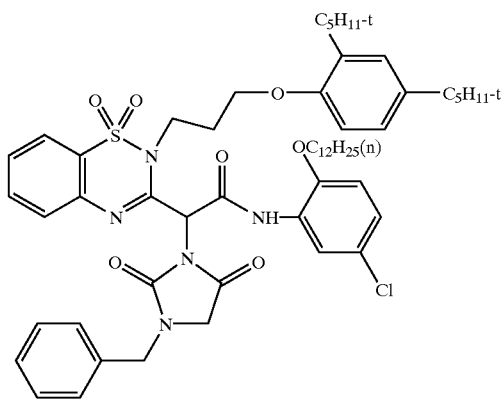 (55)
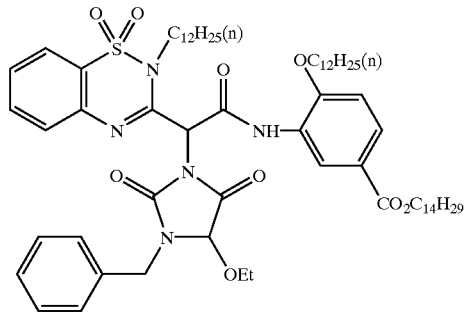 (56)
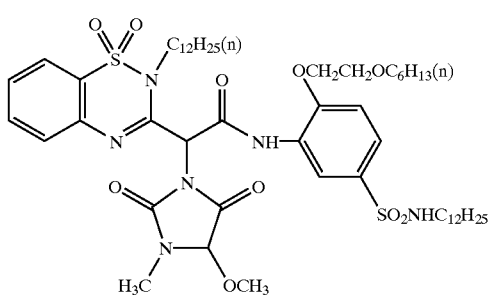 (57)
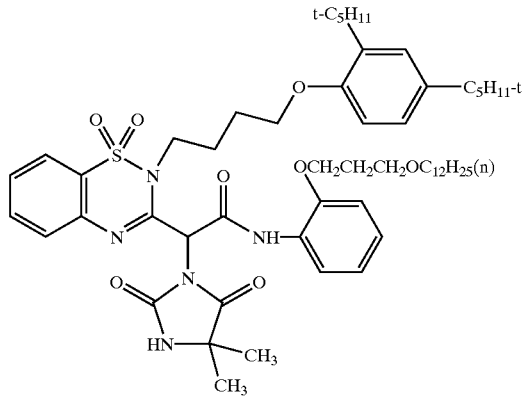 (58)
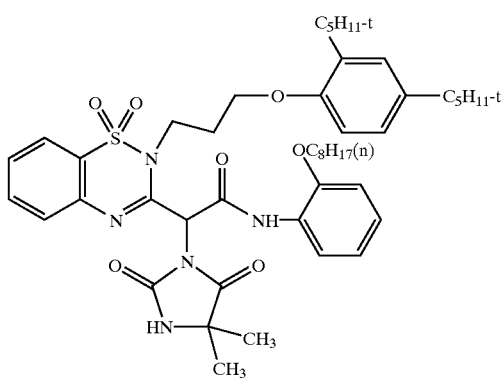 (59)
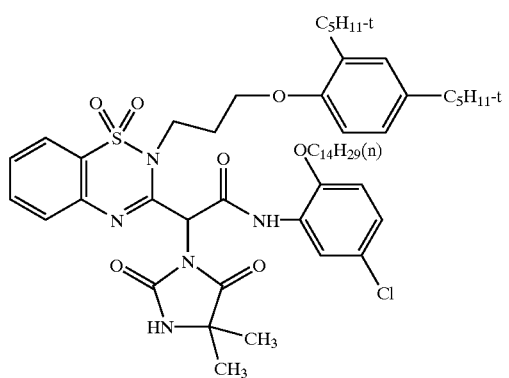 (60)
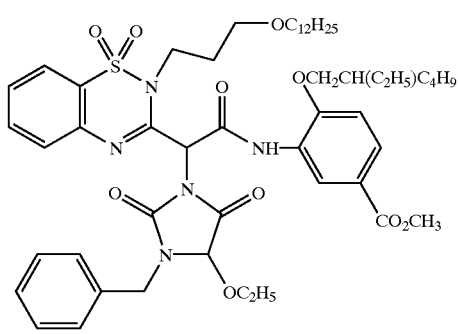 (61)
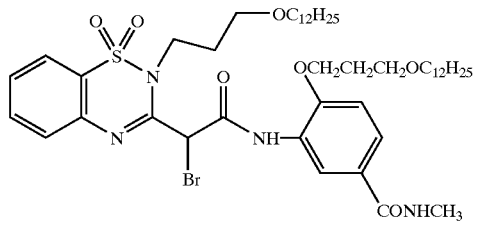 (62)

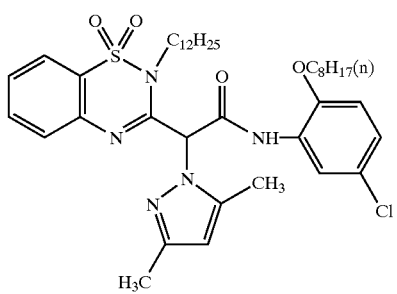
(63)
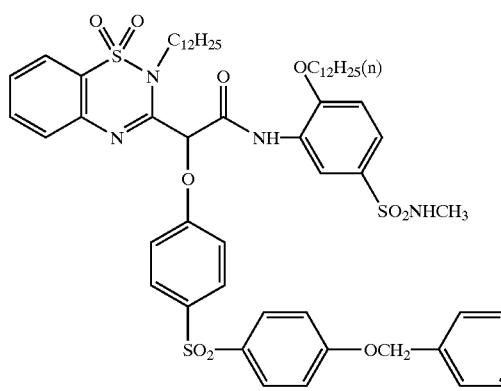
(64)
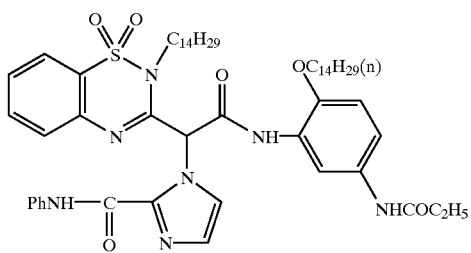
(65)
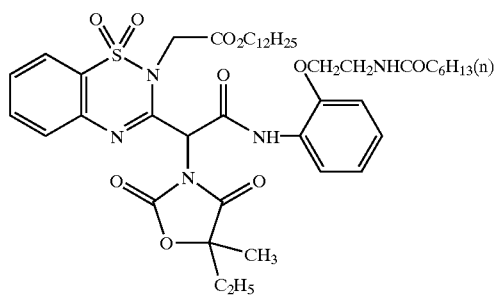
(66)
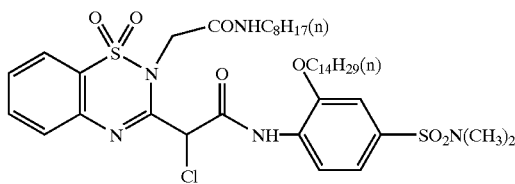
(67)
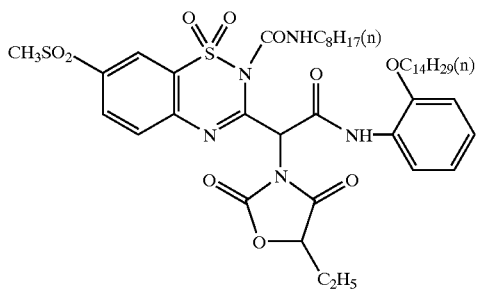
(68)
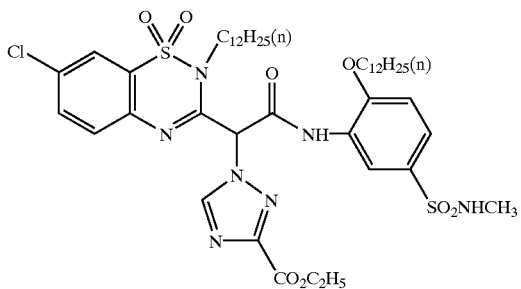
(69)
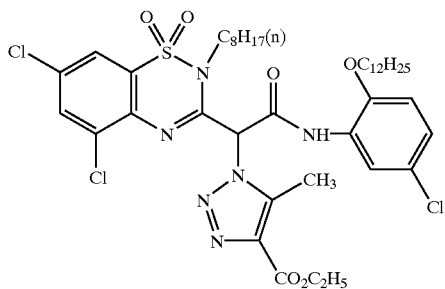
(70)
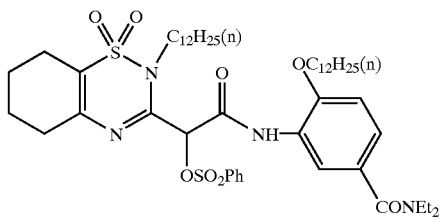
(71)
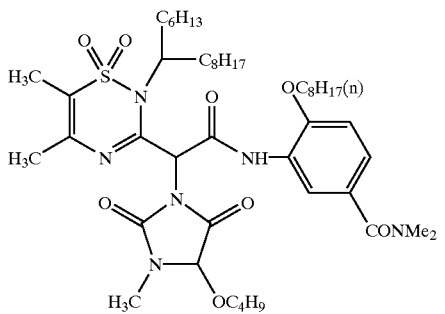
(72)

(73)
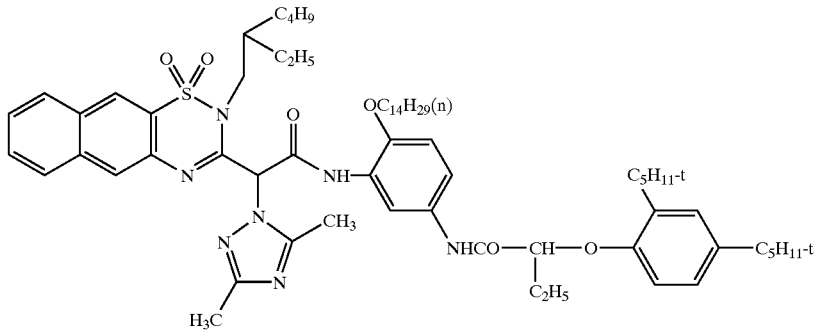
(74)
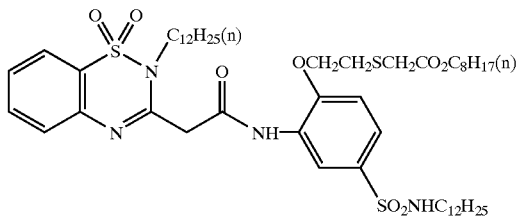
(75)
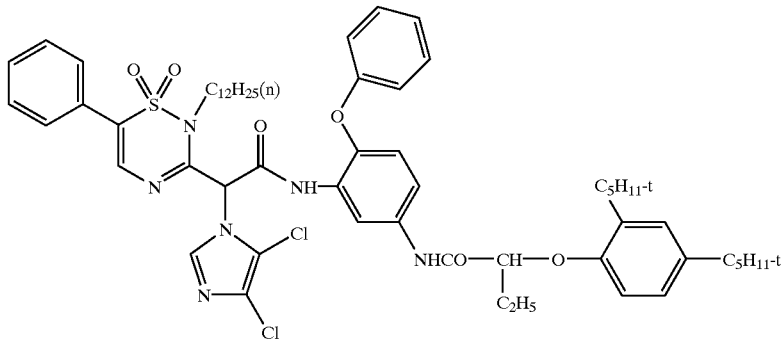
(76)
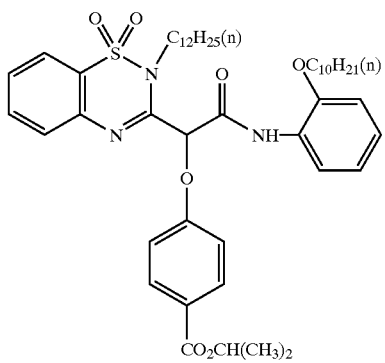
(77)
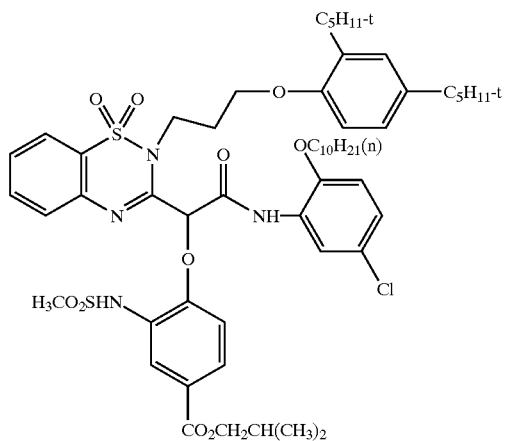

-continued
(78) 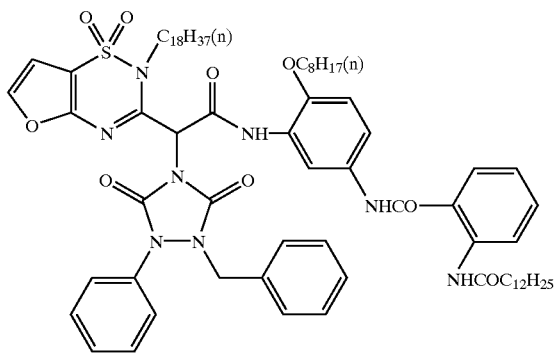
(79) 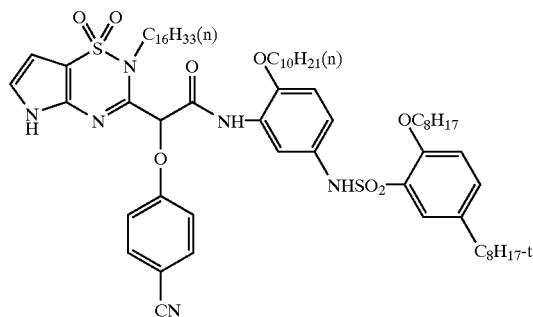
(80) 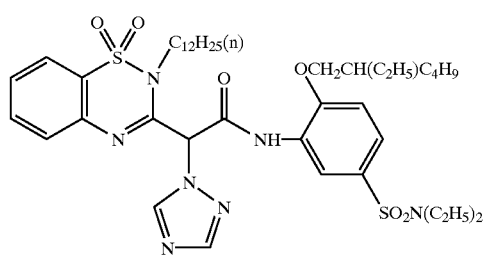
(81) 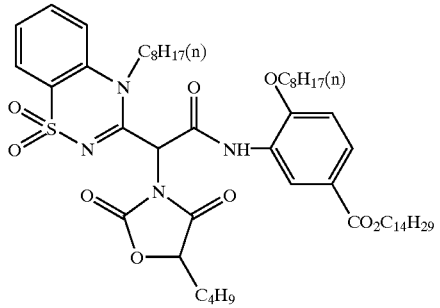
(82) 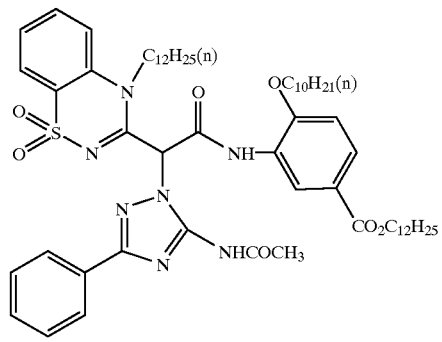
(83) 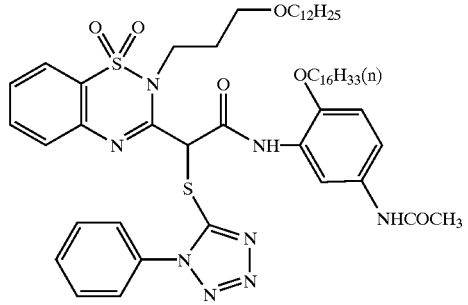
(84) 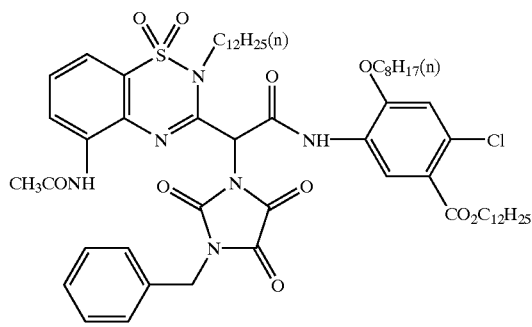
(85) 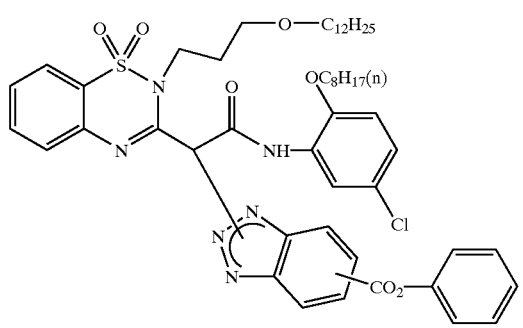

-continued
(86)
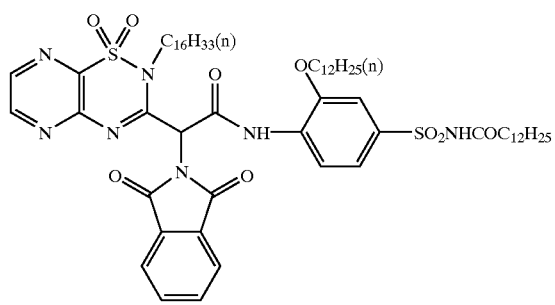
(87)
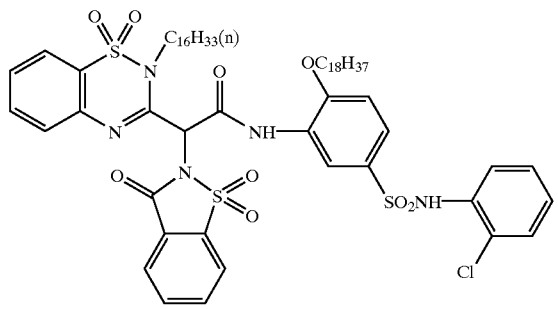
(88)
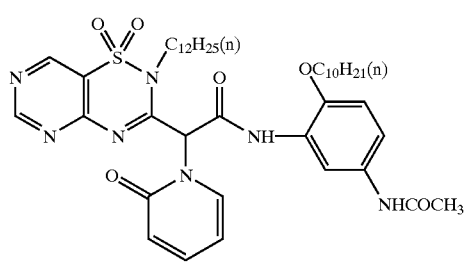
(89)
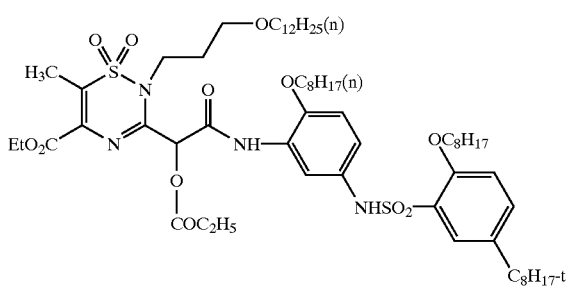
(90)
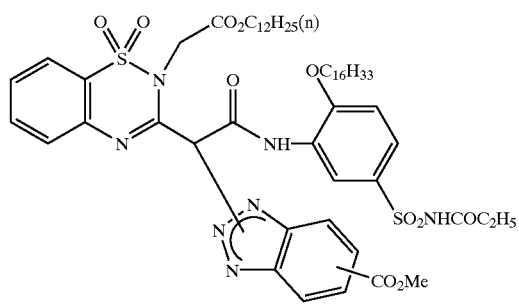
(91)
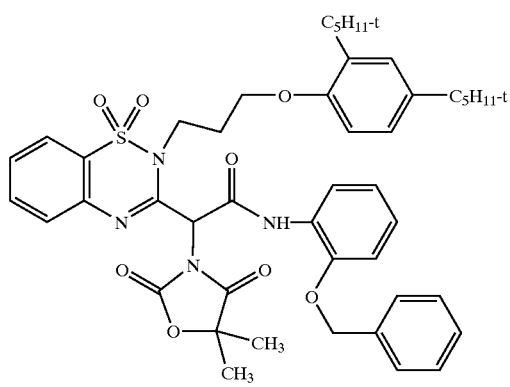
(92)
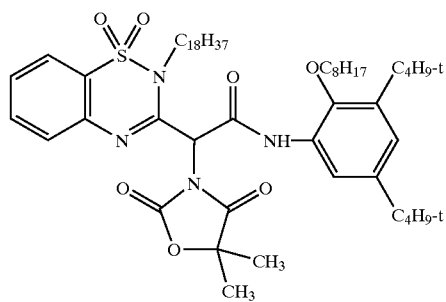
(93)
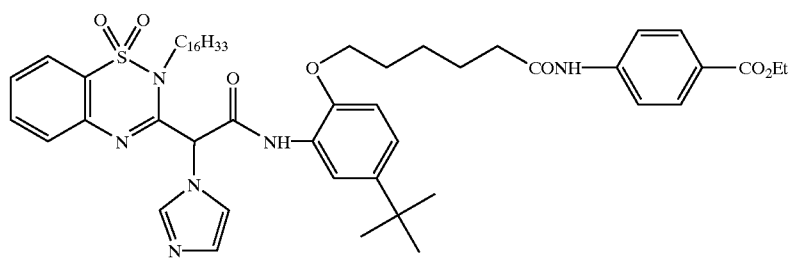

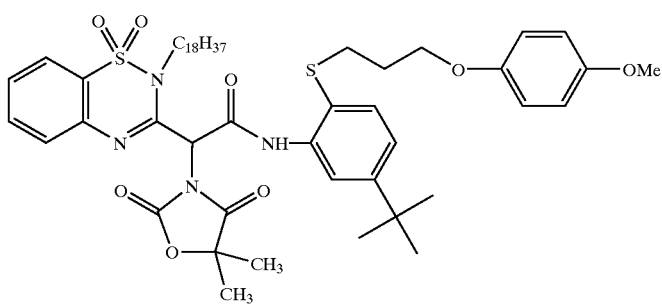
(94)
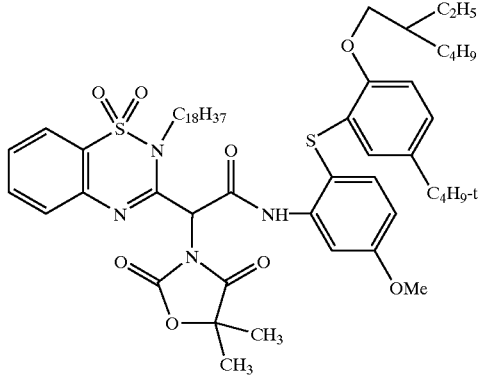
(95)
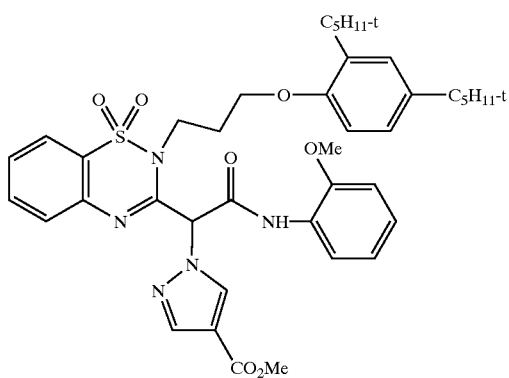
(96)
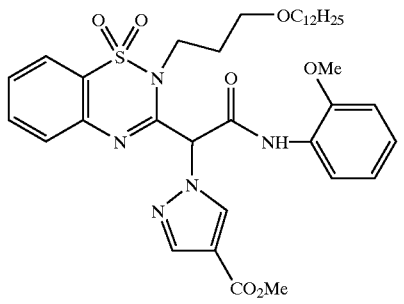
(97)
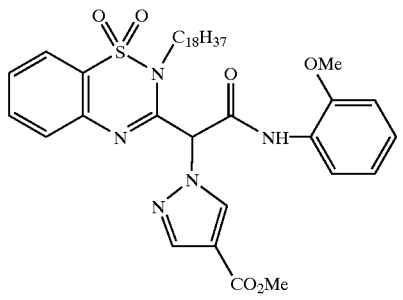
(98)
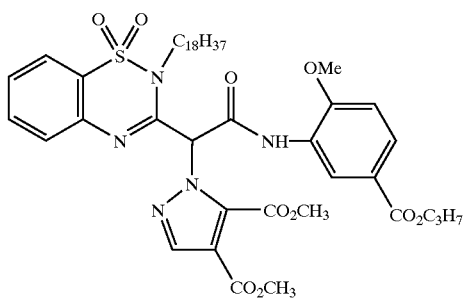
(99)
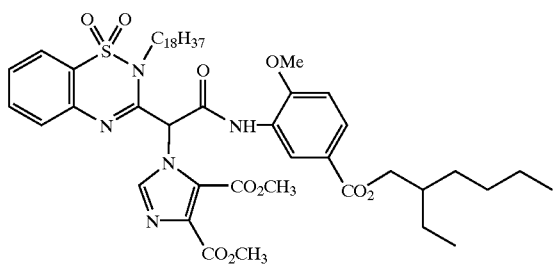
(100)
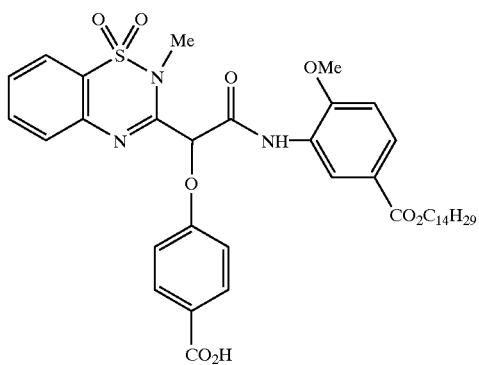
(101)

-continued
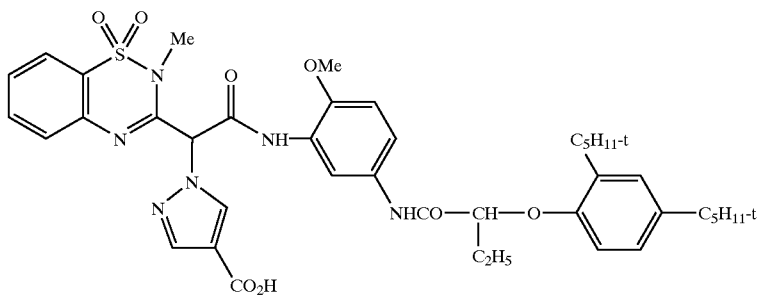
(102)
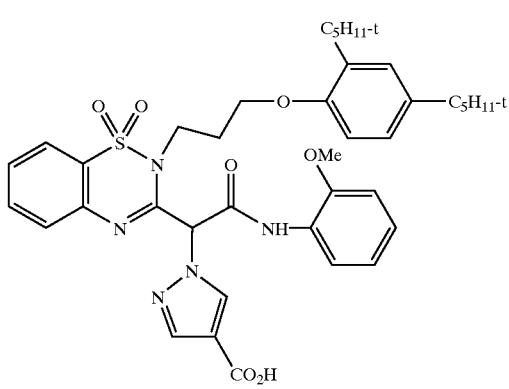
(103)
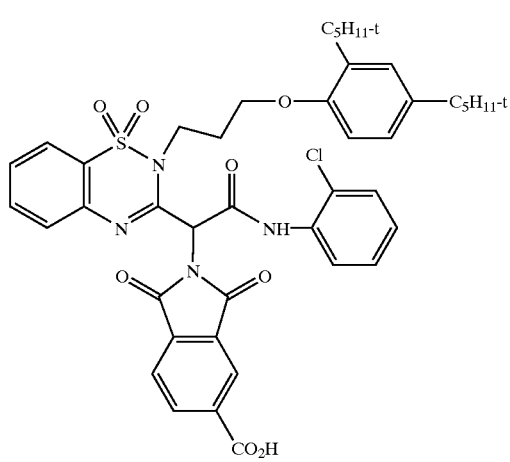
(104)
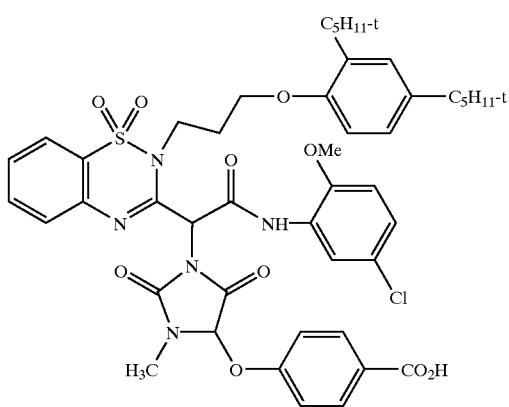
(105)
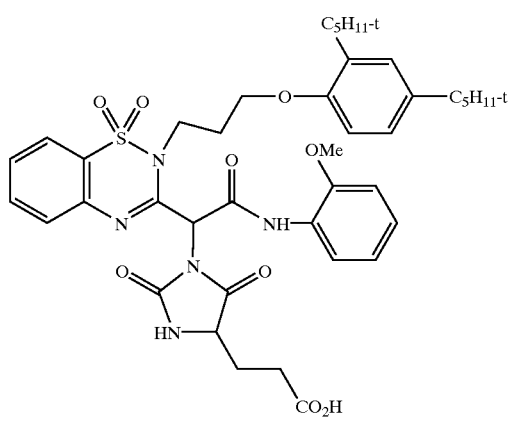
(106)
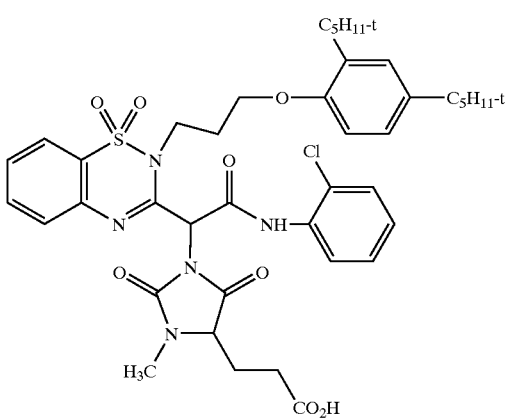
(107)
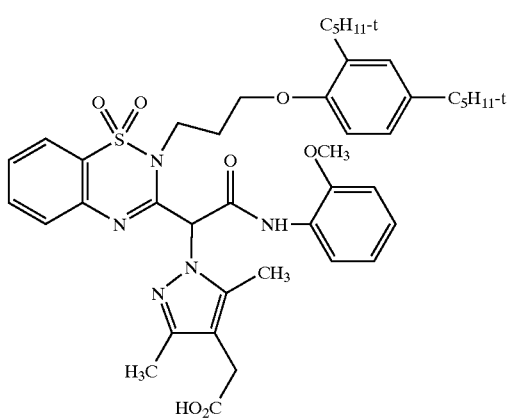
(108)

-continued
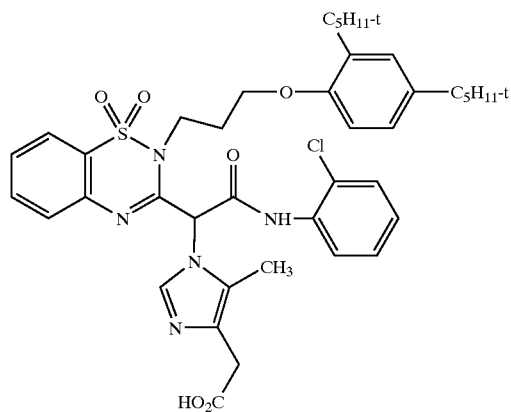 (109)
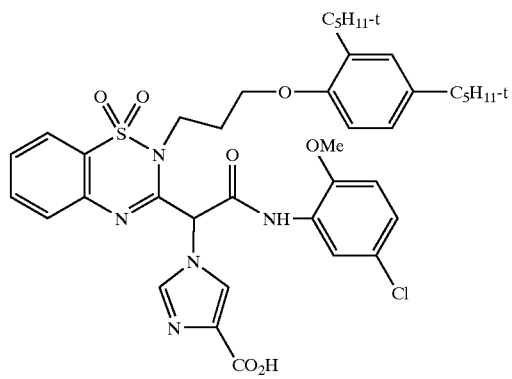 (110)
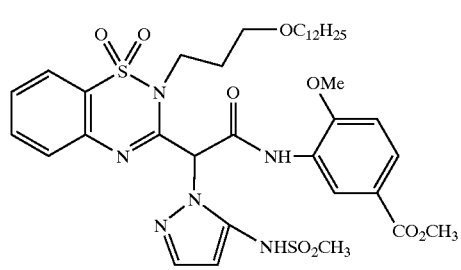 (111)
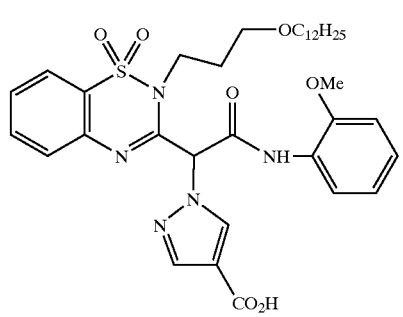 (112)
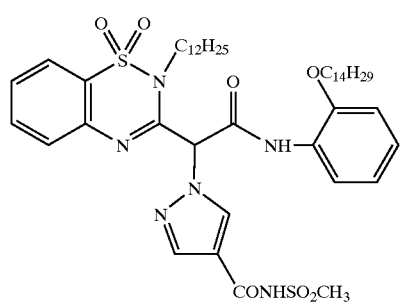 (113)
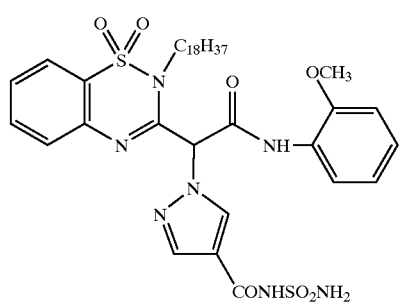 (114)
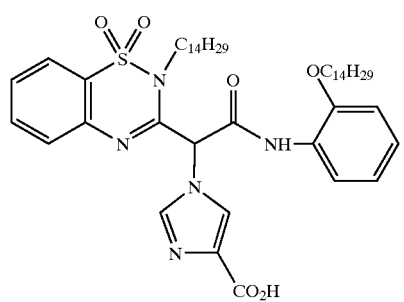 (115)
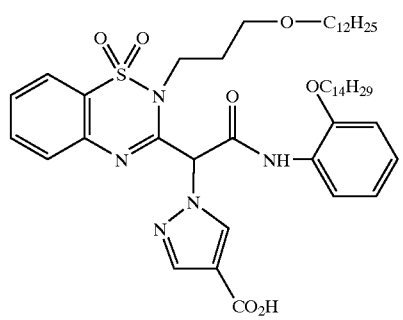 (116)

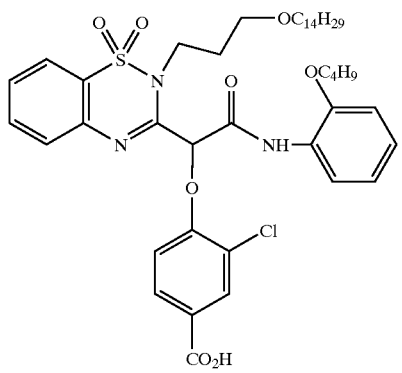
(117)
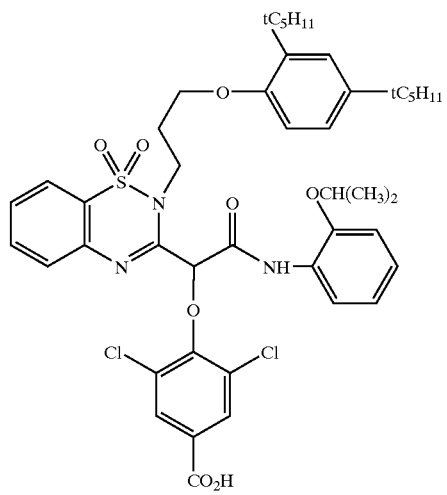
(118)
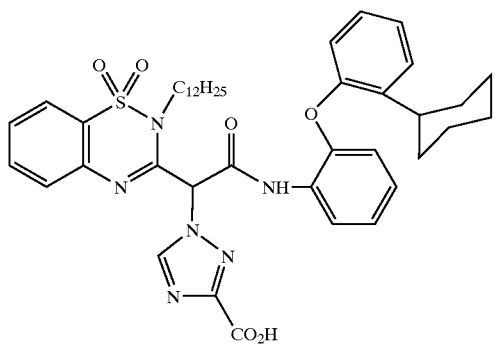
(119)
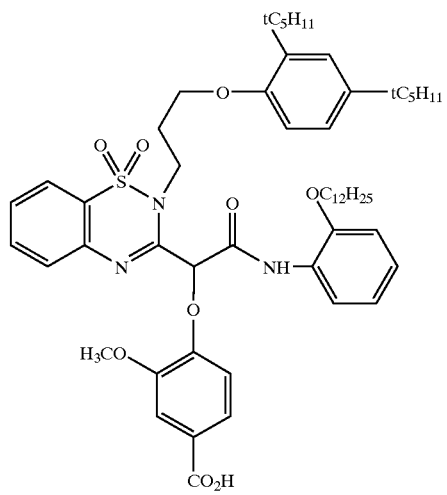
(120)
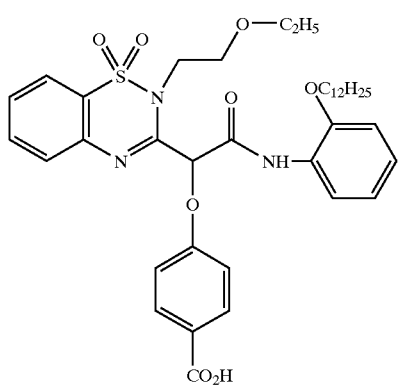
(121)
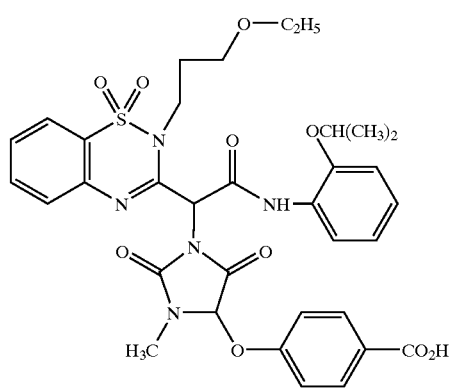
(122)

-continued
(123)
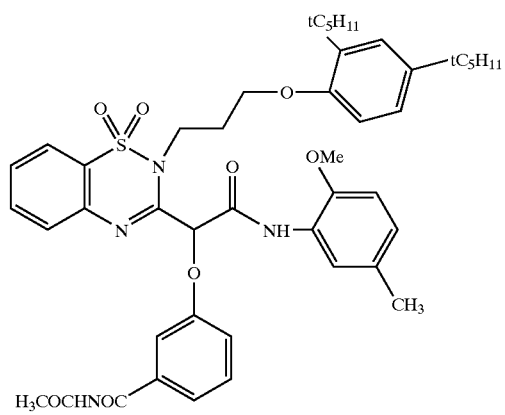
(124)
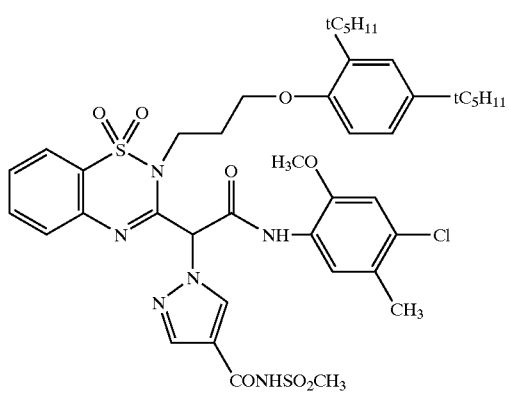
(125)
(126)
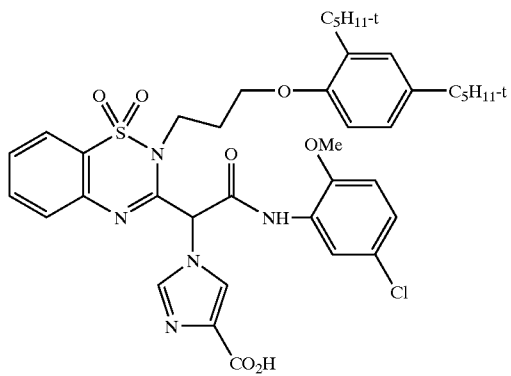
(127)
(128)
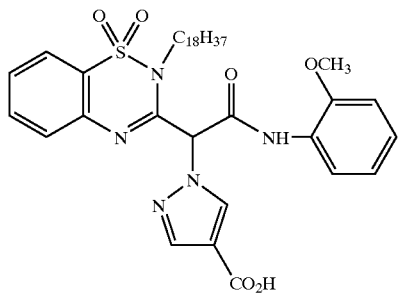
(129)
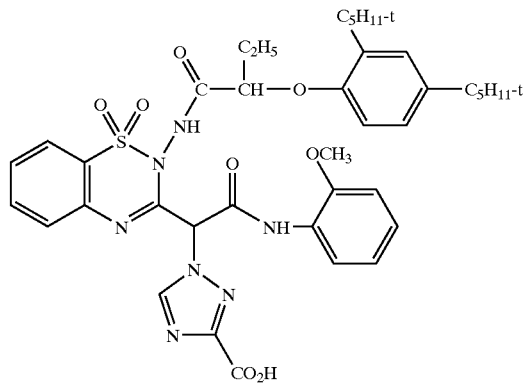
(130)

-continued
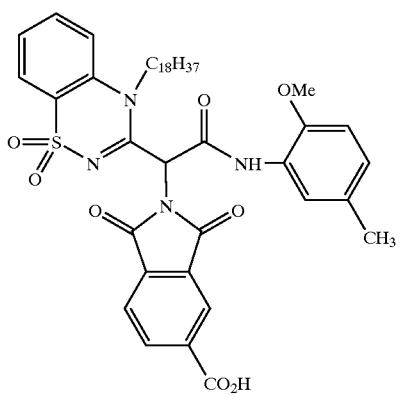
(131)
(132)
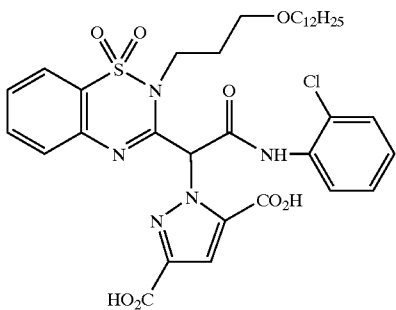
(133)
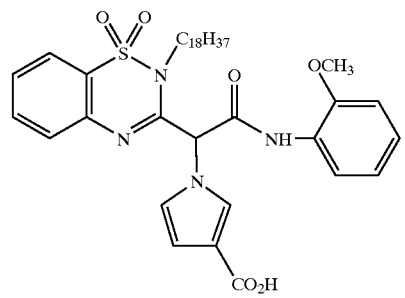
(134)
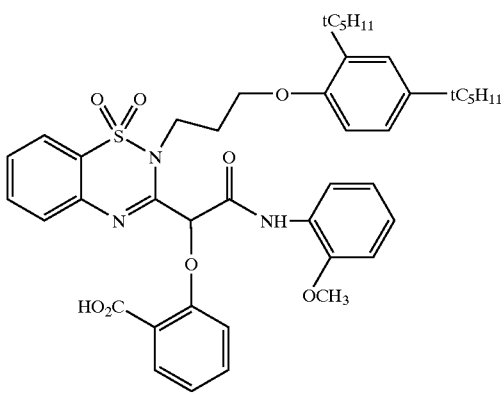
(135)
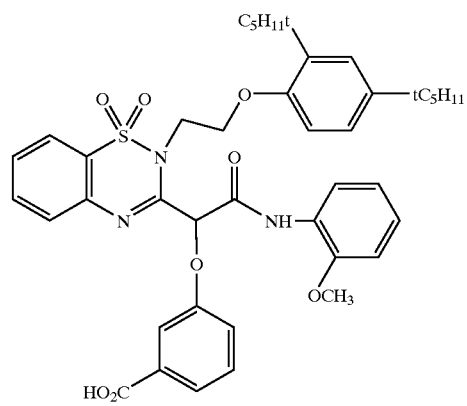
(136)
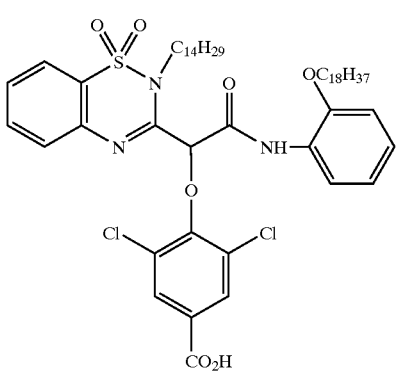
(137)
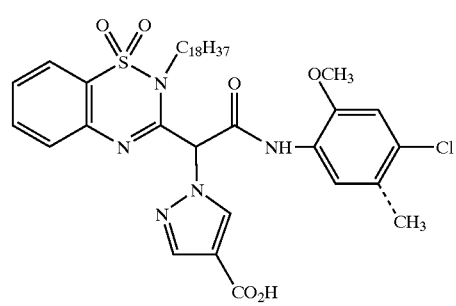
(138)

-continued
(139) 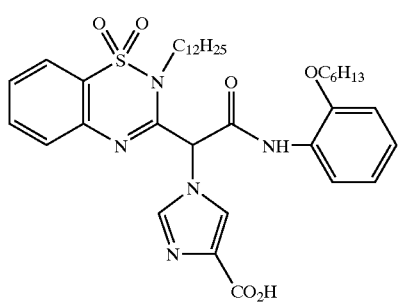
(140) 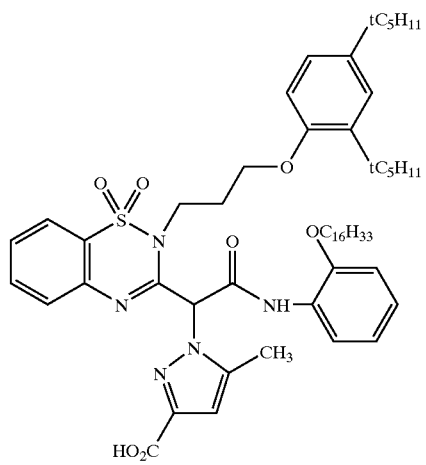
(141) 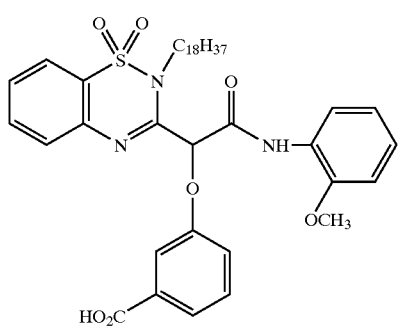
(142) 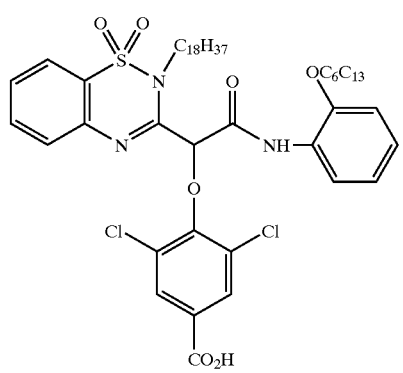
(143) 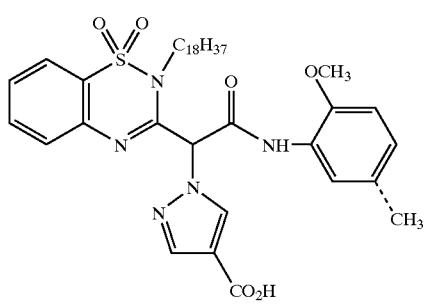
(144) 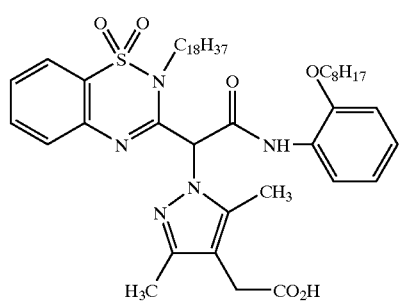
(145) 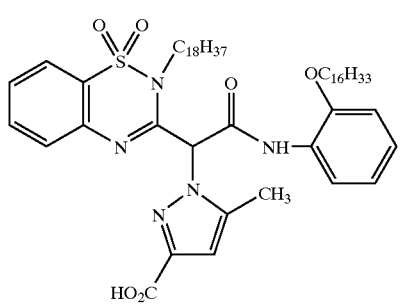
(146) 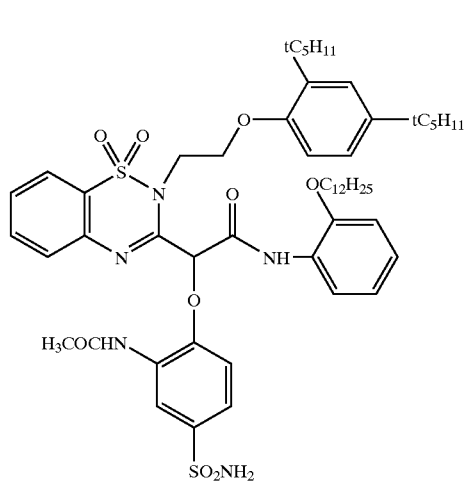

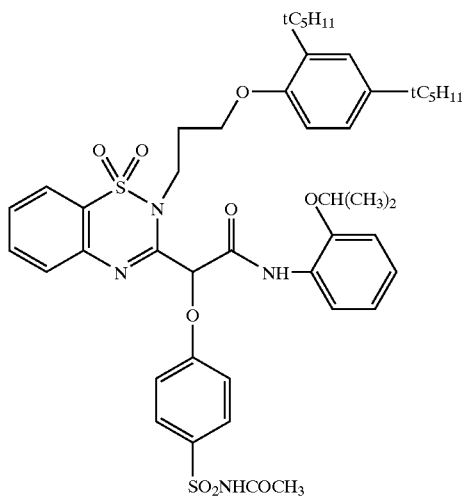
(147)
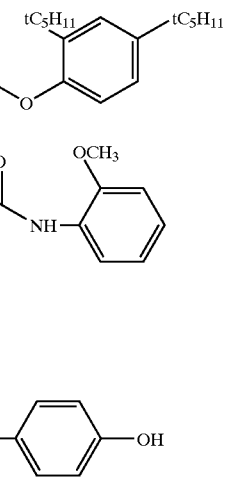
(148)
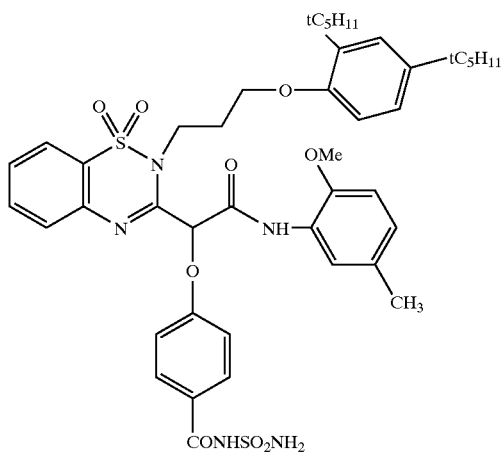
(149)
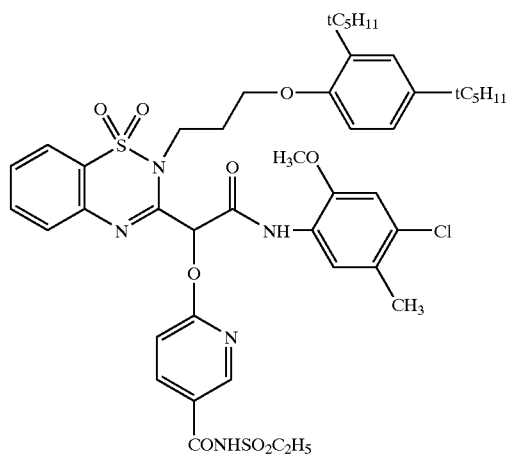
(150)
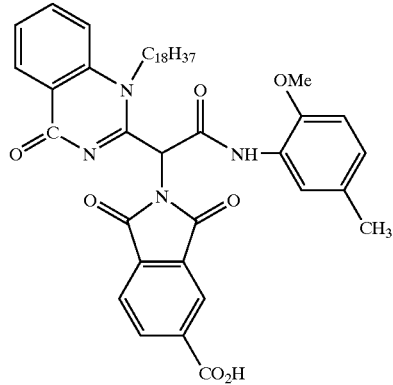
(151)
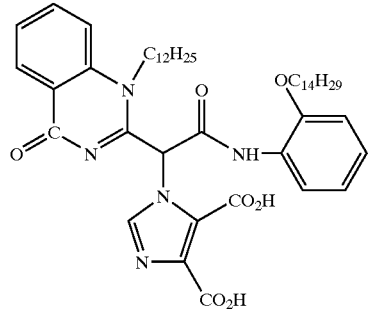
(152)
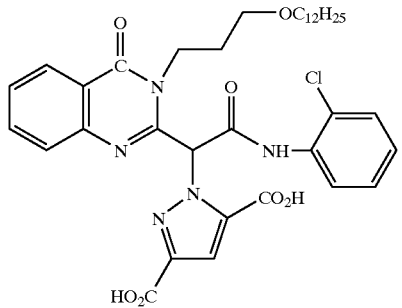
(153)
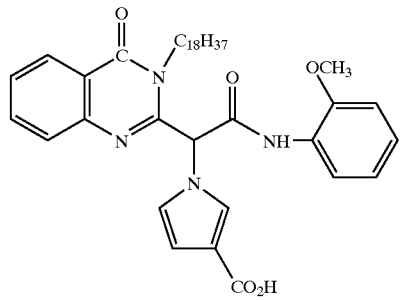
(154)

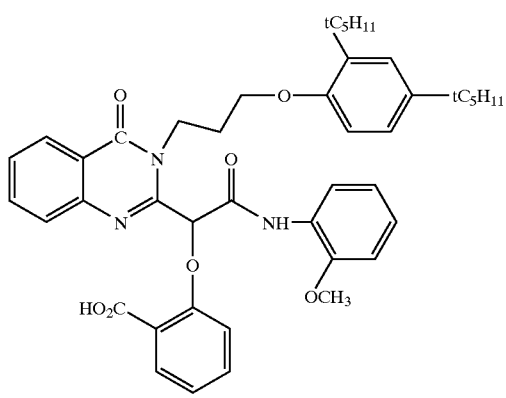
(155)
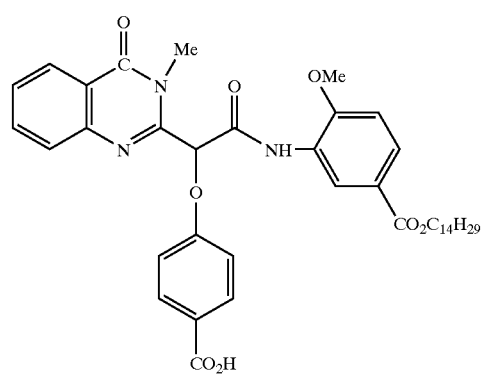
(156)
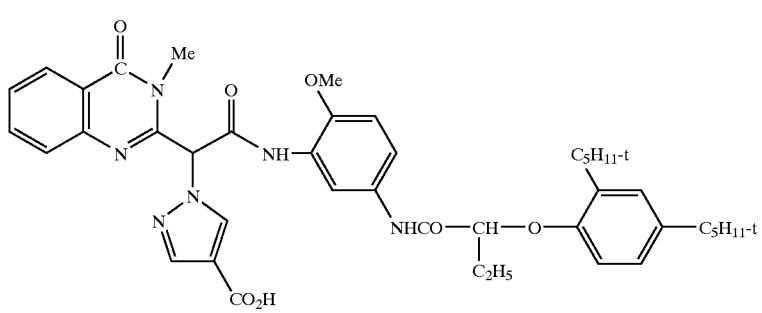
(157)
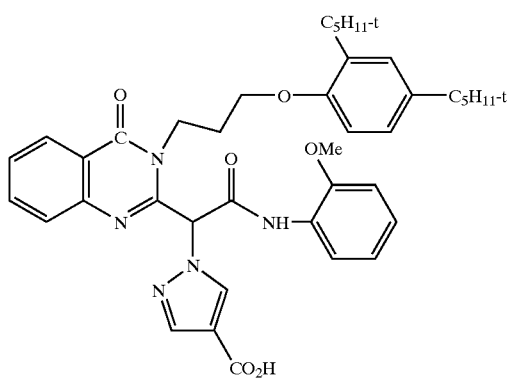
(158)
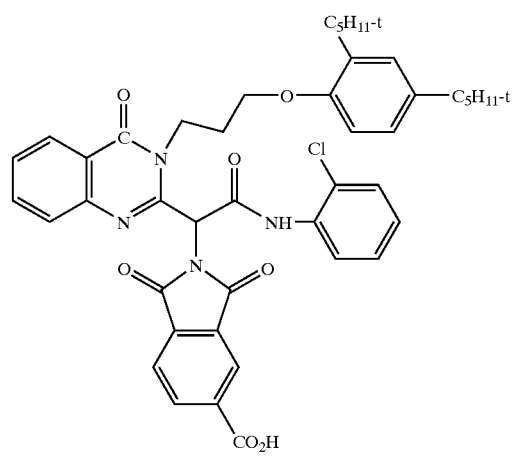
(159)
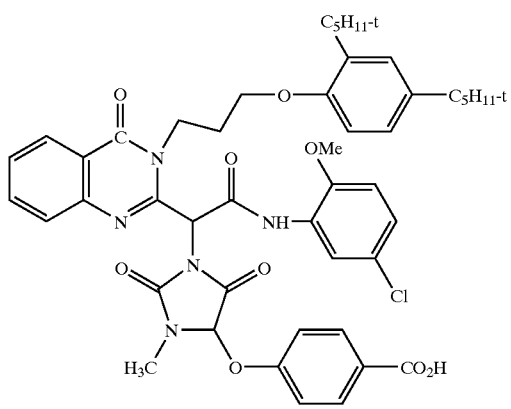
(160)

-continued
(161)
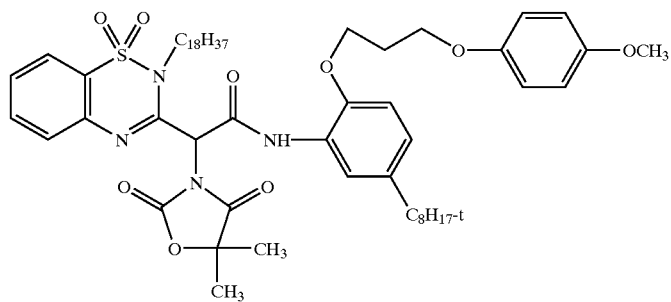
(162)
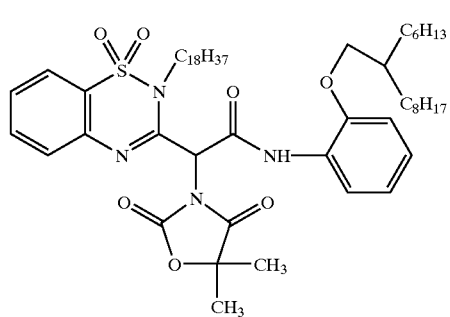
(163)
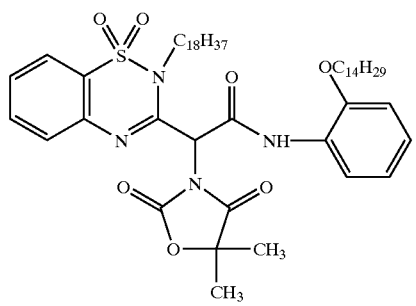
(164)
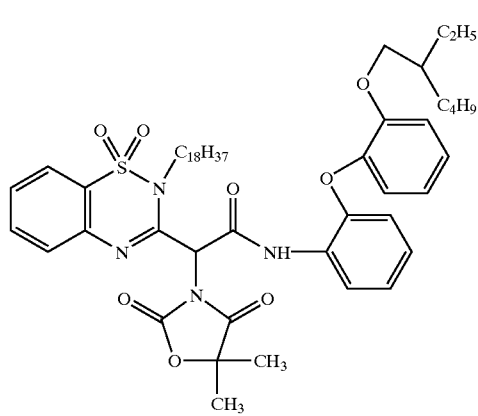
(165)
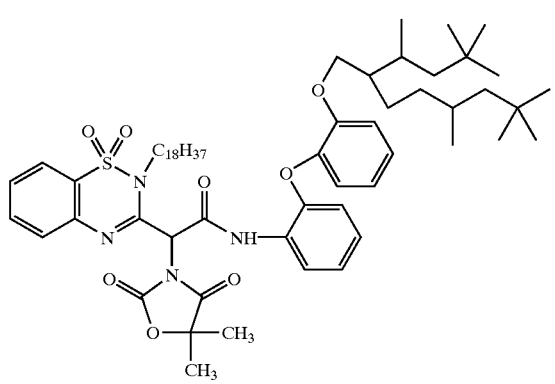
(166)
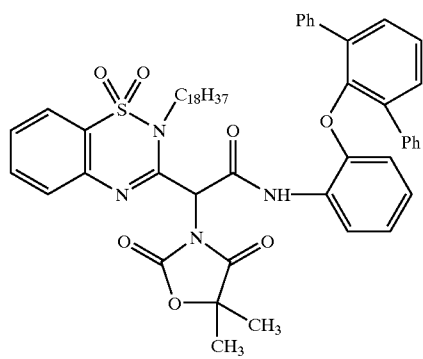
(167)
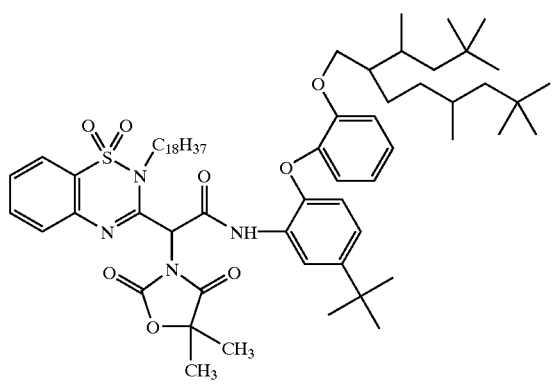

-continued
(168)
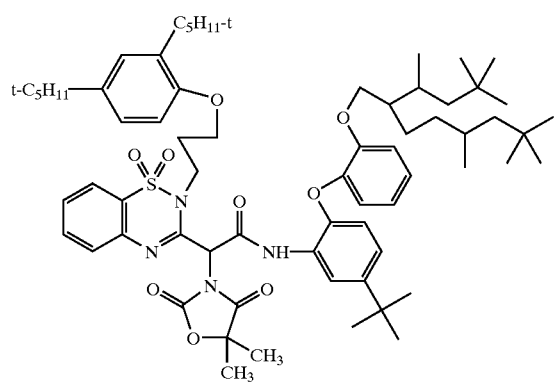
(169)
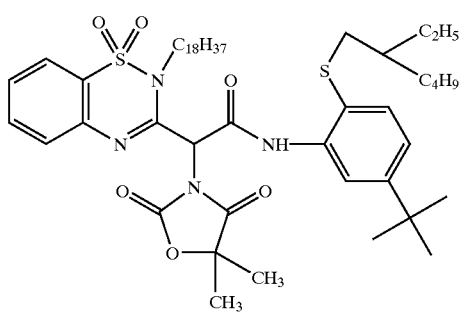
(170)
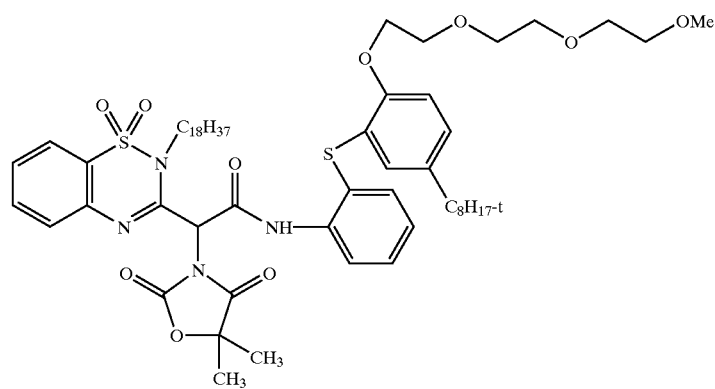
(171)
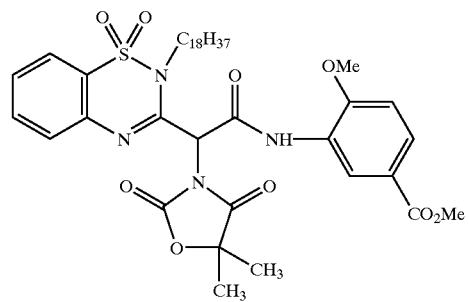
(172)
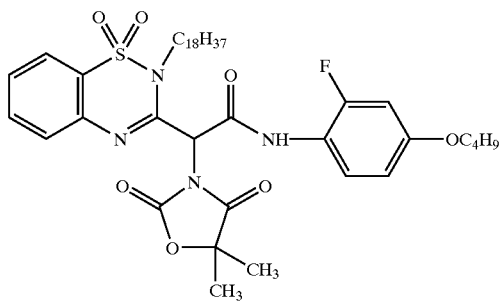
(173)
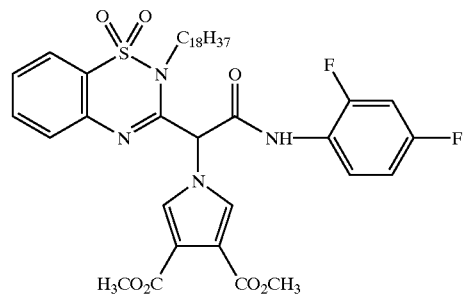
(174)
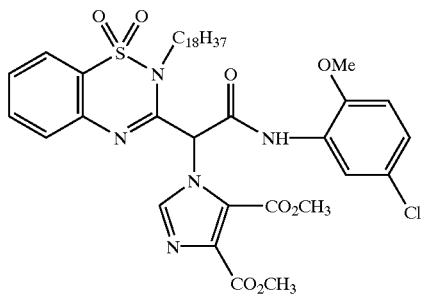

-continued
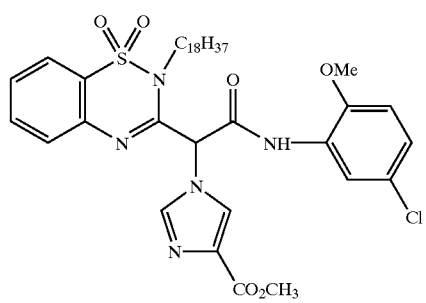 (175)
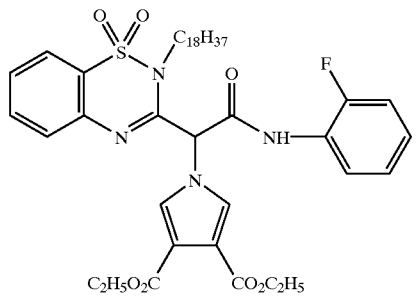 (176)
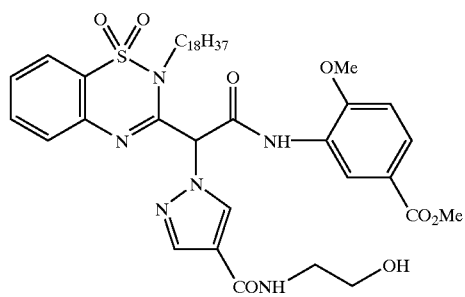 (177)
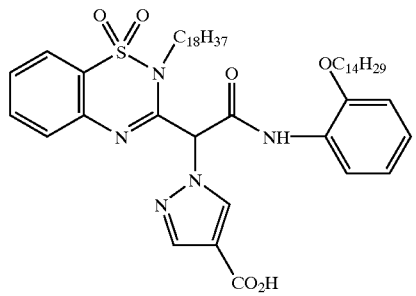 (178)
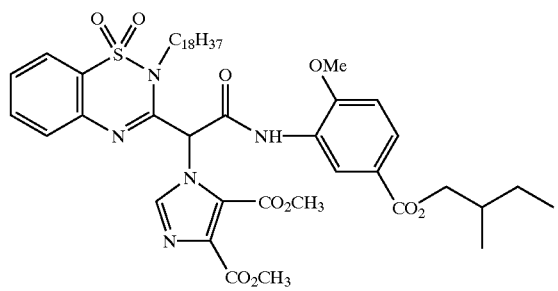 (179)
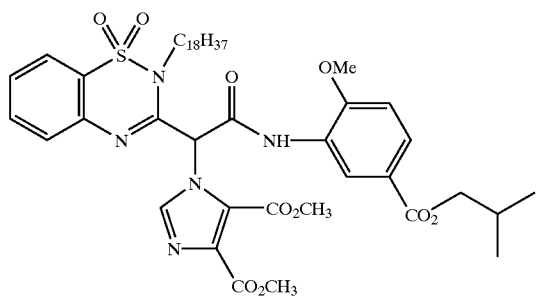 (180)
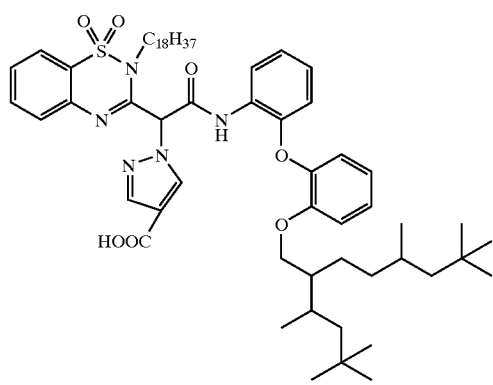 (181)
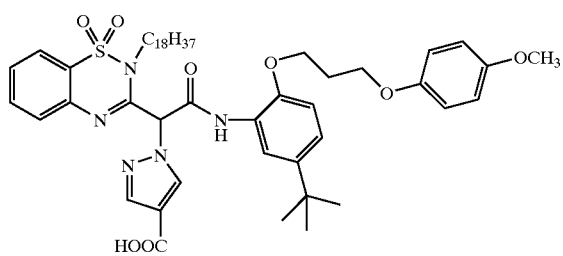 (182)
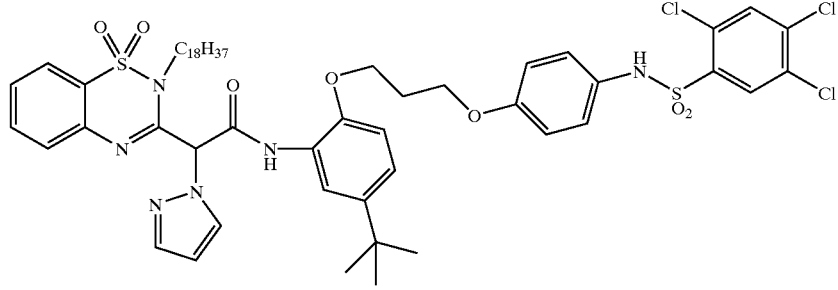 (183)

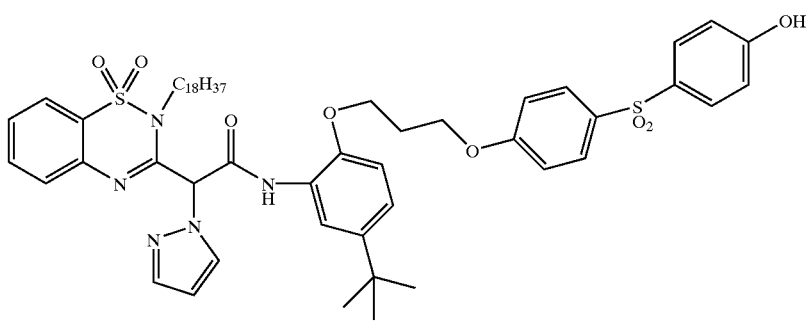
(184)
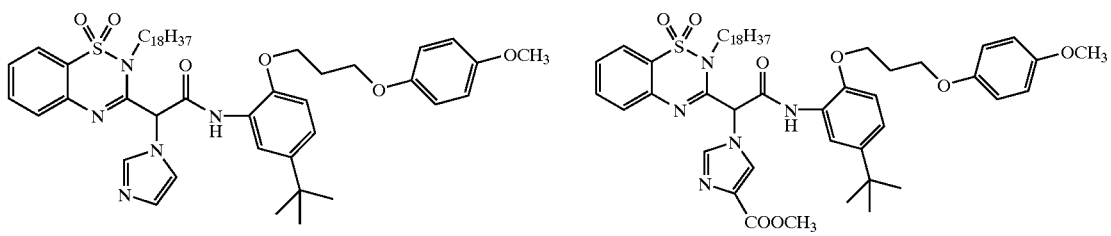
(185) (186)
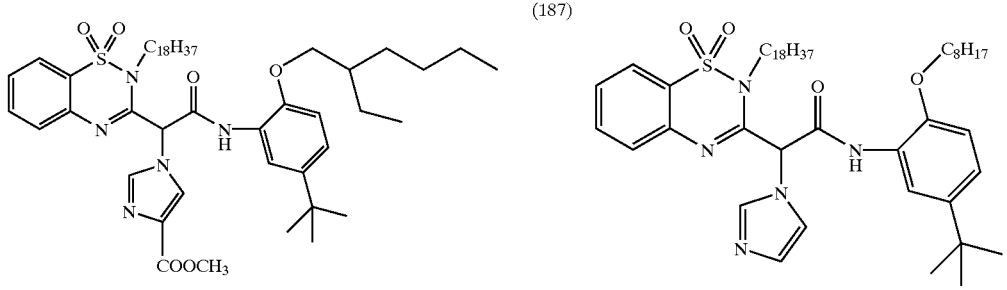
(187) (188)
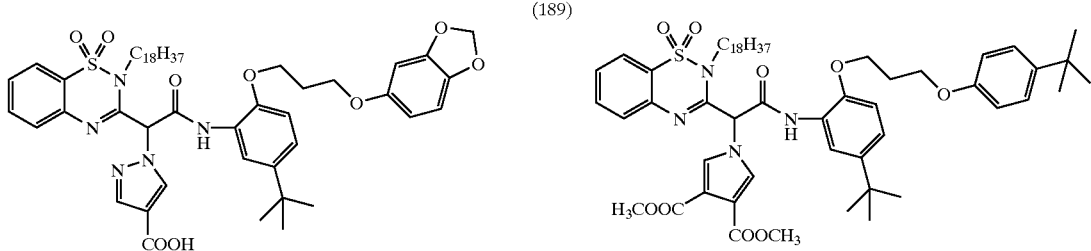
(189) (190)
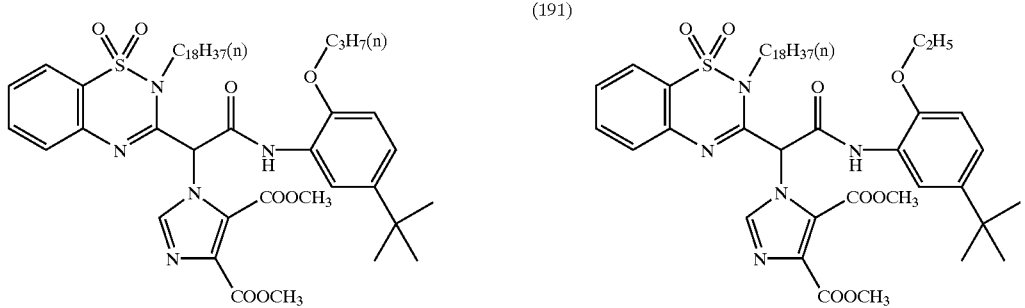
(191) (192)

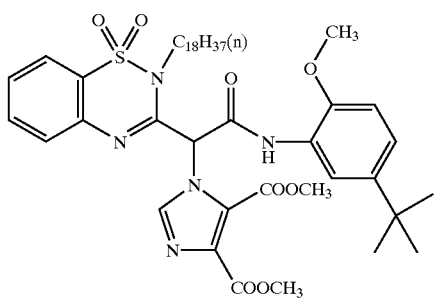
(193)

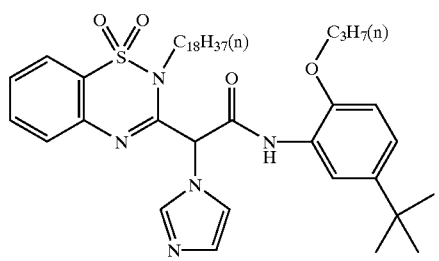
(194)

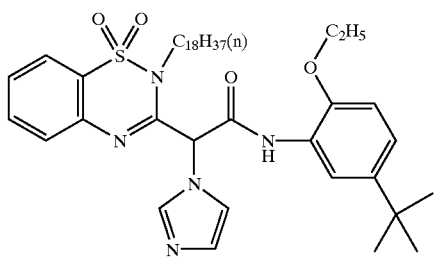
(195)

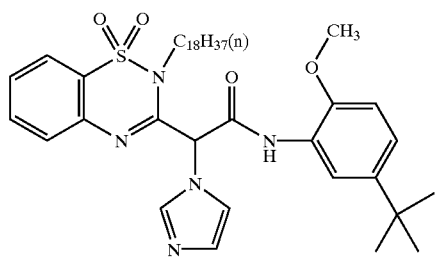
(196)

In the following explanation, when the exemplified compounds (herein also referred to as a dye-forming coupler) shown above are referred to, the number X in the parenthesis, i.e., (X), is labeled to each of the exemplified compounds, and they are expressed as "coupler (X)".

Specific Synthetic Examples of the compounds represented by the foregoing formula (I) are described below.

SYNTHETIC EXAMPLE 1

Synthesis of Coupler (1)

Coupler (1) was synthesized according to the following synthesis route:

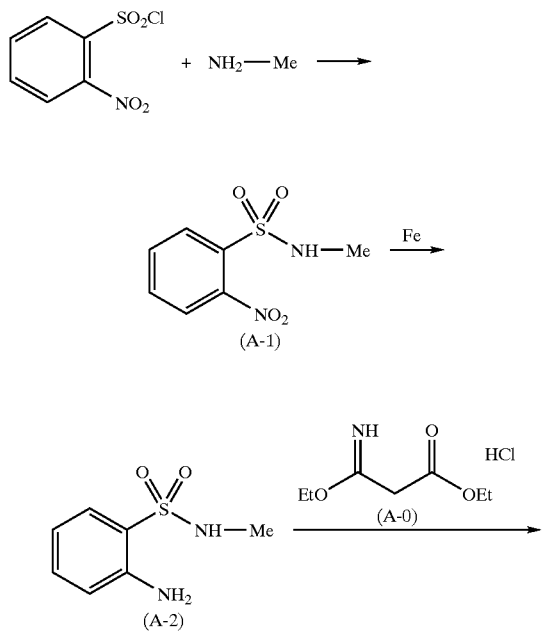

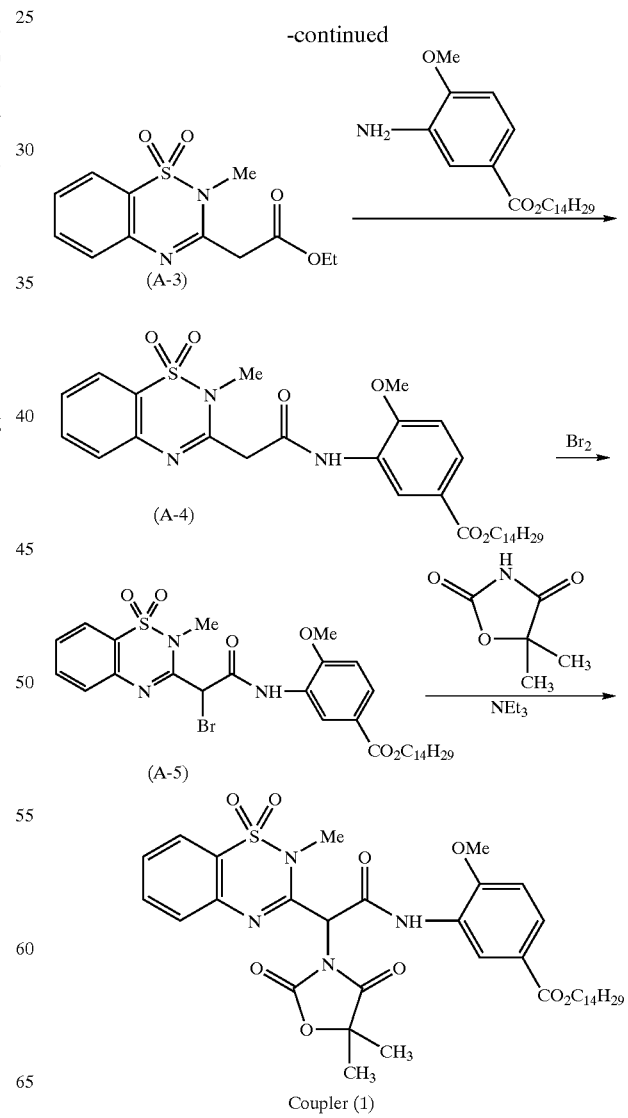

44.3 g of o-nitrobenzenesulfonyl chloride was gradually added, with stirring, to a mixture solution of 38.8 g of an aqueous 40% methylamine solution and 200 ml of acetonitrile, on an ice bath. The resulting reaction mixture was heated up to room temperature and stirred for another 1 hour. Thereafter, ethyl acetate and water were added to separate an organic layer from an aqueous layer. The organic layer was washed with dilute hydrochloric acid and then a saturated brine. After the organic layer was dried with magnesium sulfate anhydride, the solvent was removed by vacuum distillation. Crystallization from a mixed solvent of ethyl acetate and hexane gave 28.6 g of Compound (A-1).

44.8 g of reduced iron and 4.5 g of ammonium chloride were dispersed in a mixture of 270 ml of isopropanol and 45 ml of water, and stirred for 1 hour with heating under refluxing. To the resulting mixture, 25.9 g of Compound (A-1) was gradually added with stirring. After heating in refluxing for another 1 hour, insoluble matters were removed by a suction filter through Celite. Ethyl acetate and water were added to the filtrate to separate an organic layer from an aqueous layer. The organic layer was washed with a saturated brine and water, and then dried with magnesium sulfate anhydride. The solvent was removed by vacuum distillation, to yield 21.5 g of Compound (A-2) as an oily product.

A mixture of 18.9 g of Compound (A-2), 39.1 g of hydrochloride of iminoether (A-0) and 200 ml of ethyl alcohol was stirred with heating in refluxing for 1 day. Additionally 19.2 g of hydrochloride of iminoether was added and stirred with heating in refluxing for another 1 day. Ethyl acetate and water were added to separate an organic layer from an aqueous layer. The organic layer was washed with dilute hydrochloric acid and a saturated brine, and then dried with magnesium sulfate anhydride. The solvent was removed by vacuum distillation. Crystallization from a mixed solvent of ethyl acetate and hexane gave 21.0 g of Compound (A-3).

A solution of 5.6 g of Compound (A-3), 7.2 g of 2-methoxy-5-tetradecyloxycarbonylaniline and 20 ml of m-dichlorobenzene was stirred with heating in refluxing for 6 hours. After cooling, crystallization by adding hexane gave 8.8 g of Compound (A-4).

To 110 ml of methylene chloride solution containing 5.4 g of Compound (A-4), 10 ml of methylene chloride solution containing 0.45 ml of bromine was added drop-wise on an ice bath. After the resultant mixture was stirred for 30 minute at room temperature, methylene chloride and water were added to separate an organic layer from an aqueous layer. The organic layer was washed with a saturated brine, and then dried with magnesium sulfate anhydride. The solvent was removed by vacuum distillation, to obtain a crude product of Compound (A-5).

To a solution which was prepared by dissolving 3.5 g of 5,5-dimethyloxazolidine-2,4-dione and 3.8 ml of triethylamine in 110 ml of N,N-dimethyl acetoamide, a solution containing all the previously synthesized crude product of Compound (A-5) dissolved in 25 ml of acetonitrile was added drop-wise over 10 minutes at room temperature, and then stirred for 2 hours at room temperature. Ethyl acetate and water were added to separate an organic layer from an aqueous layer. The organic layer was washed with 0.1 normal aqueous potassium hydroxide solution, dilute hydrochloric acid and a saturated brine, and then dried with magnesium sulfate anhydride. The solvent was removed by vacuum distillation. The residue was purified on silica gel column chromatography using a mixed solvent of acetone and hexane as an eluate, and then recrystallized from a mixed solvent of ethyl acetate/hexane, to give 4.7 g of Coupler (1).

SYNTHETIC EXAMPLE 2

Synthesis of Coupler (3)

Coupler (3) was synthesized according to the following synthesis route:

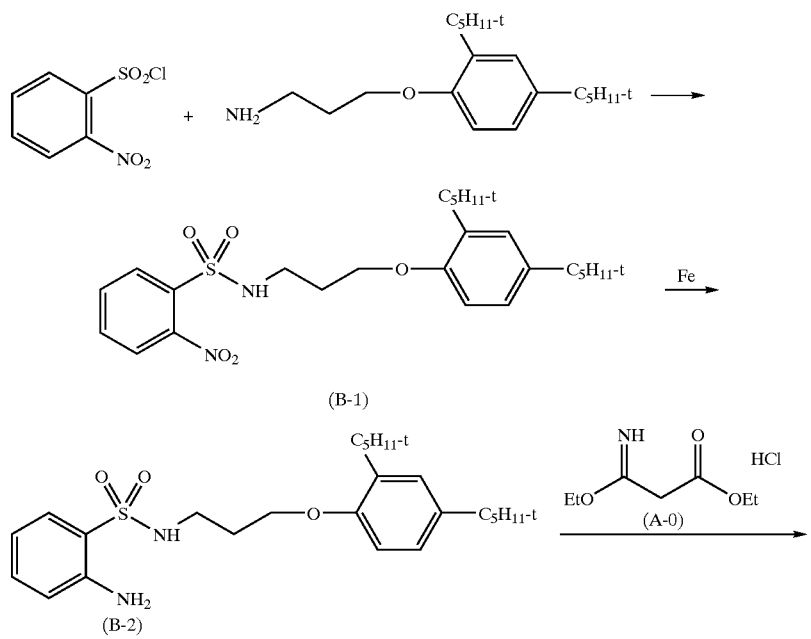

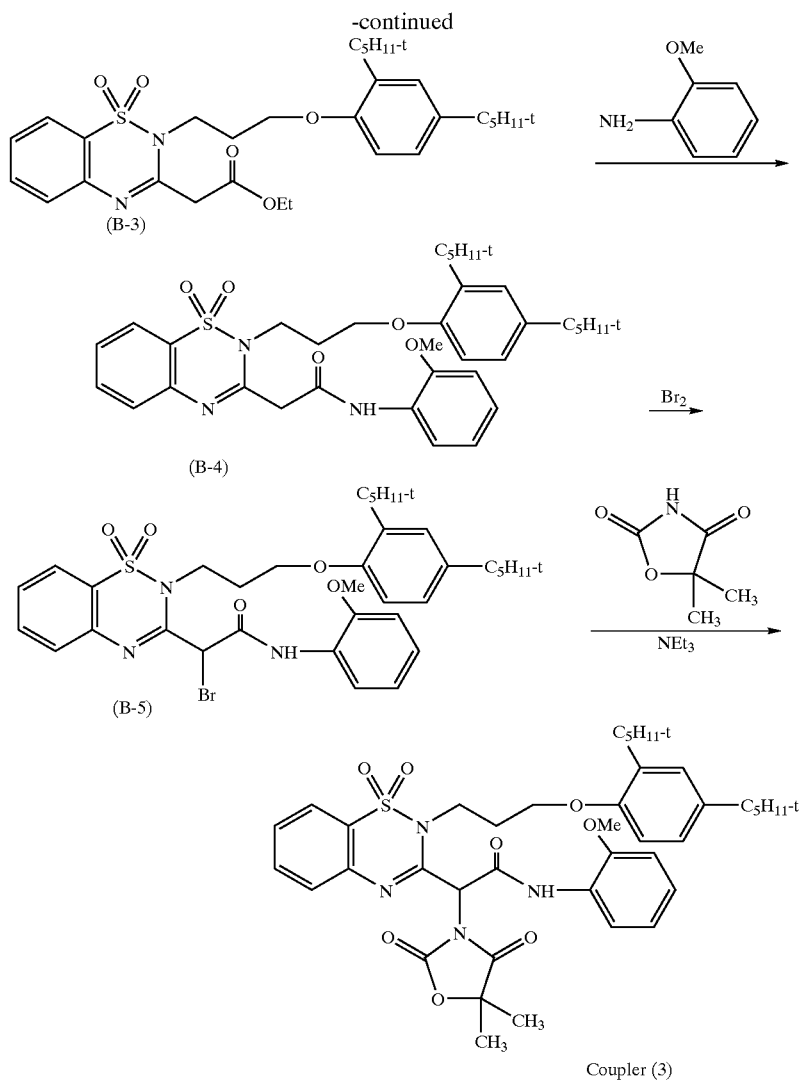

Coupler (3)

To a solution containing 438 g of 3-(2,4-di-t-amylphenoxy) propylamine, 210 ml of triethylamine and 1 liter of acetonitrile, 333 g of o-nitrobenzenesulfonyl chloride was gradually added with stirring on an ice bath. The resulting reaction mixture was heated up to room temperature and further stirred for 1 hour. Thereafter, ethyl acetate and water were added to separate an organic layer from an aqueous layer. The organic layer was washed with dilute hydrochloric acid and a saturated brine. After the organic layer was dried with magnesium sulfate anhydride, the solvent was removed by vacuum distillation. Crystallization from a mixed solvent of ethyl acetate and hexane gave 588 g of Compound (B-1).

84.0 g of reduced iron and 8.4 g of ammonium chloride were dispersed in a mixture of 540 ml of isopropanol and 90 ml of water, and heated in refluxing for 1 hour. To the resulting dispersion, 119 g of Compound (B-1) was gradually added with stirring. After heating in refluxing for another 2 hours, the reaction mixture was filtrated by a suction filter through Celite. Ethyl acetate and water were added to the filtrate to separate an organic layer from an aqueous layer. The organic layer was washed with a saturated brine, and then dried with magnesium sulfate anhydride. The solvent was removed by vacuum distillation, to yield 111 g of Compound (B-2) as an oily product.

A solution of 111 g of Compound (B-2), 68.4 g of hydrochloride of iminoether (A-0) and 150 ml of ethyl alcohol was stirred with heating in refluxing for 1 hour. Additionally 4.9 g of hydrochloride of iminoether was added and stirred with heating in refluxing for 30 minutes. After cooling the reaction mixture, it was filtered under suction, 100 ml of p-xylene was added to the filtrate and then heated in refluxing for 4 hours while removing ethyl alcohol by distillation. The reaction solution was purified by a silica gel column chromatography using a mixed solvent of ethyl acetate and hexane as the eluate. Crystallization from methanol gave 93.1 g of Compound (B-3).

A solution of 40.7 g of Compound (B-3), 18.5 g of 2-methoxyaniline and 10 ml of p-xylene was stirred with heating in refluxing for 6 hour. Ethyl acetate and water were added to separate an organic layer from an aqueous layer. The organic layer was washed with dilute hydrochloric acid and a saturated brine, and then dried with magnesium sulfate anhydride. The solvent was removed by vacuum distillation. Purification of the residue by a silica gel column chromatography using a mixed solvent of ethyl acetate and hexane as the eluate gave 37.7 g of Compound (B-4) as an oily product.

To a solution of 24.8 g of Compound (B-4) in 400 ml of methylene chloride, 35 ml of methylene chloride solution containing 2.1 ml of bromine was added drop-wise on an ice bath. After the mixture was stirred for 30 minute on an ice bath, methylene chloride and water were added to separate an organic layer from an aqueous layer. The organic layer was washed with a saturated brine, and then dried with magnesium sulfate anhydride. The solvent was removed by vacuum distillation, to obtain Compound (B-5) as a crude product.

To a solution of 15.5 g of 5,5-dimethyl oxazolidine-2,4-dione and 16.8 ml of triethylamine in 200 ml of N,N-dimethyl acetoamide, a solution containing all the previously synthesized crude product of Compound (B-5) dissolved in 40 ml of acetonitrile was added drop-wise over 10 minutes at room temperature. The resultant mixture was heated up to 40° C. and then stirred for 30 minutes. Ethyl acetate and water were added to separate an organic layer from an aqueous layer. The organic layer was washed with 0.1 normal aqueous potassium hydroxide solution, dilute hydrochloric acid and a saturated brine, and then dried with magnesium sulfate anhydride. The solvent was removed by vacuum distillation. The residue was purified by a silica gel column chromatography using a mixed solvent of acetone and hexane as the eluate. Crystallization from a mixed solvent of ethyl acetate and hexane gave 23.4 g of Coupler (3).

SYNTHETIC EXAMPLE 3

Synthesis of Coupler (6)

Coupler (6) was synthesized according to the following synthesis route:

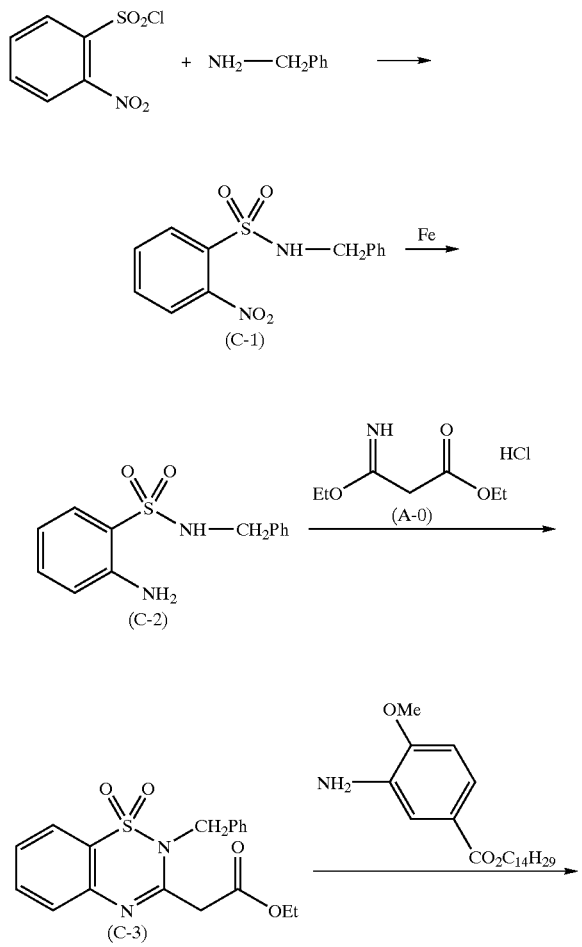

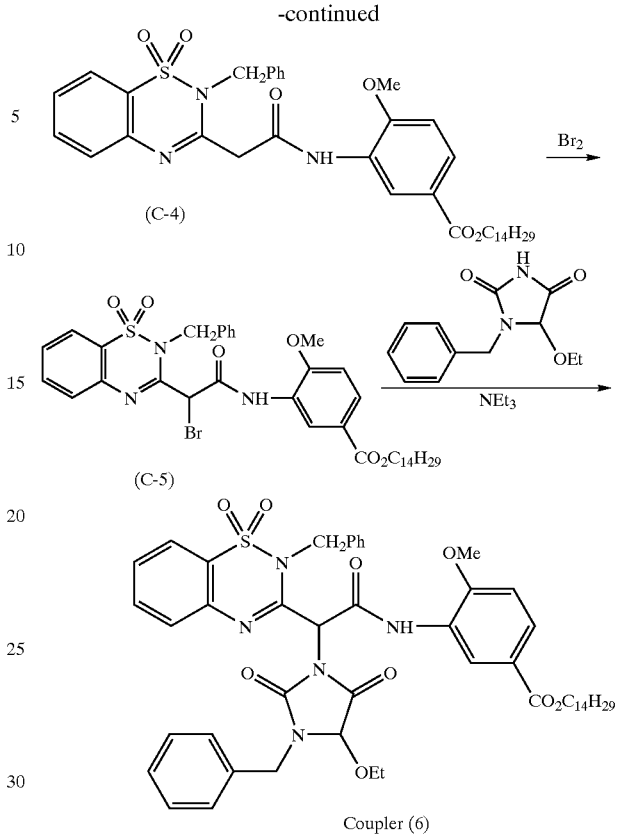

Coupler (6)

To a solution of 21.4 g benzylamine in 200 ml of acetonitrile, 39.9 g of o-nitrobenzenesulfonyl chloride was gradually added with stirring on an ice bath. The resulting reaction mixture was heated up to room temperature. Further, 30 ml of triethylamine was added drop-wise and stirred for 1 hour. Thereafter, ethyl acetate and water were added to separate an organic layer from an aqueous layer. The organic layer was washed with dilute hydrochloric acid and then a saturated brine. After the organic layer was dried with magnesium sulfate anhydride, the solvent was removed by vacuum distillation. Crystallization from a mixed solvent of ethyl acetate and hexane gave 31.2 g of Compound (C-1).

44.8 g of reduced iron and 4.5 g of ammonium chloride were dispersed in a mixture of 270 ml of isopropanol and 45 ml of water, and stirred for 1 hour with heating in refluxing. To the resulting mixture, 29.2 g of Compound (C-1) was gradually added with stirring. After heating in refluxing for another 1 hour, the reaction mixture was filtrated by a suction filter through Celite. Ethyl acetate and water were added to the filtrate to separate an organic layer from an aqueous layer. The organic layer was washed with a saturated brine, and then dried with magnesium sulfate anhydride. The solvent was removed by vacuum distillation, to yield 25.5 g of Compound (C-2) as an oily product.

A solution of 19.7 g of Compound (C-2) and 22.0 g of hydrochloride of iminoether (A-0) in 200 ml of ethyl alcohol was stirred with heating in refluxing for 4 hours. Further, 19.7 g of hydrochloride of the iminoether was added and stirred with heating under reflux for 4 hours. Additionally 13 g of p-toluene sulfonic acid monohydrate was added and stirred with heating in refluxing for 1 hour. Ethyl acetate and water were added to separate an organic layer from an aqueous layer. The organic layer was washed with dilute hydrochloric acid and a saturated brine, and then dried with magnesium sulfate anhydride. The solvent was removed by vacuum distillation. Crystallization from a mixed solvent of ethyl acetate and hexane gave 3.2 g of Compound (C-3).

A solution of 2.9 g of Compound (C-3), 2.9 g of 2-methoxy-5-tetradecyloxycarbonylaniline in 20 ml of o-dichlorobenzene was stirred for 6 hours with heating in refluxing. Ethyl acetate and water were added to separate an organic layer from an aqueous layer. The organic layer was washed with dilute hydrochloric acid and a saturated brine, and then dried with magnesium sulfate anhydride. The solvent was removed by vacuum distillation. The residue was purified by a silica gel column chromatography using a mixed solvent of ethyl acetate and hexane as the eluate. Crystallization from a mixed solvent of ethyl acetate and hexane gave 3.8 g of Compound (C-4).

To a solution containing 3.4 g of Compound (C-4) in 100 ml of methylene chloride, 10 ml of methylene chloride solution containing 0.26 ml of bromine was added drop-wise on an ice bath. After the mixture was stirred for 30 minute at room temperature, methylene chloride and water were added to separate an organic layer from an aqueous layer. The organic layer was washed with a saturated brine, and then dried with magnesium sulfate anhydride.

The solvent was removed by vacuum distillation, to obtain a crude product of Compound (C-5).

To a solution of 3.5 g of 1-benzyl-5-ethoxyhydantoin and 2.1 ml of triethylamine in 100 ml of N,N-dimethyl acetoamide, a solution containing all the previously synthesized crude product of Compound (C-5) dissolved in 20 ml of acetonitrile was added drop-wise over 30 minutes at room temperature, and then stirred at 40° C. for 2 hours. Ethyl acetate and water were added to separate an organic layer from an aqueous layer. The organic layer was washed with 0.1 normal aqueous potassium hydroxide solution, dilute hydrochloric acid and a saturated brine, and then dried with magnesium sulfate anhydride. The solvent was removed by vacuum distillation. The residue was purified by a silica gel column chromatography using a mixed solvent of ethyl acetate and hexane as the eluate. Crystallization from a mixed solvent of ethyl acetate and hexane gave 3.0 g of Coupler (6).

SYNTHETIC EXAMPLE 4

Synthesis of Coupler (31)

Coupler (31) was synthesized according to the following synthesis route:

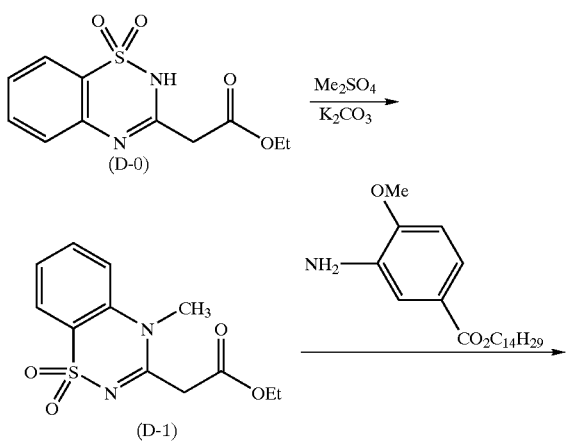

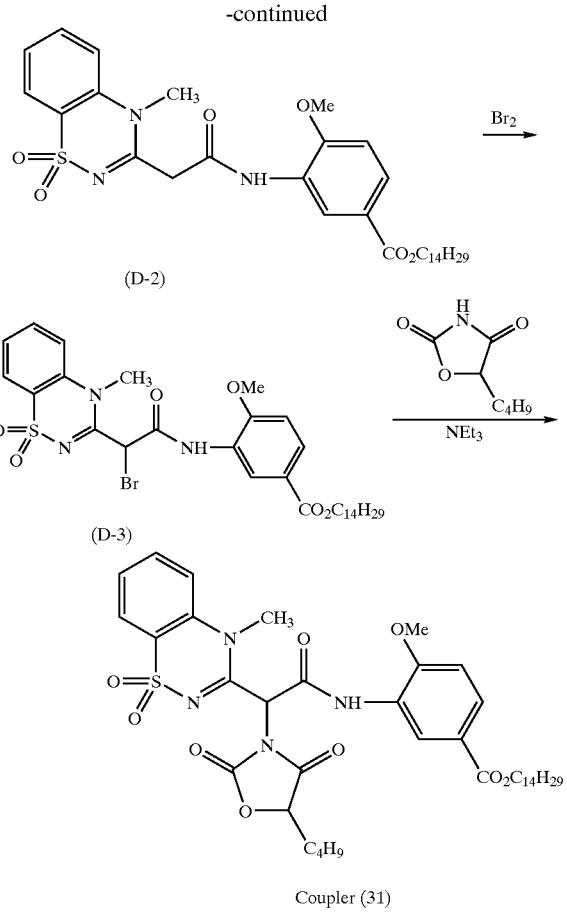

Coupler (31)

To a solution of 26.8 g of Compound (D-0) (Coupler-I described in U.S. Pat. No. 3,841,880) and 16.6 g of potassium carbonate in 300 ml of acetone, 13.9 g of dimethyl sulfate was added drop-wise and stirred for 2 hours with heating in refluxing. Ethyl acetate and water were added to separate an organic layer from an aqueous layer. The organic layer was washed with dilute hydrochloric acid and a saturated brine, and then dried with magnesium sulfate anhydride. The solvent was removed by vacuum distillation. The residue was purified by a silica gel column chromatography using a mixed solvent of acetone and hexane as the eluate. Crystallization from a mixed solvent of ethyl acetate and hexane gave 5.6 g of Compound (D-1). At the same time, 10.9 g of Compound (A-3) was obtained as a by-product. Coupler (1) may be produced from Compound (A-3) thus prepared.

A solution of 5.4 g of Compound (D-1) and 7.3 g of 2-methoxy-5-tetradecyloxycarbonylaniline in 50 ml of o-dichlorobenzene was stirred for 6 hours with heating in refluxing. Ethyl acetate and water were added to separate an organic layer from an aqueous layer. The organic layer was washed with dilute hydrochloric acid and a saturated brine, and then dried with magnesium sulfate anhydride. The solvent was removed by vacuum distillation. Crystallization from a mixed solvent of ethyl acetate and methanol gave 9.1 g of Compound (D-2).

To a solution of 4.8 g of Compound (D-2) in 100 ml of methylene chloride, 10 ml of a methylene chloride solution containing 0.4 ml of bromine was added drop-wise on an ice bath. The reaction mixture was stirred for 30 minutes on an ice bath. Thereafter, methylene chloride and water were added to separate an organic layer from an aqueous layer. The organic layer was washed with a saturated brine, and then dried with magnesium sulfate anhydride. The solvent was removed by vacuum distillation, to obtain a crude product of Compound (D-3).

To a solution of 3.8 g of 5-butyloxazolidine-2,4-dione and 3.4 ml of triethylamine dissolved in 100 ml of N,N-dimethyl acetamide, a solution containing all the previously synthesized crude product of Compound (D-3) dissolved in 50 ml of N,N-dimethylacetamide was added drop-wise at room temperature over 30 minutes, and the resultant mixture was stirred for 1 hour at room temperature. Ethyl acetate and water were added to separate an organic layer from an aqueous layer. The organic layer was washed with 0.1 normal aqueous potassium hydroxide solution, dilute hydrochloric acid and a saturated brine, and then dried with magnesium sulfate anhydride. The solvent was removed by vacuum distillation. The residue was purified by a silica gel column chromatography using a mixed solvent of acetone, tetrahydrofuran and hexane as the eluate. Crystallization from a mixed solvent of ethyl acetate and hexane gave 2.1 g of Coupler (31).

SYNTHETIC EXAMPLE 5

Synthesis of Coupler (51)

Coupler (51) was synthesized in the synthesis route shown below.

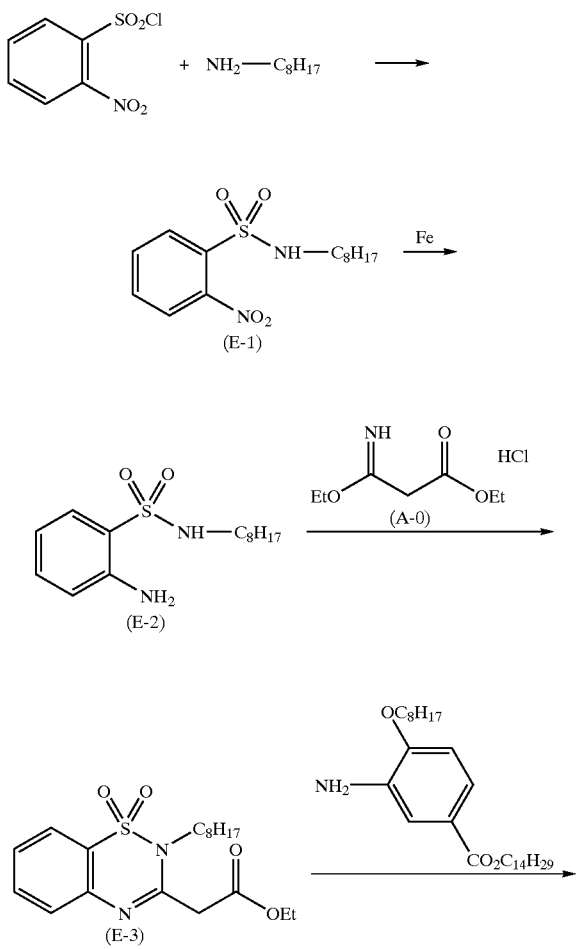

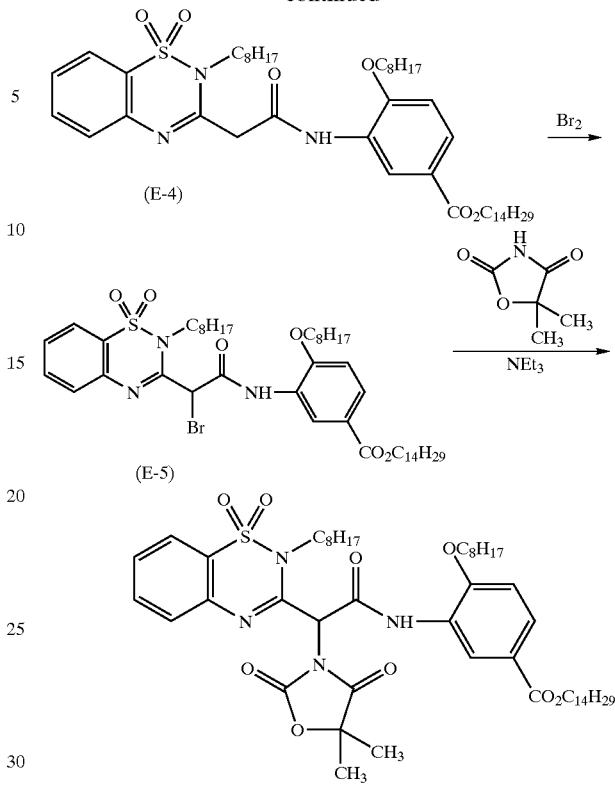

Coupler (51)

To a solution of 25.8 g of octylamine in 200 ml of acetonitrile, 44.3 g of o-nitrobenzenesulfonyl chloride was gradually added with stirring, while cooling on ice. The resulting reaction mixture was heated up to room temperature and further stirred for 1 hour. Thereafter, ethyl acetate and water were added to separate an organic layer from an aqueous layer. The organic layer was washed with dilute hydrochloric acid and saturated brine. After the organic layer was dried with magnesium sulfate anhydride, the solvent was removed by vacuum distillation, to yield 55.6 g of Compound (E-1).

44.8 g of reduced iron and 4.5 g of ammonium chloride were dispersed in a mixture of 270 ml of isopropanol and 45 ml of water, and the resulting dispersion was stirred under reflux for 1 hour. To the resulting mixture, 24.9 g of Compound (E-1) was gradually added with stirring. After heating in reflux for another 1 hour, insoluble matters were removed by a suction filter through Celite. Ethyl acetate and water were added to the filtrate to separate an organic layer from an aqueous layer. The organic layer was washed with saturated brine, and then dried with magnesium sulfate anhydride. The solvent was removed by vacuum distillation, to yield 20.5 g of Compound (E-2).

A solution of 19.0 g of Compound (E-2), 40.1 g of hydrochloride of iminoether (A-0), and 200 ml of ethyl alcohol was stirred with heating in reflux for 1 day. Additionally 20.2 g of hydrochloride of iminoether was added and stirred while heating under reflux for another 1 day. Ethyl acetate and water were added to separate an organic layer from an aqueous layer. The organic layer was washed with dilute hydrochloric acid and saturated brine, and then dried with magnesium sulfate anhydride. The solvent was removed by vacuum distillation, to yield 19.0 g of Compound (E-3).

A solution of 5.6 g of Compound (E-3), 9.2 g of 2-octyloxy-5-tetradecyloxycarbonylaniline and 20 ml of m-dichlorobenzene was stirred while heating under reflux for 6 hours. After cooling, methanol was added thereto, and crystallization from methanol gave 9.2 g of Compound (E-4).

To 110 ml of methylene chloride solution containing 5.4 g of Compound (E-4), 10 ml of methylene chloride solution containing 0.45 ml of bromine was added drop-wise, while cooling on ice. After the resultant mixture was stirred for 30 minute at room temperature, methylene chloride and water were added to separate an organic layer from an aqueous layer. The organic layer was washed with saturated brine, and then dried with magnesium sulfate anhydride. The solvent was removed by vacuum distillation, to obtain a crude product of Compound (E-5).

To a solution which was prepared by dissolving 3.5 g of 5,5-dimethyloxazolidine-2,4-dione and 3.8 ml of triethylamine in 110 ml of N,N-dimethyl acetoamide, a solution containing all the previously synthesized crude product of Compound (E-5) dissolved in 25 ml of acetonitrile was added drop-wise over 10 minutes at room temperature, and then the resultant mixture was stirred for 2 hours at room temperature. Ethyl acetate and water were added to separate an organic layer from an aqueous layer. The organic layer was washed with 0.1 normal aqueous potassium hydroxide solution, dilute hydrochloric acid and saturated brine, and then dried with magnesium sulfate anhydride. The solvent was removed by vacuum distillation. The residue was purified by means of a silica gel column chromatography using a mixed solvent of acetone and hexane, as an eluate, to obtain 4.5 g of Coupler (51).

SYNTHETIC EXAMPLE 6

Synthesis of Coupler (53)

Coupler (53) was synthesized in the synthesis route shown below.

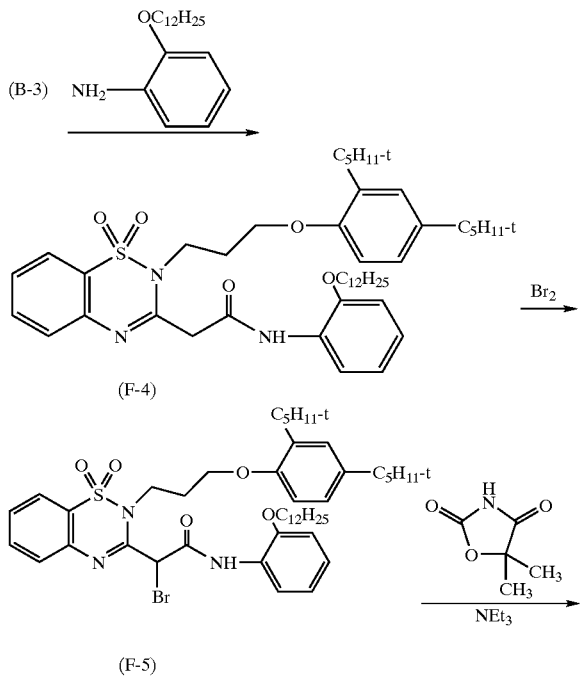

-continued

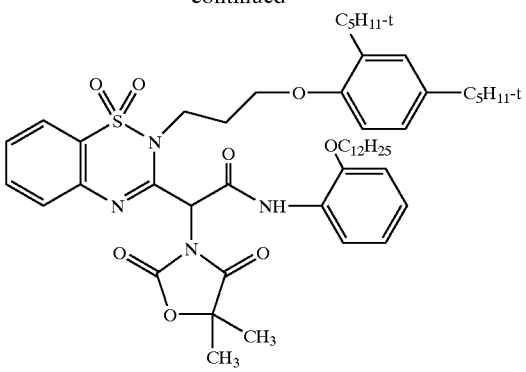

Coupler (53)

A solution of 40.7 g of Compound (B-3), 25.5 g of 2-dodecyloxyaniline and 10 ml of p-xylene was stirred while heating under reflux for 6 hour. Ethyl acetate and water were added to separate an organic layer from an aqueous layer. The organic layer was washed with dilute hydrochloric acid and saturated brine, and then dried with magnesium sulfate anhydride. The solvent was removed by vacuum distillation. The residue was purified by means of a silica gel column chromatography using a mixed solvent of ethyl acetate and hexane as an eluate, to obtain 38.7 g of Compound (F-4) as an oily product.

To 400 ml of methylene chloride solution containing 23.8 g of Compound (F-4), 35 ml of methylene chloride solution containing 2.1 ml of bromine was added drop-wise, while cooling on ice. After the resultant mixture was stirred for 30 minute while cooling on an ice bath, methylene chloride and water were added to separate an organic layer from an aqueous layer. The organic layer was washed with saturated brine, and then dried with magnesium sulfate anhydride. The solvent was removed by vacuum distillation, to obtain a crude product of Compound (F-5).

To a solution of 15.6 g of 5,5-dimethyl oxazolidine-2,4-dione and 16.5 ml of triethylamine in 200 ml of N,N-dimethyl acetoamide, a solution containing all the previously synthesized crude product of Compound (F-5) dissolved in 40 ml of acetonitrile was added drop-wise over 10 minutes at room temperature. The resultant mixture was heated up to 40° C. and then stirred for 30 minutes. Ethyl acetate and water were added to separate an organic layer from an aqueous layer. The organic layer was washed with 0.1 normal aqueous potassium hydroxide solution, dilute hydrochloric acid and saturated brine, and then dried with magnesium sulfate anhydride. The solvent was removed by vacuum distillation. The residue was purified by means of a silica gel column chromatography using a mixed solvent of acetone and hexane as an eluate, to yield 22.4 g of Coupler (53).

SYNTHETIC EXAMPLE 7

Synthesis of Coupler (103)

Coupler (103) was synthesized in the synthesis route shown below.

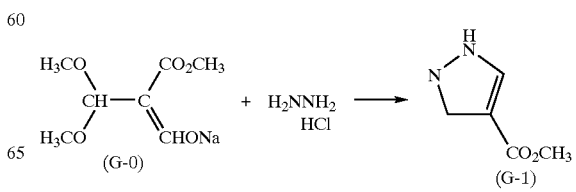

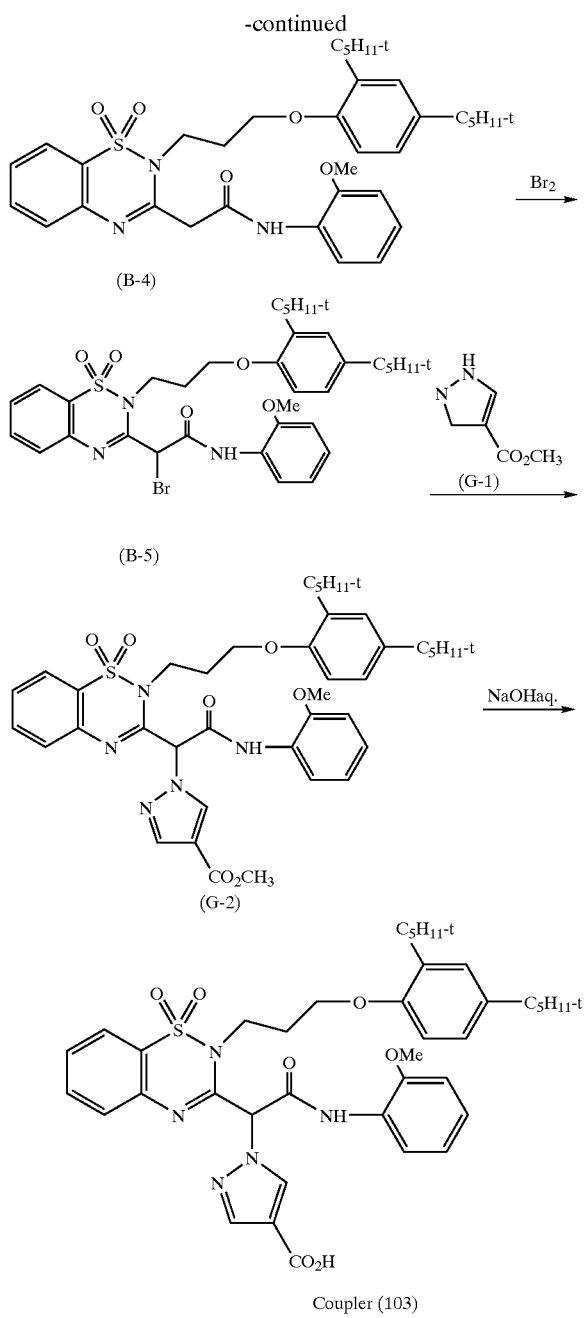

(B-4)

(B-5)

(G-2)

Coupler (103)

aqueous layer. The organic layer was washed with saturated brine, and then dried with magnesium sulfate anhydride. The solvent was removed by vacuum distillation, to obtain a crude product of Compound (B-5).

To a solution of 13.5 g of Compound (G-1) in 250 ml of N,N-dimethylacetoamide, 16.0 ml of 1,8-diazabicyclo [5,4,0]-7-undecene was added. Thereto, a solution of the above-prepared compound (B-5) in 250 ml of N,N-dimethylacetoamide was further added drop-wise. After the completion of dropwise addition, the resultant mixture was heated up to 50° C. and stirred for 1 hour. Ethyl acetate and water were added to separate an organic layer from an aqueous layer. The organic layer was washed with dilute hydrochloric acid and saturated brine, and then dried with magnesium sulfate anhydride. The solvent was removed by vacuum distillation. Crystallization from a mixed solvent of ethyl acetate and hexane gave 27.6 g of Compound (G-2).

To a solution of 27.6 g of Compound (G-2) in a mixture of 80 ml of tetrahydrofuran and 220 ml of methyl alcohol, 110 ml of 2N-aqueous sodium hydroxide solution was added. The resultant mixture was heated up to 50° C. and stirred for 5 hours. After neutralization with dilute hydrochloric acid, ethyl acetate was added to separate an organic layer from an aqueous layer. The organic layer was dried with magnesium sulfate anhydride. The solvent was removed by vacuum distillation. Crystallization from a mixed solvent of ethyl acetate and hexane gave 24.8 g of Coupler (103).

SYNTHETIC EXAMPLE 8

Synthesis of Coupler (112)

Coupler (112) was synthesized in the synthesis route shown below.

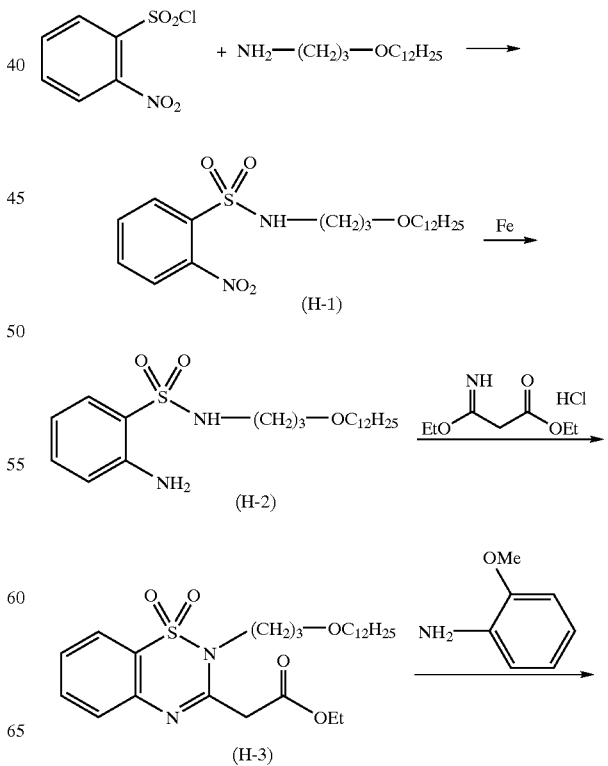

To 1.0 liter of a methyl alcohol solution containing 83.4 g of compound (G-0) (purity 95%), 27.4 g of hydrazine hydrochloride was added, and then the resultant mixture was stirred at room temperature for one night. 400 ml of water and 800 ml of ether were added to the mixture and stirred, and then insoluble matters were filtered. The filtrate was extracted with ether. The resultant organic layer was dried with magnesium sulfate anhydride. The solvent was removed by vacuum distillation. Crystallization from acetonitrile gave 40.0 g of Compound (G-1).

To 400 ml of methylene chloride solution containing 24.8 g of Compound (B-4), 35 ml of methylene chloride solution containing 2.1 ml of bromine was added drop-wise, while cooling on ice. After the resultant mixture was stirred for 30 minute while cooling on an ice bath, methylene chloride and water were added to separate an organic layer from an

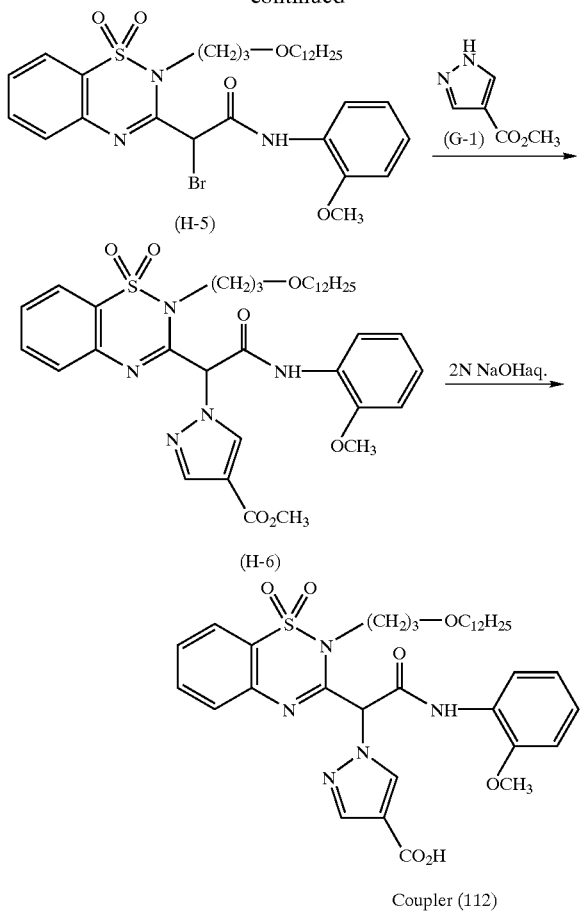

To a solution of 57.8 g of 3-lauryloxy-propylamine and 33.6 ml of triethylamine in 300 ml of acetonitrile, 52.5 g of o-nitrobenzenesulfonyl chloride was gradually added with stirring, while cooling on ice. The resulting reaction mixture was heated up to room temperature and further stirred for one night. Crystallization by pouring the mixture into dilute hydrochloric acid gave 105.8 g of Compound (H-1).

109.0 g of reduced iron and 10.9 g of ammonium chloride were dispersed in a mixture of 550 ml of isopropanol and 50 ml of water, and the resultant dispersion was heated under reflux for 1 hour. To the resulting mixture, 105.8 g of Compound (H-1) was gradually added with stirring. After heating under reflux for another 1 hour, the reaction mixture was filtrated by a suction filter through Celite. Ethyl acetate and water were added to the filtrate to separate an organic layer from an aqueous layer. The separated organic layer was washed with saturated brine, and then dried with magnesium sulfate anhydride. The solvent was removed by vacuum distillation, to yield 77.1 g of Compound (H-2) as an oily product.

A solution of 60.0 g of Compound (H-2) and 45.0 g of hydrochloride of iminoether in 300 ml of ethyl alcohol was stirred while heating under reflux for 1 hour. Additionally, 3.0 g of hydrochloride of iminoether was added, and the resultant mixture was stirred with heating in reflux for 2 hours. After cooling, 300 ml of p-xylene was added, and heated under reflux for 8 hours, while distilling off ethanol. Ethyl acetate and water were added thereto to separate an organic layer from an aqueous layer. The organic layer was washed with dilute hydrochloric acid and saturated brine, and then dried with magnesium sulfate anhydride. The dried organic layer was concentrated by vacuum distillation, to remove the solvent. The residue was purified by means of a silica gel column chromatography, to obtain 54.7 g of Compound (H-3) as an oily product.

A solution of 25.4 g of Compound (H-3), 7.6 g of 2-methoxyaniline in 60 ml of o-xylene was stirred while heating under reflux for 1 hour. Thereafter, 2-methoxyaniline was added in an amount of 3.5 g of a time in total three times at 1 hour-interval, and then the resultant mixture was stirred while heated under reflux for 6 hours. Ethyl acetate and water were added to separate an organic layer from an aqueous layer. The organic layer was washed with dilute hydrochloric acid and saturated brine, and then dried with magnesium sulfate anhydride. The solvent was removed by vacuum distillation. The residue was purified by means of a silica gel column chromatography using a mixed solvent of ethyl acetate and hexane, as an eluate. Crystallization from a mixed solvent of ethyl acetate and hexane gave 14.2 g of Compound (H-4).

To a solution containing 14.2 g of Compound (H-4) in 100 ml of methylene chloride, 8.7 g of perbromic acid pyridine was added. After the mixture was stirred for 30 minute at room temperature, methylene chloride and water were added to separate an organic layer from an aqueous layer. The organic layer was washed with saturated brine, and then dried with magnesium sulfate anhydride. The dried organic layer was concentrated by vacuum distillation to remove the solvent, to obtain a crude product of Compound (H-5).

To a solution of 9.5 g of Compound (G-1) in 200 ml of N,N-dimethylacetoamide, 11.3 ml of 1,8-diazabicyclo [5,4,0]-7-undecene was added. Thereto, a solution of the above-prepared Compound (H-5) in 100 ml of N,N-dimethylacetoamide was further added drop-wise. After the completion of dropwise addition, the resultant mixture was heated up to 50° C. and stirred for 1 hour. Ethyl acetate and water were added to separate an organic layer from an aqueous layer. The organic layer was washed with dilute hydrochloric acid and saturated brine, and then dried with magnesium sulfate anhydride. The solvent was removed by vacuum distillation. Crystallization from a mixed solvent of ethyl acetate and hexane gave 15.7 g of Compound (H-6).

To a-solution of 15.7 g of Compound (H-6) in a mixture of 50 ml of tetrahydrofuran and 140 ml of methyl alcohol, 70 ml of 2N-aqueous sodium hydroxide solution was added. The resultant mixture was heated up to 50° C. and stirred for 3 hours. After neutralization with dilute hydrochloric acid, ethyl acetate was added to separate an organic layer from an aqueous layer. The organic layer was dried with magnesium sulfate anhydride. The solvent was removed by vacuum distillation. Crystallization from a mixed solvent of ethyl acetate and hexane gave 13.8 g of Coupler (112).

SYNTHETIC EXAMPLE 9

Synthesis of Coupler (126)

Coupler (126) was synthesized in the synthesis route shown below.

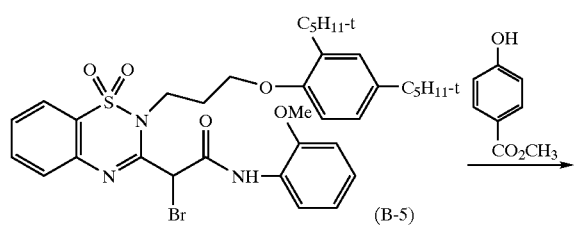

93

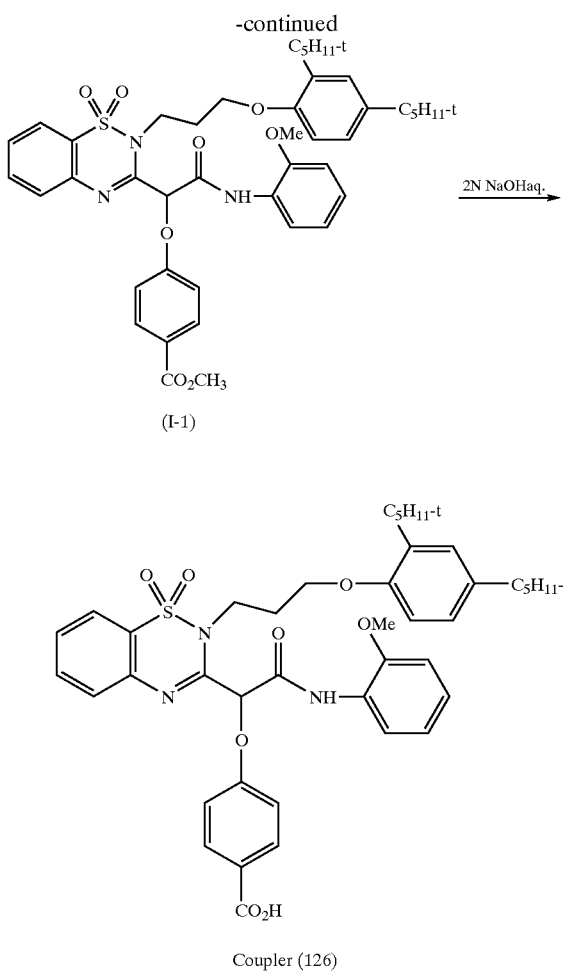

To a solution of 8.4 g of methyl p-hydroxybenzoate in 100 ml of N,N-dimethylacetoamide, 8.3 ml of 1,8-diazabicyclo [5,4,0]-7-indecene was added. To the resultant mixture, a solution of 100 ml of N,N-dimethylacetoamide containing 12.9 g of the crude product of Compound (B-5) prepared under the above-mentioned conditions, was added dropwise. After stirring at room temperature for 3 hours, ethyl acetate and water were added to separate an organic layer from an aqueous layer. The organic layer was washed with saturated brine, and then dried with magnesium sulfate anhydride. The solvent was removed by vacuum distillation. The residue was purified by means of a silica gel column chromatography, to yield 11.0 g of Compound (I-1) as an oily product.

To a solution of 11.0 g of Compound (I-1) in a mixed solvent of 30 ml of tetrahydrofuran and 50 ml of methyl alcohol, 45 ml of 2-N aqueous solution of sodium hydroxide was added. After stirring at 50° C. for 3 hours, the mixture was neutralized with dilute hydrochloric acid. Ethyl acetate and water were added to separate an organic layer from an aqueous layer. The organic layer was washed with aqueous sodium bicarbonate solution and saturated brine, and then dried with magnesium sulfate anhydride. The solvent was removed by vacuum distillation. The residue was purified by means of a silica gel column chromatography. Crystallization from a mixed solvent of ethyl acetate and hexane gave 5.7 g of coupler (126).

94

SYNTHETIC EXAMPLE 10

Synthesis of Coupler (129)

Coupler (129) was synthesized in the synthesis route shown below.

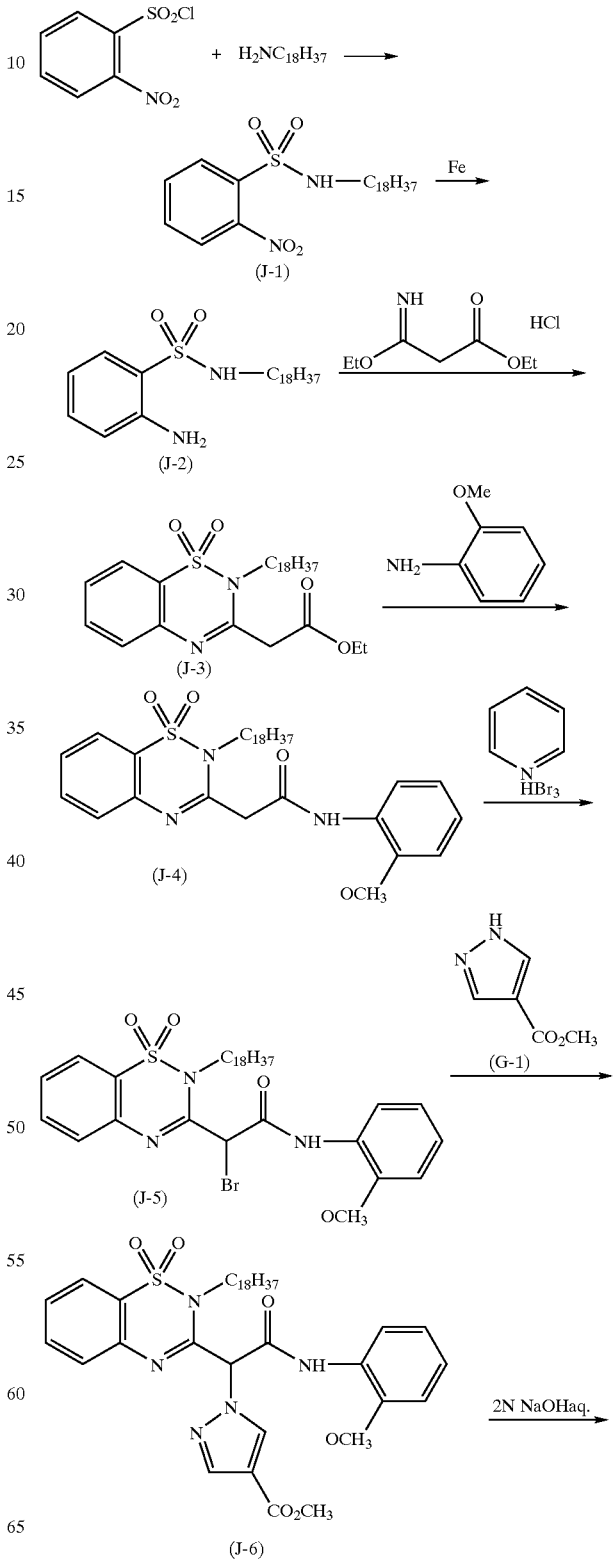

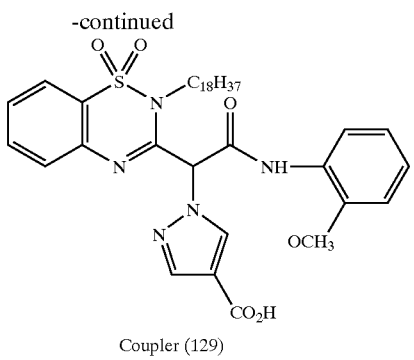

Coupler (129)

To a solution of 61.0 g of stearylamine and 32.0 ml of triethylamine in 300 ml of N,N-dimethylacetoamide, 50.0 g of o-nitrobenzenesulfonyl chloride was gradually added with stirring, while cooling on ice. The resulting mixture was stirred at 40° C. for 2 hours. Crystallization by pouring the mixture into water gave 79.8 g of Compound (J-1).

77.0 g of reduced iron and 7.7 g of ammonium chloride were dispersed in a mixture of 400 ml of isopropanol and 40 ml of water, and the resultant dispersion was heated under reflux for 1 hour. To the resulting mixture, 78.0 g of Compound (J-1) was gradually added with stirring. After heating under reflux for 3 hours, the reaction mixture was filtrated by a suction filter through Celite. Ethyl acetate and water were added to the filtrate to separate an organic layer from an aqueous layer. The organic layer was washed with saturated brine, and then dried with magnesium sulfate anhydride. The solvent was removed by vacuum distillation. Crystallization from methyl alcohol gave 45.8 g of Compound (J-2).

A solution of 45.0 g of Compound (J-2) and 31.0 g of hydrochloride of iminoether in 400 ml of ethyl alcohol was stirred while heating under reflux for 1 hour. Additionally 3.0 g of hydrochloride of iminoether was added and stirred while heating under reflux for 3 hours. After cooling, 300 ml of p-xylene was added, and heated under reflux for 18 hours, while distilling off ethanol. Ethyl acetate and water were added to the filtrate to separate an organic layer from an aqueous layer. The organic layer was washed with dilute hydrochloric acid and saturated brine, and then dried with magnesium sulfate anhydride. The solvent was removed by vacuum distillation. Crystallization from methyl alcohol gave 30.6 g of Compound (J-3).

A solution of 15.0 g of Compound (J-3), 4.7 g of 2-methoxyaniline in 50 ml of o-xylene was stirred while heating under reflux for 6 hours. Ethyl acetate and water were added to separate an organic layer from an aqueous layer. The organic layer was washed with dilute hydrochloric acid and saturated brine, and then dried with magnesium sulfate anhydride. The solvent was removed by vacuum distillation. Crystallization from methyl alcohol gave 14.4 g of Compound (J-4).

To a solution containing 14.0 g of Compound (J-4) in 200 ml of methylene chloride, 8.2 g of perbromic acid pyridine was added. After the resultant mixture was stirred for 1 hour at room temperature, ethyl acetate and water were added to separate an organic layer from an aqueous layer. The organic layer was washed with saturated brine, and then dried with magnesium sulfate anhydride. The dried organic layer was concentrated by vacuum distillation, to obtain 15.5 g of a crude product of Compound (J-5).

To a solution of 8.7 g of Compound (G-1) in 200 ml of N,N-dimethylacetoamide, 10.3 ml of 1,8-diazabicyclo [5,4,0]-7-undecene was added. To the resultant mixture, a solution of 15.5 g of Compound (J-5) in 100 ml of N,N-dimethylacetoamide was added drop-wise. After the completion of dropwise addition, the mixture was heated up to 50° C. and stirred for 1 hour. Ethyl acetate and water were added to separate an organic layer from an aqueous layer. The organic layer was washed with dilute hydrochloric acid and saturated brine, and then dried with magnesium sulfate anhydride. The solvent was removed by vacuum distillation. The residue was purified by means of a silica gel column chromatography, to yield 15.0 g of Compound (J-6).

To a solution of 15.0 g of Compound (J-6) in a mixed solvent of 50 ml of tetrahydrofuran and 140 ml of methyl alcohol, 60 ml of 2-N aqueous solution of sodium hydroxide was added. The mixture was heated up to 50° C. and stirred for 3 hours. After neutralization with dilute hydrochloric acid, ethyl acetate was added for separation of an organic layer from an aqueous layer. The organic layer was dried with magnesium sulfate anhydride. The solvent was removed by vacuum distillation. The residue was purified by means of a silica gel column chromatography. Crystallization from a mixed solvent of ethyl acetate and hexane gave 13.2 g of coupler (129).

SYNTHETIC EXAMPLE 11

Synthesis of Coupler (191)

Coupler (191) was synthesized in the synthesis route shown below.

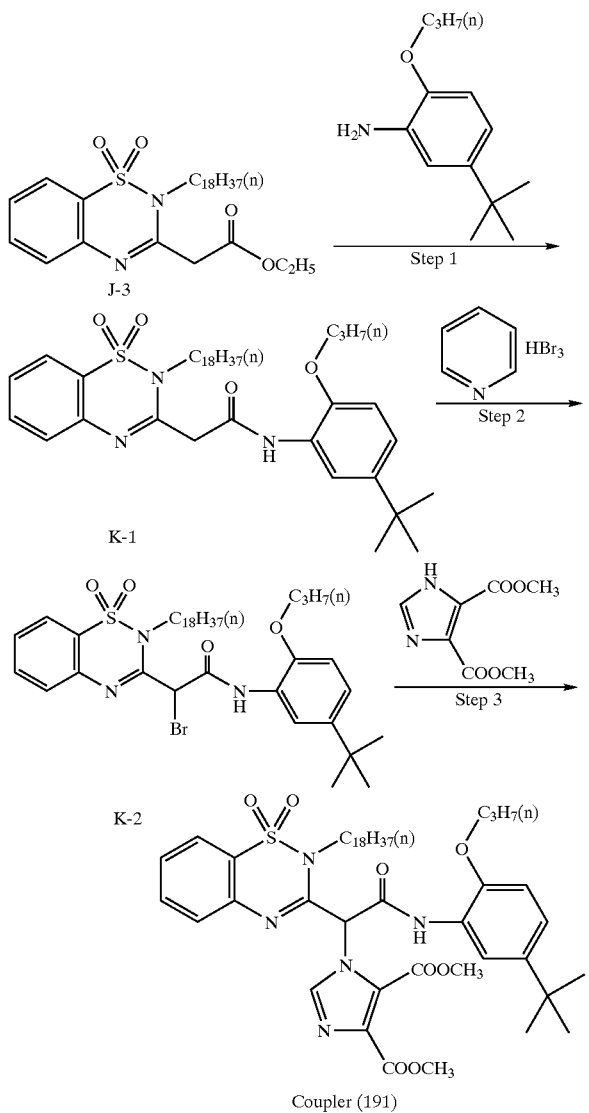

Coupler (191)

Step 1

62.2 g (105 mmol) of Compound J-3, 21.8 g (105 mmol) of 2-propoxy-5-t-butyl aniline, and 300 ml of xylene were reacted at 150° C. for 3 hours. Thereafter, 150 ml of xylene was distilled away, and the reaction mixture was further reacted for 4 hours. The reaction mixture was cooled to room temperature, and 100 ml of methanol and 200 ml of acetonitrile were added, and the precipitated crystals were collected by filtration, and the crystals were washed well with acetonitrile. The crystals were dried, to give 51.1 g of Compound (K-1) (yield 71%).

Step 2

35.8 g (52.5 mmol) of Compound (K-1), 50 ml methylene chloride, 18.5 g (57.7 mmol) of hydrobromate pyridinium perbromide were reacted at 20° C. for 1 hour. Thereto, 100 ml of water was added, and the organic layer was washed, and the resultant organic layer was dried over magnesium sulfate, and the solvent was distilled away under reduced pressure. The thus-obtained Compound (K-2) was used as such in the next step.

Step 3

The whole amount of Compound (K-2) obtained in the step 2, 14.5 g (78.8 mmol) of 4,5-bis(methoxycarbonyl) imidazole, 11.8 ml (78.8 mmol) of 1,8-diazabicyclo[5.4.0]-7-undecene and 200 ml of dimethyl acetamide were reacted at 20° C. for 30 minutes. Thereafter, to the reaction mixture, was added 500 ml of water and 500 ml of ethyl acetate to separate an organic layer from an aqueous layer. The organic layer was washed once with water and once with saturated birne, and dried over magnesium sulfate, and the solvent was distilled away under reduced pressure. The residue was purified by silica gel column chromatography (ethyl acetate/hexane=1/10 to 1/4) and then recrystallized from acetonitrile, to give 22.1 g Coupler (191) (yield 49%). The structure of the coupler was identified by 300 MHz $^1$HNMR and mass spectrometry.

The pKa of the Coupler (191), as determined at 25° C. in tetrahydrofuran:water=6:4, was 8.3.

Mass spectrum and $^1$HNMR data are shown below.
Mass spectrometric (negative) measurement results
183, 403, 629, 863 (M−1)
Data of $^1$HNMR (values of δ in CDCl$_3$)
0.79–0.92 (m, 6H), 1.05 (bs, 2H), 1.22 (bs, 30H), 1.30 (s, 9H), 1.48–1.63 (m, 2H), 2.90–3.02 (m, 1H), 3.03–3.18 (m, 1H), 3.79 (q, J=6.6 Hz, 2H), 3.84 (s, 3H), 3.98 (s, 3H), 6.72 (d, J=8.9 Hz, 1H), 7.04 (dd, J1=8.9 Hz, J2=3.0 Hz, 1H), 7.18–7.27 (m, 1H), 7.54–7.63 (m, 2H), 7.73 (m, J=8.7 Hz, 1H), 7.76 (s, 1H), 8.47 (d, 3.0 Hz, 1H)

(Silver Halide Photographic Light-Sensitive Material)

The light-sensitive material of the present invention is a silver halide photographic light-sensitive material, in which at least one light-sensitive layer is formed on a support, and the light-sensitive material contains the dye-forming coupler that is the compound represented by formula (I), (I-2), (II), (IIA), (IIB), or (II-2) described above (hereinafter referred to as a dye-forming coupler of the present invention or a coupler of the present invention) in at least one layer of the light-sensitive layer(s). The above-described coupler is generally contained in a hydrophilic colloid layer composed of an ordinary gelatin binder. An ordinary light-sensitive material can be made by providing light-sensitive emulsion layers (light-sensitive layers) composed of at least one blue-sensitive silver halide emulsion layer, at least one green-sensitive silver halide emulsion layer, and at least one red-sensitive silver halide emulsion layer, on a support. The order of these light-sensitive layers to be provided may be selected arbitrarily. An infrared ray-sensitive silver halide emulsion layer may be used instead of at least one of the above-mentioned light-sensitive emulsion layers. Color reproduction based on subtractive color processes can be performed by incorporating, into each of these light-sensitive emulsion layers, a silver halide emulsion having sensitivity in the corresponding wavelength range, and a coupler for forming a dye having a color complementary to the color of sensitizing light. However, the light-sensitive emulsion layer and the developed hue of the coupler may not have a corresponding relationship as described above.

The dye-forming coupler of the present invention can be incorporated into any one of the light-sensitive emulsion layers (preferably, the blue-sensitive silver halide emulsion layer or the green-sensitive silver halide emulsion layer, particularly preferably the blue-sensitive silver halide emulsion layer).

The dye-forming coupler of the present invention is useful mainly as a yellow coupler or a magenta coupler, particularly as a yellow coupler, when combined with a p-phenylenediamine color-developing agent. Therefore, in the case that a p-phenylenediamine is used as a color-developing agent for the silver halide photographic light-sensitive material of the present invention, the dye-forming coupler of the present invention is incorporated preferably into the yellow coupler- or magenta coupler-containing color-forming layer, particularly preferably into the yellow color-forming layer. In systems wherein a color-developing agent other than p-phenylenediamines is used, the dye-forming coupler of the present invention is useful as a dye-forming coupler that can give a dye having various types of hue.

In the silver halide photographic light-sensitive material of the present invention, the coupler is added preferably in an amount of $1 \times 10^{-3}$ to 1 mole, more preferably in an amount of $2 \times 10^{-3}$ to $3 \times 10^{-1}$ mole, per mole of silver halide.

The coupler of the present invention may be incorporated in a light-sensitive material by various known dispersion processes. It is preferred to use an oil-in-water dispersion process in which first a compound is dissolved in a high-boiling-point organic solvent (in combination with a low-boiling-point organic solvent as occasion demands), thereby forming a solution and then the resulting solution is emulsified and dispersed in an aqueous gelatin solution, which is then added to a silver halide emulsion. Examples of the high-boiling-point organic solvent for use in the oil-in-water dispersion process are described in, for example, JP-A-5-313327, JP-A-5-323539, JP-A-5-323541, JP-A-6-258803, JP-A-8-262662, and U.S. Pat. No. 2,322,027. Further, the steps, effects and specific examples of latex polymers for impregnation, which are used in the latex dispersion process as one of polymer dispersion process, are described in, for example, U.S. Pat. No. 4,199,363, West German Patent Application (OLS) Nos. 2,541,274 and 2,541,230, JP-B-53-41091 ("JP-B" means examined Japanese patent publication), and European Patent Publication No. 029104. Further, dispersion processes using an organic solvent-soluble polymer are described in, for example, PCT International Publication WO 88/00723 and JP-A-5-150420. Methacrylate-series or acrylamide-series polymers are preferred. In particular, the use of acrylamide-series polymers is preferred, in view of enhancing image-fastness.

The term "high boiling point" herein used refers to a boiling point of 175° C. or more at ordinary pressure.

Examples of the high-boiling-point solvent that can be used in the present invention are described in, for example, U.S. Pat. No. 2,322,027. Specific examples of the high-boiling-point organic solvent having a boiling point of 175°

C. or more at ordinary pressure include phthalic acid esters {e.g., dibutyl phthalate, dicyclohexyl phthalate, di-2-ethylhexyl phthalate, decyl phthalate, bis(2,4-di-tert-amylphenyl) phthalate, bis(2,4-di-tert-amylphenyl) isophthalate, bis(1,1-di-ethylpropyl) phthalate}, esters of phosphoric acid or phosphonic acid (e.g., triphenyl phosphate, tricresyl phosphate, 2-ethylhexyldiphenyl phosphate, tricyclohexyl phosphate, tri-2-ethlhexyl phosphate, tridodecyl phosphate, tributoxyethyl phosphate, trichloropropyl phosphate, di-2-ethylhexylphenyl phosphonate), benzoic acid esters (e.g., 2-ethylhexyl benzoate, dodecyl benzoate, 2-ethylhexyl p-hydroxybenzoate), amides (e.g., N,N-diethyldodecaneamide, N,N-diethyllaurylamide, N-tetradecylpyrrolidone), sulfonamides (e.g., N-butylbenzenesulfonamide), alcohols and phenols (e.g., isostearyl alcohol, 2,4-di-tert-amylphenol), aliphatic carboxylic acid esters (e.g., bis-(2-ethylhexyl) sebacate, dioctyl azelate, glycerol tributylate, isostearyl lactate, trioctyl citrate), aniline derivatives (e.g., N,N-dibutyl-2-butory-5-tert-octylaniline), hydrocarbons (e.g., paraffin, dodecylbenzene, diisopropylnaphthalate), and chlorinated paraffins. In particular, the foregoing phosphoric acid esters, and hydrogen-providing compounds described in JP-A-6-258803 and JP-A-8-262662 are preferably used, since they help to provide an excellent hue.

In order to reduce a load to environment, it is preferred to use compounds described in European Patent Nos. EP-969320A1 and EP-969321A1, in place of the foregoing phthalic acid esters. In addition to the above-mentioned compounds, tributyl citrate, pentaglycelol triesters and the like may be used.

The dielectric constant of the high-boiling-point organic solvent varies depending on the purpose for use, but it is preferably in the range of 2.0 to 7.0, more preferably in the range of 3.0 to 6.0.

The high-boiling-point organic solvent is used preferably in an amount of 0 to 10 times of the mass of the coupler, more preferably in an amount of 0 to 4 times thereof.

Further, as an auxiliary solvent, an organic solvent having a boiling point of generally 30° C. or more, preferably in the range of from 50° C. to about 160° C. may be used. Typical examples of the auxiliary solvent include ethyl acetate, butyl acetate, ethyl propionate, methyl ethyl ketone, cyclohexane, 2-ethoxyethyl acetate and dimethylformamide.

All or a part of the auxiliary solvent may be removed from an emulsified dispersion by means of a vacuum distillation, a noodle washing, an ultrafiltration, or the like, as occasion demands, for the purpose of improving storage stability with the lapse of time in the state of the emulsified dispersion, or inhibiting a fluctuation in photographic properties or improving storage stability with the lapse of time of the final coating composition in which the emulsified dispersion is mixed with a silver halide emulsion.

The average particle size of the oleophilic fine particle dispersion thus obtained is preferably in the range of 0.001 to 1.0 $\mu$m, more preferably in the range of 0.05 to 0.30 $\mu$m, and most preferably in the range of 0.08 to 0.20 $\mu$m. The average particle size can be determined with a measuring device such as Coulter submicron particle analyzer model N4 (trade name, made by Coulter Electronics Co., Ltd.). If the average particle size of the oleophilic fine particles dispersion is too large, such problems easily arise that a color-formation efficiency of a coupler is lessened, or gloss on the surface of a light-sensitive material deteriorates. In contrast, if the average particle size is too small, viscosity of the dispersion increases and consequently a handling becomes difficult at the time of production.

The amount to be used (in terms of weight ratio) of a dispersion of oleophilic fine-particles composed of the coupler of the present invention to a dispersion medium is preferably in the range of 2 to 0.1, more preferably in the range of 1.0 to 0.2, per 1 part by weight of the dispersion medium. Examples of the dispersion medium include gelatin that is a typical example, and in addition thereto mention can be made of hydrophilic polymers, such as polyvinyl alcohol. The oleophilic fine-particle dispersion may contain various compounds, together with the coupler of the present invention, according to the purpose of use.

The silver halide photographic light-sensitive material of the present invention is suitable for a light-sensitive material of the type that uses a coupler. Particularly the light-sensitive material is suitable for various color photographic light-sensitive materials, such as color negative films for general purposes or movies, color reversal films for slides or television, color papers, color positive films for general purposes or movies, photosensitive materials for display, color reversal papers, and color proofs for scanning exposure or area-wise exposure; and black-and-white photosensitive materials using a coupler. Further, color negative films are suitable for film unites with a lens, as described in JP-B-2-32615 and JU-B-3-39784 ("JU-B" means examined Japanese Utility-model Registration Publication).

In case where the coupler of the present invention is applied to a color paper, the light-sensitive material and the like described in JP-A-11-7109, particularly descriptions in paragraph numbers 0071 to 0087 in JP-A-11-7109 are preferable, and therefore the above descriptions in JP-A-11-7109 are incorporated herein by reference.

In case where the coupler of the present invention is applied to a color negative film, the descriptions at paragraph Nos. 0115 to 0217 of the specification of JP-A-11-305396 can be preferably applied thereto, and therefore incorporated herein by reference.

In case where the coupler of the present invention is applied to a color reversal film, the descriptions at paragraph Nos. 0018 to 0021 of the specification of JP-A-11-84601 can be preferably applied thereto, and therefore incorporated herein by reference.

A preferable embodiment of the silver halide photographic light-sensitive material of the present invention is explained in detail below.

The coupler of the present invention is mainly preferable applying in the following two embodiments.

First, the first embodiment is explained.
(First Embodiment)

Other known photographic materials and additives may be used in the silver halide photographic light-sensitive material of the present invention.

For example, as a photographic support (base), a transmissive type support and a reflective type support may be used. As the transmissive type support, it is preferred to use transparent supports, such as a cellulose nitrate film, and a transparent film of polyethylene terephthalate, or a polyester of 2,6-naphthalenedicarboxylic acid (NDCA) and ethylene glycol (EG), or a polyester of NDCA, terephthalic acid and EG, provided thereon with an information-recording layer such as a magnetic layer. As the reflective type support, it is especially preferable to use a reflective support having a substrate laminated thereon with a plurality of polyethylene layers or polyester layers (water-proof resin layers or laminate layers), at least one of which contains a white pigment such as titanium oxide.

A more preferable reflective support for use in the present invention is a support having a paper substrate provided with a polyolefin layer having fine holes, on the same side as silver halide emulsion layers. The polyolefin layer may be composed of multi-layers. In this case, it is more preferable for the support to be composed of a fine hole-free polyolefin (e.g., polypropylene, polyethylene) layer adjacent to a gelatin layer on the same side as the silver halide emulsion layers, and a fine hole-containing polyolefin (e.g., polypropylene, polyethylene) layer closer to the paper substrate. The density of the multi-layer or single-layer of polyolefin layer(s) existing between the paper substrate and photographic constituting layers is preferably in the range of 0.40 to 1.0 g/ml, more preferably in the range of 0.50 to 0.70 g/ml. Further, the thickness of the multi-layer or single-layer of polyolefin layer(s) existing between the paper substrate and photographic constituting layers is preferably in the range of 10 to 100 µm, more preferably in the range of 15 to 70 µm. Further, the ratio of thickness of the polyolefin layer(s) to the paper substrate is preferably in the range of 0.05 to 0.2, more preferably in the range 0.1 to 0.5.

Further, it is also preferable for enhancing rigidity (mechanical strength) of the reflective support, by providing a polyolefin layer on the surface of the foregoing paper substrate opposite to the side of the photographic constituting layers, i.e., on the back surface of the paper substrate. In this case, it is preferable that the polyolefin layer on the back surface be polyethylene or polypropylene, the surface of which is matted, with the polypropylene being more preferable. The thickness of the polyolefin layer on the back surface is preferably in the range of 5 to 50 µm, more preferably in the range of 10 to 30 µm, and further the density thereof is preferably in the range of 0.7 to 1.1 g/ml. As to the reflective support for use in the present invention, preferable embodiments of the polyolefin layer provide on the paper substrate include those described in JP-A-10-333277, JP-A-10-333278, JP-A-11-52513, JP-A-11-65024, European Patent Nos. 0880065 and 0880066.

Further, it is preferred that the above-described waterproof resin layer contains a fluorescent whitening agent. Further, the fluorescent whitening agent also may be dispersed in a hydrophilic colloid layer of the light-sensitive material. Preferred fluorescent whitening agents that can be used, include benzoxazole series, coumarin series, and pyrazoline series compounds. Further, fluorescent whitening agents of benzoxazolylnaphthalene series and benzoxazolylstilbene series are more preferably used. The amount of the fluorescent whitening agent to be used is not particularly limited, and it is preferably in 2 the range of 1 to 100 mg/m. When a fluorescent whitening agent is mixed with a waterproof resin, a mixing ratio of the fluorescent whitening agent to be used to the water-proof resin is preferably in the range of 0.0005 to 3% by mass, and more preferably in the range of 0.001 to 0.5% by mass of the resin.

Further, a transmissive type support or the foregoing reflective type support each having coated thereon a hydrophilic colloid layer containing a white pigment may be used as the reflective type support.

Furthermore, a reflective type support having a mirror plate reflective metal surface or a secondary diffusion reflective metal surface may be employed as the reflective type support.

As the support for use in the light-sensitive material of the present invention, a support of the white polyester type, or a support provided with a white pigment-containing layer on the same side as the silver halide emulsion layer, may be adopted for display use. Further, it is preferable for improving sharpness that an antihalation layer is provided on the silver halide emulsion layer side or the reverse side of the support. In particular, it is preferable that the transmission density of support is adjusted to the range of 0.35 to 0.8 so that a display may be enjoyed by means of both transmitted and reflected rays of light.

In the light-sensitive material of the present invention, in order to improve, e.g., sharpness of an image, a dye (particularly an oxonole-series dye) that can be discolored by processing, as described in European Patent No. 0337490 A2, pages 27 to 76, is preferably added to the hydrophilic colloid layer such that an optical reflection density at 680 nm in the light-sensitive material is 0.70 or more. It is also preferable to add 12% by mass or more (more preferably 14% by mass or more) of titanium oxide that is surface-treated with, for example, dihydric to tetrahydric alcohols (e.g., trimethylolethane) to a water-proof resin layer of the support.

The light-sensitive material of the present invention preferably contains, in their hydrophilic colloid layers, dyes (particularly oxonole dyes and cyanine dyes) that can be discolored by processing, as described in European Patent No. 0337490 A2, pages 27 to 76, in order to prevent irradiation or halation or enhance safelight safety (immunity). Further, dyes described in European Patent No. 0819977 are also preferably used in the present invention.

Among these water-soluble dyes, some deteriorate color separation or safelight safety when used in an increased amount. Preferable examples of the dye which can be used and which does not deteriorate color separation include water-soluble dyes described in JP-A-5-127324, JP-A-5-127325 and JP-A-5-216185.

In the present invention, it is possible to use a colored layer that can be discolored during processing, in place of the water-soluble dye, or in combination with the water-soluble dye. The colored layer capable of being discolored with a processing to be used may contact with a light-sensitive emulsion layer directly, or indirectly through an interlayer containing an agent for preventing color-mixing during processing, such as hydroquinone and gelatin. The colored layer is preferably provided as a lower layer (closer to a support) with respect to the light-sensitive emulsion layer that develops the same primary color as the color of the colored layer. It is possible to provide colored layers independently, each corresponding to respective primary colors. Alternatively, only one or some layer(s) selected from the above colored layers may be provided. In addition, it is possible to provide a colored layer subjected to coloring so as to match a plurality of primary-color regions. With respect to the optical reflection density of the colored layer, at the wavelength which provides the highest optical density in a range of wavelengths used for exposure (a visible light region from 400 nm to 700 nm for an ordinary printer exposure, and the wavelength of the light generated from the light source in the case of scanning exposure), the optical density is preferably within the range of 0.2 to 3.0, more preferably 0.5 to 2.5, and particularly preferably 0.8 to 2.0.

The colored layer described above may be formed by a known method. For example, there are a method in which a dye in a state of a dispersion of solid fine-particles is incorporated in a hydrophilic colloid layer, as described in JP-A-2-282244, from page 3, upper right column to page 8, and JP-A-3-7931, from page 3, upper right column to page 11, left under column; a method in which an anionic dye is mordanted in a cationic polymer, a method in which a dye is adsorbed onto fine grains of silver halide or the like and fixed in the layer, and a method in which a colloidal silver is used, as described in JP-A-1-239544. As to a method of dispersing fine-powder of a dye in solid state, for example, JP-A-2-308244, pages 4 to 13 describes a method in which solid fine-particles of dye which is at least substantially water-insoluble at the pH of 6 or less, but at least substantially water-soluble at the pH of 8 or more, are incorporated. The method of mordanting an anionic dye in a cationic polymer is described, for example, in JP-A-2-84637, pages 18 to 26. U.S. Pat. Nos. 2,688,601 and 3,459,563 disclose a method of preparing colloidal silver for use as a light absorber. Among these methods, preferred are the methods of incorporating fine-particles of dye and of using colloidal silver.

Silver halide grains in the silver halide emulsion which can be used in the present invention, are preferably cubic or tetradecahedral crystal grains substantially having {100} planes (these grains may be rounded at the apexes thereof and further may have planes of higher order), or octahedral crystal grains. Alternatively, a silver halide emulsion in which the proportion of tabular grains having an aspect ratio of 2 or more and composed of {100} or {111} planes accounts for 50% or more in terms of the total projected area, can also be preferably used. The term "aspect ratio" refers to the value obtained by dividing the diameter of the circle having an area equivalent to the projected area of an individual grain by the thickness of the grain. In the present invention, cubic grains, or tabular grains having {100} planes as major faces, or tabular grains having {111} planes as major faces are preferably used.

As a silver halide emulsion which can be used in the present invention, for example, a silver chloride, silver bromide, silver iodobromide, or silver chloro(iodo)bromide emulsion may be used. It is preferable for a rapid processing to use a silver chloride or silver chlorobromide emulsion having a silver chloride content of 95 mole % or greater, more preferably a silver halide emulsion having a silver chloride content of 98 mole % or greater. Especially preferred of these silver halide emulsions are those containing silver chloride grains having a silver bromide localized phase on the surface thereof, since both high sensitivity and stabilization of photographic properties are attained.

The silver bromide localized phase is preferably formed by epitaxial growth of the localized phase having a total silver bromide content of at least 10 mole % in the silver bromide localized phase. A silver bromide content of the silver bromide localized phase is preferably in the range of 10 to 60 mole %, and most preferably in the range of 20 to 50 mole %. The silver bromide localized phase is preferably composed of silver having population of 0.1 to 5 mole %, more preferably 0.3 to 4 mole %, to the molar amount of entire silver which constitutes silver halide grains for use in the present invention. The silver bromide localized phase is preferably doped with complex ions of a metal of Group VIII in the periodic table, such as iridium (III) chloride, iridium (III) bromide, iridium (IV) chloride, sodium hexachloroiridate (III), potassium hexachloroiridate (IV), hexaammineiridium (IV) salts, trioxalatoiridium (III) salt, and trioxalatoiridium (IV) salt. The amount of these compounds to be added can be varied in a wide range depending on the purposes for use, and it is preferably in the range of $10^{-9}$ to $10^{-2}$ mole, per mole of silver halide.

In a silver halide emulsion for use in the present invention, various kinds of polyvalent metal ion impurities other than iridium may be incorporated, during grain formation or in the course of physical ripening of the emulsion. AS for examples of the impurities to be used, salts or complex salts of metals of Group VIII of the periodic table, such as iron, ruthenium, osmium, rhenium, rhodium, cadmium, zinc, lead, copper and thallium, may be used in combination thereof. In the present invention, compounds of metals, such as iron, ruthenium, osmium and rhenium, which have at least four cyano ligands, are particularly preferred, since high-illumination-intensity sensitivity is further enhanced and latent-image sensitization is also inhibited. Iridium compounds provide an outstanding effect on the high-illumination intensity exposure suitability. The amount of these compounds to be added can be varied in a wide range depending on the purposes, and it is preferably in the range of $10^{-9}$ mole to $10^{-2}$ mole, per mole of silver halide.

The silver halide grains contained in the silver halide emulsion for use in the present invention have an average grain size (the grain size herein refers to the diameter of a circle equivalent to the projected area of an individual grain, and the number average is taken as the average grain size) of preferably from 0.1 μm to 2 μm.

With respect to the distribution of sizes of these grains, a so-called monodisperse emulsion having a variation coefficient (the value obtained by dividing the standard deviation of the grain size distribution by the average grain size) of 20% or less, more preferably 15% or less, and further preferably 10% or less, is preferred. For obtaining wide latitude, it is also preferred to blend the above-described monodisperse emulsions in the same layer or to form a multilayer structure by multilayer-coating of the monodisperse emulsions.

Various compounds or precursors thereof can be contained in the silver halide emulsion for use in the present invention to prevent fogging from occurring or to stabilize photographic performance during manufacture, storage or photographic processing of the photographic material. Specific examples of compounds useful for the above purposes are disclosed in JP-A-62-215272, pages 39 to 72, and they can be preferably used. In addition, 5-arylamino-1,2,3,4-thiatriazole compounds (in which the aryl residual group has at least one electron-attractive group), as disclosed in European Patent No. 0447647, are also preferably used.

Further, in the present invention, in order to enhance stability of the silver halide emulsion, it is preferable to use hydroxamic acid derivatives described in JP-A-11-109576; cyclic ketones having a double bond both ends of which are substituted with an amino group or a hydroxyl group, in adjacent to a carbonyl group, as described in JP-A-11-327094 (particularly those represented by formula (SI) and the descriptions of paragraph numbers 0036 to 0071 of JP-A-11-327094 can be incorporated herein by reference); catechols and hydroquinones each substituted with a sulfo group, as described in JP-A-11-143011 (e.g., 4,5-dihydroxy-1,3-benzenedisulfonic acid, 2,5-dihydroxy-1,4-benzenedisulfonic acid, 3,4-dihydroxybenzenesulfonic acid, 2,3-dihydroxybenzenesulfonic acid, 2,5-dihydroxybenzenesulfonic acid, 3,4,5-trihydroxybenzenesulfonic acid, and salts thereof); water-soluble reducing agents represented by any of formulae (I) to (III) of JP-A-11-102045, and hydroxylamines represented by the formula (A) in U.S. Pat. No. 5,556,741 (the descriptions of column 4, line 56 to column 11, line 22 in the U.S. Pat. No. 5,556,741 can be preferably applied to the present invention, and incorporated herein by reference).

Spectral sensitization is generally carried out, for the purpose of imparting spectral sensitivity in a desired light wavelength region to the light-sensitive emulsion in each layer of the photographic material of the present invention.

Spectral sensitizing dyes which are used in the photographic material of the present invention for spectral sensitization of blue, green and red light regions, include, for example, those disclosed by F. M. Harmer, in *Heterocyclic Compounds—Cyanine Dyes and Related Compounds*, John Wiley & Sons, New York, London (1964). Specific examples of the compounds and spectral sensitization processes that are preferably used in the present invention include those described in the above JP-A-62-215272, from page 22, right upper column to page 38. In addition, the spectral sensitizing dyes described in JP-A-3-123340 are very preferred as red-sensitive spectral sensitizing dyes for silver halide emulsion grains having a high silver chloride content, from the viewpoint of stability, adsorption strength and the temperature dependency of exposure, and the like.

The amount of these spectral sensitizing dyes to be added can be varied in a wide range depending on the occasion, and it is preferably in the range of $0.5 \times 10^{-6}$ mole to $1.0 \times 10^{-2}$ mole, more preferably in the range of $1.0 \times 10^{-6}$ mole to $5.0 \times 10^{-3}$ mole, per mole of silver halide.

The silver halide emulsion that can be used in the present invention is generally chemically sensitized. Chemical sensitization can be performed by utilizing a sulfur sensitization, represented by the addition of an unstable sulfur compound, noble metal sensitization represented by gold sensitization, and reduction sensitization, each singly or in combination thereof. Compounds that are preferably used in chemical sensitization include those described in JP-A-62-215272, from page 18, right lower column to page 22, right upper column. Of these chemical sensitization, gold-sensitized silver halide emulsion are particularly preferred, since fluctuation in photographic properties which occurs when scanning exposure to laser beams or the like is conducted, can be further reduced by gold sensitization. In order to conduct gold sensitization, compounds such as chloroauric acid or a salt thereof, gold thiocyanates, gold thiosulfates, and colloidal gold sulfide may be used. The amount of these compounds to be added can be varied in a wide range depending on the occasion, and it is generally in the range of $5 \times 10^{-7}$ mole to $5 \times 10^{-3}$ mole, preferably in the range of $1.0 \times 10^{-6}$ mole to $1 \times 10^{-4}$ mole, per mole of silver halide. In the present invention, gold sensitization may be used in combination with other sensitizing methods, for example, sulfur sensitization, selenium sensitization, tellurium sensitization, reduction sensitization, or noble metal sensitization using a noble metal compound other than gold compounds.

The silver halide photographic light-sensitive material of the present invention can be used for a color negative film, a color positive film, a color reversal film, a color reversal photographic printing paper, a color photographic printing paper and the like, as described above. Among these materials, the light-sensitive material of the present invention is preferably used for a color photographic printing paper in the first embodiment.

The color photographic printing paper preferably has at least one yellow color-forming silver halide emulsion layer, at least one magenta color-forming silver halide emulsion layer, and at least one cyan color-forming silver halide emulsion layer, on a support. Generally, these silver halide emulsion layers are in the order, from the support, of the yellow color-forming silver halide emulsion layer, the magenta color-forming silver halide emulsion layer, and the cyan color-forming silver halide emulsion layer.

However, another layer arrangement which is different from the above, may be adopted.

When, for example, the coupler of the present invention functions as a yellow coupler, a yellow coupler-containing silver halide emulsion layer may be provided at any position on a support. However, in the case where silver halide tabular grains are contained in the yellow coupler-containing layer, it is preferable that the yellow coupler-containing layer is positioned more apart from a support than at least one of a magenta coupler-containing silver halide emulsion layer and a cyan coupler-containing silver halide emulsion layer. Further, it is preferable that the yellow coupler-containing silver halide emulsion layer is positioned most apart from a support of other silver halide emulsion layers, from the viewpoint of color-development acceleration, desilvering acceleration, and lowering of a residual color due to a sensitizing dye. Further, it is preferable that the cyan coupler-containing silver halide emulsion layer is positioned in the middle of other silver halide emulsion layers, from the viewpoint of reduction in a blix fading. On the other hand, it is preferable that the cyan coupler-containing silver halide emulsion layer is the lowest layer, from the viewpoint of reduction in a light fading. Further, each of a yellow-color-forming layer, a magenta-color-forming layer and a cyan-color-forming layer may be composed of two or three layers. It is also preferable that a color-forming layer is formed by disposing a silver halide emulsion-free layer containing a coupler, in adjacent to a silver halide emulsion layer, as described in, for example, JP-A-4-75055, JP-A-9-114035, JP-A-10-246940, and U.S. Pat. No. 5,576,159.

Preferred examples of silver halide emulsions and other materials (additives or the like) for use in the present invention, photographic constitutional layers (arrangement of the layers or the like), and processing methods for processing the photographic materials and additives for processing are disclosed in JP-A-62-215272, JP-A-2-33144 and European Patent No. 0355660 A2. Particularly, those disclosed in European Patent No. 0355660 A2 are preferably used. Further, it is also preferred to use silver halide color photographic light-sensitive materials and processing methods therefor disclosed in, for example, JP-A-5-34889, JP-A-4-359249, JP-A-4-313753, JP-A-4-270344, JP-A-5-66527, JP-A-4-34548, JP-A-4-145433, JP-A-2-854, JP-A-1-158431, JP-A-2-90145, JP-A-3-194539, JP-A-2-93641 and European Patent Publication No. 0520457 A2.

In particular, as the above-described reflective support and silver halide emulsion, as well as the different kinds of metal ions to be doped in the silver halide grains, the storage stabilizers or antifogging agents of the silver halide emulsion, the methods of chemical sensitization (sensitizers), the methods of spectral sensitization (spectral sensitizing dyes), the cyan, magenta, and yellow couplers and the emulsifying and dispersing methods thereof, the dye stability-improving agents (stain inhibitors and discoloration inhibitors), the dyes (colored layers), the kinds of gelatin, the layer structure of the light-sensitive material, and the film pH of the light-sensitive material, those described in the patent publications as shown in the following Table 1 are preferably used in the present invention.

TABLE 1

| Element | JP-A-7-104448 | JP-A-7-77775 | JP-A-7-301895 |
|---|---|---|---|
| Reflective-type bases | Column 7, line 12 to Column 12, line 19 | Column 35, line 43 to Column 44, line 1 | Column 5, line 40 to Column 9, line 26 |
| Silver halide emulsions | Column 72, line 29 to Column 74, line 18 | Column 44, line 36 to Column 46, line 29 | Column 77, line 48 to Column 80, line 28 |
| Different metal ion species | Column 74, lines 19 to 44 | Column 46, line 30 to Column 47, line 5 | Column 80, line 29 to Column 81, line 6 |
| Storage stabilizers or antifoggants | Column 75, lines 9 to 18 | Column 47, lines 20 to 29 | Column 18, line 11 to Column 31, line 37 (Especially, mercaptoheterocyclic compounds) |
| Chemical sensitizing methods (Chemical sensitizers) | Column 74, line 45 to Column 75, line 6 | Column 47, lines 7 to 17 | Column 81, lines 9 to 17 |
| Spectrally sensitizing methods (Spectral sensitizers) | Column 75, line 19 to Column 76, line 45 | Column 47, line 30 to Column 49, line 6 | Column 81, line 21 to Column 82, line 48 |
| Cyan couplers | Column 12, line 20 to Column 39, line 49 | Column 62, line 50 to Column 63, line 16 | Column 88, line 49 to Column 89, line 16 |
| Yellow couplers | Column 87, line 40 to Column 88, line 3 | Column 63, lines 17 to 30 | Column 89, lines 17 to 30 |
| Magenta couplers | Column 88, lines 4 to 18 | Column 63, line 3 to Column 64, line 11 | Column 31, line 34 to Column 77, line 44 and column 88, lines 32 to 46 |
| Emulsifying and dispersing methods of couplers | Column 71, line 3 to Column 72, line 11 | Column 61, lines 36 to 49 | Column 87, lines 35 to 48 |
| Dye-image-preservability improving agents (antistaining agents) | Column 39, line 50 to Column 70, line 9 | Column 61, line 50 to Column 62, line 49 | Column 87, line 49 to Column 88, line 48 |
| Anti-fading agents | Column 70, line 10 to Column 71, line 2 | | |
| Dyes (coloring layers) | Column 77, line 42 to Column 78, line 41 | Column 7, line 14 to Column 19, line 42, and Column 50, line 3 to Column 51, line 14 | Column 9, line 27 to Column 18, line 10 |
| Gelatins | Column 78, lines 42 to 48 | Column 51, lines 15 to 20 | Column 83, lines 13 to 19 |
| Layer construction of light-sensitive materials | Column 39, lines 11 to 26 | Column 44, lines 2 to 35 | Column 31, line 38 to Column 32, line 33 |
| Film pH of light-sensitive materials | Column 72, lines 12 to 28 | | |
| Scanning exposure | Column 76, line 6 to Column 77, line 41 | Column 49, line 7 to Column 50, line 2 | Column 82, line 49 to Column 83, line 12 |
| Preservatives in developing solution | Column 88, line 19 to Column 89, line 22 | | |

As other cyan, magenta and yellow couplers which can be used in combination in the present invention, those disclosed in JP-A-62-215272, page 91, right upper column line 4 to page 121, left upper column line 6; JP-A-2-33144, page 3, right upper column line 14 to page 18, left upper column bottom line, and page 30, right upper column line 6 to page 35, right under column, line 11 and; European Patent No. 0355,660 (A2), page 4 lines 15 to 27, page 5 line 30 to page 28 bottom line, page 45 lines 29 to 31, page 47 line 23 to page 63 line 50, are also advantageously used.

Further, it is preferred for the present invention to add compounds represented by formula (II) or (III) in WO 98/33760 or compounds represented by formula (D) described in JP-A-10-221825.

In the silver halide photographic light-sensitive material of the present invention, the dye-forming coupler of the present invention may be used singly or in combination. In the case where the coupler is used as a yellow coupler, the other yellow couplers which may be preferably used in combination with the above-said coupler, are acylacetoanilide yellow couplers in which the acyl group has a 3-membered to 5-memberd cyclic structure, as described in European Patent No.0447969A1; malondianilide yellow couplers having a cyclic structure, as described in European Patent No. 0482552A1; pyrrol-2- or 3-yl- or indole-2- or 3-yl-carbonylacetoanilide-series couplers, as described in European Patent Nos. 0953870A1, 0953871A1, 0953872A1, 0953873A1, 0953874A1 and 0953875A1; acylacetamide yellow couplers having a dioxane structure, as described in U.S. Pat. No. 5,118,599, in addition to the compounds described in the above-mentioned table. Above all, the acylacetamide yellow coupler in which the acyl group is an 1-alkylcyclopropane-1-carbonyl group, or the malondianilide yellow coupler in which one anilide moiety constitutes an indoline ring, is especially preferably used in combination with the above-said coupler of the present invention.

The cyan coupler used in the present invention is preferably a phenol-series or naphthol-series cyan coupler, or a heterocyclic coupler.

The phenol coupler is preferably, for example, the cyan coupler represented by formula (ADF), as described in JP-A-10-333297, as well as any coupler in the above-mentioned table.

A 2,5-diacylaminophenol coupler, which is improved in hue and fastness of the resulting dye and which is described in U.S. Pat. No. 5,888,716, is preferably used.

As the heterocyclic coupler, the followings are preferred to use in combination with the coupler of the present invention: pyrroloazole-type cyan couplers described in EP 0488248 and EP 0491197A1, and pyrazoloazole-type cyan couplers having a hydrogen bond group or an electron withdrawing group at its 6 position, as described in U.S. Pat. No. 4,873,183 and U.S. Pat. No. 4,916,051, particularly preferably pyrazoloazole-type cyan couplers having a carbamoyl group at its 6 position, as described in JP-A-8-171185, JP-A-8-311360 and JP-A-8-339060.

Among these cyan couplers, pyrroloazole-series cyan couplers represented by formula (I), as described in JP-A-11-282138, are particularly preferred. The descriptions in paragraph Nos. 0012 to 0059 of this publication, as well as the exemplified cyan couplers (1) to (47), can be applied to the present invention, and are preferably incorporated herein by reference.

In addition, the coupler of the present invention can also be used in combination with a diphenylimidazole-series cyan coupler described in JP-A-2-33144; a 3-hydroxypyridine-series cyan coupler (particularly a 2-equivalent coupler formed by allowing a coupler (42) of a 4-equivalent coupler to have a chlorine splitting-off group, and couplers (6) and (9), enumerated as specific examples are preferable) described in EP 0333185 A2; a cyclic active methylene-series cyan coupler (particularly couplers 3, 8, and 34 enumerated as specific examples are preferable) described in JP-A-64-32260; a pyrrolopyrozole-type cyan coupler described in European Patent No. 0456226 A1; or a pyrroloimidazole-type cyan coupler described in European Patent No. 0484909.

As the magenta coupler that can be used in the present invention, use can be made of a 5-pyrazolone-series magenta coupler or a pyrazoloazole-series magenta coupler, such as those described in the above-mentioned patent publications in the above Table. Among these, preferred to be used are pyrazolotriazole couplers in which a secondary or tertiary alkyl group is directly bonded to the 2-, 3- or 6-position of the pyrazolotriazole ring, as described in JP-A-61-65245; pyrazoloazole couplers having a sulfonamido group in its molecule, as described in JP-A-61-65246; pyrazoloazole couplers having an alkoxyphenylsulfonamido ballasting group, as described in JP-A-61-147254; and pyrazoloazole couplers having an alkoxy or aryloxy group on its 6-position, as described in European Patent Nos. 0226849 A and 0294785 A, in view of the hue and stability of image to be formed therefrom and color-forming property of the couplers.

Particularly as the magenta coupler, pyrazoloazole couplers represented by formula (M-I), as described in JP-A-8-122984, are preferred. The descriptions of paragraph Nos. 0009 to 0026 of the patent publication can be entirely applied to the present invention and therefore are incorporated herein by reference.

In addition, pyrazoloazole couplers having a steric hindrance group at both the 3- and 6-positions, as described in European Patent Nos. 845384 and 884640, are also preferably used.

It is preferred that magenta or cyan couplers, as well as the (yellow) coupler of the present invention, are also pregnated into a loadable latex polymer (as described, for example, in U.S. Pat. No. 4,203,716) in the presence (or absence) of the high-boiling-point organic solvent described in the foregoing table, or they are dissolved in the presence (or absence) of the foregoing high-boiling-point organic solvent with a polymer insoluble in water but soluble in an organic solvent, and then emulsified and dispersed into an aqueous hydrophilic colloid solution.

The water-insoluble but organic solvent-soluble polymers that can be preferably used, include the homo-polymers and co-polymers disclosed in U.S. Pat. No. 4,857,449, from column 7 to column 15 and WO 88/00723, from page 12 to page 30. The use of methacrylate-series or acrylamide-series polymers, especially acrylamide-series polymers are more preferable in view of color-image stabilization and the like.

To suppress Blix discoloration (leuco dye reciprocity failure) by a bleaching solution or bleach-fixing solution, it is preferred to use a polymer described in JP-A-8-62797, JP-A-9-17240 and JP-A-9-329861, in the hydrophilic colloid layer.

In the present invention, known color mixing-inhibitors may be used. Among these compounds, those described in the following patent publications are preferred.

For example, high-molecular-weight redox compounds described in JP-A-5-333501; phenidone- or hydrazine-series compounds as described in, for example, WO 98/33760 and U.S. Pat. No. 4,923,787; and white couplers as described in, for example, JP-A-5-249637, JP-A-10-282615 and German Patent No. 19629142 A1, may be used. Further, in order to accelerate developing speed by increasing the pH of a developing solution, redox compounds described in, for example, German Patent Nos. 19,618,786 A1 and 19,806, 846 A1, European Patent Nos. 0,839,623 A1 and 0,842,975 A1, and French Patent No. 2,760,460 $\mu$l, are also preferably used.

In the present invention, as an ultraviolet ray absorbent, it is preferred to use a compound having a high molar extinction coefficient. Examples of the compound include those having a triazine skeleton. Among these compounds, use can be made of those described, for example, in JP-A-46-3335, JP-A-55-152776, JP-A-5-197074, JP-A-5-232630, JP-A-5-307232, JP-A-6-211813, JP-A-8-53427, JP-A-8-234364, JP-A-8-239368, JP-A-9-31067, JP-A-10-115898, JP-A-10-147577, JP-A-10-182621, JP-T-8-501291 ("JP-T" means searched and published International patent application), European Patent No. 0,711,804 A and German Patent No. 19,739,797A.

In the present invention, examples of a decoloration inhibitor (anti-fading agent), a hue adjusting agent, and the like other than those described in the above Table, include vinyl compounds represented by formula (II), aniline derivatives represented by formula (III) having an oxygen-nitrogen bond or substituted with an alkoxy group, non-diffusible phenydone derivatives represented by formula (IV), nondiffusion carboxylic acids represented by formula (V), non-diffusible arylcarbamoyl derivatives represented by formula (VI), arylamide derivatives represented by formula (VII), and cyclic imide derivatives represented by formula (VIII), each of which are described in JP-A-11-258748, and all of them can be preferably used.

As the binder or protective colloid that can be used in the light-sensitive material of the present invention, gelatin is used advantageously, but another hydrophilic colloid can be used singly or in combination with gelatin. It is preferable for the gelatin for use in the present invention that the content of heavy metals, such as Fe, Cu, Zn and Mn, as impurities therein, is reduced to 5 ppm or below, more preferably 3 ppm or below.

Further, the amount of calcium contained in the light-sensitive material is preferably 20 mg/m$^2$ or less, more preferably 10 mg/m$^2$ or less, and most preferably 5 mg/m$^2$ or less.

In the present invention, it is preferred to add an antibacterial (fungi-preventing) agent and antimold agent, as described in JP-A-63-271247, in order to destroy various kinds of molds and bacteria which propagate in a hydrophilic colloid layer and deteriorate the image.

Further, the pH of the film of the light-sensitive material is preferably in the range of 4.0 to 7.0, more preferably in the range of 4.0 to 6.5.

The light-sensitive material of the present invention can preferably be used, in addition to the printing system using a general negative printer, in a scanning exposure system using a cathode ray tube (CRT).

The cathode ray tube exposure apparatus is simpler and more compact, and therefore less expensive than a laser-emitting apparatus. Further, optical axis and color (hue) can easily be adjusted.

In a cathode ray tube that is used for image-wise exposure, various light-emitting substances which emit a For example, any one of red-light-emitting substances, green-light-emitting substances, blue-light-emitting substances, or a mixture of two or more of these light-emitting substances may be used. The spectral regions are not limited to the above red, green and blue, and fluorophoroes which can emit a light in a region of yellow, orange, purple or infrared can be used. Particularly, a cathode ray tube that emits a white light by means of a mixture of these light-emitting substances is often used.

In the case where the light-sensitive material has a plurality of light-sensitive layers each having different spectral sensitivity distribution from each other and also the cathode ray tube has fluorescent substances which emit light in a plurality of spectral regions, exposure to a plurality of colors may be carried out at the same time. Namely, color image signals may be input into a cathode ray tube, to allow light to be emitted from the surface of the tube. Alternatively, a method in which an image signal of each of colors is successively input and light of each of colors is emitted in order, and then exposure is carried out through a film capable of cutting a color other than the emitted color, i.e., a surface successive exposure, may be used. Generally, among these methods the surface successive exposure is preferred from the viewpoint of high quality enhancement, because a cathode ray tube having high resolution can be used.

The light-sensitive material of the present invention can preferably be used in the digital scanning exposure system using monochromatic high density light, such as a gas laser, a light-emitting diode, a semiconductor laser, a second harmonic generation light source (SHG) comprising a combination of nonlinear optical crystal with a semiconductor or a solid state laser using a semiconductor laser as an excitation light source. It is preferred to use a semiconductor laser, or a second harmonic generation light source (SHG) comprising a combination of nonlinear optical crystal with a solid state laser or a semiconductor laser, to make a system more compact and inexpensive. In particular, to design a compact and inexpensive apparatus having a longer duration of life and high stability, use of a semiconductor laser is preferable; and it is preferred that at least one of exposure light sources should be a semiconductor laser.

When such a scanning exposure light source is used, the maximum spectral sensitivity wavelength of the light-sensitive material of the present invention can be arbitrarily set up in accordance with the wavelength of a scanning exposure light source to be used. Since oscillation wavelength of a laser can be made half, using a SHG light source obtainable by a combination of a nonlinear optical crystal with a semiconductor laser or a solid state laser using a semiconductor as an excitation light source, blue light and green light can be obtained. Accordingly, it is possible to have the spectral sensitivity maximum of a photographic material in normal three wavelength regions of blue, green and red.

The exposure time in such a scanning exposure is defined as the time necessary to expose the size of the picture element (pixel) with the density of the picture element being 400 dpi, and preferred exposure time is $10^{-4}$ sec or less and more preferably $10^{-6}$ sec or less.

The scanning exposure system that can preferably be used for the present invention is described in detail in the patent publications as shown in the above table.

With respect to the processing of the photographic material of the present invention, processing materials and processing methods, as disclosed in JP-A-2-207250, from page 26, right under column, line 1 to page 34, right upper column, line 9, and JP-A-4-97355, from page 5, left upper column, line 17 to page 18, right under column, line 20, can be preferably applied. Further, as preservatives which are used in the developing solution, compounds described in the patent publications as shown in the above table can be preferably used.

The present invention is preferably applied to a light-sensitive material having rapid processing suitability.

The term "color-developing time" as used herein refers to a period of time required from the beginning of dipping a light-sensitive material into a color-developing solution until the light-sensitive material is dipped into a blix solution in the subsequent processing step. In the case where a processing is carried out using, for example, an autoprocessor, the color-developing time is the sum total of a time in which a light-sensitive material has been dipped in a color-developing solution (so-called "time in the solution") and a time in which the light-sensitive material has been conveyed in air toward a bleach-fixing bath in the step subsequent to color development (so-called "time in the air"). Likewise, the term "blix time" as used herein refers to a period of time required from the beginning of dipping a light-sensitive material into a blix solution until the light-sensitive material is dipped into a washing bath or a stabilizing bath in the subsequent processing step. Further, the term "washing or stabilizing time" as used herein refers to a period of time required from the beginning of dipping a light-sensitive material into a washing solution or a stabilizing solution until the end of the dipping toward a drying step (so-called "time in the solution").

In the present invention, the color-developing time is preferably 60 sec or less, more preferably from 50 sec to 6 sec, further preferably from 30 sec to 6 sec. Likewise, the blix time is preferably 60 sec or less, more preferably from 50 sec to 6 sec, further preferably from 30 sec to 6 sec. Further, the washing or stabilizing time is preferably 150 sec or less, more preferably from 130 sec to 6 sec.

Examples of a development method applicable to the photographic material of the present invention after exposure, include a conventional wet system, such as a development method using a developing solution containing an alkali agent and a developing agent, and a development method wherein a developing agent is incorporated in the photographic material and an activator solution, e.g., a developing agent-free alkaline solution is employed for the development, as well as a heat development system using no processing solution. In particular, the activator method using a developing agent-free alkaline solution is preferred over the other methods, because the processing solution contains no developing agent, thereby it enables easy management and handling of the processing solution, and reduction in waste disposal load to make for environmental preservation.

The preferable developing agents or their precursors to be incorporated in the photographic materials in the case of adopting the activator method include the hydrazine compounds described in, for example, JP-A-8-234388, JP-A-9-152686, JP-A-9-152693, JP-A-9-211814 and JP-A-9-160193.

Further, the processing method in which the photographic material reduced in the amount of silver to be applied undergoes the image amplification processing using hydrogen peroxide (intensification processing), can be employed preferably. In particular, it is preferably to apply this processing method to the activator method. Specifically, the image-forming methods utilizing an activator solution containing hydrogen peroxide, as disclosed in JP-A-8-297354 and JP-A-9-152695 can be preferably used.

The processing with an activator solution is generally followed by a desilvering step in the activator method, but the desilvering step can be omitted in the case of applying the image amplification processing method to photographic materials of a low silver amount. In such a case, washing or stabilization processing can follow the processing with an activator solution to result in simplification of the processing process. On the other hand, when the system of reading the image information from photographic materials by means of a scanner or the like is employed, the processing form requiring no desilvering step can be applied, even if the photographic materials are those of a high silver amount, such as photographic materials for shooting.

The activator solution, desilvering solution (bleach-fixinging solution), washing solution and stabilizing solution for use in the present invention can contain known ingredients and can be used in conventional manners. Preferably, those described in *Research Disclosure*, Item 36544, pp. 536–541 (September 1994), and JP-A-8-234388 can be used in the present invention.

It is preferred to use a band stop filter, as described in U.S. Pat. No. 4,880,726, when the photographic material of the present invention is subjected to exposure with a printer. Color mixing of light can be excluded and color reproducibility is remarkably improved by the above means.

In the present invention, a yellow microdot pattern may be previously formed by pre-exposure before giving an image information, to thereby perform copy restraint, as described in European Patent Nos. 0789270 μl and 0789480 A1.

The light-sensitive material of the present invention can be preferably used as a light-sensitive material for the advanced photo-system, which has a magnetic recording layer. The light-sensitive material of the present invention can be preferably used in a system wherein a small amount of water is used to perform heat-development, or in a complete dry system wherein no water is used to perform heat-development. Detailed descriptions on these systems are found, for example, in JP-A-6-35118, JP-A-6-17528, JP-A-56-146133, JP-A-60-119557, and JP-A-1-161236.

In the present invention, the wording "a silver halide photographic light-sensitive material" means to include not only a light-sensitive material for forming a color image but also a light-sensitive material for forming a monotone image, an example of which is a black and white image.

Next, the second embodiment of the present invention is explained.

(Second Embodiment)

The light-sensitive material of the present invention comprises, on a support, at least one red-sensitive layer, at least one green-sensitive layer and at least one blue-sensitive layer. A typical example thereof is a silver halide photographic light-sensitive material comprising, on a support, at least one light-sensitive layer consisting of two or more silver halide emulsion layers whose color sensitivities are substantially the same, but whose light-sensitivities are different. Said light-sensitive layer is a unit light-sensitive layer that has a color sensitivity to any of blue light, green light and red light. In a multi-layer silver halide color photographic light-sensitive material, such unit light-sensitive layers are generally arranged in the order of a red-sensitive layer, a green-sensitive layer and a blue-sensitive layer from the support side. However, according to the intended use, this order of arrangement can be reversed. Alternatively, the layers may be arranged such that sensitive layers sensitive to the same color can sandwich another sensitive layer sensitive to a different color. Non-sensitive layers can be formed as an interlayer between the silver halide light-sensitive layers, or as the uppermost layer or the lowermost layer. These non-sensitive layers can contain, for example, couplers, DIR compounds, and color mixing inhibitors to be described below. Each of the silver halide emulsion layers constituting unit photosensitive layers respectively can preferably take a two-layer constitution composed of a high-sensitive emulsion layer and a low-sensitive emulsion layer, as described in DE 1 121 470 or GB Patent No.923 045. Generally, they are preferably arranged such that the sensitivities are decreased toward the support. As described, for example, in JP-A-57-112751, JP-A-62-200350, JP-A-62-206541, and JP-A-62-206543, a low-sensitive emulsion layer may be placed away from the support, and a high-sensitive emulsion layer may be placed nearer to the support.

A specific example of the order includes an order of a low-sensitive blue-sensitive layer (BL)/high-sensitive blue-sensitive layer (BH)/high-sensitive green-sensitive layer (GH)/low-sensitive green-sensitive layer (GL)/high-sensitive red-sensitive layer (RH)/low-sensitive red-sensitive layer (RL), or an order of BH/BL/GL/GH/RH/RL, or an order of BH/BL/GH/GL/RL/RH, stated from the side most away from the support.

As described in JP-B-55-34932, an order of a blue-sensitive layer/GH/RH/GL/RL stated from the side most away from the support is also possible. Further as described in JP-A-56-25738 and JP-A-62-63936, an order of a blue-sensitive layer/GL/RL/GH/RH stated from the side most away from the support is also possible.

Further as described in JP-B-49-15495, an arrangement is possible wherein the upper layer is a silver halide emulsion layer highest in sensitivity, the intermediate layer is a silver halide emulsion layer lower in sensitivity than that of the upper layer, the lower layer is a silver halide emulsion layer further lower in sensitivity than that of the intermediate layer, so that the three layers different in sensitivity may be arranged with the sensitivities successively lowered toward the support.

Even in such a constitution comprising three layers different in sensitivity, an order of a medium-sensitive emulsion layer/high-sensitive emulsion layer/low-sensitive emulsion layer stated from the side away from the support may be taken in layers identical in color sensitivity, as described in JP-A-59-202464.

Further, for example, an order of a high-sensitive emulsion layer/low-sensitive emulsion layer/medium-sensitive emulsion layer, or an order of a low-sensitive emulsion layer/medium-sensitive emulsion layer/high-sensitive emulsion layer can be taken.

In the case of four layers or more layers, the arrangement can be varied as above.

The use of an interlayer inhibiting effect as means for improving color reproduction is preferable. The light-sensitive material is preferably spectrally sensitized such that a barycentric sensitivity wavelength ($\lambda_G$) of a spectral sensitivity distribution of the above-mentioned green-sensitive silver halide emulsion layer (if a plurality of layers, as a whole of the layers) satisfies 520 nm<$\lambda_G$≦580 nm, and a barycentric wavelength ($\lambda_R$) of a spectral sensitivity distribution of the magnitude of an interlayer effect given to the above-mentioned red-sensitive silver halide emulsion layer (if a plurality of layers, as a whole of the layers) from another layer (interlayer effect donor layer) at a wavelength of 500 to 600 nm satisfies 500 nm<$\lambda_R$≦560 nm, and $\lambda_G - \lambda_R \geq 5$ nm.

As the sensitizing dye and the solid dispersion of a dye that are used in the above light-sensitive materials, use can be made of those described in JP-A-11-305396. Besides, the above-mentioned specific sensitivities, and the barycentric wavelength in a spectral sensitivity distribution as a result of an interlayer effect given to the red-sensitive silver halide emulsion layer from another layer (interlayer effect donor layer), can be measured by the method described in JP-A-11-305396.

The silver halide photographic light-sensitive material of the present invention preferably contains at least one compound that releases a development inhibitor or a precursor thereof upon a reaction with an oxidized product of a developing agent formed by development. Examples of the compound include DIR (Development Inhibitor-Releasing) couplers, DIR-hydroquinones, and couplers that release a DIR-hydroquinone or a precursor thereof.

The silver halide grains for use in a layer that gives an interlayer effect to a red-sensitive layer are not particularly limited in terms of their size, shape, and the like. However, so-called tabular grains having a high aspect ratio, mono-disperse emulsions in which grain size of the silver halide is uniform, and silver iodobromide grains having a layered structure of iodide are preferably used. Besides, as means for enlarging the exposure latitude, it is preferable to mix two or more kinds of silver halide emulsions whose grain sizes are different from each other.

The donor layer that gives an interlayer effect to a red-sensitive layer may be placed at any location on a support. However, the donor layer is preferably placed nearer the support than a blue-sensitive layer, but farther from the support than the red-sensitive layer. Besides, the donor layer is more preferably placed nearer the support than a yellow filter layer.

The donor layer that gives an interlayer effect to a red-sensitive layer is furthermore preferably placed nearer the support than a green-sensitive layer, but farther from the support than the red-sensitive layer. The donor layer is most preferably placed in adjacent to the support-side of the green-sensitive layer. The term "in adjacent to" as used herein is intended that the intended two layers are not placed via any another layer such as an intermediate layer between them.

The donor layer that gives an interlayer effect to a red-sensitive layer may be composed of at least two layers. In this case, they may be located in adjacent to each other, or separately.

The emulsion that is used in light-sensitive material of the present invention may be any of a surface latent image type emulsion which predominantly forms a latent image on the surface of the silver halide grain, an internal latent image type emulsion which predominantly forms a latent image in the interior of the silver halide grain, and another type of emulsion which forms a latent image both on the surface and in the interior of the silver halide grain. However, the emulsion for use in the present invention must be a negative type emulsion. The internal latent image type emulsion may be a core/shell internal latent image type emulsion described in JP-A-63-264740. The method of preparing this core/shell internal latent image type emulsion is described in JP-A-59-133542. Although the thickness of the shell of this emulsion depends on, for example, development conditions, it is preferably 3 to 40 nm, and especially preferably 5 to 20 nm.

A silver halide emulsion is normally subjected to physical ripening, chemical sensitization, and spectral sensitization steps before it is used. Additives for use in these steps are described in R.D. Nos. 17643, 18716, and 307105, and they are summarized in a table, which will be shown later.

In the light-sensitive material of the present invention, it is possible to mix, in a single layer, two or more types of emulsions different in at least one of characteristics of a light-sensitive silver halide emulsion, i.e., a grain size, a grain size distribution, halogen composition, grain shape, and sensitivity.

In the present invention, it is preferable to apply surface-fogged silver halide grains described in U.S. Pat. No. 4,082,553, internally fogged silver halide grains described in U.S. Pat. No. 4,626,498 and JP-A-59-214852, or colloidal silver, in light-sensitive silver halide emulsion layers and/or substantially non-light-sensitive hydrophilic colloid layers. The internally or surface-fogged silver halide grain means a silver halide grain which can be developed uniformly (non image-wise) regardless of whether it exists at a non-exposed portion or an exposed portion of the light-sensitive material. A method of preparing the internally or surface-fogged silver halide grain is described in U.S. Pat. No. 4,626,498 and JP-A-59-214852. Silver halides that form the internal nuclei of an internally fogged core/shell type silver halide grain may have different halogen compositions. As the internally or surface-fogged silver halide, any of silver chloride, silver chlorobromide, silver iodobromide and silver chloroiodobromide can be used. The average grain size of these fogged silver halide grains is preferably 0.01 to 0.75 $\mu$m, and particularly preferably 0.05 to 0.6 $\mu$m. The grain shape may be a regular grain shape. Although the emulsion may be a polydisperse emulsion, it is preferably a mono-disperse emulsion (in which at least 95% in mass or in number of silver halide grains have grain diameters falling within a range of ±40% of the average grain diameter).

In the present invention, it is preferable to use non-light-sensitive fine grain silver halide. The non-light-sensitive fine grain silver halide is a silver halide fine grain which is not sensitive to light during imagewise exposure for obtaining a dye image, and is not substantially developed during processing. These silver halide fine grains are preferably not fogged in advance. In the fine grain silver halide, the content of silver bromide is 0 to 100 mole %. The fine grain silver halide may contain silver chloride and/or silver iodide, if necessary. The fine grain silver halide preferably contains silver iodide of 0.5 to 10 mol %. The average grain diameter (the average value of equivalent circle diameter of projected area) of the fine grain silver halide is preferably 0.01 to 0.5 $\mu$m, more preferably 0.02 to 0.2 $\mu$m.

The fine grain silver halide may be prepared following the same procedure as for a conventional light-sensitive silver halide grains. The surface of each silver halide grain need not be optically sensitized nor spectrally sensitized. However, before the silver halide grains are added to a coating solution, it is preferable to add known stabilizers such as triazole-series compounds, azaindene-series compounds, benzothiazolium-series compounds, mercapto-series compounds and zinc compounds. Colloidal silver may be added to this fine grain silver halide-containing layer.

In a light-sensitive material in relation to the present technique, the above-mentioned various additives are used, in addition to these, other various additives can be used, depending on purposes.

These additives are described in more detail, in Research Disclosure (RD) No. 17643 (December, 1978); RD No. 18716 (November, 1979); and RD No. 308119 (December, 1989), whose particular parts are given below in a table.

| Kind of Additive | RD 17643 | RD 18716 | RD 308119 |
|---|---|---|---|
| 1 Chemical sensitizers | p. 23 | p. 648 (right column) | p. 996 |
| 2 Sensitivity-enhancing agents | | p. 648 (right column) | |
| 3 Spectral sensitizers and Supersensitizers | pp. 23–24 | pp. 648 (right column)–649 (right column) | pp. 996 (right column)–998 (right column) |
| 4 Brightening agents | p. 24 | | p. 998 (right column) |
| 5 Antifogging agents and Stabilizers | pp. 24–25 | p. 649 (right column) | pp. 998 (right column)–1000 (right column) |
| 6 Light absorbers, Filter dyes, and UV Absorbers | pp. 25–26 | pp. 649 (right column)–650 (left column) | p. 1003 (left column)–1003 (right column) |
| 7 Antistaining agents | p. 25 (right column) | p. 650 (left column–right column) | p. 1002 (right column) |
| 8 Dye-image stabilizers | p. 25 | | p. 1002 (right column) |
| 9 Hardeners | p. 26 | p. 651 (left column) | pp. 1004 (right column)–1005 (left column) |
| 10 Binders | p. 26 | p. 651 (left column) | pp. 1003 (right column)–1004 (right column) |
| 11 Plasticizers and Lubricants | p. 27 | p. 650 (right column) | p. 1006 (left column)–1006 (right column) |
| 12 Coating aids and Surfactants | pp. 26–27 | p. 650 (right column) | pp. 1005 (left column)–1006 (left column) |
| 13 Antistatic agents | p. 27 | p. 650 (right column) | pp. 1006 (right column)–1007 (left column) |
| 14 Matting agents | | | pp. 1008 (left column)–1009 (left column) |

In the light-sensitive material of the present invention, various dye-forming couplers may be used in combination with couplers of the present invention. The following couplers are preferred.

Yellow coupler: a coupler represented by formula (I) or (II) in EP 502,424A; a coupler represented by formula (I) or (II) in EP 513,496A (especially, Y-28 on page 18); a coupler represented by formula (I) in claim 1 in EP 568,037A; a coupler represented by formula (I) in lines 45 to 55 in column 1 in U.S. Pat. No. 5,066,576; a coupler represented by formula (I) in paragraph 0008 in JP-A-4-274425; a coupler described in claim 1 on page 40 in EP 498,381A1 (especially, D-35 on page 18); a coupler represented by formula (Y) on page 4 in EP 447,969A1 (especially, Y-1 on page 17, Y-54 on page 41); a coupler represented by formula (II) to (IV) in lines 36 to 58 in column 7 in U.S. Pat. No. 4,476,219 (especially, II-17, 19 (column 17), II-24 (column 19)).

Magenta coupler: L-57 (page 11, right and lower column), L-68 (page 12, right and lower column), L-77 (page 13, right and lower column) in JP-A-3-39737; [A-4]-63 (page 134), [A-4]-73, -75 (page 139) in EP 456,257; M-4, -6 (page 26), M-7 (page 27) in EP 486,965; M-45 (page 19) in EP 571,959A; (M−1) (page 6) in JP-A-5-204106; M-22 in paragraph [0237] in JP-A-4-362631.

Cyan coupler: CX-1, 3, 4, 5, 11, 12, 14, 15 (pages 14 to 16) in JP-A-4-204843; C-7, 10 (page 35), 34, 35 (page 37), (1-1), (1-17) (pages 42 to 43) in JP-A-4-43345; a coupler represented by formula (Ia) or (Ib) in claim 1 in JP-A-6-67385.

Polymer coupler: P-1, P-5 (page 11) in JP-A-2-44345.

Preferable examples of couplers, which form a color dye having a suitable diffusive property, include those described in U.S. Pat. No. 4,366,237, GB 2,125,570, EP 96,873B, and DE 3,234,533.

Examples of the coupler, which is used for compensating unnecessary absorption of a color dye, include a yellow-colored cyan coupler represented by formulae (CI), (CII), (CIII), and (CIV) described on page 5 in EP 456,257A1 (especially, YC-86 on page 84), a yellow-colored magenta coupler, ExM-7 (page 202), EX-1 (page 249), EX-7 (page 251), described in EP 456,257A1, a magenta-colored cyan coupler, CC-9 (column 8), CC-13 (column 10), described in U.S. Pat. No. 4,833,069, and a colorless masking coupler, represented by Formula (2) (column 8) in U.S. Pat. No. 4,837,136, and formula (A) in claim 1 in WO92/11575 (particularly the exemplified compounds on pages 36 to 45).

Examples of the compound (including a coupler), which reacts with an oxidized product of a developing agent, to release a photographically useful compound's residue, include the followings:

Development inhibitor releasing compounds: compounds represented by any one of Formulae (I), (II), (III), and (IV) described on page 11 in EP 378,236A1, (especially, T-101 (page 30), T-104 (page 31), T-113 (page 36), T-131 (page 45), T-144 (page 51), T-158 (page 58)); compounds represented by Formula (I) described on page 7 in EP 436,938A2, (especially, (D-49) (page 51); compounds represented by Formula (I) in EP 568,037A (especially, (23) (page 11), and compounds represented by Formula (I), (II), or (III) described on pages 5 to 6 in EP440,195A2, (especially, I-(1) on page 29).

Bleaching accelerator releasing compounds: compounds represented by Formula (I) or (I') described on page 5 in EP 310,125A2, (especially, (60), (61) on page 1) and compounds represented by Formula (I) described in claim 1 of JP-A-6-59411, (especially, (7) on page 7).

Ligand releasing compounds: compounds represented by LIG-X described in claim 1 of U.S. Pat. No. 4,555,478, (especially, a compound in lines 21 to 41 in column 12).

Leuco dye releasing compounds: compounds 1 to 6 in U.S. Pat. No. 4,749,641, columns 3 to 8; Fluorescent dye releasing compounds: compounds represented by COUP-DYE described in claim 1 of U.S. Pat. No. 4,774,181, (especially, compounds 1 to 11 in column 7 to 10).

Compounds, which release a development accelerator or a fogging agent: compounds represented by Formula (I), (2) or (3) in U.S. Pat. No. 4,656,123, column 3, (especially, (I-22) in column 25), and the compound ExZK-2 described on page 75, lines 36 to 38, in EP 450,637A2.

Compounds which release a group capable of becoming a dye only after being split-off: compounds represented by Formula (I) described in claim 1 of U.S. Pat. No. 4,857,447, (especially, Y-1 to Y-19 in column 25 to 36).

As additives other than the coupler, the following ones are preferable.

Dispersion media for an oil-soluble organic compound: P-3, 5, 16, 19, 25, 30, 42, 49, 54, 55, 66, 81, 85, 86 and 93 (page 140 to page 144) in JP-A-62-215272; latex for impregnation with the oil-soluble organic compound: latex described in U.S. Pat. No. 4,199,363; scavengers for an oxidized product of a developing agent: compounds represented by the formula (I) in U.S. Pat. No. 4,978,606, column 2, line 54 to line 62 (particularly I-, (1), (2), (6), (12) (columns 4 to 5)) and compounds represented by the formula in U.S. Pat. No. 4,923,787, column 2, line 5 to line 10 (particularly Compound 1 (column 3)); stain preventive agents: compounds represented by one of the formulae (I) to (III) in EP 298321A, page 4, line 30 to line 33 (particularly, I-47, 72, III-1, 27 (page 24 to page 48)); anti-fading agents: A-6, 7, 20, 21, 23, 24, 25, 26, 30, 37, 40, 42, 48, 63, 90, 92, 94 and 164 (page 69 to page 118) in EP 298321A, and II-1 to III-23 in U.S. Pat. No. 5,122,444, columns 25 to 38 (particularly, III-10), I-1 to III-4 in EP 471347A, page 8 to page 12 (particularly, II-2), and A-1 to 48 in U.S. Pat. No. 5,139,931, columns 32 to 40 (particularly A-39 and 42); materials reducing the amount of a color development-enchancing agent or a color contamination preventive agent to be used: I-1 to II-15 in EP 411324A, page 5 to page 24 (particularly, I-46); formalin scavengers: SCV-1 to 28 in EP 477932A, page 24 to page 29 (particularly SCV-8); hardener: H-1, 4, 6, 8 and 14 in JP-A-1-214845 in page 17, compounds (H-1 to H-54) represented by one of the formulae (VII) to (XII) in U.S. Pat. No. 4,618,573, columns 13 to 23, compounds (H-1 to 76) represented by the formula (6) in JP-A-2-214852, page 8, the lower right (particularly, H-14) and compounds described in claim 1 in U.S. Pat. No. 3,325,287; precursors of developing inhibitor: P-24, 37, 39 (page 6 to page 7) in JP-A-62-168139 and compounds described in claim 1 of U.S. Pat. No. 5,019,492 (particularly 28 to 29 in column 7); antiseptics and mildew-proofing agents: I-1 to III-43 in U.S. Pat. No. 4,923,790, columns 3 to 15 (particularly II-1, 9, 10 and 18 and III-25); stabilizers and antifoggants: I-1 to (14) in U.S. Pat. No. 4,923,793, columns 6 to 16 (particularly, I-1, 60, (2) and (13)) and compounds 1 to 65 in U.S. Pat. No. 4,952,483, columns 25 to 32 (particularly, 36); chemical sensitizers: triphenylphosphine selenide and compound 50 in JP-A-5-40324; dyes: a-1 to b-20 in JP-A-3-156450, page 15 to page 18 (particularly, a-1, 12, 18, 27, 35, 36, b-5 and V-1 to 23 on pages 27 to 29, particularly, V-1), F-I-1 to F-II-43 in EP 445627A, page 33 to page 55 (particularly F-I-11 and F-II-8), III-1 to 36 in EP 457153A, page 17 to page 28 (particularly III-1 and 3), microcrystal dispersions of Dye-1 to 124 in WO88/04794, 8 to 26, compounds 1 to 22 in EP319999A, page 6 to page 11 (particularly, compound 1), compounds D-1 to 87 (page 3 to page 28) represented by one of the formulae (1) to (3) in EP 519306A, compounds 1 to 22 (columns 3 to 10) represented by the formula (I) in U.S. Pat. No. 4,268,622, compounds (1) to (31) (columns 2 to 9) represented by the formula (I) in U.S. Pat. No. 4,923,788; UV absorbers: compound (18b) to (18r) and 101 to 427 (page 6 to page 9) represented by the formula (1) in JP-A-46-3335, compounds (3) to (66) (page 10 to page 44) represented by the formula (1) and compounds HBT-1 to HBT-10 (page 14) represented by the formula (III) in EP 520938A, and compounds (1) to (31) (columns 2 to 9) represented by the formula (1) in EP 521823A.

The present invention can be applied to various color light-sensitive materials such as color negative films for general purposes or movies, color reversal films for slides or television, color paper, color positive films and color reversal paper. Additionally, the present invention can be suitably applied to a film unit with a lens described in JP-B-2-32615 or JU-B-3-39784 ("JU-B" means an "examined Japanese Utility model application"). Particularly the second embodiment can be preferably applied to color negative films and color reversal films.

A support that can be suitably used in the present invention is described in, for example, the above-described R.D. No. 17643 (page 28), R.D. No. 18716 (page 647, right column to page 648, left column) and R.D. No. 307105 (page 879).

In a light-sensitive material of the present invention, the total thickness of the layers from the light-sensitive silver halide emulsion layer closest to the support, to the surface of the photographic light-sensitive material, is preferably 30 $\mu$m or less, and more preferably 28 $\mu$m or less. A film swelling speed $T_{1/2}$ is preferably 30 sec or less, and more preferably 20 sec or less. $T_{1/2}$ is defined as a time required to reach ½ the saturated film thickness, which is 90% of the maximum swelled film thickness reached when the film is processed with a color developer at 30° C. for 3 min and 15 sec. The film thickness means the thickness of a film measured under controlled moisture condition, at a temperature of 25° C. and a relative humidity of 55% (two days). $T_{1/2}$ can be measured by using a swellometer of a type described in Photogr. Sci. Eng., by A. Green et al., Vol. 19, 2, pp. 124 to 129. $T_{1/2}$ can be adjusted adding a film hardener to gelatin as a binder, or changing aging conditions after coating. The swell ratio is preferably 150 to 400%. The swell ratio can be calculated from the maximum swollen film thickness under the conditions above by using the expression (maximum swollen film thickness–film thickness)/film thickness.

In the light-sensitive material of the present invention, hydrophilic colloid layers (referred to as backing layers) having a total dried film thickness of 2 to 20 $\mu$m are preferably formed on the side opposite to the side having emulsion layers. The backing layers preferably contain, the aforementioned light absorbents, filter dyes, ultraviolet absorbents, antistatic agents, film hardeners, binders, plasticizers, lubricants, coating aids, and surfactants. The swell ratio of the backing layer is preferably 150 to 500%.

The light-sensitive materials of the present invention can be developed by conventional methods described in the above-mentioned R.D. No. 17643, pp. 28 to 29, R.D. No.

18716, page 615, left to right columns, and R.D. No. 307105, pp. 880 to 881.

Next, color negative film processing solutions for use in the present invention will be described below.

Compounds described in JP-A-4-121739, from page 9, upper right column, line 1, to page 11, lower left column, line 4, can be used in a color developer that can be used in the present invention. As a color developing agent used when particularly rapid processing is to be performed, 2-methyl-4-[N-ethyl-N-(2-hydroxyethyl)amino]aniline, 2-methyl-4-[N-ethyl-N-(3-hydroxypropyl)amino]aniline, and 2-methyl-4-[N-ethyl-N-(4-hydroxybutyl)amino]aniline are preferable.

The use amount of any of these color-developing agents is preferably 0.01 to 0.08 mole, more preferably 0.015 to 0.06 mole, and especially preferably 0.02 to 0.05 mole per liter of a color developer. Also, a replenisher of a color developer preferably contains a color-developing agent at concentration 1.1 to 3 times, particularly 1.3 to 2.5 times the above concentration.

As a preservative of a color developer, hydroxylamine can be extensively used. When higher preservability is necessary, the use of a hydroxylamine derivative having a substituent such as an alkyl group, a hydroxyalkyl group, a sulfoalkyl group, and a carboxyalkyl group is preferable. Preferable examples include N,N-di-(sulfoethyl) hydroxylamine, monomethylhydroxylamine, dimethylhydroxylamine, monoethylhydroxylamine, diethylhydroxylamine, and N,N-di(carboxylethyl) hydroxylamine. Of these derivatives, N,N-di-(sulfoethyl) hydroxylamine is particularly preferable. Although these derivatives can be used together with hydroxylamine, it is preferable to use one or two types of these derivatives instead of hydroxylamine.

The use amount of a preservative is preferably 0.02 to 0.2 mole, more preferably 0.03 to 0.15 mole, and especially preferably 0.04 to 0.1 mole per liter. As in the case of a color-developing agent, a replenisher preferably contains a preservative at concentration 1.1 to 3 times the concentration of a mother solution (processing tank solution).

A color developer contains sulfite as an agent for preventing an oxide of a color-developing agent from changing into tar. The use amount of this sulfite is preferably 0.01 to 0.05 mole, more preferably 0.02 to 0.04 mole per liter. Sulfite is preferably used in a replenisher at concentration 1.1 to 3 times the above concentration.

The pH of a color developer is preferably 9.8 to 11.0, and more preferably 10.0 to 10.5. In a replenisher, the pH is preferably set to be higher by 0.1 to 1.0 than the above values. To stably maintain such a pH, a known buffer agent such as carbonate, phosphate, sulfosalicylate, or bolate is used.

The replenishment rate of a color developer is 2 preferably 80 to 1,300 ml per $m^2$ of a light-sensitive material. However, the replenishment rate is preferably smaller in order to reduce environmental-pollution-load. For example, the replenishment rate is preferably 80 to 600 ml, and more preferably 80 to 400 ml.

The bromide ion concentration in a color developer is usually 0.01 to 0.06 mole per liter. However, this bromide ion concentration is preferably set at 0.015 to 0.03 mole per liter for the purpose of suppressing fog to improve discrimination with maintaining sensitivity, and of improving graininess at the same time. To set the bromide ion concentration in this range, it is only necessary to add bromide ion calculated by the following equation, to a replenisher. When C takes a negative value, however, no bromide ions are preferably added to a replenisher.

$$C=(A-W)/V$$

in which
C: a bromide ion concentration (mole/L) in a color developer replenisher
A: a target bromide ion concentration (mole/L) in a color developer
W: an amount (mole) of bromide ions dissolving into a color developer from a light-sensitive material when 1 $m^2$ of the light-sensitive material is color-developed
V: a replenishiment rate (L) of a color developer replenisher to 1 $m^2$ of a light-sensitive material As a method of increasing the sensitivity when the replenishiment rate is decreased or high bromide ion concentration is set, it is preferable to use a development accelerator such as pyrazolidones represented by 1-phenyl-3-pyrazolidone, and 1-phenyl-2-methyl-2-hydroxylmethy-3-pyrazolidone, or a thioether compound represented by 3,6-dithia-1,8-octanediol.

Compounds and processing conditions described in JP-A-4-125558, from page 4, lower left column, line 16, to page 7, lower left column, line 6, can be applied to a processing solution having a bleaching capacity in the present invention.

The bleaching agent preferably has an oxidation-reduction potential of 150 mV or more. Preferable specific examples of the bleaching agent are described in JP-A-5-72694 and JP-A-5-173312. In particular, 1,3-diaminopropane tetraacetic acid and ferric complex salt of a compound shown as specific example 1 in JP-A-5-173312, page 7, are preferable.

Further, to improve the biodegradability of a bleaching agent, it is preferable to use ferric complex salt of a compound described in JP-A-4-251845, JP-A-4-268552, EP 588,289, EP 591,934 and JP-A-6-208213, as a bleaching agent. The concentration of any of these bleaching agents is preferably 0.05 to 0.3 mole per liter of a solution having a bleaching capacity. To reduce the amount of discharge to the environment, the concentration is preferably designed to be 0.1 to 0.15 mole per liter of the solution having a bleaching capacity. When the solution having a bleaching capacity is a bleaching solution, preferably 0.2 to 1 mole, and more preferably 0.3 to 0.8 mole of a bromide is added per liter.

A replenisher of the solution having a bleaching capacity basically contains components at concentrations calculated by the following equation. This makes it possible to maintain the concentrations in a mother solution constant.

$$C_R=C_T \times (V_1+V_2)/V_1+C_P$$

In which
$C_R$: concentration of a component in a replenisher
$C_T$: concentration of a component in a mother solution (processing tank solution)
$C_P$: concentration of a component consumed during processing
$V_1$: a replenishiment rate (ml) of a replenisher having a bleaching capacity per $m^2$ of a light-sensitive material
$V_2$: an amount (ml) of carryover from a preceding bath by $m^2$ of a light-sensitive material Additionally, a bleaching solution preferably contains a pH buffering agent, and particularly preferably, it contains a dicarboxylic acid with little odor, such as succinic acid, maleic acid, malonic acid, glutaric acid, and adipic acid. Also, the use of known bleaching accelerators described in JP-A-53-95630, RD No.17129, and U.S. Pat. No. 3,893,858 is preferable.

It is preferable to replenish 50 to 1,000 ml of a bleaching replenisher to a bleaching solution, per $m^2$ of a light-sensitive material. The replenishiment rate is more preferably 80 to 500 ml, and especially preferably 100 to 300 ml. Conducting aeration of a bleaching solution is also preferable.

Compounds and processing conditions described in JP-A-4-125558, from page 7, lower left column, line 10, to page 8, lower right column, line 19, can be applied to a processing solution with a fixing capacity.

To improve the fixing speed and preservability, the compound represented by formulae (I) or (II) described in JP-A-6-301169 is preferably added singly or in combination, a processing solution with a fixing capacity. To improve preservability, the use of sulfinic acid, including p-toluenesulfinate, described in JP-A-1-224762 is also preferable.

To improve the desilvering characteristics, ammonium is preferably used as cation, in a processing solution with a bleaching capacity or a processing solution with a fixing capacity. However, the amount of ammonium is preferably reduced, or not used at all, to reduce environmental pollution.

In the bleaching, bleach-fixing, and fixing steps, it is particularly preferable to perform jet stirring described in JP-A-1-309059.

The replenishiment rate of a replenisher in the bleach-fixing, or fixing step is preferably 100 to 1,000 ml, more preferably 150 to 700 ml, and furthermore preferably 200 to 600 ml per $m^2$ of a light-sensitive material.

In the bleach-fixing, or fixing step, an appropriate silver collecting apparatus is preferably installed either in-line or off-line to collect silver. When such an apparatus is installed in-line, processing can be performed while the silver concentration in a solution is reduced, and as a result of this, the replenishiment rate can be reduced. It is also preferable to install such an apparatus off-line to collect silver and reuse the residual solution as a replenisher.

The bleach-fixing, or fixing step can be performed using a plurality of processing tanks, and these tanks are preferably piped in a cascade manner to form a multistage counter flow system. To balance the size of a processor, two-tank cascade system is generally efficient. The processing time ratio of the preceding tank to the subsequent tank is preferably (0.5:1) to (1:0.5), and more preferably (0.8:1) to (1:0.8).

In a bleach-fixing, or fixing solution, the presence of a free chelating agent, which is not a metal complex, is preferable to improve the preservability. As these chelating agents, the use of the biodegradable chelating agents previously described in connection to a bleaching solution is preferable.

Contents described in aforementioned JP-A-4-125558, from page 12, lower right column, line 6, to page 13, lower right column, line 16, can be applied to the washing and stabilization steps. To improve the safety of the working environment, it is preferable to use azolylmethylamines described in EP 504,609 and EP 519,190 or N-methylolazoles described in JP-A-4-362943, instead of folmaldehyde, in a stabilizer, and to make a magenta coupler two-equivalent so that a solution of surfactant containing no image stabilizing agent such as folmaldehyde can be used.

To reduce adhesion of dust to a magnetic recording layer coated on a light-sensitive material, a stabilizer described in JP-A-6-289559 can be preferably used.

The replenishiment rate of washing water and a stabilizer is preferably 80 to 1,000 ml, more preferably 100 to 500 ml, and especially preferably 150 to 300 ml per $m^2$ of a light-sensitive material, to maintain the washing and stabilization functions and at the same time reduce the waste liquors for environmental conservation. In a processing performed with such a replenishment rate, it is preferable to prevent the propagation of bacteria and mildew by using known mildew-proofing agents such as thiabendazole, 1,2-methylisothiazoline-3-one, and 5-chloro-2-methylisothiazoline-3-one, antibiotics such as gentamicin, and water deionized by an ion exchange resin or the like. It is more effective to use deionized water together with a mildew-proofing agent or an antibiotic.

The replenishiment rate of a solution in a washing water tank or stabilizer tank is preferably reduced by a reverse osmosis membrane treatment described in JP-A-3-46652, JP-A-3-53246, JP-A-355542, JP-A-3-121448, and JP-A-3-126030. A reverse osmosis membrane used in this treatment is preferably a low-pressure reverse osmosis membrane.

In the processing that is used in the present invention, it is particularly preferable to perform evaporation correction of the processing solution as described in JIII Journal of Technical Disclosure No.94-4992. In particular, a method of performing correction on the basis of (formula-1) on page 2, by using temperature and humidity information of an environment in which a processor is set is preferable. Water for use in this evaporation correction is preferably taken from the washing water replenishiment tank. If this is the case, deionized water is preferably used as the washing replenishing water.

Processing agents described in aforementioned JIII Journal of Technical Disclosure No.94-4992, from page 3, right column, line 15, to page 4, left column, line 32, are preferably used in the present invention. As a processor used with these processing agents, a film processor described on page 3, right column, lines 22 to 28, is preferable.

Specific examples of processing agents, automatic processors, and evaporation correction methods suited to practicing the present invention are described in aforementioned JIII Journal of Technical Disclosure No.94-4992, from page 5, right column, line 11, to page 7, right column, last line.

Processing agents used in the present invention can be supplied in any form such as a liquid agent having the concentration as it is to be used, a concentrated liquid agent, granules, powder, tablets, paste, and emulsion. Examples of such processing agents are a liquid agent contained in a low-oxygen permeable vessel as described in JP-A-63-17453, vacuum-packed powders and granules described in JP-A-4-19655 and JP-A-4-230748, granules containing a water-soluble polymer described in JP-A-4-221951, tablets described in JP-A-51-61837 and JP-A-6-102628, and a paste described in JP—T-57-500485. Although any of these processing agents can be preferably used, the use of a liquid adjusted to have the concentration as it is to be used, in advance, is preferable for the sake of convenience in use.

As a vessel for containing these processing agents, polyethylene, polypropylene, polyinylchloride, polyethyleneterephthalate, nylon and the like, are used singly or as a composite material. These materials are selected in accordance with the level of necessary oxygen permeability. For a readily oxidizable solution such as a color developer, a low oxygen permeable material is preferable. More specifically, polyethyleneterephthalate or a composite material of polyethylene and nylon is preferable. A vessel made of any of these materials preferably has a thickness of 500 to 1,500 $\mu$m and is preferably adjusted to have oxygen permeability of 20 ml/$m^2$·24 hrs·atom or less.

Next, color reversal film processing solution used in the present invention will be described below.

Processing for a color reversal film is described in detail in Aztech Ltd., Kochi Gijutsu No. 6 (1991, April 1), from page 1, line 5, to page 10, line 5, and from page 15, line 8, to page 24, line 2, and any of the contents can be preferably applied.

In a color reversal film processing, an image-stabilizing agent is contained in a control bath or a final bath. Preferable examples of such an image-stabilizing agent are formalin, sodium formaldehyde-bisulfite, and N-methylolazoles. Sodium formaldehyde-bisulfite, and N-methylolazoles are preferable in terms of preserving working environment, and N-methyloltriazole is particularly preferable as N-methylolazoles. The contents pertaining to a color developer, bleaching solution, fixing solution, and washing water described in the color negative film processing can be preferably applied to the color reversal film processing.

Preferable examples of color reversal film processing agents containing the above contents are an E-6 processing agent manufactured by Eastman Kodak Co. and a CR-56 processing agent manufactured by Fuji Photo Film Co., Ltd.

Next, a magnetic recording layer preferably used in the present invention is explained.

The magnetic recording layer preferably used in the present invention refers to a layer provided by coating a base with an aqueous or organic solvent coating solution containing magnetic particles dispersed in a binder.

To prepare the magnetic particles used in the present invention, use can be made of a ferromagnetic iron oxide such as $\gamma Fe_2O_3$, Co-coated $\gamma Fe_2O_3$, Co-coated magnetite, Co-containing magnetite, ferromagnetic chromium dioxide, a ferromagnetic metal, a ferromagnetic alloy, hexagonal Ba ferrite, Sr ferrite, Pb ferrite, Ca ferrite, and the like. A Co-coated ferromagnetic iron oxide, such as Co-coated $\gamma Fe_2O_3$, is preferable. The shape may be any of a needle shape, a rice grain shape, a spherical shape, a cubic shape, a tabular shape, and the like. The specific surface area is preferably 20 $m^2/g$ or more, and particularly preferably 30 $m^2/g$ or more, in terms of $S_{BET}$.

The saturation magnetization (as) of the ferromagnetic material is preferably $3.0 \times 10^4$ to $3.0 \times 10^5$ A/m, and particularly preferably $4.0 \times 10^4$ to $2.5 \times 10^5$ A/m. The ferromagnetic particles may be surface-treated with silica and/or alumina or an organic material. The surface of the magnetic particles may be treated with a silane coupling agent or a titanium coupling agent, as described in JP-A-6-161032. Further, magnetic particles whose surface is coated with an inorganic or organic material, as described in JP-A-4-259911 and JP-A-5-81652, can be used.

As the binder that can be used for the magnetic particles, as described in JP-A-4-219569, a thermoplastic resin, a thermosetting resin, a radiation-setting resin, a reactive resin, an acid-degradable polymer, an alkali-degradable polymer, a biodegradable polymer, a natural polymer (e.g. a cellulose derivative and a saccharide derivative), and a mixture of these can be used. The above resins have a Tg of −40 to 300° C. and a weight-average molecular weight of 2,000 to 1,000,000. Examples include vinyl copolymers, cellulose derivatives, such as cellulose diacetates, cellulose triacetates, cellulose acetate propionates, cellulose acetate butylates, and cellulose tripropionates; acrylic resins, and polyvinyl acetal resins. Gelatin is also preferable. Cellulose di(tri)acetates are particularly preferable. To the binder may be added an epoxy, aziridine, or isocyanate crosslinking agent, to harden the binder. Examples of the isocyanate crosslinking agent include isocyanates, such as tolylene diisocyanate, 4,4',-diphenylmethane diisocyanate, hexamethylene diisocyanate, and xylylene diisocyanate; reaction products of these isocyanates with polyalcohols (e.g. a reaction product of 3 mol of tolylene diisocyanate with 1 mol of trimethylolpropane), and polyisocyanates produced by condensation of these isocyanates. Those are described, for example, in JP-A-6-59357.

The method of dispersing the foregoing magnetic material in the foregoing binder is preferably one described in JP-A-6-35092, in which method use is made of a kneader, a pin-type mill, an annular-type mill, and the like, which may be used alone or in combination. A dispersant described in JP-A-5-088283 and other known dispersants can be used. The thickness of the magnetic recording layer is generally 0.1 to 10 $\mu$m, preferably 0.2 to 5 $\mu$m, and more preferably 0.3 to 3 $\mu$m. The weight ratio of the magnetic particles to the binder is preferably from (0.5:100) to (60:100), and more preferably from (1:100) to (30:100). The coating amount of the magnetic particles is generally 0.005 to 3 $g/m^2$, preferably 0.01 to 2 $g/m^2$, and more preferably 0.02 to 0.5 $g/m^2$. The transmission yellow density of the magnetic recording layer is preferably 0.01 to 0.50, more preferably 0.03 to 0.20, and particularly preferably 0.04 to 0.15.

The magnetic recording layer can be provided to the undersurface of the photographic base by coating or printing through all parts or in a striped fashion. To apply the magnetic recording layer, use can be made of an air doctor, blade, air knife, squeezing, impregnation, reverse roll, transfer roll, gravure, kiss, cast, spraying, dipping, bar, extrusion, or the like. A coating solution described, for example, in JP-A-5-341436 is preferable.

The magnetic recording layer may be provided with functions, for example, of improving lubricity, of regulating curling, of preventing electrification, of preventing adhesion, and of abrading a head, or it may be provided with another functional layer that is provided with these functions. An abrasive in which at least one type of particles comprises aspherical inorganic particles having a Mohs hardness of 5 or more, is preferable. The aspherical inorganic particles preferably comprise a fine powder of an oxide, such as aluminum oxide, chromium oxide, silicon dioxide, and titanium dioxide; a carbide, such as silicon carbide and titanium carbide; diamond, or the like. The surface of these abrasives may be treated with a silane coupling agent or a titanium coupling agent. These particles may be added to the magnetic recording layer, or they may form an overcoat (e.g. a protective layer and a lubricant layer) on the magnetic recording layer. As a binder that can be used at that time, the above-mentioned binders can be used, and preferably the same binder as mentioned for the magnetic recording layer is used. Light-sensitive materials having a magnetic recording layer are described in U.S. Pat. Nos. 5,336,589, 5,250,404, 5,229,259, and 5,215,874, and European Patent No. 466,130.

A polyester support that is preferably used in the present invention will be described below. Details of the polyester support, as well as details of light-sensitive materials, processing, cartridges, and examples (to be described later), are described in JIII Journal of Technical Disclosure No.94-6023 (Japan Institute of Invention & Innovation, Mar. 15, 1994). Polyester for use in the present invention is formed from diol and aromatic dicarboxylic acid as essential components. Examples of the aromatic dicarboxylic acid are 2,6-, 1,5-, 1,4-, and 2,7-naphthalene dicarboxylic acids, terephthalic acid, isophthalic acid, and phthalic acid. Examples of the diol are diethyleneglycol, triethyleneglycol, cyclohexanedimethanol, bisphenol A, and bisphenol. Examples of the polymer are homopolymers such as polyethyleneterephthalate, and polyethylenenaphthalate, and polycyclohexanedimethanol terephthalate. Polyester containing 50 to 100 mole % of 2,6-naphthalenedicarboxylic acid is particularly preferable. Polyethylene-2,6-naphthalate is particularly preferable among the above polymers.

The average molecular weight is generally in the range of about 5,000 and 200,000. The Tg of the polymer for use in the present invention is generally 50° C. or higher, preferably 90° C. or higher.

The polyester base is heat-treated at a heat treatment temperature of generally 40° C. or over, but less than the Tg, and preferably at a heat treatment temperature of the Tg −20° C. or more, but less than the Tg, so that it will hardly have core set curl. The heat treatment may be carried out at a constant temperature in the above temperature range, or it may be carried out with cooling. The heat treatment time is generally 0.1 hours or more, but 1,500 hours or less, and preferably 0.5 hours or more, but 200 hours or less. The heat treatment of the base may be carried out with the base rolled, or it may be carried out with it being conveyed in the form of web. The surface of the base may be made rough (unevenness, for example, by applying electroconductive inorganic fine-particles, such as $SnO_2$ and $Sb_2O_5$), so that the surface state may be improved. Further, it is desirable to provide, for example, a rollette (knurling) at the both ends for the width of the base (both right and left ends towards the direction of rolling) to increase the thickness only at the ends, so that a trouble of deformation of the base will be prevented. The trouble of deformation of the support means that, when a support is wound on a core, on its second and further windings, the support follows unevenness of its cut edge of the first winding, deforming its flat film-shape. These heat treatments may be carried out at any stage after the production of the base film, after the surface treatment, after the coating of a backing layer (e.g. with an antistatic agent and a slipping agent), and after coating of an undercoat, with preference given to after coating of an antistatic agent.

Into the polyester may be blended (kneaded) an ultraviolet absorber. Further, prevention of light piping can be attained by blending dyes or pigments commercially available for polyesters, such as Diaresin (trade name, manufactured by Mitsubisi Chemical Industries Ltd.), and Kayaset (trade name, manufactured by Nippon Kayaku Co., Ltd.).

These supports are preferably subjected to a surface treatment, in order to achieve strong adhesion between the support and a photographic constituting layer. For the above-mentioned surface treatment, various surface-activation treatments can be used, such as a chemical treatment, a mechanical treatment, a corona discharge treatment, a flame treatment, an ultraviolet ray treatment, a high-frequency treatment, a glow discharge treatment, an active plasma treatment, a laser treatment, a mixed acid treatment, and an ozone oxidation treatment. Among the surface treatments, an ultraviolet irradiation treatment, a flame treatment, a corona treatment, and a glow treatment are preferable.

With respect to the undercoating, a single layer or two or more layers may be used. As the binder for the undercoat layer, for example, copolymers produced by using, as a starting material, a monomer selected from among vinyl chloride, vinylidene chloride, butadiene, methacrylic acid, acrylic acid, itaconic acid, maleic anhydride, and the like, as well as polyethylene imines, epoxy resins, grafted gelatins, nitrocelluloses, and gelatins, can be mentioned. As compounds that can swell the base, resorcin and p-chlorophenol can be mentioned. As gelatin hardening agents in the undercoat layer, chrome salts (e.g. chrome alum), aldehydes (e.g. formaldehyde and glutaraldehyde), isocyanates, active halogen compounds (e.g. 2,4-dichloro-6-hydroxy-s-triazine), epichlorohydrin resins, active vinyl sulfone compounds, and the like can be mentioned. $SiO_2$, $TiO_2$, inorganic fine particles, or polymethyl methacrylate copolymer fine particles (0.01 to 10 µm) may be included as a matting agent.

Further, in the present invention, an antistatic agent is preferably used. As the antistatic agent, polymers containing a carboxylic acid, a carboxylate, or a sulfonate; cationic polymers, and ionic surface-active compounds can be mentioned.

Most preferable antistatic agents are fine particles of at least one crystalline metal oxide selected from the group consisting of ZnO, $TiO_2$, $SnO_2$, $Al_2O_3$, $In_2O_3$, $SiO_2$, MgO, BaO, $MoO_3$, and $V_2O_5$, and having a specific volume resistance of $10^7$ Ω cm or less, and more preferably $10^5$ Ω cm or less and a particle size of 0.001 to 1.0 µm, or fine particles of their composite oxides (Sb, P, B, In, S, Si, C, and the like); as well as fine particles of the above metal oxides in the form of a sol, or fine particles of composite oxides of these.

The content thereof in the light-sensitive material is preferably 5 to 500 mg/m², and particularly preferably 10 to 350 mg/m². The ratio of the amount of the electroconductive crystalline oxide or its composite oxide to the amount of the binder is preferably from 1/300 to 100/1, and more preferably from 1/100 to 100/5.

A light-sensitive material of the present invention preferably has a slip property. Slip agent-containing layers are preferably formed on both the sides of a light-sensitive-layer side and a back-layer side. A preferable slip property is 0.01 to 0.25 as a coefficient of kinetic friction. This represents a value obtained when a sample is transferred against stainless steel sphere of 5 mm in diameter, at a speed of 60 cm/min (25° C., 60% RH). In this evaluation, a value of nearly the same level is obtained when the surface of a light-sensitive layer is used as a partner material in place of the stainless steel sphere.

Examples of a slip agent that can be used in the present invention are polyorganosiloxane, higher fatty acid amide, higher fatty acid metal salt, and ester of higher fatty acid and higher alcohol. As the polyorganosiloxane, it is possible to use, e.g., polydimethylsiloxane, polydiethylsiloxane, polystyrylmethylsiloxane, or polymethylphenylsiloxane. A layer to which the slip agent is added is preferably the outermost emulsion layer or a backing layer. Polydimethylsiloxane and ester having a long-chain alkyl group are particularly preferable.

The light-sensitive material of the present invention preferably contains a matting agent. This matting agent can be added to either the emulsion side or back side, and especially preferably added to the outermost layer of the emulsion layer side. The matting agent can be either soluble or insoluble in processing solution, and the use of both types of matting agents is preferable. Preferable examples are polymethylmethacrylate grains, poly (methylmethacrylate/methacrylic acid=9/1 or 5/5 (molar ratio)) grains, and polystyrene grains. The grain diameter is preferably 0.8 to 10 µm, and a narrow grain diameter distribution is preferable. It is preferable that 90% or more of all grains have grain diameters 0.9 to 1.1 times the average grain diameter. To increase the matting property, it is preferable to simultaneously add fine grains with a grain size of 0.8 µm or smaller. Examples are polymethylmethacrylate grains (0.2 µm), poly (methylmethacrylate/methacrylic acid=9/1 (molar ratio), 0.3 µm) grains, and polystyrene grains (0.25 µm), and colloidal silica grains (0.03 µm).

Next, a film magazine (patrone) used in the present invention is described below. The main material of the magazine for use in the present invention may be a metal or synthetic plastic.

Preferable plastic materials are polystyrenes, polyethylenes, polypropylenes, polyphenyl ethers, and the like. Further, the magazine that can be used in the present invention may contain various antistatic agents, and preferably, for example, carbon black, metal oxide particles; nonionic, anionic, cationic, and betaine-series surface-active agents, or polymers can be used. These antistatic magazines are described in JP-A-1-312537 and JP-A-1-312538. In particular, the resistance of the magazine at 25° C. and 25% RH is preferably $10^{12}$ Ω or less. Generally, plastic magazines are made of plastics with which carbon black or a pigment has been kneaded, to make the magazines screen light. The size of the magazine may be size 135, which is currently used, and, to make cameras small, it is effective to change the diameter of the 25-mm cartridge of the current size 135, to 22 mm or less. Preferably the volume of a case of the magazine is 30 cm or less, and more preferably 25 $cm^3$ or less. The weight of the plastic to be used for the magazine or the magazine case is preferably 5 to 15 g.

Further, the magazine may be one in which a spool is rotated to deliver a film. Also the structure may be such that the forward end of a film is housed in the magazine body, and by rotating a spool shaft in the delivering direction, the forward end of the film is delivered out from a port of the magazine. These magazines are disclosed in U.S. Pat. No. 4,834,306, and U.S. Pat. No. 5,226,613. A photographic film for use in the present invention may be a so-called raw film, which is before being subjected to development, and may be a photographic film after being processed. Further, a raw film and a photographic film after development may be housed in the same new magazine or in different magazines.

The color photographic light-sensitive material of the present invention can be advantageously used also as a negative film for advanced photo system (hereinafter referred to as AP system). Examples of the film include a film, manufactured by making the light-sensitive material film into AP system format and housing it into a cartridge for exclusive use, such as NEXIA A, NEXIA F, and NEXIA H (trade names, ISO 200/100/400 in that order) manufactured by Fuji Photo Film Co., Ltd. (hereinafter referred to as Fuji Film). These cartridge films for AP system are used after being loaded into cameras for AP system, such as EPION series, e.g. EPION 300Z (trade name) manufactured by Fuji Film. The color photographic light-sensitive material of the present invention is also preferable for use in a film unit with a lens, which is represented by Fuji Color UTSURUNDESU Super Slim (trade name) manufactured by Fuji Film.

A film thus photographed is printed through the following steps in a mini Lab system.
(1) Reception (an exposed cartridge film is received from a customer)
(2) Detaching step (the film is transferred from the cartridge to an intermediate cartridge for development steps)
(3) Film development
(4) Reattaching step (the developed negative film is returned to the original cartridge)
(5) Printing (prints of three types C, H, and P and an index print are continuously automatically printed on color paper [preferably Fuji Film SUPER FA8 (trade name)])
(6) Collation and shipment (the cartridge and the index print are collated by an ID number and shipped together with the prints)

As these systems, Fuji Film MINILAB CHAMPION SUPER FA-298, FA-278, FA-258, FA-238 (trade names) and Fuji Film DIGITAL LAB SYSTEM FRONTIER (trade name) are preferable. Examples of a film processor for MINILAB CHAMPION are FP922AL, FP562B, FP562B AL, FP362B, and FP362B AL (trade names), and recommended processing chemicals are FUJI COLOR JUST—IT CN-16L and CN-16Q (trade names). Examples of a printer processor are PP3008AR, PP3008A, PP1828AR, PP1828A, PP1258AR, PP1258A, PP728AR, and PP728A (trade names), and recommended processing chemicals are FUJI COLOR JUST—IT CP-47L and CP-40FAII (trade names).

In FRONTIER SYSTEM, Scanner & Image Processor SP-1000 and Laser Printer & Paper Processor LP-1000P or Laser Printer LP-1000W (trade names) are used. Both a detacher used in the detaching step and a reattacher used in the reattaching step are preferably Fuji Film DT200 or DT100 and AT200 or AT100 (trade names), respectively.

The AP system can also be enjoyed by PHOTO JOY SYSTEM whose main component is Fuji Film Digital Image Workstation ALADDIN 1000 (trade name). For example, a developed APS cartridge film is directly loaded into ALADDIN 1000, or image information of a negative film, positive film, or print is input to ALADIN 1000 by 35-mm Film Scanner FE-550 or Flat Head Scanner PE-550 (trade names). Obtained digital data can be easily processed and edited. This data can be printed out by Digital Color Printer NC-550AL (trade name) using a photo-fixing heat-sensitive color printing system or PICTROGRAPHY 3000 (trade name) using a laser exposure thermal development transfer system, or by existing laboratory equipment through a film recorder. ALADDIN 1000 can also output digital information directly to a floppy disk (registered trademark) or zip disk, or to CD-R via a CD writer.

In a home, a user can enjoy photographs on a TV set, simply by loading a developed AP system cartridge film into Fuji Film Photo Player AP-1 (trade name). Image information can also be continuously input to a personal computer with a high speed, by loading a developed AP system cartridge film into Fuji Film Photo Scanner AS-1 (trade name). Fuji Film Photo Vision FV-10 or FV-5 (trade names) can be used to input a film, print, or three-dimensional object, to a personal computer. Furthermore, image information recorded in a floppy disk (registered trademark), zip disk, CD-R, or hard disk can be variously processed on a computer by using Fuji Film Application Software Photo Factory. Fuji Film Digital Color Printer NC-2 or NC-2D (trade names) using a photo-fixing heat-sensitive color printing system is suited to outputting high quality prints from a personal computer.

To keep developed AP system cartridge films, FUJICOLOR POCKET ALUBUM AP-5 POP L, AP-1 POP L, AP-1 POP KG, or CARTRIDGE FILM 16 (trade names) is preferable.

As the dye-forming coupler of the present invention, the couplers represented by the above-mentioned formula (I), or (II) can be preferably applied to the first embodiment. Besides, the couplers represented by the above-mentioned formula (I), (II), (IIA), (IIB), (I-2), or (II-2) can be preferably applied to the second embodiment. More preferably, the couplers represented by formula (IIA) or (IIB) can be applied to the second embodiment. Regarding a color reversal light-sensitive material, the coupler represented by formula (IIB) can be more preferably applied.

(Azomethine Dye)

Next, the compound (herein also referred to as an azomethine dye) represented by formula (D) according to the present invention is explained in detail.

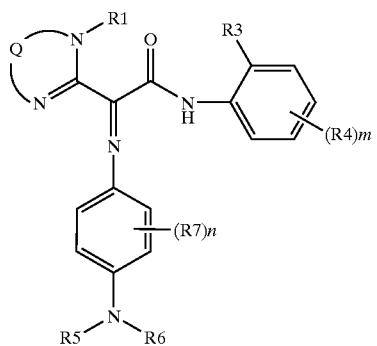

formula (D)

In formula (D), R1, R3, R4, m, and Q each have the same meanings as in formula (I). Preferable examples of these are the same as in formula (I).

In formula (D), R5 and R6 each represent a hydrogen atom or a substituent, or R5 and R6 may bond with each other to form a ring. R7 represents a substituent. n represents an integer of 0 to 4. When R5, R6 and R7 each independently represent a substituent, examples of the substituent are those enumerated as the examples of the substituent of R1 described above.

When n is 2 or more, R7s may be the same or different from each other, or they may bond with each other to form a fused ring. Alternatively, when n is 1 or more, R7 may bond with R5 or R6, to form a fused ring.

In formula (D), however, at least one group selected from the group consisting of R1, R3, R4, the substituent represented by $R_{11}$ the substituent represented by $R_{12}$, and at least one substituent on the ring that is formed by a combination of $R_{11}$ and $R_{12}$, is a group having 10 or more (preferably 10 to 50) carbon atoms, preferably 12 or more (preferably 12 to 45) carbon atoms, in total.

R7 is preferably a substituted or unsubstituted alkyl group having 1 to 30 carbon atoms, a substituted or unsubstituted alkenyl group having 1 to 30 carbon atoms, a substituted or unsubstituted aryl group having 6 to 30 carbon atoms, a substituted or unsubstituted alkoxy group having 1 to 30 carbon atoms, a halogen atom, or a substituted or unsubstituted acylamino group having 1 to 30 carbon atoms, more preferably R7 is the alkyl group. Further preferably, R7 is a methyl group bonded at the o-position to the nitrogen atom of the azomethine group.

R5 and R6 each are preferably a substituted or unsubstituted alkyl group having 1 to 30 carbon atoms, or a substituted or unsubstituted aryl group having 6 to 30 carbon atoms, more preferably the foregoing alkyl group. Further more preferably, one of R5 and R6 is an ethyl group and the other is a 2-hydroxyethyl group or 2-methanesulfonamidoethyl group.

Among the compounds represented by formula (D) of the present invention, the preferable compounds can be represented by the following formula (III).

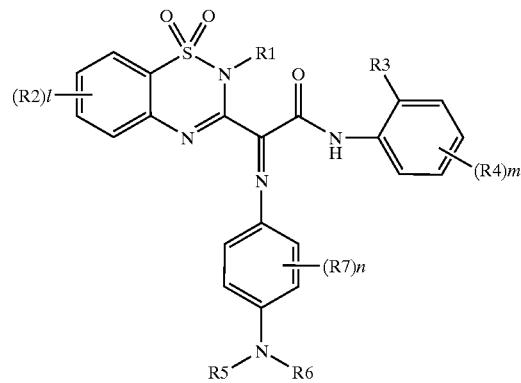

formula (III)

In formula (III), R1, R2, R3, R4, l, and m each have the same meanings as in formula (II). Preferable examples of these are the same as in formula (II).

In formula (III), R5, R6, R7, and n each have the same meanings as in formula (D). Preferable examples of these are the same as in formula (D).

However, in formula (III), at least one selected from R1, R2, R3, and R4 is a group having 10 or more (preferably 10 to 50), more preferably 12 or more (preferably 12 to 45) carbon atoms in total.

Among the azometine dyes represented by formula (D) or (III), preferable in the present invention is a dye having a maximum absorption wavelength of 400 to 500 nm, more preferably 410 to 480 nm, further preferably 420 to 460 nm.

Preferable specific examples of the azomethine dye represented by formula (D) or formula (III) according to the present invention are shown below, but the present invention should not be construed as being limited to them.

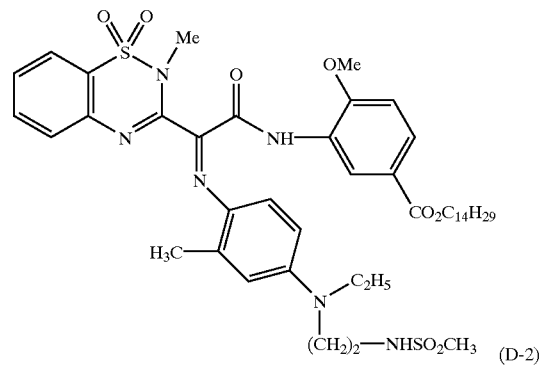

(D-1)

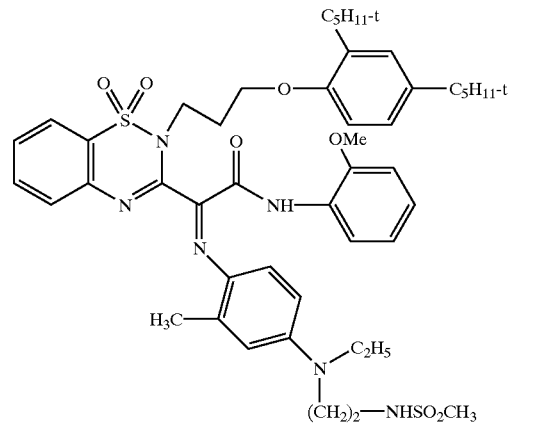

(D-2)

-continued
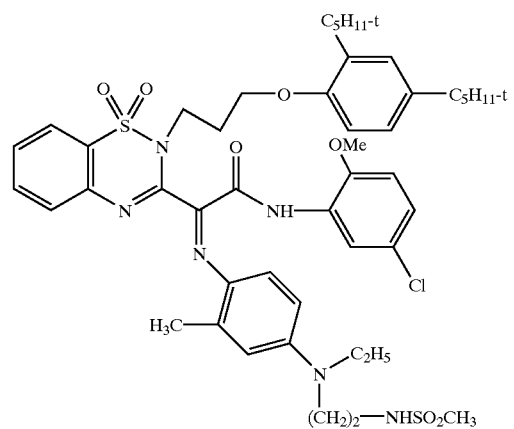
(D-3)
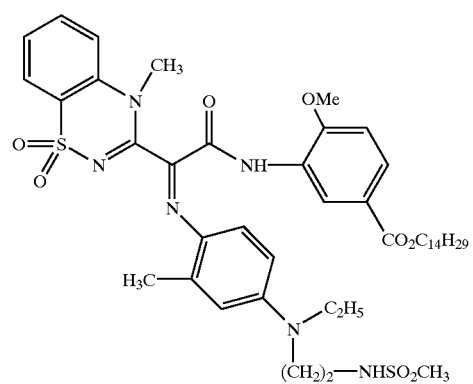
(D-4)
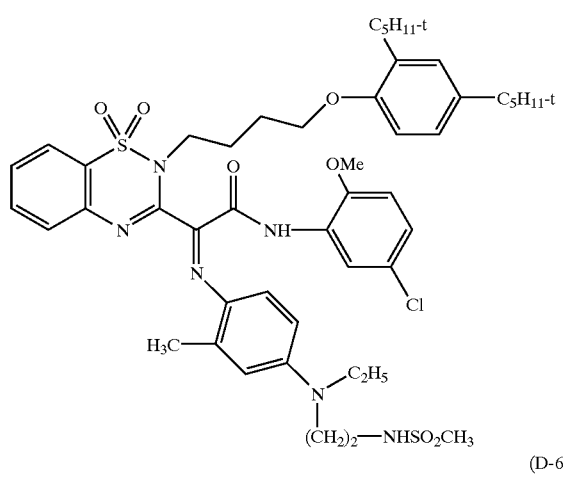
(D-5)
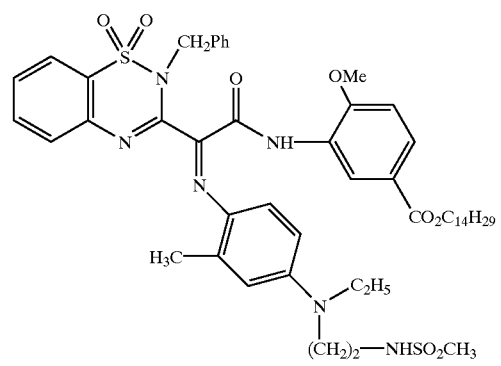
(D-6)
-continued
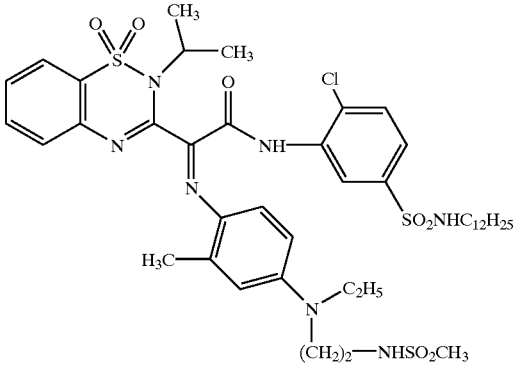
(D-7)
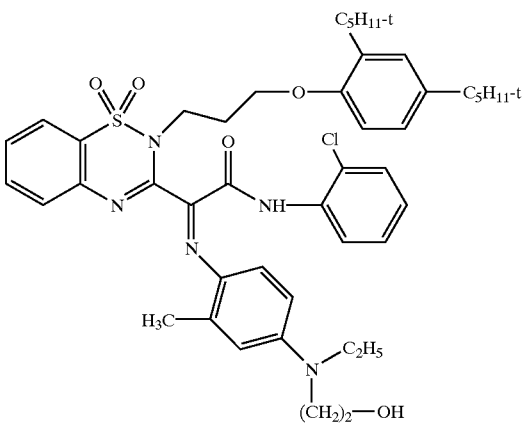
(D-8)
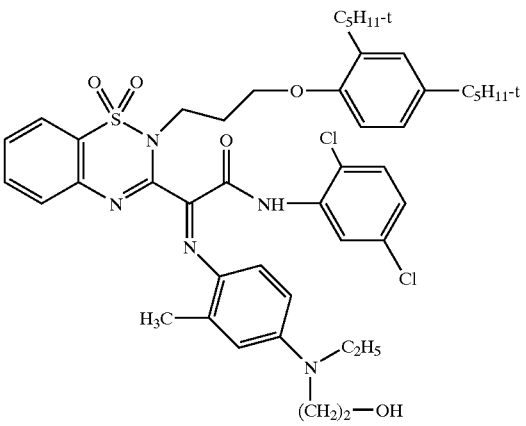
(D-9)
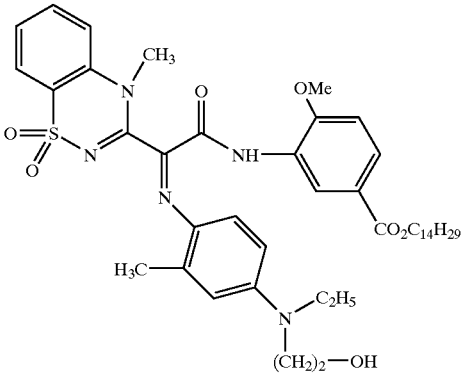
(D-10)

(D-11)
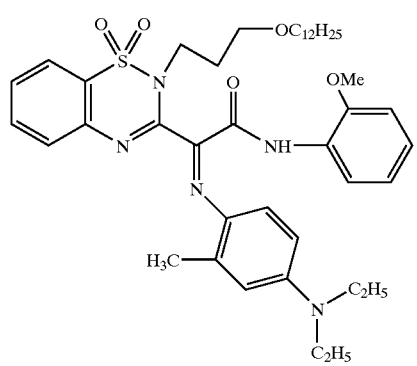
(D-12)
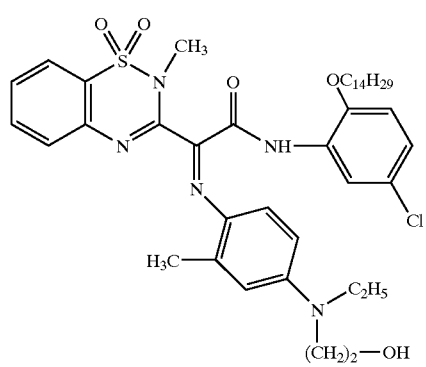
(D-13)
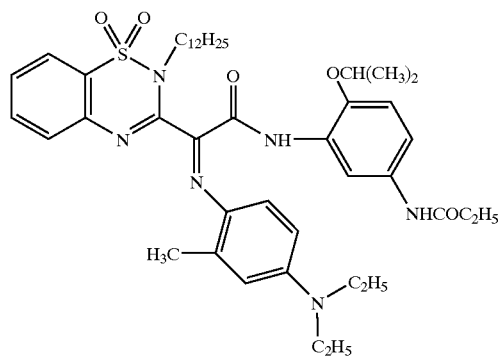
(D-14)
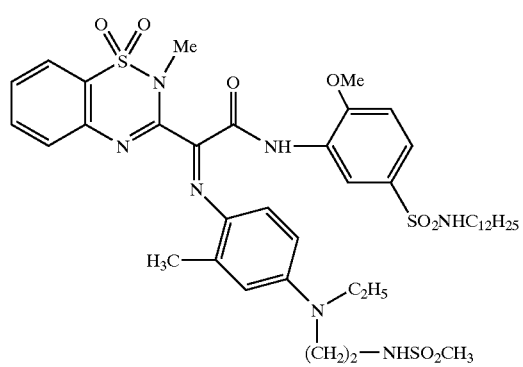
(D-15)
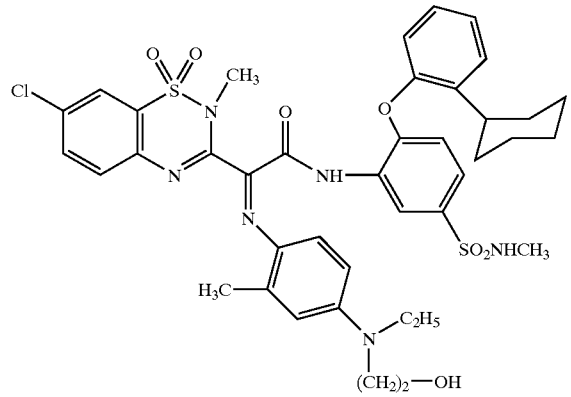
(D-16)
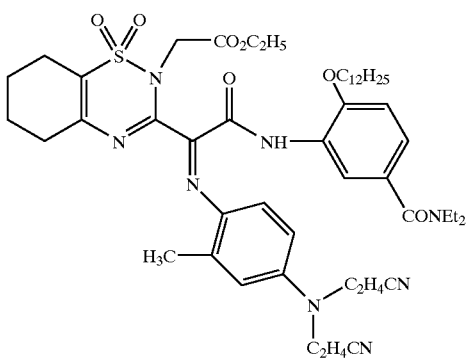
(D-17)
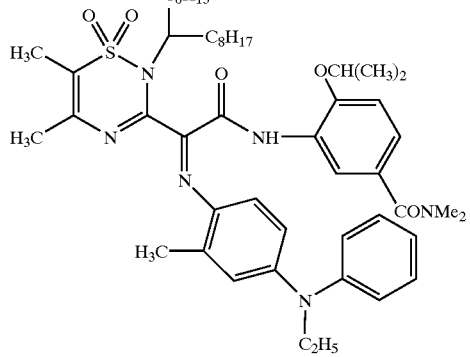
(D-18)
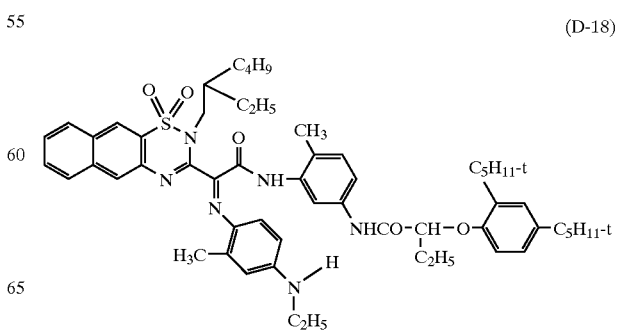

(D-19)
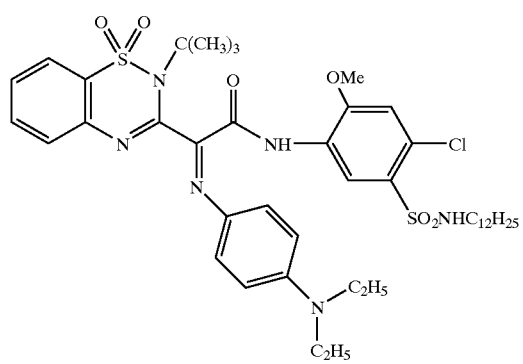
(D-20)
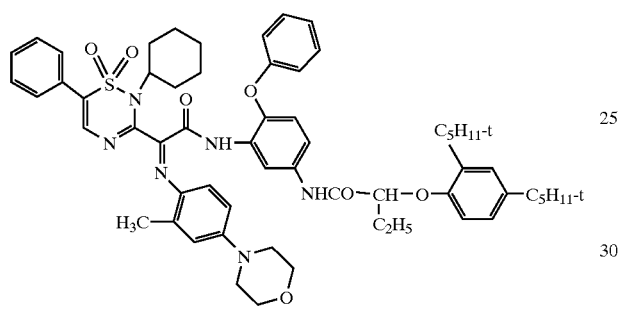
(D-21)
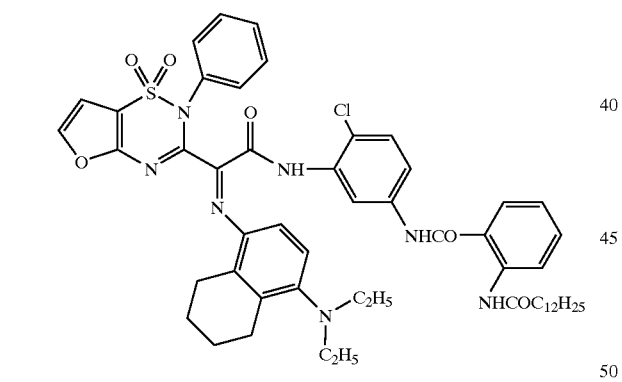
(D-22)
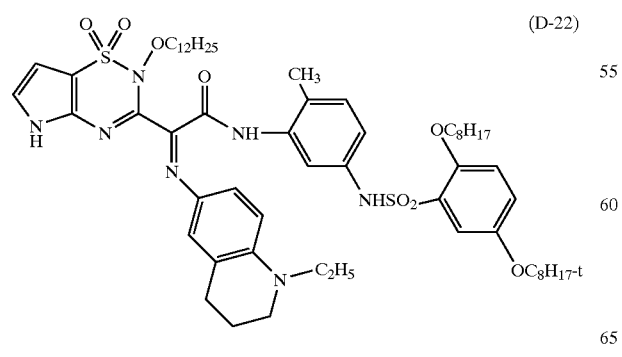
(D-23)
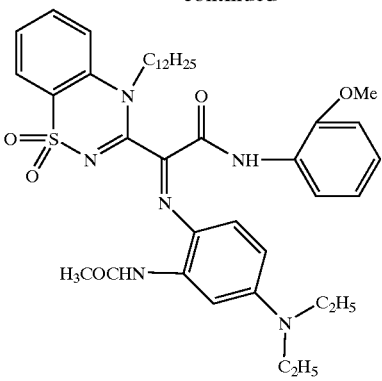
(D-24)
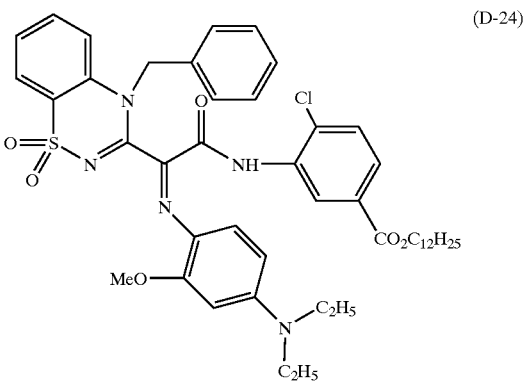
(D-25)
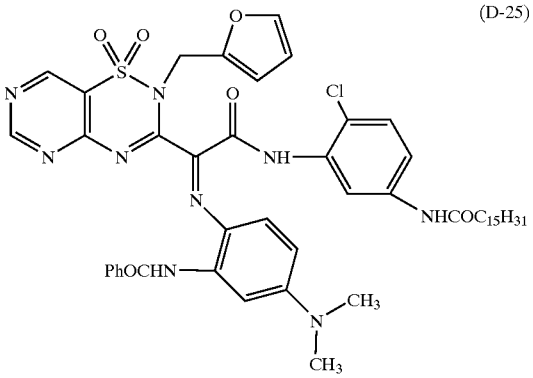
(D-26)
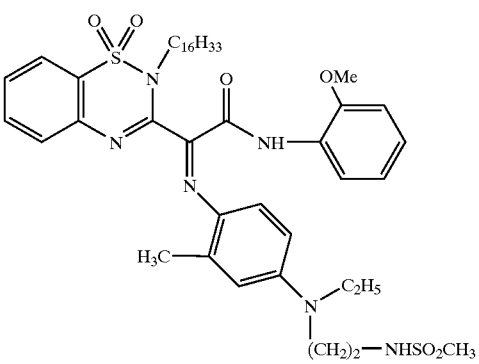

-continued
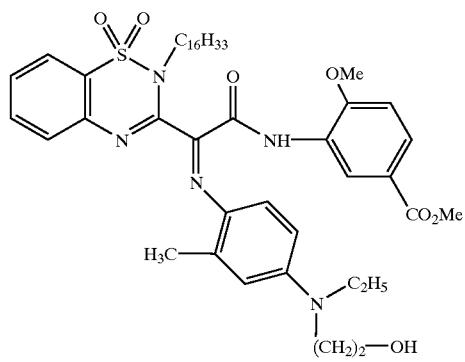
(D-27)
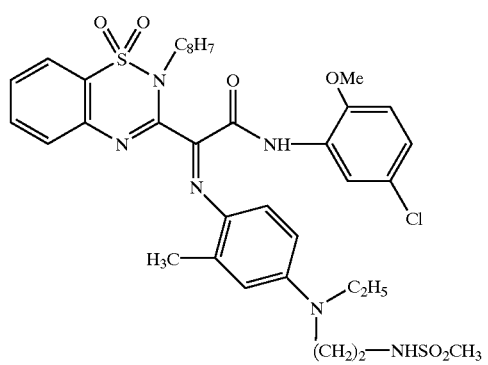
(D-28)
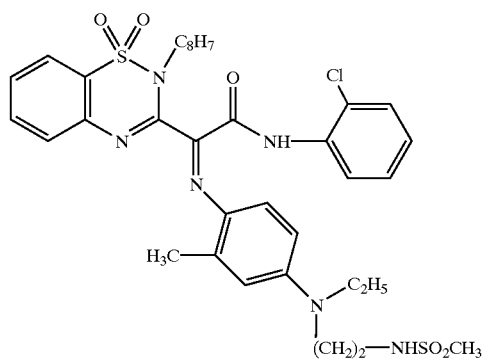
(D-29)
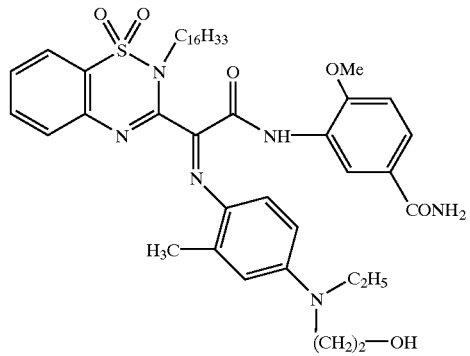
(D-30)
-continued
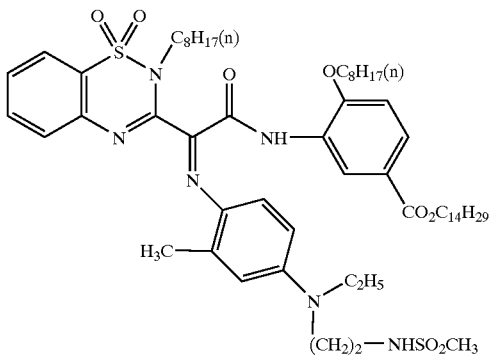
(D-31)
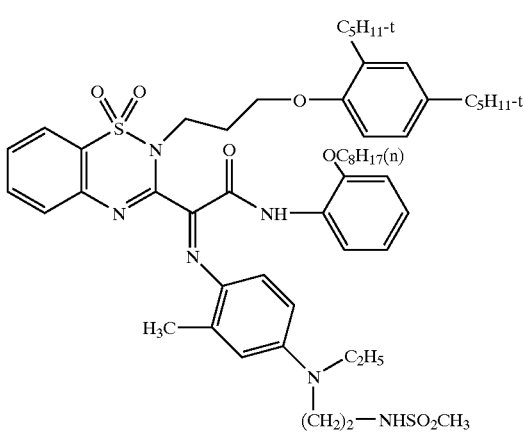
(D-32)
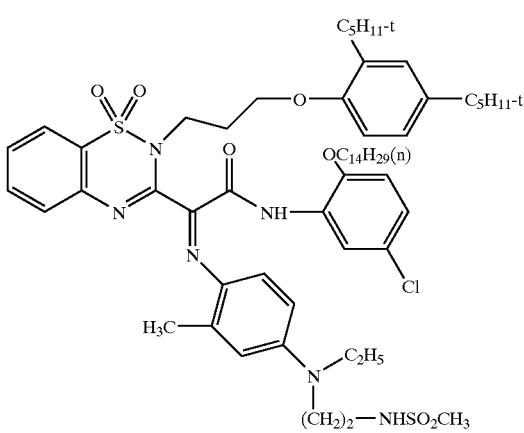
(D-33)
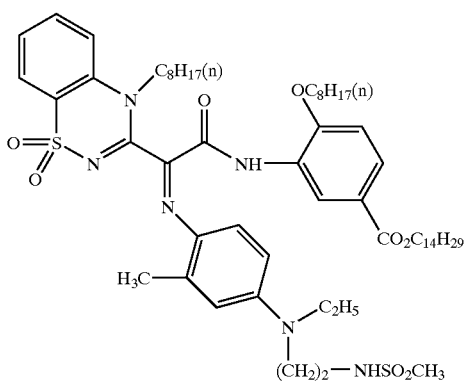
(D-34)

(D-35)
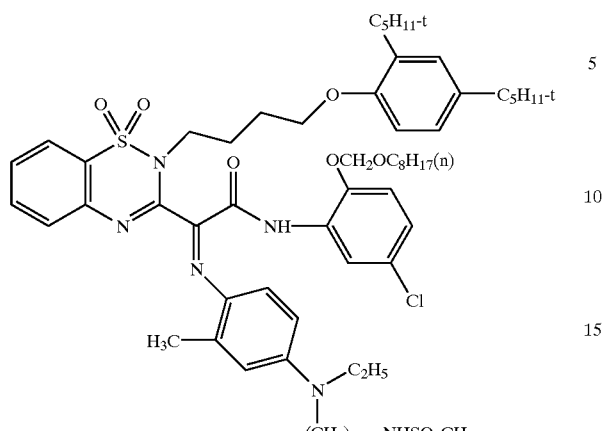
(D-36)
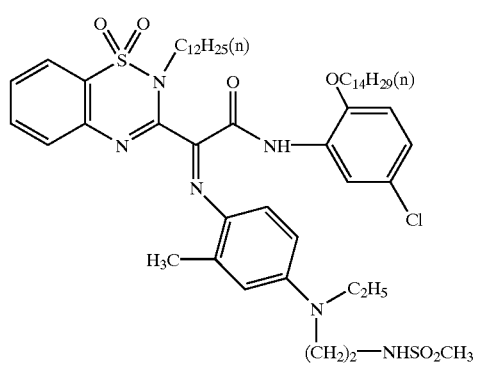
(D-37)
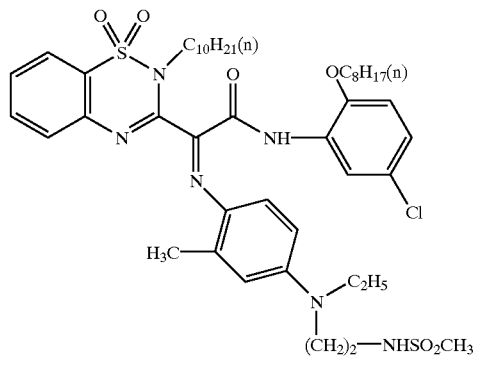
(D-38)
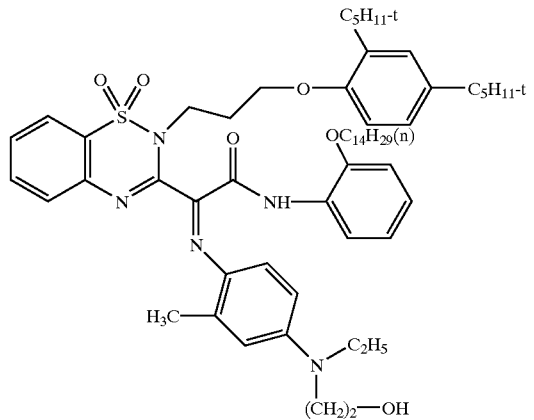
(D-39)
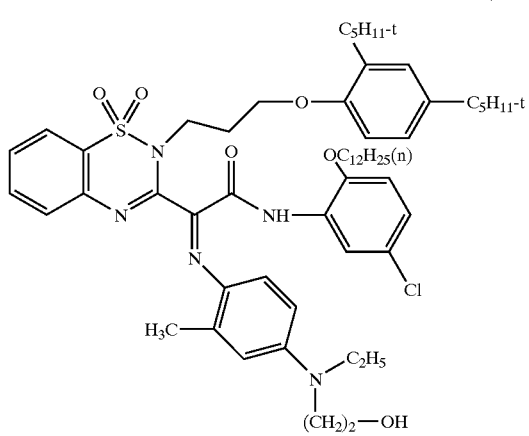
(D-40)
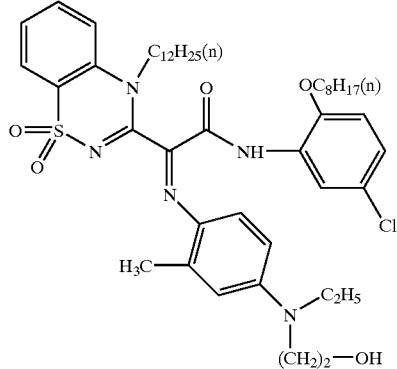
(D-41)
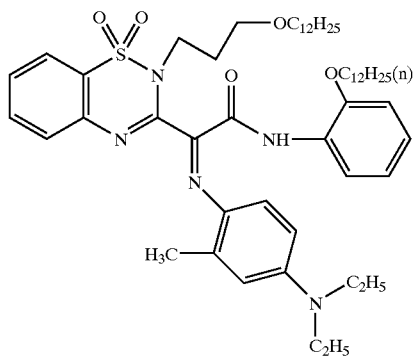
(D-42)
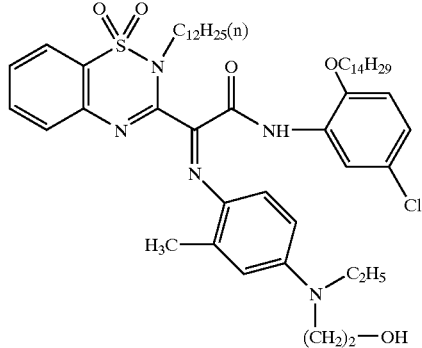

-continued
(D-43)
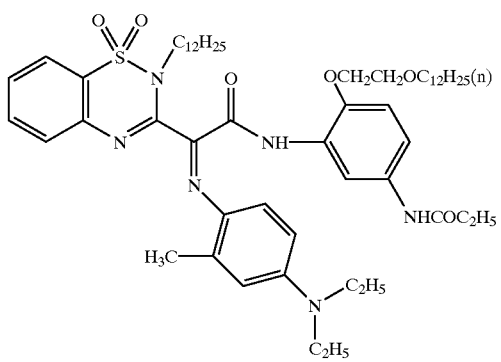
(D-44)
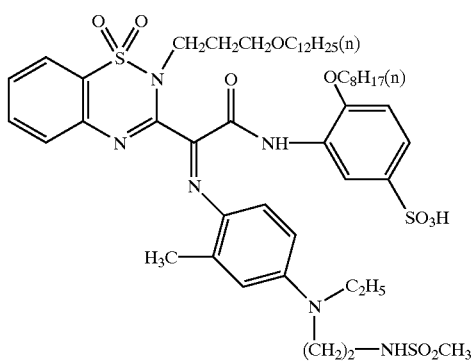
(D-45)
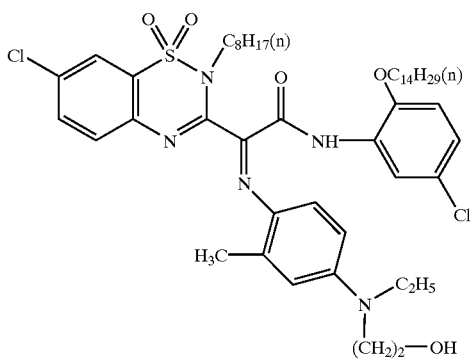
(D-46)
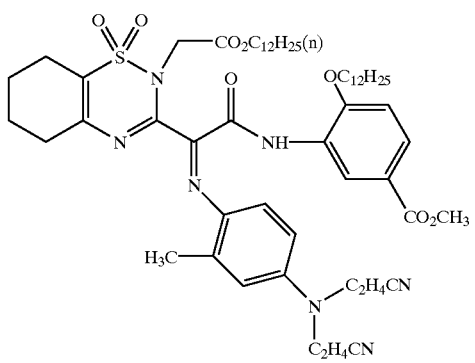
-continued
(D-47)
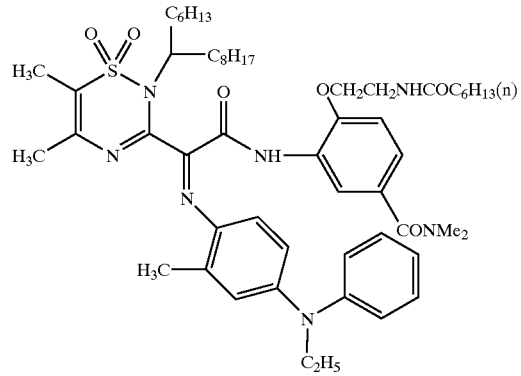
(D-48)
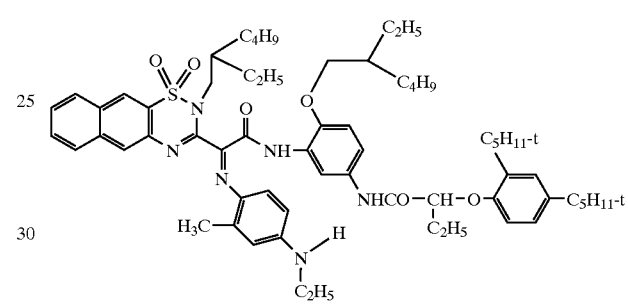
(D-49)
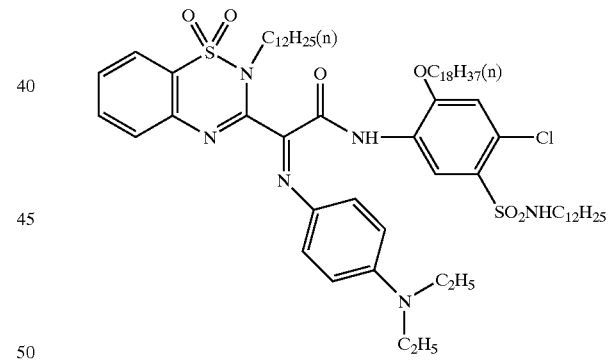
(D-50)
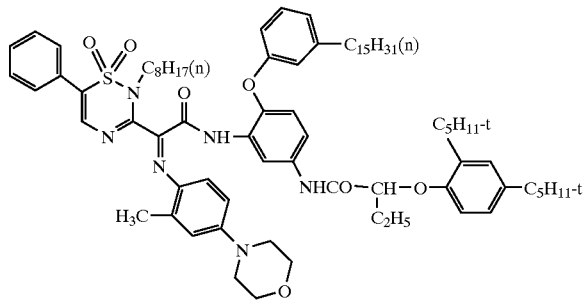

(D-51)

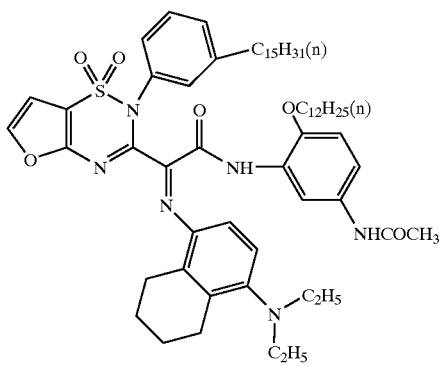

(D-55)

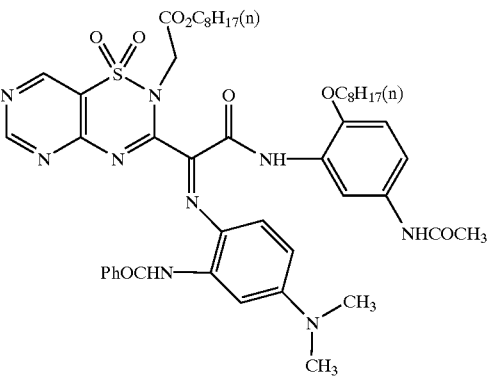

(D-52)

(D-53)

(D-54)

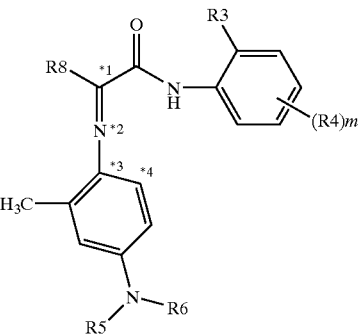

The compound represented by formula (D) or (III) of the present invention can be synthesized, for example, by a coupling reaction of the compound represented by formula (I) or (II) of the present invention, with an oxidized product of a phenylenediamine-series developing agent, especially preferably an N,N-disubstituted p-phenylenediamine derivative. Alternatively, the compound of the formula (D) or (III) can be synthesized by a reaction of the compound represented by formula (I) or (II) of the present invention in which X is a hydrogen atom, with a 4-nitrosoaniline-series compound. The preparation method is explained in EXAMPLES below.

The azomethine dye compounds of the present invention are applicable for many uses on account of their excellent properties such as hue and fastness. For example, they are useful for ink, dyestuffs, and the like. Especially, they are useful as the image-forming dyes, for example, dyestuffs in the ink for use in an ink-jet printer, and dyestuffs for use in color photography.

Next, the azomethine dye compound represented by formula (IV) of the present invention are explained in detail below.

formula (IV)

In formula (IV), R3, R4, R5, R6 and m each have the same meanings as in formula (III). Preferable examples of these are the same as in formula (III).

In formula (IV), R8 represents an aryl group or a heterocyclic group. More minutely the aryl group is preferably a substituted or unsubstituted aryl group having 6 to 30 carbon atoms (e.g., phenyl, p-tolyl, naphthyl, 2,6-dimethylphenyl). More minutely the heterocyclic group is preferably a 5- to 7-membered, substituted or unsubstituted, saturated or unsaturated, aromatic or non-aromatic, monocyclic or condensed heterocyclic group having 3 to 30 carbon atoms, more preferably a heterocyclic group having at least one ring-constituting atom selected from nitrogen atom, sulfur atom and oxygen atom in addition to carbon atom.

Especially preferable examples of the heterocyclic group include 6- or 7-membered, monocyclic or condensed, saturated or unsaturated heterocyclic groups having at least one ring-constituting atom selected from nitrogen atom and/or sulfur atom in addition to carbon atom.

R8 is preferably a group represented by the following formula (V), more preferably a group represented by the following formula (VI).

formula (V)

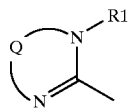

In formula (V), Q represents a group represented by —C(—$R_{11}$)=C(—$R_{12}$)—$SO_2$— (in the present invention, this expression of the foregoing group should not be construed as limited to the direction of the bonds belonging to the group as represented by this expression); $R_{11}$ and $R_{12}$ represent a group forming, together with the —C=C— portion, a 5- to 7-membered ring when they bond with each other, or $R_{11}$ and $R_{12}$ each independently represent a hydrogen atom or a substituent; and R1 represents a substituent.

formula (VI)

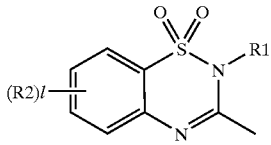

In formula (VI), R1 represents a substituent; R2 represents a substituent; l represents an integer of 0 to 4, and when l is 2 or more, R2s may be the same or different, or they may bond with each other to form a ring.

In formula (IV), R3 is more preferably a halogen atom (e.g., chlorine, florine), an alkoxy group (a substituted or unsubstituted alkoxyl group generally having 1 to 30 carbon atoms, e.g., methoxy, butoxy, dodecyloxy, hexadecyloxy), an aryloxy group (a substituted or unsubstituted aryloxy group generally having 6 to 30 carbon atoms, e.g., phenoxy, 4-methylphenoxy), an alkylthio group (a substituted or unsubstituted alkylthio group generally having 1 to 30 carbon atoms, for example, methylthio, and dodecylthio), or an arylthio group (a substituted or unsubstituted arylthio group generally having 6 to 30 carbon atoms, for example, phenylthio, and 4-methylphenylthio).

In formula (IV), at least one group selected from the group consisting of R1, R2, R3, R4, at least one substituent on an aryl ring or heterocyclic ring of $R_8$, a substituent represented by $R_{11}$ in Q, a substituent represented by $R_{12}$ in Q, and at least one substituent on a ring formed by $R_{11}$ and $R_{12}$ in Q, is a group having 10 or more (preferably 10 to 50), more preferably 12 or more (preferably 12 to 45) carbon atoms in total.

In the azomethine dye compound represented by formula (IV), the angle defined by the dihedral angle C*1 N*2 C*3 C*4 when the angle takes the most stabilized stereochemical structure in terms of energy, which is measured by quantum chemistry calculations, is within the range between −28° and 28°, preferably within the range between −24° and 24°.

In the present invention, to determine the dihedral angle C*1 N*2 C*3 C*4, the quantum chemistry calculations, which are also called as molecular orbital calculations, are conducted using the basis function of 6–31G* or more according to the widely used B3LYP method (density functional method) among methods of the ab initio MO (molecular orbital) methods. Strictly speaking, the B3LYP method is a hybridized method in which the density functional method and the Hartree-Fock's method are hybridized. That is a reason why the method is called a hybrid method. For example, Gaussian 98 (trade name) which is a program package soft available from Gaussian Inc in the U.S.A., may be used.

In brief, the theory of the quantum chemistry calculations is a computational method, by which the stereochemical structure of the molecule having the lowest whole energy can be figured out by calculating a kinetic energy of electrons, interaction between electron and electron, interaction between electron and nucleus, and interaction between nucleus and nucleus, in the whole molecule. Briefly speaking, the term "stereochemical structure having the lowest energy" means that the molecule exists as such a stereochemical structure. Details of the theory are published in a book form. For example, many text books as listed below are commercially available:

Ryoshi Kagaku Nyumon (Introduction to Quantum Chemistry) (the First and Second volumes) by Sadajiro Yonezawa et al. (Kagaku Dojin, 1983), Ryoshi Kagaku •Bunshi-kidoho Nyumon (Introduction to Quantum Chemistry and Method of Molecular Orbitals) by Kiyoshi Mutai (Shokodo, 1991), Bunshi-kidoho (Method of Molecular Orbitals) by Minoru Hirota (Shokabo, 1999), and Keisan Kagaku Gaido-bukku Sandai bunshi keisan puroguramu no Kaisetsu (A HAND BOOK OF COMPUTATIONAL CHEMISTRY—Commentary of three major molecular computation programs by Tim Clark, joint translated by Eiji Ohsawa et al. (Maruzen, 1988)

With respect to calculation of azomethine dyes which are compounds without the definition in the present invention, for example, the following report is known: Journal of Physical Chemistry A (American Chemical Society, 2001), page 1214. This report is an example in which calculations are conducted using the basis function of 6–31 G* or more according to the B3LYP method.

In the quantum chemistry calculations, accuracy of calculations depends on the method (for example, the density functional method and the Hartree-Fock's method) and the basis function (for example, 6–31 G**, 3–21G) which are used in combination. In the present invention, the present inventors have found that the azomethine dye represented by formula (IV) exhibits excellent properties, when the basis function of 6–31G* or more (for example, 6–31 G*, 6–31+G*, 6–31 G**, or 6–311 G*) is used in the B3LYP method (density functional method), and in addition the dihedral angle C*1 N*2 C*3 C*4 of the resulting stereochemical structure is 28° or less, more preferably 24° or less, in terms of the absolute value respectively. Namely, we have found that the nearer plane the dihedral angle is (in other words, the nearer 0° the absolute value of the dihedral angle is), the higher the molar extinction coefficient is attained in an absorption spectrum of the dye. The high molar extinction coefficient which enables to reduce the amount of the dye to be used in order to obtain a definite level of the optical density, is one of the important fundamental properties of the dye. Further, the nearer plane the dihedral angle is, the more effectively the electronic condition of the chromophore is stabilized with resonance. Therefore, it is assumed that such angle is of advantage to the storage stability of the dye.

Recently, the quantum chemistry calculations can be carried out on a work station or a personal computer. In the field of computational chemistry, the calculation method is becoming a common use as a tool of chemical studies. However, in the case of large molecules, it takes a long period of time to calculate. Therefore, a model except for important portions is generally used, to calculate, for example, by replacing a long-chain alkyl group with a methyl group, likewise replacing a long-chain alkoxy group with a methoxy group. Similar replacement may be optionally done.

The quantum chemistry calculations are explained with reference to the following specific examples.

The dihedral angle $C^*1\ N^*2\ C^*3\ C^*4$ defined in formula (IV) is indicated by theta below. VR-1 to VR-8 shown below are examples of the compounds for comparison which are not the compounds of the present invention. These were calculated for comparison. VD1 to VD20 are model dyes of azomethine dye compounds of the present invention. All the theta's shown below are values obtained by calculations using a program package available from Gaussian Inc. in the U.S.A., and using the basis function of 6–31 G** according to the B3LYP method. However, the present invention should not be construed as being limited to these.

In the present invention, as mentioned above, in formula (IV), at least one group selected from the group consisting of R1, R2, R3, R4, at least one substituent on the aryl ring or hetero ring of R8, the substituent represented by $R_{11}$ in Q, the substituent represented by $R_{12}$ in Q, and at least one substituent on the ring that is formed by a combination of $R_{11}$ and $R_{12}$ in Q, is a group having 10 or more carbon atoms in total.

A unit of value of theta shown below is "°".

VR-1

A model of a dye for comparison (CD-1)

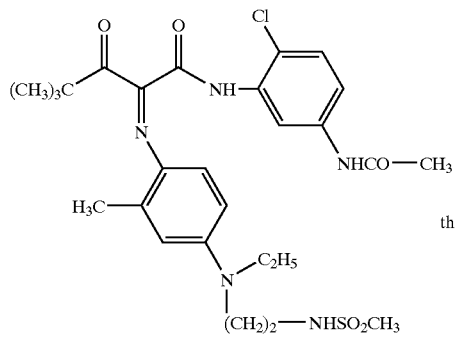

theta = −36.1

VR-2

A model of a dye for comparison (CD-2)

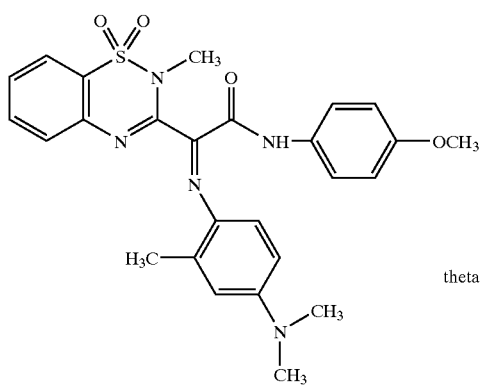

theta = 19.7

VR-3

A model of a dye for comparison (CD-3)

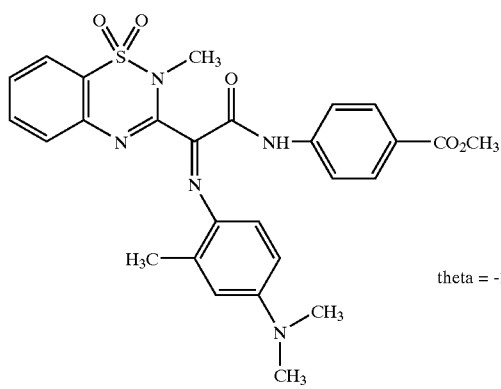

theta = −17.2

VR-4

A model of dyes formed from Coupler A3 or A4, described in EP0953873A1

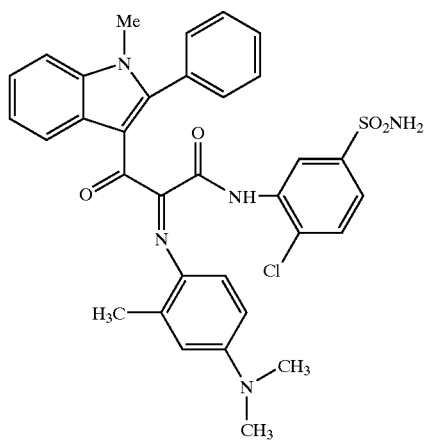

theta = 29.6

VR-5

A model of dyes formed from the couplers described in JP-A-5-11, 416

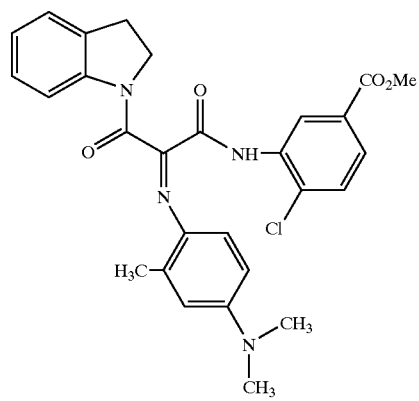

theta = −28.4

VR-6
A model of dyes formed from the couplers described in JP-A-4-218, 042
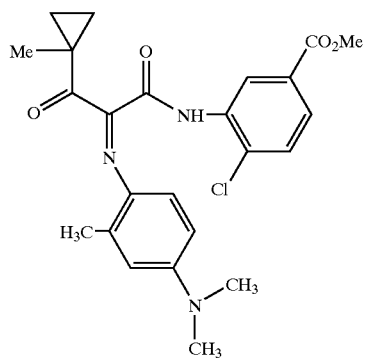
theta = −30.9
VR-7
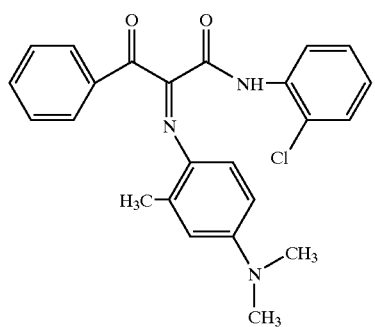
theta = −34.2
VR-8
A model of a dye for comparison (CD-4) A model of dyes formed from the couplers described in JP-A-10-198, 008
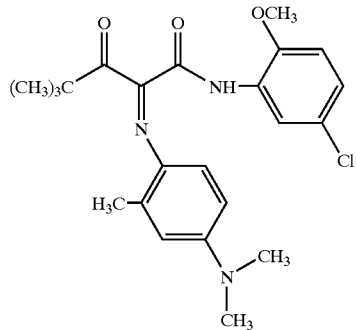
theta = 35.7
VD1
(A model of D-1, D-31, and D-46)
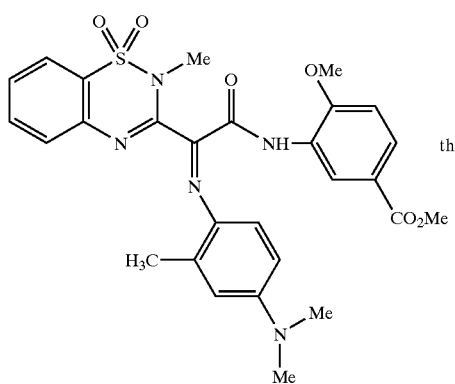
theta = −21.1
VD2
(A model of D-2, D-11, D-32, D-38, and D-41)
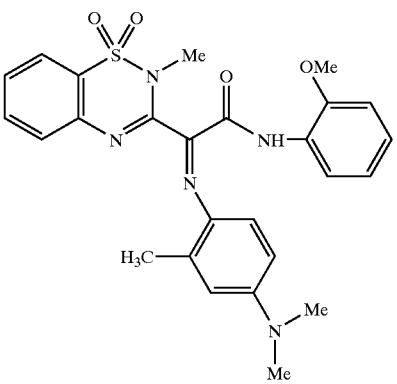
theta = −21.0
VD3
(A model of D-3, D-5, D-12, D-33, D-35, D-36, D-37, D-39, D-42, and D-45)
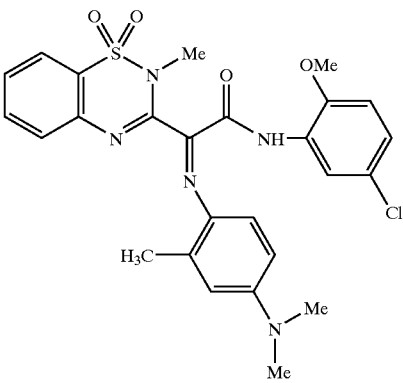
theta = −19.5
VD4
(A model of D-4, D-10, and D-34)
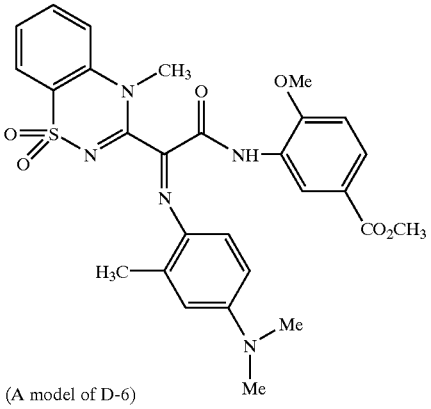
theta = 9.8
VD5
(A model of D-6)
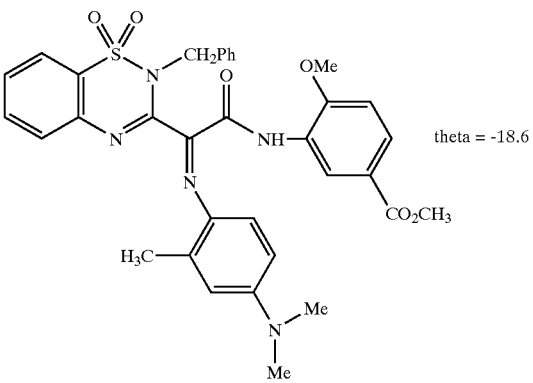
theta = −18.6

VD6
(A model of D-7)
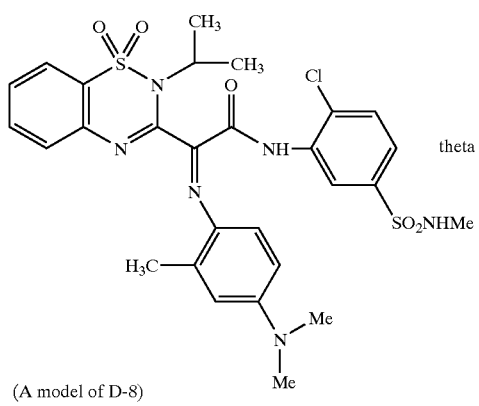
theta = −10.2
VD7
(A model of D-8)
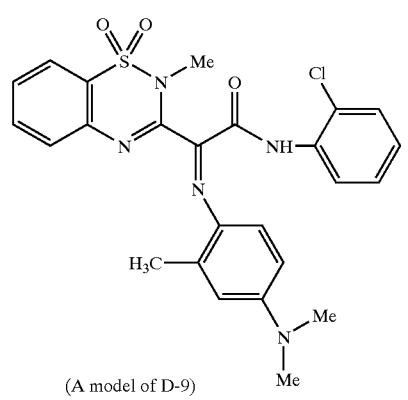
theta = −17.6
VD8
(A model of D-9)
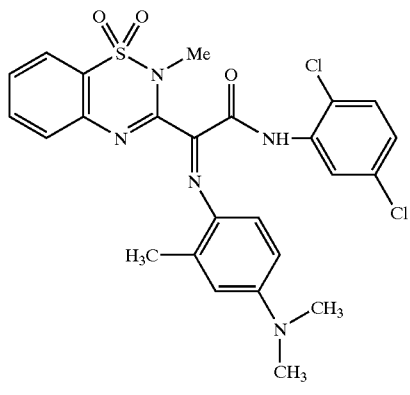
theta = −19.9
VD9
(A model of D-44)
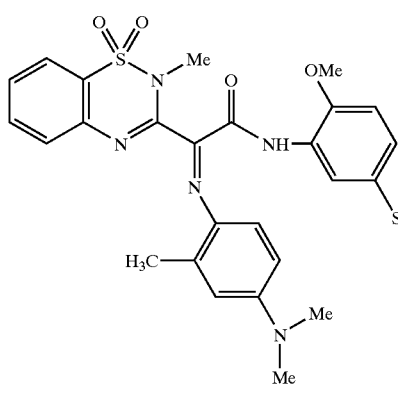
theta = −18.9
VD10
(A model of D-15)
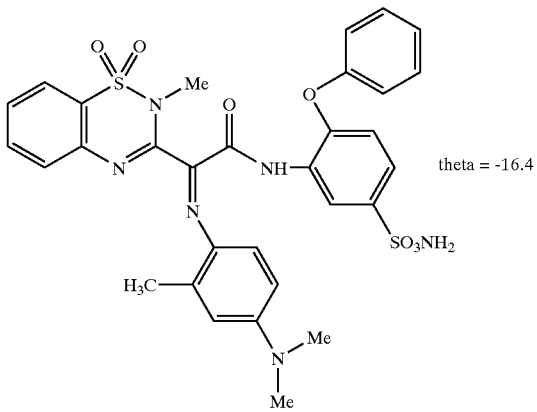
theta = −16.4
VD11
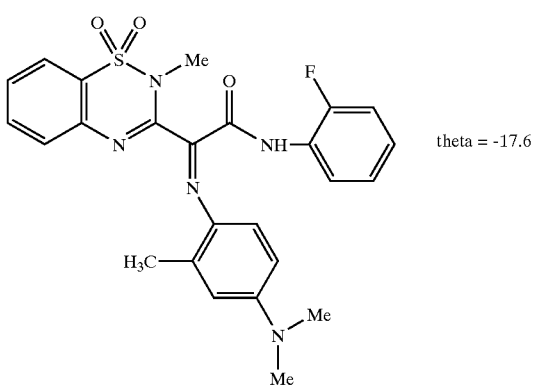
theta = −17.6
VD12
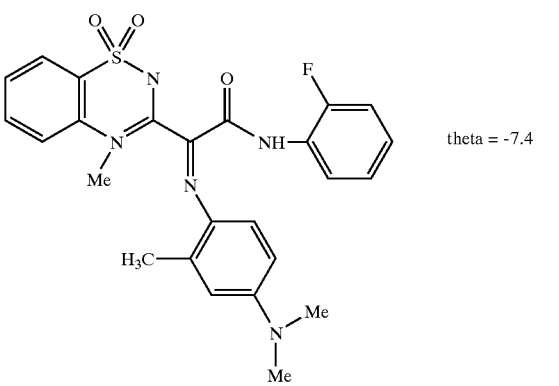
theta = −7.4
VD13
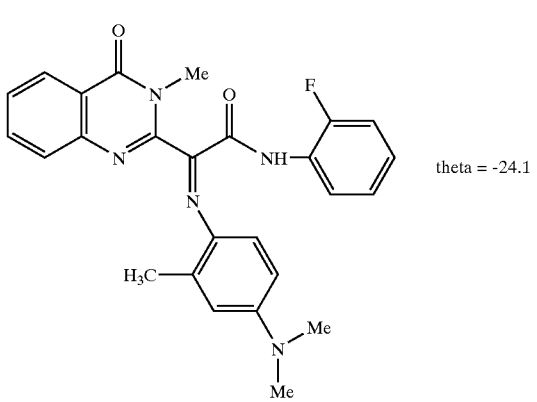
theta = −24.1

VD14

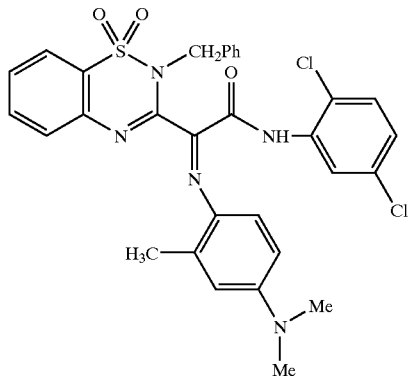

theta = -19.6

VD15

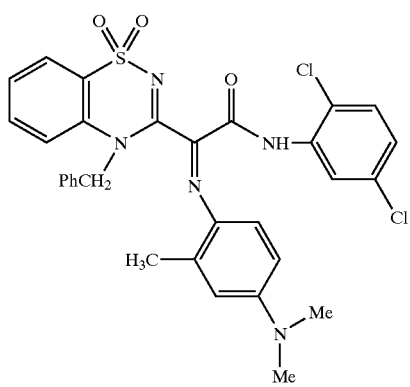

theta = 8.4

VD16

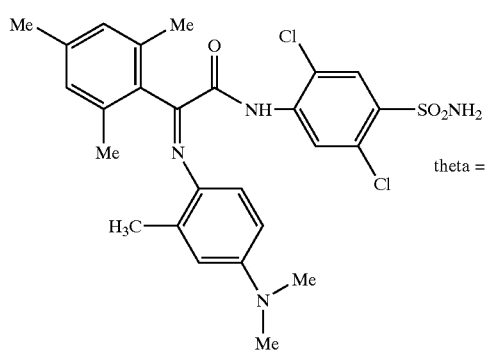

theta = -27.8

VD17

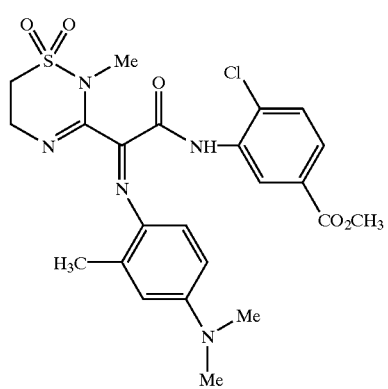

theta = -15.6

VD18

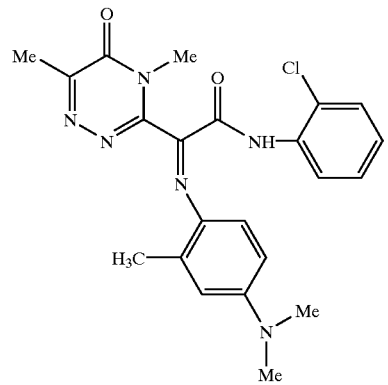

theta = -27.7

VD19

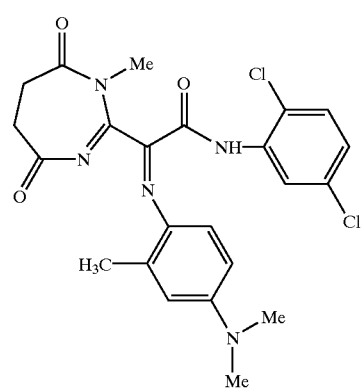

theta = -19.5

VD20

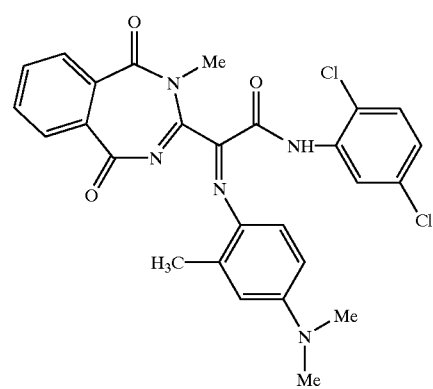

theta = -21.7

Among these dyes, each of D11 to DV13, DV17, DV19 and DV20 is a model dye of the dye in which, in formula (V), the Me group in the moiety corresponding to R1 is —C$_{12}$H$_{25}$; or, in formula (IV), the Me group corresponding to R5 is an ethyl group and the Me group corresponding to R6 is a 2-(methanesulfonamido)ethyl group. Each of DV14 and VD15 is a model dye of the dye in which, in formula (V), the —CH$_2$Ph group in the moiety corresponding to R1 is a p-octyloxybenzyl group; or, in formula (IV), the Me group corresponding to R5 is an ethyl group and the Me group corresponding to R6 is a 2-hydroxyethyl group. VD16 is a model dye of the dye in which, in formula (IV), the —SO$_2$NH$_2$ group on the anilido group is a —SO$_2$NHC$_{12}$H$_{25}$, the Me group corresponding to R5 is an ethyl group, and the Me group corresponding to R6 is a 2-hydroxyethyl group. DV18 is a model dye of the dye in which, in formula (V), the Me group in the moiety corresponding to R1 is —C$_{12}$H$_{25}$; or, in formula (IV), the Me group corresponding to R5 is an ethyl group and the Me group corresponding to R6 is a 2-hydroxyethyl group.

In the present invention, among the azometine dyes represented by formula (IV), preferred is the dye having a maximum absorption wavelength of 400 to 500 nm, more preferably 410 to 480 nm, further preferably 420 to 460 nm.

The compounds represented by formula (IV) of the present invention can be synthesized in the same manner as the compounds represented by formula (D) or (III).

The compounds represented by formula (IV), which are excellent in both hue and fastness, are preferably used in the same use as the azomethine dyes represented by formula (D) or (III). More preferably, the compounds of the formula (IV) are useful for image formation, particularly as dyestuffs for use in color photography.

Therefore, a preferable embodiment of the present invention is a color photograph containing a compound represented by formula (IV).

In a silver halide photographic light-sensitive material, the above compound may be used and incorporated as a dyestuff. However, a preferable embodiment of the present invention is a use of the compound of the formula (IV) as a coupler. This use is, for example, that a silver halide photographic light-sensitive material contains a coupler (specifically the same compound as the above dye of formula (IV), except for replacing the =N—Ph group bonding to C*1 in formula (IV) with the X group, in which X has the same meaning as in formula (I), with preferable examples of X being the same as in formula (I)), which gives the dye of formula (IV) upon a coupling reaction with an oxidized product of an aromatic primary amine (an oxidized product of an aniline derivative which has a —NR5(R6) group at the p-position and a methyl group at the o-position), so that the resulting dye is used as a dye consisting a color image for a photograph.

The present invention can provide a dye-forming coupler that gives a dye having an excellent hue, a large molecular extinction coefficient and excellent storage stability. Further, the present invention can provide a dye-forming coupler that gives a dye having an excellent hue, especially excellent in sharpness at the foot portion of a peak of the absorption curve (there is no subsidiary absorption) at the longer wavelength side, having a large molecular extinction coefficient, and being excellent in storage stability, and that exhibits a high color-forming property, and that can be produced with a low production cost in a small number of steps. Further, the present invention can provide a silver halide photographic light-sensitive material containing said coupler, that exhibits not only excellent color reproduction and sharpness but also good dye-image fastness. Further, the present invention can provide an azomethine dye having a large molecular extinction coefficient as well as being excellent in both hue and storage stability. Still further, the present invention can provide an azomethine dye compound that is excellent in sharpness at the foot portion of a peak of the absorption curve at the longer wavelength side, that has a large molecular extinction coefficient, and that is excellent in hue, sharpness and storage stability.

The present invention will now be described in more detail with reference to the following examples, but the invention is not limited to those. Numbering system of the compounds and simplified symbols, and the like, as utilized in each of the examples are independent in each of the examples, unless otherwise specified.

EXAMPLE

Comparative Example 1

1. Preparation of a Dye for Comparison (CD-1)

To a mixture of 0.85 g of the following coupler for comparison (C-1), 0.80 g of N-ethyl-N-(β-methanesulfoneamidoethyl)-3-methyl-4-aminoaniline sulfate, 3.75 g of sodium carbonate, 60 ml of ethyl acetate and 50 ml of water, was gradually added a solution of 1.45 g of ammonium persulfate dissolved in 10 ml of water, at room temperature under stirring. The reaction liquid was stirred for 1 hour and then the organic phase was separated. The organic phase was purified by silica gel chromatography, to give a dye for comparison (CD-1), which was the following yellow azomethine dye for comparison.

Coupler for comparison

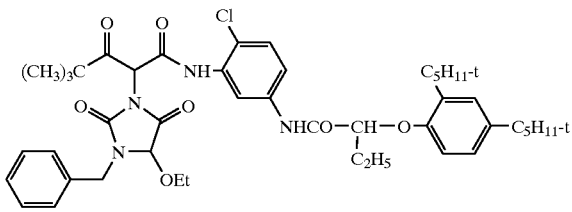

(C-1)

Dye for comparison

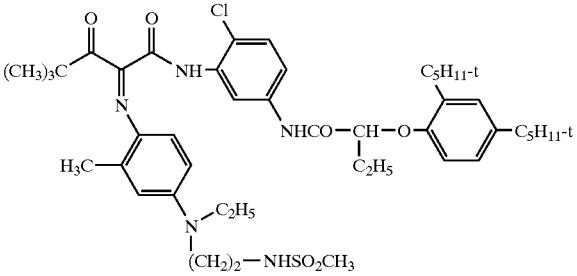

(CD-1)

2. Preparation of Dyes for Comparison (CD-2), (CD-3), and (CD-4)

Yellow azomethine dyes for comparison (CD-2), (CD-3), and (CD-4) were obtained in the same manner as in the section 1 "Preparation of a dye for comparison (CD-1)" in Comparative Example 1, except for replacing the coupler for comparison (C-1) with the following coupler for comparison (C-2) (Compound (XV) described in U.S. Pat. No. 3,841,880), the following coupler for comparison (C-3) (Compound (17) described in JP-A-52-82423), and the following coupler for comparison (C-4) (compound (27) described in JP-A-10-198008) respectively.

Coupler for comparison

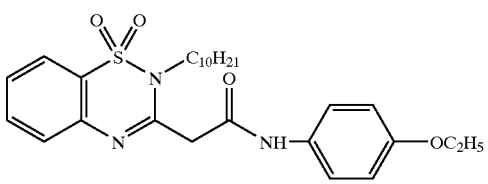

(Compound(XV) described in U.S. Pat. No. 3841880)

(C-2)

159
-continued

Coupler for comparison

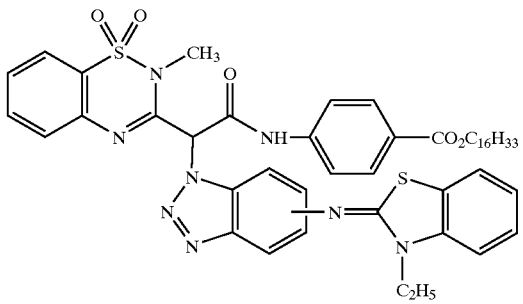

(Compound (17) described in JP-A-52-82423)

Dye for comparison

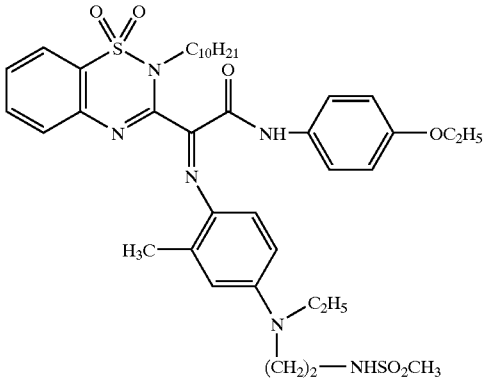

Dye for comparison

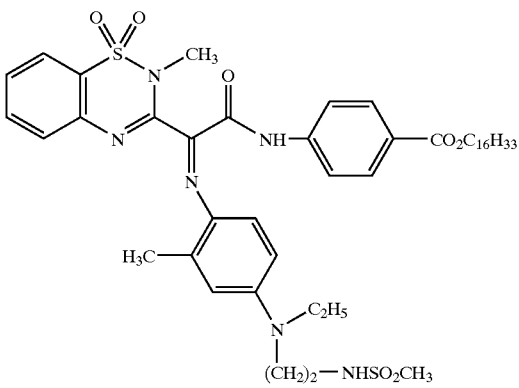

Coupler for comparison

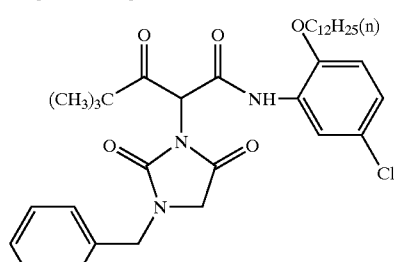

(Compound (27) described in JP-A-10-198008)

160
-continued

Dye for comparison

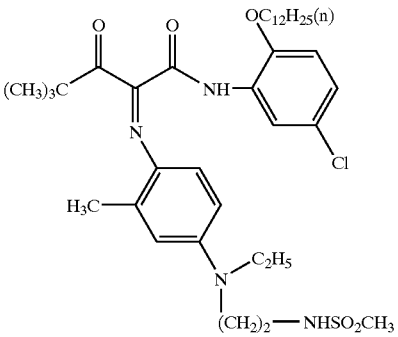

Example 1

1. Preparation of Dyes (D-1) to (D-4), (D-26), (D-28), (D-31) to (D-34)

The dyes (D-1) to (D-4), (D-26), (D-28), (D-31) to (D-34), were synthesized in the same manner as in Comparative Example 1, except that in the section 1. "Preparation of a dye for comparison (CD-1)" in Comparative Example 1, the above-mentioned exemplified couplers (1), (3), (5), (31), (41), (43), (51), (59), (60) and (81) of the present invention were used, respectively, instead of the coupler for comparison (C-1), to give the following azomethine dye D-1 wherein the coupler (1) was used, dye D-2 wherein the coupler (3) was used, dye D-3 wherein the coupler (5) was used, dye D-4 wherein the coupler (31) was used, dye D-26 wherein the coupler (41) was used, dye D-28 wherein the coupler (43) was used, dye D-31 wherein the coupler (51) was used, dye D-32 wherein the coupler (59) was used, dye D-33 wherein the coupler (60) was used, and dye D-34 wherein the coupler (81) was used, each of which was the azomethine dye obtained from the dye-forming coupler of the present invention. $^1$H-NMR (CDCl$_3$, 200 MHz, TMS), the maximum absorption wavelength (max, in ethyl acetate) of the dyes are shown below.

D-1: $^1$H-NMR, 10.22 (s, 1H), 9.08 (s, 1H), 7.96 (d, 1H), 7.85 (d, 1H), 7.75~7.45 (m, 3H), 7.16 (d, 1H), 6.97 (d, 1H), 6.65 (s, 1H), 6.43 (d, 1H), 4.50 (t, 1H), 4.28 (t, 2H), 4.02 (s, 3H), 3.62~3.22 (m, 9H), 2.95 (s, 3H), 2.60 (s, 3H), 1.82~1.62 (m, 2H), 1.48~1.08 (m, 22H), 0.87 (t, 3H), λmax=436.2 nm D-2: $^1$H-NMR, 10.36 (s, 1H), 8.50 (d, 1H), 7.98 (d, 1H), 7.78~7.45 (m, 3H), 7.28 (d, 1H), 7.13~6.85 (m, 5H), 6.70~6.54 (m, 2H), 6.45 (d, 1H), 4.50 (t, 1H), 4.25~3.75 (m, 7H), 3.60~3.18 (m, 6H), 2.91 (s, 3H), 2.58 (s, 3H), 2.45~2.06 (m, 2H), 1.70~1.40 (m, 4H), 1.29~1.00 (m, 15H), 0.61 (t, 3H), 0.42 (t, 3H), λmax=433.1 nm D-3: $^1$H-NMR, 10.30 (s, 1H), 8.57 (s, 1H), 7.98 (d, 1H), 7.78~7.47 (m, 3H), 7.29 (d, 1H), 7.10~6.90 (m, 3H), 6.82 (d, 1H), 6.68~6.53 (m, 2H), 6.46 (d, 1H), 4.48 (t, 1H), 4.20~3.70 (m, 7H), 3.60~3.20 (m, 6H), 2.90 (s, 3H), 2.58 (s, 3H), 2.46~2.00 (m, 2H), 1.70~1.43 (m, 4H), 1.28~1.00 (m, 15H), 0.61 (t, 3H), 0.43 (t, 3H), λmax=439.4 nm D-4: $^1$H-NMR, 10.16 (s, 1H), 9.01 (s, 1H), 8.06 (d, 1H), 7.81 (d, 1H), 7.72 (d, 1H), 7.56 (t, 1H), 7.37 (d, 1H), 7.04 (d, 1H), 6.95 (d, 1H), 6.65 (s, 1H), 6.47 (d, 1H), 4.97 (t, 1H), 4.32~4.10 (m, 2H), 4.00 (s, 3H), 3.56 (s, 3H), 3.54~3.13 (m, 6H), 2.90 (s, 3H), 2.56 (s, 3H), 1.82~1.56 (m, 2H), 1.47~1.02 (m, 25H), 0.86 (t, 3H), λmax=441.2 nm D-26: $^1$H-NMR, 10.30 (s, 1H), 8.49 (s, 1H), 7.95 (d, 1H), 7.75~7.43 (m, 3H), 7.25 (d, 1H), 7.14~6.87 (m, 3H), 6.65 (s, 1H), 6.44 (d, 1H), 4.48 (t, 1H), 3.95 (s, 3H), 3.93~3.20 (m, 8H), 2.92 (s, 3H), 2.56 (s, 3H), 1.82~1.43 (m, 2H), 1.42~1.00 (m, 29H), 0.90 (t, 3H), λmax=434.5 nm D-28: ¹H-NMR, 10.30 (s, 1H), 8.56 (s, 1H), 7.94 (d, 1H), 7.76~7.45 (m, 3H), 7.25 (d, 1H), 7.04 (d, 1H), 6.82 (d, 1H), 6.65 (s, 1H), 6.44 (d, 1H), 4.67 (t, 1H), 3.93 (s, 3H), 3.92~3.16 (m, 8H), 2.90 (s, 3H), 2.55 (s, 3H), 1.82~1.43 (m, 2H), 1.42~1.00 (m, 33H), 0.90 (t, 3H), λmax=440.5 nm
D-31: ¹H-NMR, 10.01 (s, 1H), 9.11 (s, 1H), 7.96 (d, 1H), 7.85 (d, 1H), 7.75~7.43 (m, 3H), 7.15 (d, 1H), 6.96 (d, 1H), 6.66 (s, 1H), 6.43 (d, 1H), 4.51 (t, 1H), 4.28 (t, 2H), 4.15 (t, 2H), 3.62~3.22 (m, 8H), 2.95 (s, 3H), 2.58 (s, 3H), 1.82~1.05 (m, 51H), 0.95~0.72 (m, 9H), λmax=438.2 nm
D-32: ¹H-NMR, 10.16 (s, 1H), 8.55 (d, 1H), 7.93 (d, 1H), 7.78~7.45 (m, 3H), 7.27 (d, 1H), 7.11~6.85 (m, 5H), 6.68~6.54 (m, 2H), 6.45 (d, 1H), 4.51 (t, 1H), 4.25~3.72 (m, 6H), 3.60~3.18 (m, 6H), 2.91 (s, 3H), 2.55 (s, 3H), 2.45~2.04 (m, 2H), 2.00~1.80 (m, 2H), 1.72~1.00 (m, 29H), 0.83 (t, 3H), 0.61 (t, 3H), 0.42 (t, 3H), λmax=434.0 nm
D-33: ¹H-NMR, 10.17 (s, 1H), 8.62 (s, 1H), 7.98 (d, 1H), 7.78~7.47 (m, 3H), 7.28 (d, 1H), 7.08~6.90 (m, 3H), 6.82 (d, 1H), 6.66~6.53 (m, 2H), 6.46 (d, 1H), 4.49 (t, 1H), 4.20~3.67 (m, 6H), 3.60~3.20 (m, 6H), 2.90 (s, 3H), 2.58 (s, 3H), 2.46~2.02 (m, 2H), 2.00~1.80 (m, 2H), 1.70~1.00 (m, 41H), 0.83 (s, 3H), 0.61 (t, 3H), 0.43 (t, 3H), λmax=440.2 nm
D-34: ¹H-NMR, 10.01 (s, 1H), 9.05 (s, 1H), 8.06 (d, 1H), 7.82 (d, 1H), 7.71 (d, 1H), 7.54 (t, 1H), 7.37 (d, 1H), 7.04 (d, 1H), 6.95 (d, 1H), 6.64 (s, 1H), 6.47 (d, 1H), 4.98 (t, 1H), 4.32~4.05 (m, 4H), 3.80~3.15 (m, 8H), 2.90 (s, 3H), 2.54 (s, 3H), 1.82~1.02 (m, 51H), 0.95~0.72 (m, 9H), λmax=442.8 nm
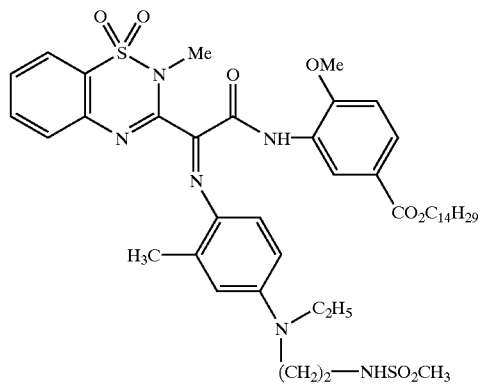
(D-1)
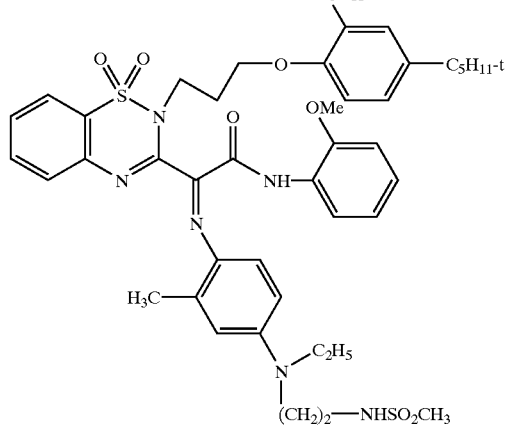
(D-2)
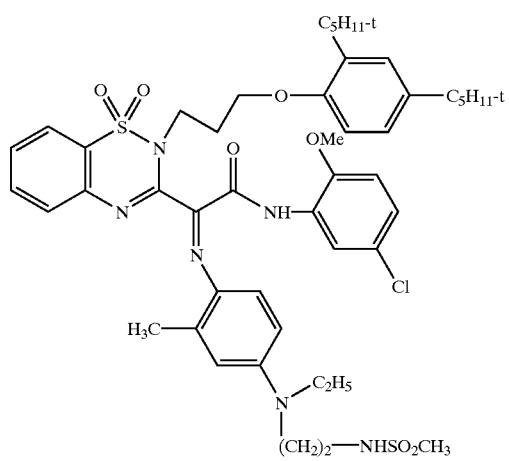
(D-3)
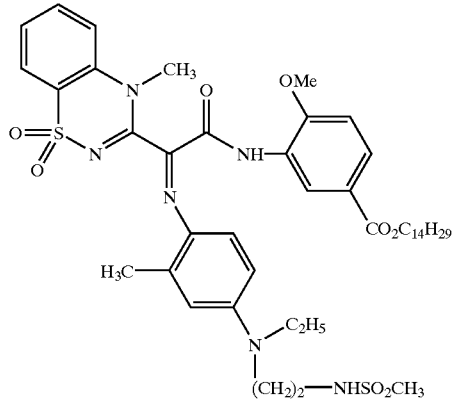
(D-4)
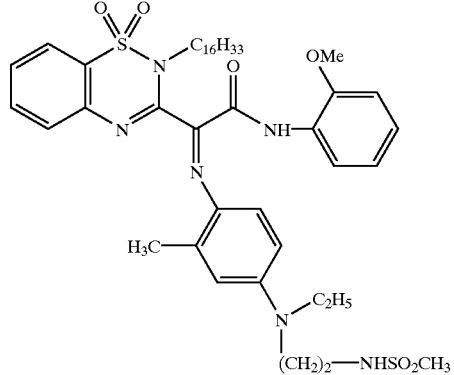
(D-26)
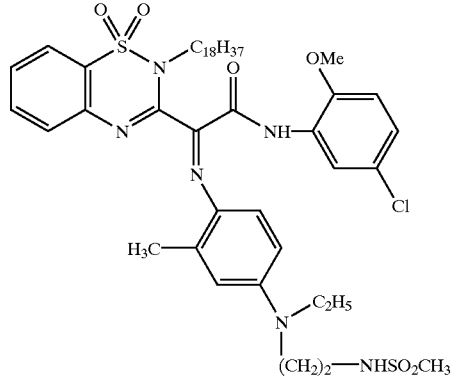
(D-28)

(D-31)

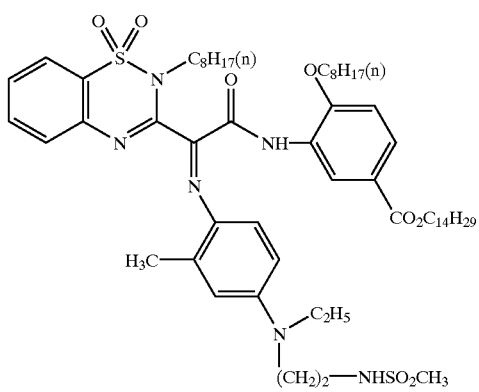

(D-34)

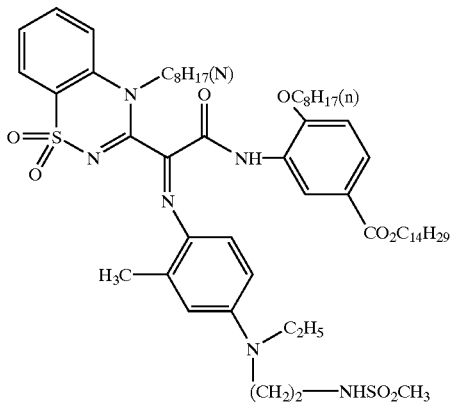

(D-32)

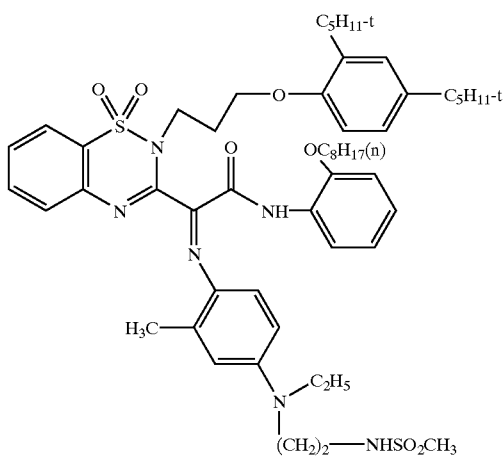

(D-33)

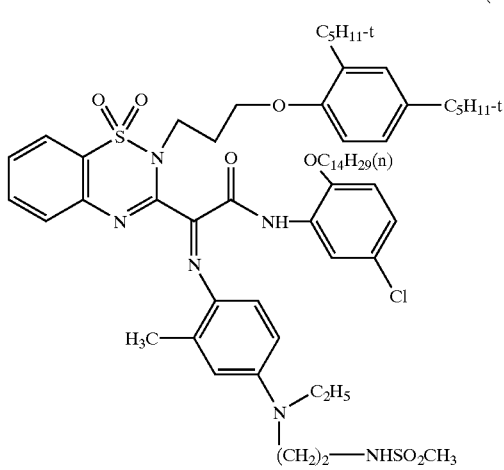

<Measurement of Absorption Spectrum>

With regard to each of the dyes for comparison (CD-1) to (CD-4) and the dyes (D-1) to (D-4), (D-26), (D-28), (D-31) to (D-34) obtained in the above Comparative Example 1 and Example 1, the absorption spectrum was measured in the following manner.

1.5 mg of any one of the dyes for comparison (CD-1) to (CD-4) and the dyes (D-1) to (D-4), (D-26), (D-28), (D-31) to (D-34) was precisely weighted in a 100 ml measuring flask, and then 100 ml of ethyl acetate was added thereto, to dissolve the dye, then the resultant solution was diluted with ethyl acetate, to prepare a sample solution 101 wherein the dye for comparison (CD-1) was used, a sample solution 102 wherein the dye for comparison (CD-2) was used, a sample solution 103 wherein the dye for comparison (CD-3) was used, a sample solution 104 wherein the dye (D-1) was used, a sample solution 105 wherein the dye (D-2) was used, a sample solution 106 wherein the dye (D-3) was used, a sample solution 107 wherein the dye (D-4) was used, a sample solution 108 wherein the dye (D-26) was used, a sample solution 109 wherein the dye (D-28) was used, a sample solution 110 wherein the dye (D-31) was used, a sample solution 111 wherein the dye (D-32) was used, a sample solution 112 wherein the dye (D-33) was used, a sample solution 113 wherein the dye (D-34) was used, and a sample solution 114 wherein the dye for comparison (CD-4) was used, respectively.

Each of the resultant sample solutions 101 to 114 was put in a quartz cell of 1-cm thickness, and then the visible absorption spectrum thereof was measured with an ultraviolet/visible spectrophotometer made by Shimadzu Corp, to calculate the molecular extinction coefficient thereof.

Further, a dihedral angle C*1 N*2 C*3 C*4 defined in formula (IV) of each dyes was calculated. In the calculation of the dihedral angle, model dyes of the obtained dyes were used and a program package Gaussian 98 (Trade name, Gaussian, Inc., US, in which a base function of 6–31G* was used) was used.

The obtained results are shown in Table 2.

TABLE 2

| Sample No. | Kind of coupler | Kind of dye | $\epsilon$ | Dihedral angle (theta) | Model dye used for the calculation | Remarks |
|---|---|---|---|---|---|---|
| 101 | Coupler for comparison (C-1) | CD-1 | $1.65 \times 10^4$ | $-36.1°$ | VR-1 | Comparative example |
| 102 | Coupler for comparison (C-2) | CD-2 | $2.13 \times 10^4$ | $-19.7°$ | VR-2 | Comparative example |
| 103 | Coupler for comparison (C-3) | CD-3 | $2.45 \times 10^4$ | $-17.2°$ | VR-3 | Comparative example |
| 104 | Coupler (1) | D-1 | $2.80 \times 10^4$ | $-21.1°$ | VD1 | This invention |
| 105 | Coupler (3) | D-2 | $2.83 \times 10^4$ | $-21.0°$ | VD2 | This invention |
| 106 | Coupler (5) | D-3 | $3.05 \times 10^4$ | $-19.5°$ | VD3 | This invention |
| 107 | Coupler (31) | D-4 | $2.93 \times 10^4$ | $9.8°$ | VD4 | This invention |
| 108 | Coupler (41) | D-26 | $2.69 \times 10^4$ | $-21.0°$ | VD2 | This invention |
| 109 | Coupler (43) | D-28 | $2.88 \times 10^4$ | $-19.5°$ | VD3 | This invention |
| 110 | Coupler (51) | D-31 | $2.60 \times 10^4$ | $-21.1°$ | VD1 | This invention |
| 111 | Coupler (59) | D-32 | $2.65 \times 10^4$ | $-21.0°$ | VD2 | This invention |
| 112 | Coupler (60) | D-33 | $2.58 \times 10^4$ | $-19.5°$ | VD3 | This invention |
| 113 | Coupler (81) | D-34 | $2.68 \times 10^4$ | $9.8°$ | VD4 | This invention |
| 114 | Coupler for comparison (C-4) | CD-4 | $1.60 \times 10^4$ | $35.7°$ | VR-8 | Comparative example |

Table 2 shows that each of the dyes obtained from the dye-forming couplers of the present invention exhibited higher molecular extinction coefficient than dyes from the dye-forming couplers for comparison. Therefore, it is understood that each of the dye-forming couplers of the present invention enables to give a density of the same level as the conventional dye-forming coupler even it is used in a thinner layer. These results mean that a silver halide color photographic light-sensitive material is improved in sharpness by using the above-said coupler of the present invention. Further, the dye-forming couplers of the present invention enable to give a density of the same level as the conventional dye-forming coupler even though both the coupler and the silver are used in smaller amounts, resulting in more reduction in production costs of the light-sensitive material.

<Test of Fading Resistance to an Acid of Dyes>

Each of the dyes for comparison (CD-1) to (CD-4) and the dyes (D-1) to (D-4), (D-26), (D-28), (D-31) to (D-34) obtained in the above Comparative Example 1 and Example 1 was subjected to test of fading resistance to an acid in the following manner.

Into 15 ml of NMP (1-methyl-2-pyrrolidinone, for peptide synthesis, purity: 99%), was dissolved 1.0 mg of any one of the dyes for comparison (CD-1) to (CD-4) or the dyes (D-1) to (D-4), (D-26), (D-28), (D-31) to (D-34), to prepare a sample solution 201 wherein the dye for comparison (CD-1) was used, a sample solution 202 wherein the dye for comparison (CD-2) was used, a sample solution 203 wherein the dye for comparison (CD-3) was used, a sample solution 204 wherein the dye (D-1) was used, a sample solution 205 wherein the dye (D-2) was used, a sample solution 206 wherein the dye (D-3) was used, a sample solution 207 wherein the dye (D-4) was used, a sample solution 208 wherein the dye (D-26) was used, a sample solution 209 wherein the dye (D-28) was used, a sample solution 210 wherein the dye (D-31) was used, a sample solution 211 wherein the dye (D-32) was used, a sample solution 212 wherein the dye (D-33) was used, a sample solution 213 wherein the dye (D-34) was used, and a sample solution 214 wherein the dye for comparison (CD-4) was used, respectively.

Phosphoric acid was added to a solution prepared by mixing 0.49 g of boric acid, 8 ml of a 1-N aqueous acetic acid solution, and 16 ml of a 1-N aqueous phosphoric acid solution in a 200-ml measuring flask (Britton-Robinson buffer solution, which will be referred to as B.R. buffer A solution hereinafter), to adjust the pH of the resultant solution to 1.15. The temperature of the solution was kept at a constant temperature of 60° C. This buffer solution was added to each of the previously-prepared sample solutions 201 to 214 until the total amount would be 25 ml. Visible absorption spectra of the solution immediately after the preparation thereof and of the solution after the storage thereof at a constant temperature of 60° C. for 3 hours, were measured with the ultraviolet/visible spectrometer made by Shimadzu Corp. Thus, respective absorbances were calculated at a maximum absorption wavelength.

The ratio of the concentration of the dye in the sample before the test of fading resistance to an acid, to the concentration of the dye in the sample after the test of fading resistance to an acid (that is, remaining ratio (%)) was calculated, using the ratio of the absorbance of the sample before the test of fading resistance to an acid, to the absorbance of the sample after the test of fading resistance to an acid. This ratio was used as an index for evaluation of fastness of a dye to an acid. The results are shown in Table 3.

TABLE 3

| Sample No. | Kind of coupler | Kind of dye | Remaining ratio (%) | Remarks |
|---|---|---|---|---|
| 201 | Coupler for comparison (C-1) | CD-1 | 20 | Comparative example |
| 202 | Coupler for comparison (C-2) | CD-2 | 83 | Comparative example |

TABLE 3-continued

| Sample No. | Kind of coupler | Kind of dye | Remaining ratio (%) | Remarks |
|---|---|---|---|---|
| 203 | Coupler for comparison (C-3) | CD-3 | 81 | Comparative example |
| 204 | Coupler (1) | D-1 | 93 | This invention |
| 205 | Coupler (3) | D-2 | 97 | This invention |
| 206 | Coupler (5) | D-3 | 98 | This invention |
| 207 | Coupler (31) | D-4 | 92 | This invention |
| 208 | Coupler (41) | D-26 | 96 | This invention |
| 209 | Coupler (43) | D-28 | 97 | This invention |
| 210 | Coupler (51) | D-31 | 92 | This invention |
| 211 | Coupler (59) | D-32 | 95 | This invention |
| 212 | Coupler (60) | D-33 | 97 | This invention |
| 213 | Coupler (81) | D-34 | 93 | This invention |
| 214 | Coupler for comparison (C-4) | CD-4 | 25 | Comparative example |

As is apparent from the results in Table 3, the dyes obtained from the dye-forming couplers of the present invention were quite excellent in fastness to an acid. Additionally, as is apparent from the results in Tables 2 and 3, the dyes represented by formula (III), and the dyes represented by formula (IV) of the present invention, which had the dihedral angle satisfying the definition of the present invention, were high in molecular absorption coefficient and excellent in fastness.

Comparative Example 2

The Numbers of Compounds are Same as Those in the Comparative Example 1

1. Preparation of an Emulsified Dispersion of the Coupler for Comparison (C-1)

Into 10 ml of ethyl acetate were dissolved 0.62 g of the coupler for comparison (C-1) and 2.6 g of tricresyl phosphate while heating. (This will be referred to as an oil phase solution.) Separately, 4.2 g of gelatin was added to 25 ml of water at room temperature, to swell the gelatin sufficiently. Thereafter, the resultant admixture was heated to 40° C., so that the gelatin was completely dissolved in water. While the temperature of this gelatin solution was kept at about 40° C., were added thereto 3 ml of a 5% aqueous sodium dodecylbenzenesulfonate solution and the previously-prepared oil phase solution. The resultant admixture was emulsified and dispersed with a homogenizer, to prepare an emulsified dispersion. The coupler for comparison (C-1) is same as that in the Comparative Example 1.

2. Preparation of a Light-Sensitive Material for Comparison

The thus-obtained emulsified dispersion of the coupler (C-1) for comparison was used, to produce a coating solution having the following composition. Then, this coating solution was applied onto a polyethylene-laminated paper having an undercoat layer, in the manner that the amount of the silver halide emulsion would be 0.33 mmol/m$^2$ in terms of silver and the amount of the coupler would be 0.7 mmol/m$^2$. Gelatin was applied, as a protective layer, onto the resultant surface of the paper in the manner that the amount of the gelatin would be 2 g/m, to produce a sample 301 as a light-sensitive material for comparison.

(Composition of the coating solution)

| | |
|---|---|
| Emulsion: silver chlorobromide (This was composed of cubic grains, the substrate of which was silver chloride. A part of its surface locally contained 0.3 mol % (in total) of silver | 13 g |

-continued (Composition of the coating solution)

| | |
|---|---|
| bromide. The average grain size thereof was 60 μm. Each of sensitizing dyes A, B and C was added thereto in an amount of 1.4 × 10$^{-4}$ mole per mole of silver halide, to give spectral sensitivity.) | |
| 10% Gelatin | 28 g |
| Emulsified dispersion of the coupler for comparison (C-1) | 22 g |
| Water | 37 ml |
| 4% Sodium 1-hydroxy-3,5-dichloro-s-triazine aqueous solution | 5 ml |

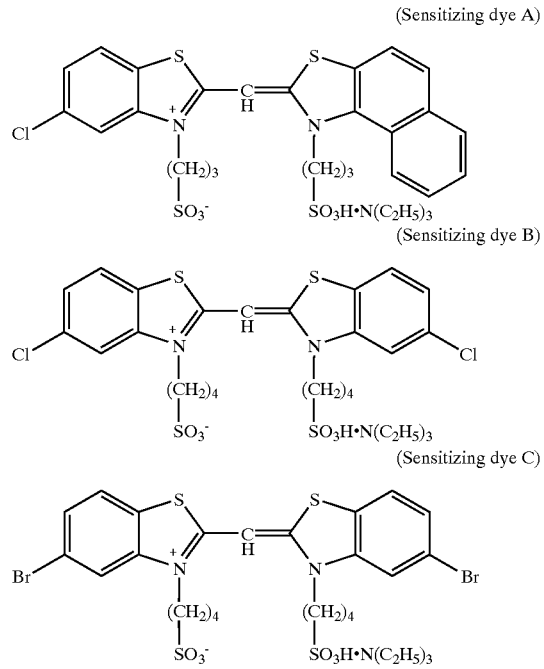

(Sensitizing dye A)

(Sensitizing dye B)

(Sensitizing dye C)

Comparative Example 3

The Numbers of Compounds are Same as Those in the Comparative Example 1

1. Preparation of Emulsified Dispersion of Coupler for Comparison (C-2), Emulsified Dispersion of Coupler for comparison (C-3), Emulsified Dispersion of Coupler for comparison (C-4), and Emulsified Dispersion of Coupler for comparison (C-5)

Emulsified dispersion of Coupler for comparison (C-2), emulsified dispersion of Coupler for comparison (C-3), emulsified dispersion of Coupler for comparison (C-4), and emulsified dispersion of Coupler for comparison (C-5), were prepared in the same manner as in the section 1 "Preparation of Emulsified Dispersion of Coupler for comparison (C-1)" in Comparative Example 2, except for replacing the Coupler for comparison (C-1) with the Coupler for comparison (C-2) (Compound (XV) described in U.S. Pat. No. 3,841,880), the Coupler for comparison (C-3) (Compound (17) described in JP-A-52-82423), the Coupler for comparison (C-4) (Compound (27) described in JP-A-10-198008), and the Coupler for comparison (C-5) (Compound (6) described in JP-A-58-111943), respectively. The couplers for comparison (C-2) to (C-4) are the same as those used in the Comparative Example 1.

was used, Sample 310 wherein the coupler (51) was used, Sample 311 wherein the coupler (59) was used, Sample 312 wherein the coupler (60) was used, Sample 313 wherein the (81) was used, were prepared in the same manner as in the section 2 "Preparation of light-sensitive material for comparison" in Comparative Example 2, except for replacing the emulsified dispersion of the coupler (C-1) for comparison with the emulsified dispersions of the exemplified couplers (1), (3), (5), (31), (41), (43), (51), (59), (60), and (81) of the present invention, respectively.

<Evaluation Tests of Color-Forming Property and Color Image Fastness>

Using samples 301 to 315, which were obtained in the foregoing Comparative Examples 2 to 3 and Example 2, the evaluation tests of color-forming property and color image fastness were carried out in the following way.

First, each of the samples was subjected to wedge-wise exposure with a white light, and then subjected to color- Coupler for comparison (C-5)

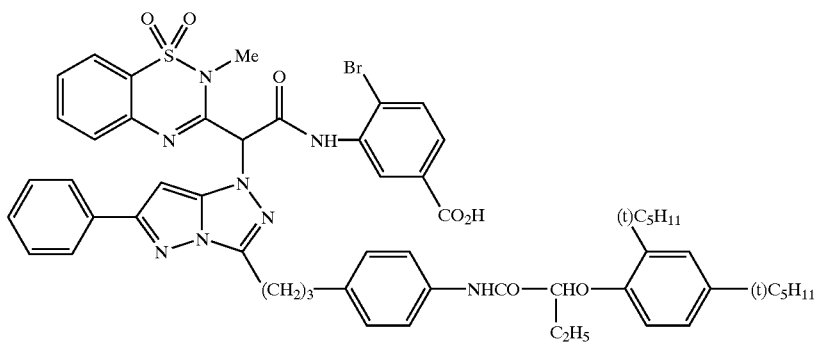

(Compound (6) described in JP-A-58-111943)

2. Preparation of Light-Sensitive Material for Comparison

Light-sensitive material samples 302, 303, 314, and 315 for comparison were prepared in the same manner as in the section 2 "Preparation of light-sensitive material for comparison" in Comparative Example 2, except for replacing the emulsified dispersion of Coupler for comparison (C-1) with the emulsified dispersion of Coupler for comparison (C-2) (Compound (XV) described in U.S. Pat. No. 3,841,880), the emulsified dispersion of Coupler for comparison (C-3) (Compound (17) described in JP-A-52-82423), the emulsified dispersion of the Coupler for comparison (C-4) (Compound (27) described in JP-A-10-198008), and the emulsified dispersion of the Coupler for comparison (C-5) (Compound (6) described in JP-A-58-111943), respectively.

Example 2

1. Preparation of each of Emulsified Dispersions of Couplers (1), (3), (5), (31), (41), (43), (51), (59), (60), and (81)

Each of emulsified dispersions of couplers according to of the present invention was prepared in the same manner as in the section 1 "Preparation of Emulsified Dispersion of Coupler for comparison (C-1)" in Comparative Example 2, except for replacing the coupler for comparison (C-1) with the foregoing exemplified couplers (1), (3), (5), (31), (41), (43), (51), (59), (60), and (81) of the present invention.

2. Preparation of Light-Sensitive Material of the Present Invention

Light-sensitive material Sample 304 wherein the coupler (1) was used, Sample 305 wherein the coupler (3) was used, Sample 306 wherein the coupler (5) was used, Sample 307 wherein the coupler (31) was used, Sample 308 wherein the coupler (41) was used, Sample 309 wherein the coupler (43)

development processing according to the processing steps shown below.

(Processing steps)

| Step | Temperature | Time |
|---|---|---|
| Color developing | 38.5° C. | 45 seconds |
| Bleach-fixing | 30 to 36° C. | 45 seconds |
| Stabilization (1) | 30 to 37° C. | 20 seconds |
| Stabilization (2) | 30 to 37° C. | 20 seconds |
| Stabilization (3) | 30 to 37° C. | 20 seconds |
| Drying | 70 to 85° C. | 70 seconds |

The respective steps of the color developing, the bleach-fixing, and the stabilization (1), (2) and (3) were carried out by immersing each of the samples into the following respective processing solutions under the above-mentioned conditions.

(Color-developer in the color-developing step)

| | |
|---|---|
| Water | 800 ml |
| Dimethylpolysiloxane-series surfactant (Silicone KF351A (trade name), manufactured by Shin-Etsu Chemical Co., Ltd.) | 0.1 g |

-continued

| | |
|---|---|
| Triethanolamine | 11.6 g |
| Ethylenediaminetetraacetic acid | 4.0 g |
| Sodium 4,5-dihydroxybenzene-1,3-disulfonate | 0.5 g |
| Potassium chloride | 10.0 g |
| Potassium bromide | 0.040 g |
| Triazinylaminostylbene-series fluorescent whitening agent (Hakkol FWA-SF (trade name), manufactutured by Showa Chemicals Inc.) | 2.5 g |
| Sodium sulfite | 0.1 g |
| Disodium-N,N-bis(sulfonatoethyl)hydroxylamine | 8.5 g |
| N-ethyl-N-(β-methanesulfonamidoethyl)-3-methyl-4-aminoaniline · 3/2 · sulfate · monohydrate | 5.0 g |
| Potassium carbonate | 26.3 g |
| Water to make | 1000 ml |
| pH (adjusted with potassium hydroxide and sulfuric acid at 25° C.) | 10.15 |
| (Bleach-fixing solution in the bleach-fixing step) | |
| Water | 800 ml |
| Iron (III) ammonium ethylenediaminetetraacetate | 47.0 g |
| Ethylenediaminetetraacetic acid | 1.4 g |
| m-Carboxymethylbenzenesulfinic acid | 8.3 g |
| Nitric acid (67%) | 16.5 g |
| Imidazole | 14.6 g |
| Ammonium thiosulfate aq. solution (750 g/liter) | 107 ml |
| Ammonium sulfite | 16.0 g |
| Potassium metabisulfite | 23.1 g |
| Water to make | 1000 ml |
| pH (adjusted with acetic acid and ammonia at 25° C.) | 6.0 |
| (Stabilizing solution in the stabilization (1) to (3) steps) | |
| Sodium chlorinated-isocyanurate | 0.02 g |
| Deionized water (electroconductivity: 5 µS/cm or less) | 1000 ml |
| pH | 6.5 |

The processed samples 301 to 314 each colored yellow. Each of the light-sensitive material samples 304 to 313 of the present invention exhibited higher Dmax than those of light-sensitive material samples 301 to 303 and 314 for comparison. Further, in each of the samples of the present invention, a hue of the dye image was sharp. On the other hand, sample 315 generated a magenta color, resulting in no yellow dye image.

Next, each of the processed samples 301 to 314 was subjected to a test of fading resistance to humidity and heat under the conditions of 80° C. and relative humidity of 70%.

The color density of each of samples before and after the test of fading resistance to humidity and heat was measured by means of TCD type densitometer made by Fuji Photo Film Co., Ltd. Further, a proportion of color density (rate of remaining density: %) before and after the test of fading resistance to humidity and heat at the point of 1.0 of color density was calculated. The rate of remaining density was used to evaluate the dye image fastness.

Then, these samples were subjected to exposure to light in the condition of 14 day-illumination under a Xe light source of 100,000 lux (5-hour light/1-hour dark intermittent illumination), to evaluate fastness of dye image. The results which were obtained are shown in Table 4.

TABLE 4

| Sample No. | Kind of coupler | Kind of dye | Dmax. | Fastness to humidity and heat Remaining rate (%) | Fastness to light Remaining rate (%) | Remarks |
|---|---|---|---|---|---|---|
| 301 | Coupler for comparison (C-1) | CD-1 | 1.41 | 80 | 85 | Comparative example |
| 302 | Coupler for comparison (C-2) | CD-2 | 1.01 | 93 | 68 | Comparative example |
| 303 | Coupler for comparison (C-3) | CD-3 | 1.23 | 92 | 61 | Comparative example |
| 304 | Coupler (1) | D-1 | 1.92 | 99 | 81 | This invention |
| 305 | Coupler (3) | D-2 | 2.05 | 99 | 83 | This invention |
| 306 | Coupler (5) | D-3 | 2.12 | 99 | 82 | This invention |
| 307 | Coupler (31) | D-4 | 1.83 | 98 | 81 | This invention |
| 308 | Coupler (41) | D-26 | 2.01 | 99 | 82 | This invention |
| 309 | Coupler (43) | D-28 | 2.08 | 98 | 83 | This invention |
| 310 | Coupler (51) | D-31 | 1.85 | 99 | 86 | This invention |
| 311 | Coupler (59) | D-32 | 1.90 | 99 | 88 | This invention |
| 312 | Coupler (60) | D-33 | 1.83 | 99 | 89 | This invention |
| 313 | Coupler (81) | D-34 | 1.93 | 98 | 88 | This invention |
| 314 | Coupler for comparison (C-4) | CD-4 | 1.35 | 92 | 82 | Comparative example |

As is apparent from Table 4, it is understood that the light-sensitive materials according to the present invention exhibited a high color-forming property, and in addition they were excellent in fastness to humidity and heat. It is also understood that an excellent fastness to light was attained particularly in the case where both R1 and R3 were a nondiffusible group, respectively.

Example 3

After corona discharge treatment was performed on the surface of a paper support whose both surfaces were laminated with polyethylene, a gelatin subbing layer containing sodium dodecylbenzenesulfonate was formed on that surface. In addition, photographic constituting layers from the first layer to the seventh layer were coated on the support to make a silver halide color photographic light-sensitive material (sample 001) having the following layer arrangement. The coating solution for each of the photographic constituting layers were prepared as follows.

(Preparation of Coating Solution for First Layer)

62 g of a yellow coupler (ExY), 8 g of a dye image stabilizer (Cpd-1), 4 g of a dye image stabilizer (Cpd-2), 8 g of a dye image stabilizer (Cpd-3) and 2 g of a dye image stabilizer (Cpd-8) were dissolved in 23 g of a solvent (Solv-1) and 80 ml of ethyl acetate, and the resultant solution was added to 220 g of an aqueous 23.5% by mass gelatin solution containing 4 g of sodium dodecylbenzenesulfonate. The resultant mixture was emulsified and dispersed by a high speed stirring emulsifier (DISOLVER), followed by addition of water to prepare 900 g of emulsified dispersion A.

Separately, a silver chlorobromide emulsion A (cubic, a 3:7 mixture (Ag molar ratio) of a large-size emulsion A with an average grain size of 0.72 μm and a small-size emulsion A with an average grain size of 0.60 μm. The variation coefficients of grain size distributions of the large-size and the small-size emulsions were 0.08 and 0.10, respectively. Each emulsion consisted of silver halide grains in which 0.3 mole % of silver bromide was locally contained in a portion of the grain surface and the remainder was silver chloride) was prepared.

To this emulsion were added blue-sensitive sensitizing dyes A, B and C shown below in $1.4 \times 10^{-4}$ mole for the large-size emulsion and $1.7 \times 10^{-4}$ mole for the small-size emulsion, per mole of silver halide, respectively. Chemical ripening of this emulsion was optimized by adding a sulfur sensitizer and a gold sensitizer.

The emulsified dispersion A described above and this silver chlorobromide emulsion A were mixed and dissolved to prepare a coating solution of the first layer having the following composition. The coating amount of each silver halide emulsion is represented by the coating amount of silver.

(Preparation of Coating Solutions for Second Layer to Seventh Layer)

The coating solutions for the second layer to the seventh layer were prepared following the same procedures as for the coating solution of the first layer. 1-oxy-3,5-dichloro-s-triazine sodium salt was used as a gelatin hardener in each layer. In addition, Ab-1, Ab-2, Ab-3 and Ab-4 were added to each layer such that their total amounts were 15.0 mg/m², 60.0 mg/m², 5.0 mg/m² and 10.0 mg/m² respectively.

Antiseptic (Ab-1)

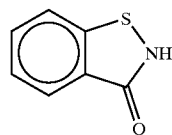

Antiseptic (Ab-2)

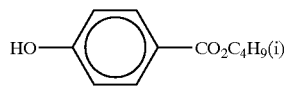

Antiseptic (Ab-3)

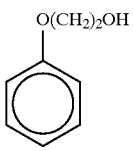

Antiseptic (Ab-4)

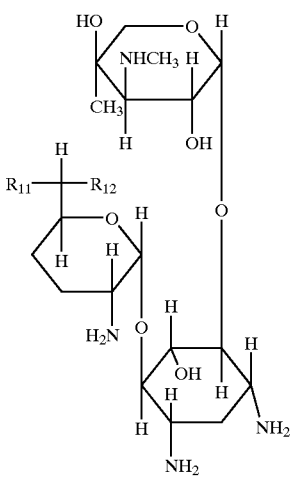

A mixture in 1:1:1:1 (molar ratio) of a, b, c, and d

For the silver chlorobromide emulsions of the respective light-sensitive emulsion layers, the following spectral sensitizing dyes were used.

Blue-Sensitive Emulsion Layer (Sensitizing dye A)

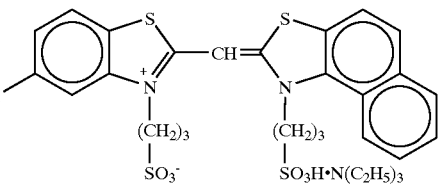

(Sensitizing dye B)

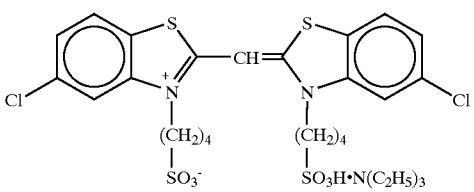

(Sensitizing dye C)

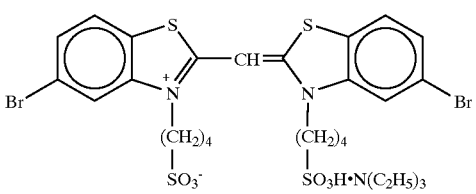

(The sensitizing dyes A, B, and C were added to the large-size emulsion in an amount of $1.4 \times 10^{-4}$ mol, respectively per mol of silver halide, and to the small-size emulsion in an amount of $1.7\times10^{-4}$ mol, respectively per mol of silver halide.)

Green-Sensitive Emulsion Layer

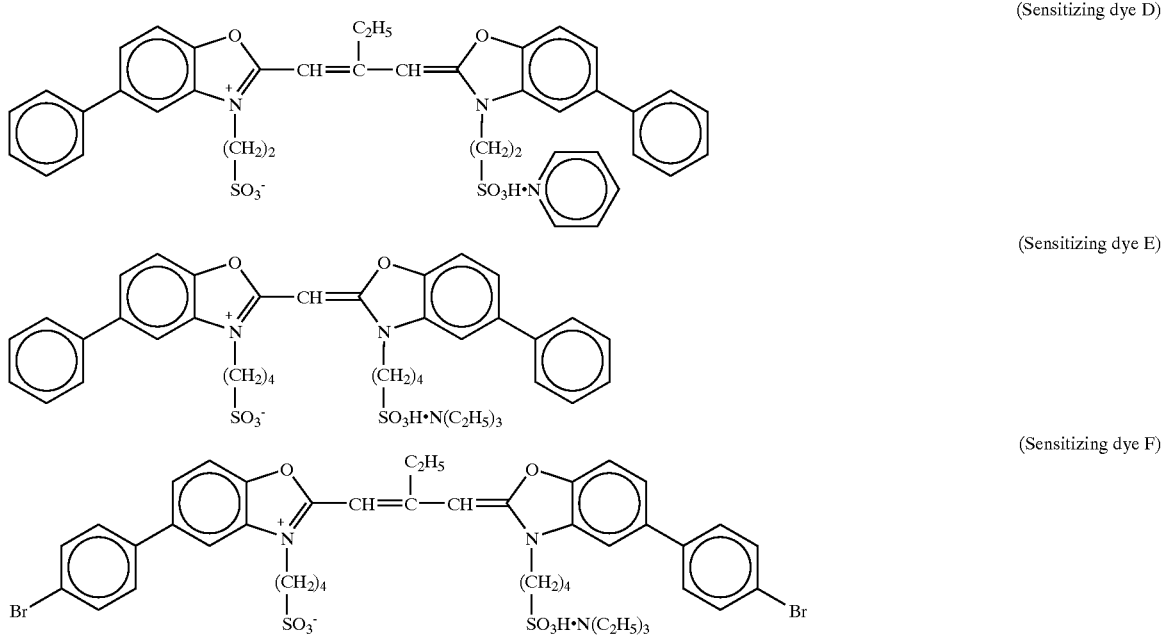

(Sensitizing dye D)

(Sensitizing dye E)

(Sensitizing dye F)

(The sensitizing dye D was added to the large-size emulsion in an amount of $3.0\times10^{-4}$ mol, and to the small-size emulsion in an amount of $3.6\times10^{-4}$ mol, per mol of the silver halide; the sensitizing dye E was added to the large-size emulsion in an amount of $4.0\times10^{-5}$ mol, and to the small-size emulsion in an amount of $7.0\times10^{-5}$ mol, per mol of the silver halide; and the sensitizing dye F was added to the large-size emulsion in an amount of $2.0\times10^{-4}$ mol, and to the small-size emulsion in an amount of $2.8\times10^{-4}$ mol, per mol of the silver halide.)

Red-Sensitive Emulsion Layer (Sensitizing dye G)

(Sensitizing dye H)

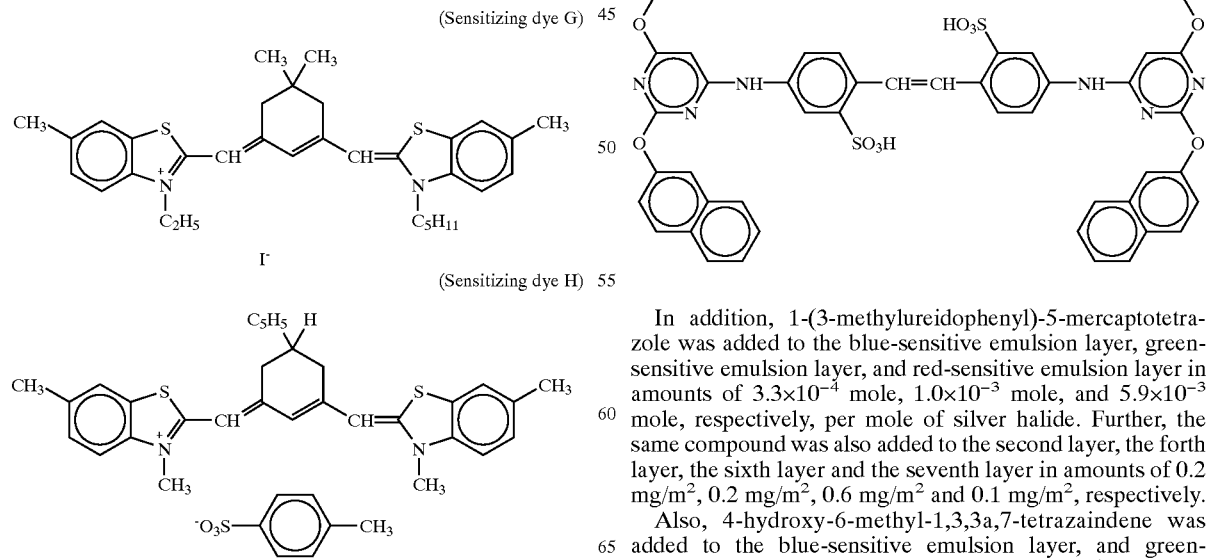

(The sensitizing dyes G, and H were added to the large-size emulsion in an amount of $6.0\times10^{-5}$ mol, respectively, per mol of silver halide, and to the small-size emulsion in an amount of $9.0\times10^{-5}$ mol, respectively, per mol of silver halide.)

Further, the following compound I was added to the red-sensitive emulsion layer in an amount of $2.6\times10^{-3}$ mol per mol of the silver halide.

(Compound I)

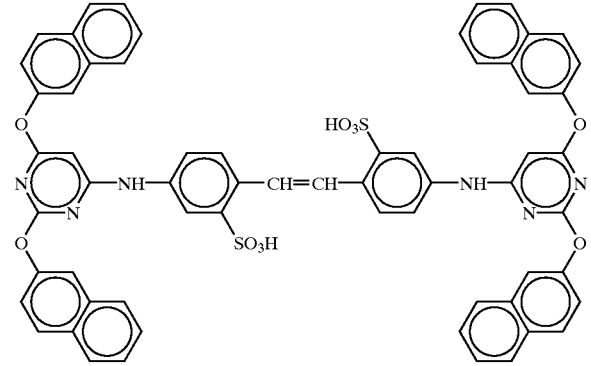

In addition, 1-(3-methylureidophenyl)-5-mercaptotetrazole was added to the blue-sensitive emulsion layer, green-sensitive emulsion layer, and red-sensitive emulsion layer in amounts of $3.3\times10^{-4}$ mole, $1.0\times10^{-3}$ mole, and $5.9\times10^{-3}$ mole, respectively, per mole of silver halide. Further, the same compound was also added to the second layer, the forth layer, the sixth layer and the seventh layer in amounts of 0.2 mg/m$^2$, 0.2 mg/m$^2$, 0.6 mg/m$^2$ and 0.1 mg/m$^2$, respectively.

Also, 4-hydroxy-6-methyl-1,3,3a,7-tetrazaindene was added to the blue-sensitive emulsion layer, and green-sensitive emulsion layer in amounts of $1\times10^{-4}$ mole and $2\times10^{-3}$ mole, respectively, per mole of silver halide.

Further, a copolymer of methacrylic acid and butyl acrylate (ratio by mass, 1:1; average molecular weight, 200,000 to 400,000) was added to the red-sensitive emulsion layer in an amount of 0.05 g/m².

Further, a mixture (molar ratio 9:1) of disodium catechol-3,5-disulfonate and 2,6-bishydroxyamino-4-diethylamino-1,3,5-triazine was added to the second layer, the fourth layer and the sixth layer in an amount of 6 mg/m², 6 mg/m² and 18 mg/m², respectively.

Furthermore, to prevent irradiation, the following dyes (the number given in parenthesis represents the coating amount) were added to the emulsion layers.

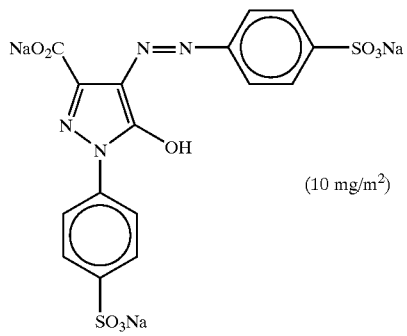
(10 mg/m²)

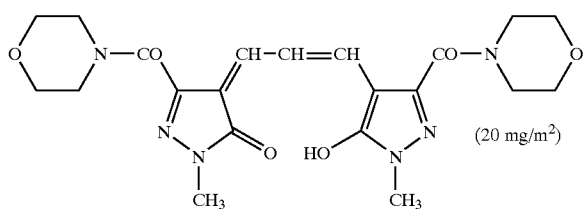
(20 mg/m²)

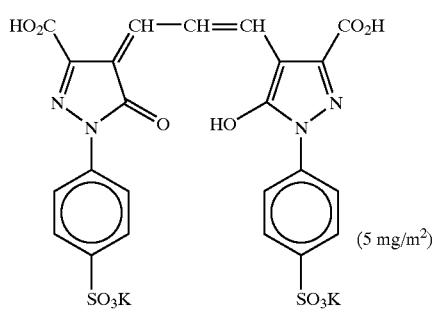
(5 mg/m²)

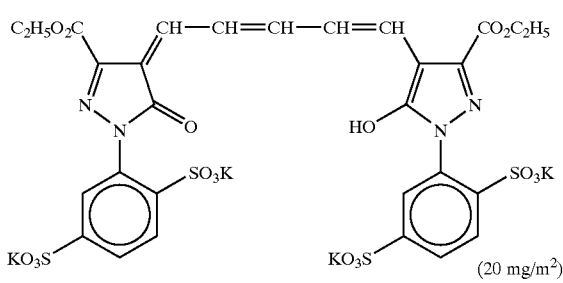
(20 mg/m²)

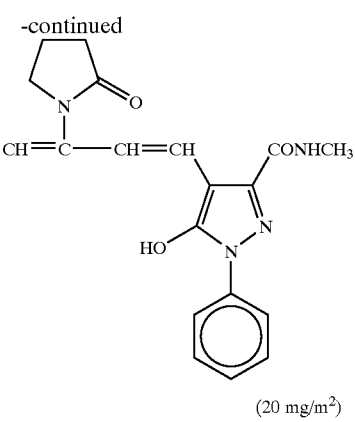
(20 mg/m²)

(Layer Constitution)

The composition of each layer is shown below. The numbers show coating amounts (g/m²). In the case of the silver halide emulsion, the coating amount is in terms of silver.

Support

Polyethylene Resin Laminated Paper

{The polyethylene resin on the first layer side contained a white pigment ($TiO_2$; content of 16 mass %, ZnO; content of 4 mass %), a fluorescent whitening agent (a mixture of 4,4'-bis(benzoxazolyl)stilbene and 4,4'-bis(5-methylbenzoxazolyl)stilbene mixed in a ratio of 8/2; content of 0.05 mass %) and a bluish dye (ultramarine)}

| First Layer (Blue-Sensitive Emulsion Layer) | |
| --- | --- |
| A silver chlorobromide emulsion A (cubic, a 3:7 mixture of a large-size emulsion A having an average grain size of 0.72 μm, and a small-size emulsion A having an average grain size of 0.60 μm (in terms of mol of silver). The deviation coefficients of the grain size distribution were 0.08 and 0.10, respectively. Each emulsion had 0.3 mol % of silver bromide contained locally in part of the grain surface whose substrate was made up of silver chloride) | 0.26 |
| Gelatin | 1.35 |
| Yellow coupler (ExY) | 0.62 |
| Color-image stabilizer (Cpd-1) | 0.08 |
| Color-image stabilizer (Cpd-2) | 0.04 |
| Color-image stabilizer (Cpd-3) | 0.08 |
| Color-image stabilizer (Cpd-8) | 0.02 |
| Solvent (Solv-1) | 0.23 |
| Second Layer (Color-Mixing Inhibiting Layer) | |
| Gelatin | 0.99 |
| Color-mixing inhibitor (Cpd-4) | 0.09 |
| Color-mixing inhibiting auxiliary (Cpd-5) | 0.018 |
| Stabilizer (Cpd-6) | 0.13 |
| Color-mixing inhibitor (Cpd-7) | 0.01 |
| Solvent (Solv-1) | 0.06 |
| Solvent (Solv-2) | 0.22 |
| Third Layer (Green-Sensitive Emulsion Layer) | |
| A silver chlorobromide emulsion B (cubic, a 1:3 mixture of a large-size emulsion B having an average grain size of 0.45 μm, and a small-size emulsion B having an average grain size of 0.35 μm (in terms of mol of silver). The deviation coefficients of the grain size distribution were 0.10 and 0.08, respectively. Each emulsion had 0.4 mol % of silver bromide contained locally in part of the grain surface whose substrate | 0.14 |

-continued

| | |
|---|---|
| was made up of silver chloride) | |
| Gelatin | 1.36 |
| Magenta coupler (ExM) | 0.15 |
| Ultraviolet absorbing agent (UV-1) | 0.05 |
| Ultraviolet absorbing agent (UV-2) | 0.03 |
| Ultraviolet absorbing agent (UV-3) | 0.02 |
| Ultraviolet absorbing agent (UV-4) | 0.03 |
| Ultraviolet absorbing agent (UV-6) | 0.01 |
| Color-image stabilizer (Cpd-2) | 0.02 |
| Color-mixing inhibitor (Cpd-4) | 0.002 |
| Stabilizer (Cpd-6) | 0.09 |
| Color-image stabilizer (Cpd-8) | 0.02 |
| Color-image stabilizer (Cpd-9) | 0.03 |
| Color-image stabilizer (Cpd-10) | 0.01 |
| Color-image stabilizer (Cpd-11) | 0.0001 |
| Solvent (Solv-3) | 0.11 |
| Solvent (Solv-4) | 0.22 |
| Solvent (Solv-5) | 0.20 |
| Fourth Layer (Color-Mixing Inhibiting Layer) | |
| Gelatin | 0.71 |
| Color-mixing inhibitor (Cpd-4) | 0.06 |
| Color-mixing inhibiting auxiliary (Cpd-5) | 0.013 |
| Stabilizer (Cpd-6) | 0.10 |
| Color-mixing inhibitor (Cpd-7) | 0.007 |
| Solvent (Solv-1) | 0.04 |
| Solvent (Solv-2) | 0.16 |
| Fifth Layer (Red-Sensitive Emulsion Layer) | |
| A silver chlorobromide emulsion C (cubic, a 1:4 mixture of a large-size emulsion C having an average grain size of 0.50 μm, and a small-size emulsion C having an average grain size of 0.41 μm (in terms of mol of silver). The deviation coefficients of the grain size distribution were 0.09 and 0.11, respectively. Each emulsion had 0.5 mol % of silver bromide contained locally in part of the grain surface whose substrate was made up of silver chloride) | 0.20 |
| Gelatin | 1.11 |
| Cyan coupler (ExC-2) | 0.13 |
| Cyan coupler (ExC-3) | 0.03 |
| Color-image stabilizer (Cpd-1) | 0.05 |
| Stabilizer (Cpd-6) | 0.05 |
| Color-mixing inhibitor (Cpd-7) | 0.02 |
| Color-image stabilizer (Cpd-9) | 0.04 |
| Color-image stabilizer (Cpd-10) | 0.01 |
| Color-image stabilizer (Cpd-14) | 0.01 |
| Color-image stabilizer (Cpd-15) | 0.03 |
| Color-image stabilizer (Cpd-16) | 0.05 |
| Color-image stabilizer (Cpd-17) | 0.05 |
| Color-image stabilizer (Cpd-18) | 0.06 |
| Color-image stabilizer (Cpd-19) | 0.06 |
| Solvent (Solv-5) | 0.15 |
| Solvent (Solv-8) | 0.05 |
| Solvent (Solv-9) | 0.10 |
| Sixth Layer (Ultraviolet Absorbing Layer) | |
| Gelatin | 0.66 |
| Ultraviolet absorbing agent (UV-1) | 0.19 |
| Ultraviolet absorbing agent (UV-2) | 0.06 |
| Ultraviolet absorbing agent (UV-3) | 0.06 |
| Ultraviolet absorbing agent (UV-4) | 0.05 |
| Ultraviolet absorbing agent (UV-5) | 0.08 |
| Ultraviolet absorbing agent (UV-6) | 0.01 |
| Solvent (Solv-7) | 0.25 |
| Seventh Layer (Protective Layer) | |
| Gelatin | 1.00 |
| Acryl-modified copolymer of polyvinyl alcohol (modification degree: 17%) | 0.04 |
| Liquid paraffin | 0.02 |
| Surface-active agent (Cpd-13) | 0.01 |

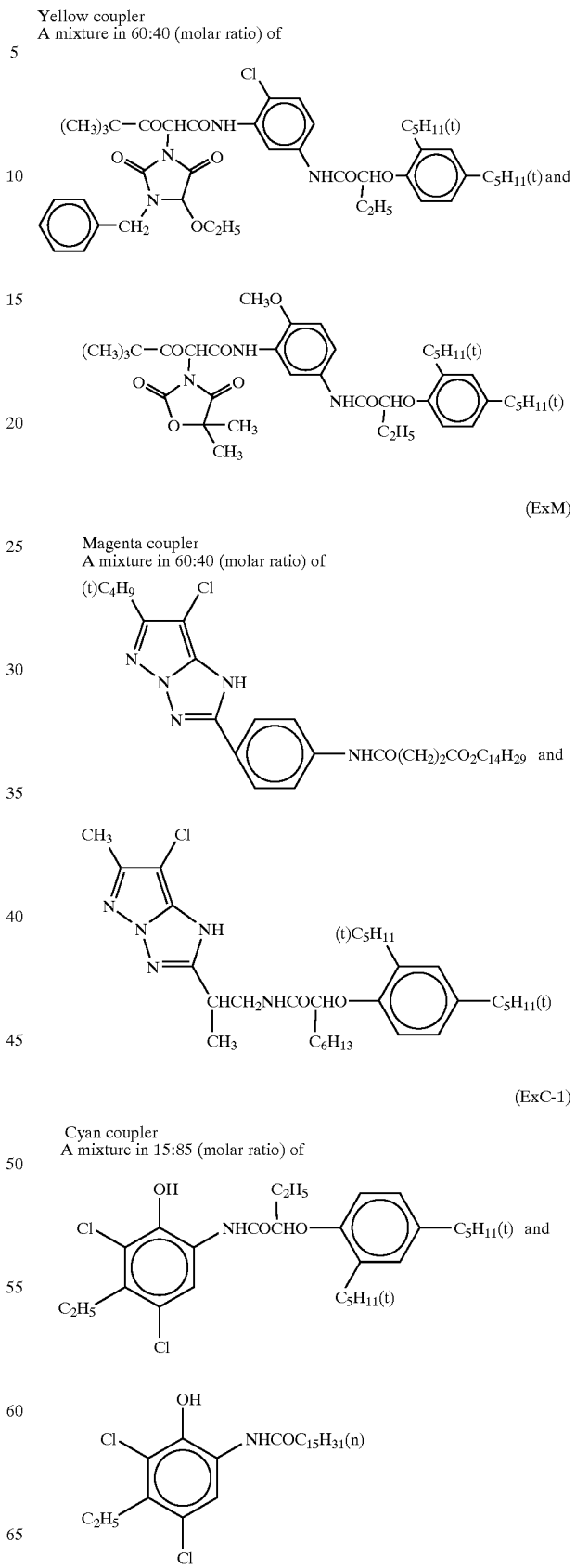

Cyan coupler (ExC-2)

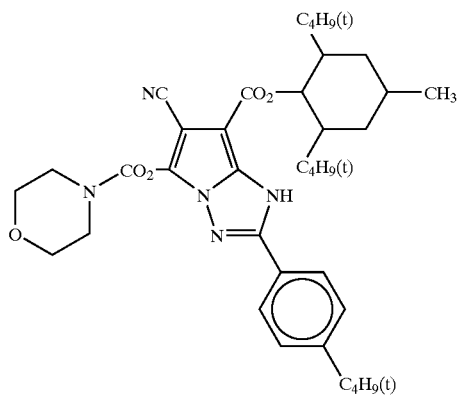

Cyan coupler (ExC-3)
A mixture in 50:25:25 (molar ratio) of

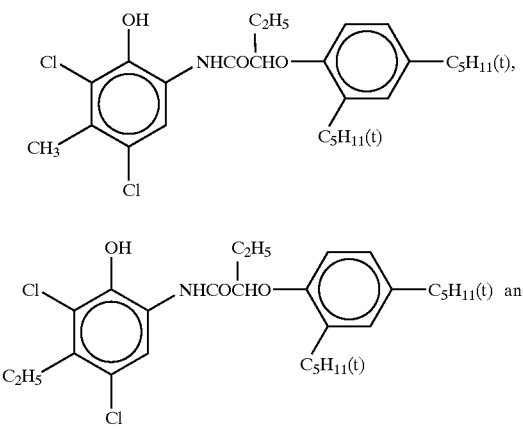

and

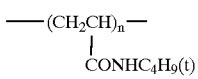

Color-image stabilizer (Cpd-1)

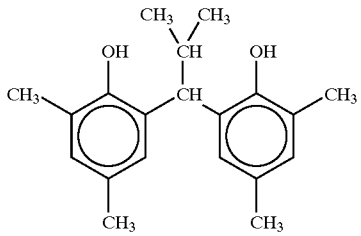

number-average molecular weight 60,000

Color-image stabilizer (Cpd-2)

—(CH₂CH)ₙ—
      |
      CONHC₄H₉(t)

Color-image stabilizer (Cpd-3)

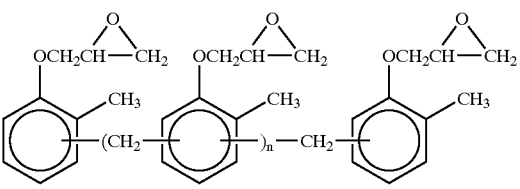

N = 7~8 (average value)

Color-mixing inhibitor (Cpd-4)
A mixture in 1:1:1(molar) of

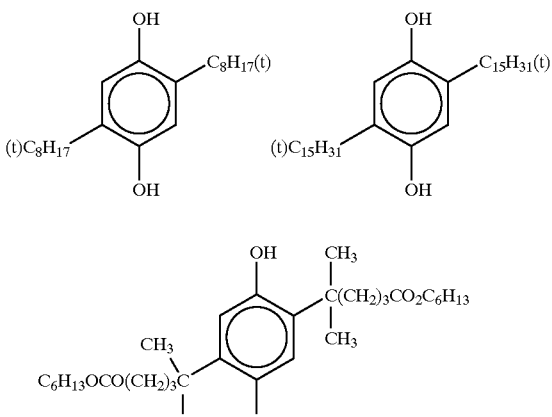

Color-mixing inhibiting auxiliary (Cpd-5)

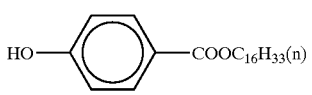

Stabilizer (Cpd-6)

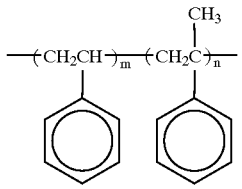

number-average
molecular weight 600
m/n = 10/90

Color-mixing inhibitor (Cpd-7)

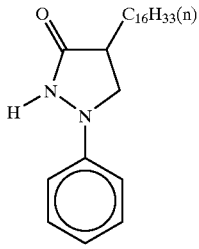

Color-image stabilizer (Cpd-8)

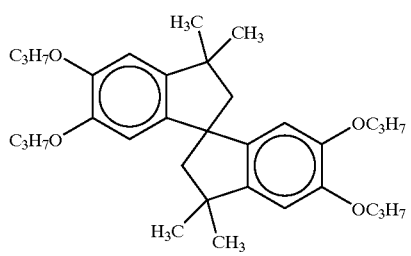

Color-image stabilizer (Cpd-9)

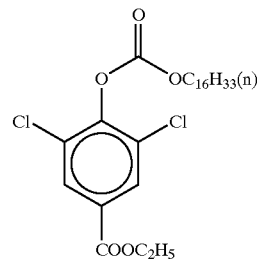

Color-image stabilizer (Cpd-10)

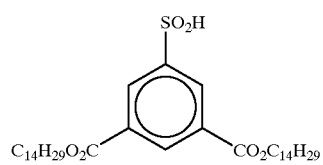

(Cpd-11)

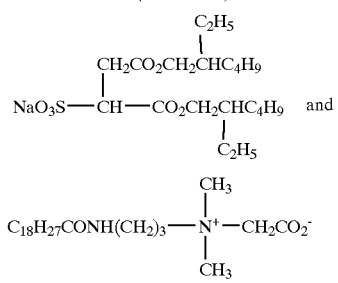

(Cpd-12)

A mixture in 7:3 (molar ratio) of (Cpd-13)

$C_{2}H_{5}$
$\qquad|$
$CH_{2}CO_{2}CH_{2}CHC_{4}H_{9}$
$NaO_{3}S-CH-CO_{2}CH_{2}CHC_{4}H_{9}$ and
$\qquad\qquad|$
$C_{2}H_{5}$ $\qquad\qquad CH_{3}$
$\qquad\qquad\quad|$
$C_{18}H_{27}CONH(CH_{2})_{3}-N^{+}-CH_{2}CO_{2}^{-}$
$\qquad\qquad\quad|$
$\qquad\qquad CH_{3}$ (Cpd-14)

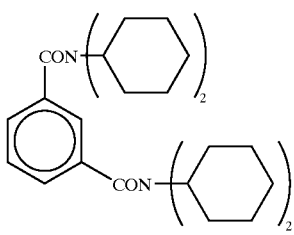

A mixture in 1:1 (molar ratio) of (Cpd-15)

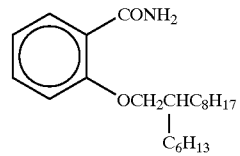

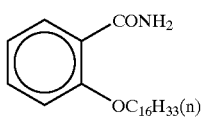

(Cpd-16)

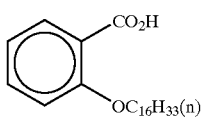

(Cpd-17)

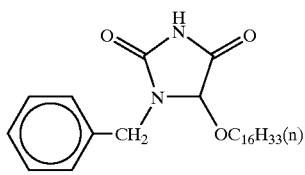

(Cpd-18)

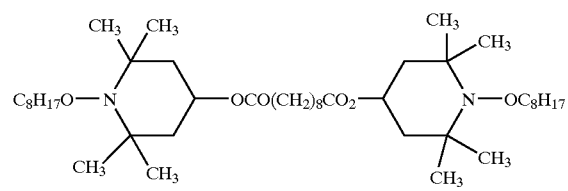

(Cpd-19)

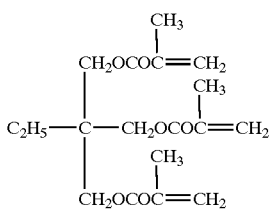

Ultraviolet absorbing agent (UV-1)

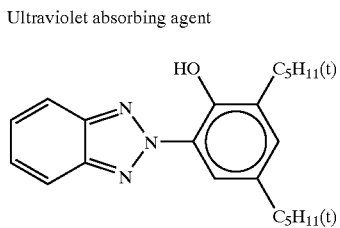

Ultraviolet absorbing agent (UV-2)

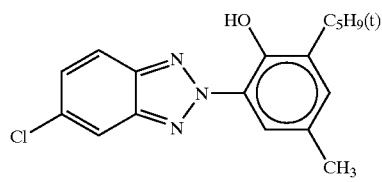

Ultraviolet absorbing agent (UV-3)

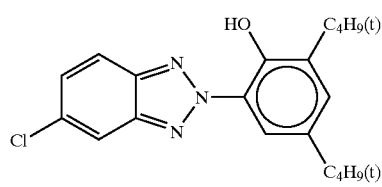

Ultraviolet absorbing agent (UV-4)

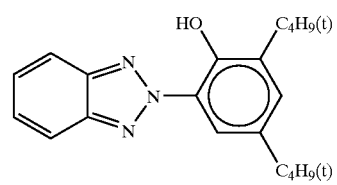

Ultraviolet absorbing agent (UV-5)

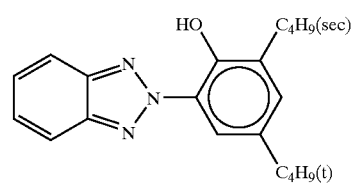

Ultraviolet absorbing agent (UV-6)

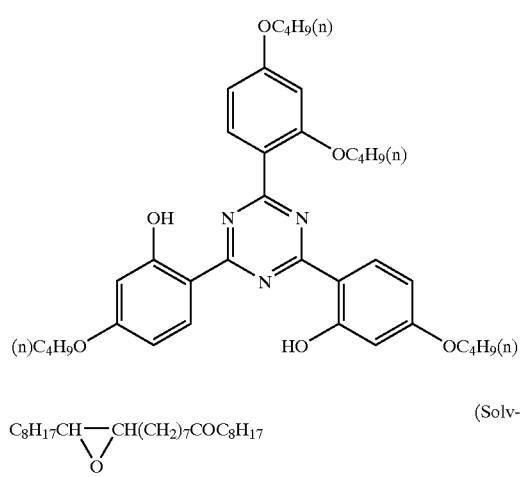

(Solv-1)

$C_8H_{17}CH\!-\!\!-\!\!CH(CH_2)_7COC_8H_{17}$
         \\ /
          O

A mixture in 1:1 (mass ratio) of (Solv-2)

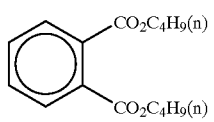 and 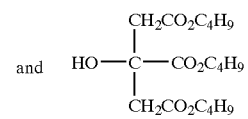

(Solv-3)

$C_4H_9OCO(CH_2)_8CO_2C_4H_9$ (Solv-4)

$O\!=\!P(OC_6H_{13}(n))_3$ (Solv-5)

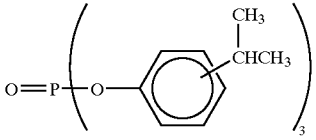

A mixture in 1:1 (Mass ratio) of (Solv-6)

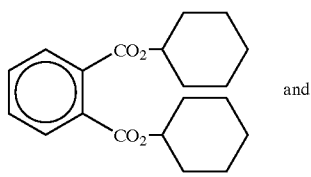 and

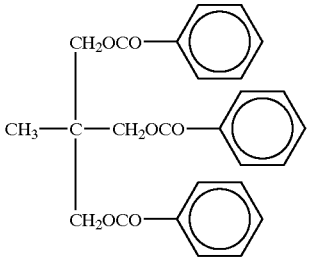

(Solv-7)

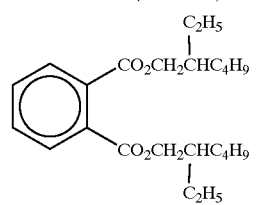

(Solv-8)

$C_8H_{17}OCO(CH_2)_8CO_2C_8H_{17}$

A mixture in 1:1 (mass ratio) of (Solv-9)

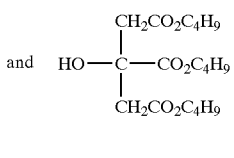

Further, light-sensitive material 401 was made in the same manner as the silver halide color photographic light-sensitive material (001), except for replacing the yellow coupler (ExY) of the emulsified dispersion A for the first layer of the silver halide color photographic light-sensitive material (001) prepared as described above, with the coupler for comparison (C-1) which was used in the foregoing section 1 in Comparative Example 1, in an equivalent amount. Likewise, light-sensitive material 402 was made in the same manner as above, except for replacing the yellow coupler (ExY) with the coupler for comparison (C-2) which was used in the foregoing section 2 in Comparative Example 1, in an equivalent amount. Further, light-sensitive material 403 was made in the same manner as above, except for replacing the yellow coupler (ExY) with the coupler for comparison (C-3) which was used in the foregoing section 2 in Comparative Example 1, in an equivalent amount. Further, light-sensitive material 414 was made in the same manner as above, except for replacing the yellow coupler (ExY) with the coupler for comparison (C-4) which was used in the foregoing section 2 in Comparative Example 1, in an equivalent amount. Furthermore, light-sensitive materials (404) to (413) according to the present invention were made in the same manner as above, except for replacing the yellow coupler (ExY) with the dye-forming couplers (1), (3), (5), (31), (41), (43), (51), (59), (60), and (81) of the present invention which were used in Example 1, in an equivalent amount, respectively.

The average particle sizes of the thus-prepared yellow-coupler-containing oleophilic fine-particle dispersions each were in the range of 0.10 to 0.20 μm.

The above-described light-sensitive material (001) was stored in the condition of 25° C.-55% RH, for 10 days, and then, made into a roll with a width of 127 mm; the rolled light-sensitive material was exposed to light imagewise, using a mini-lab printer processor PP1258AR, trade name, manufactured by Fuji Photo Film Co., Ltd.; and then, the continuous processing (running test) in the following processing steps was carried out, until the replenishment reached to be equal to twice the color-development tank volume.

| Processing step | Temperature | Time | Replenishment rate* |
|---|---|---|---|
| Color development | 38.5° C. | 45 sec | 45 ml |
| Bleach-fixing | 38.0° C. | 45 sec | 35 ml |
| Rinse (1) | 38.0° C. | 20 sec | — |
| Rinse (2) | 38.0° C. | 20 sec | — |
| Rinse (3) | **38.0° C. | 20 sec | — |
| Rinse (4) | **38.0° C. | 30 sec | 121 ml |

*Replenishment rate per m² of the light-sensitive material to be processed.
**A rinse cleaning system RC50D (trade name), manufactured by Fuji Photo Film Co., Ltd., was installed in the rinse (3), and the rinse solution was taken out from the rinse (3) and sent to a reverse osmosis membrane module (RC50D) by using a pump. The permeated water obtained in that tank was supplied to the rinse (4), and the concentrated water was returned to the rinse (3). Pump pressure was controlled such that the water to be permeated in the reverse osmosis module would be maintained in an amount
[001b]#of 50 to 300 ml/min, and the rinse solution was circulated under controlled temperature for 10 hours a day. (The rinse was made in a tank counter-current system from (1) to (4).)

The composition of each processing solution was as follows.

| | (Tank solution) | (Replenisher) |
|---|---|---|
| (Color developer) | | |
| Water | 800 ml | 800 ml |
| Dimethylpolysiloxane-series surfactant (Silicone KF351A/ trade name, Shin-Etsu Chemical Co., Ltd.) | 0.1 g | 0.1 g |
| Triethanolamine | 11.6 g | 11.6 g |
| Ethylenediamine tetraacetic acid | 4.0 g | 4.0 g |
| Sodium 4,5-dihydroxybenzene-1,3-disulfonate | 0.5 g | 0.5 g |
| Potassium chloride | 10.0 g | — |
| Potassium bromide | 0.040 g | 0.010 g |
| Triazinylaminostilbene-series fluorescent whitening agent (Hakkol FWA-SF/trade name, Showa Chemical Industry Co., Ltd.) | 2.5 g | 5.0 g |
| Sodium sulfite | 0.1 g | 0.1 g |
| Disodium-N,N-bis(sulfonatoethyl) hydroxylamine | 8.5 g | 11.1 g |
| N-ethyl-N-(β-methanesulfonamidoethyl)-3-methyl-4-amino-4-aminoaniline · 3/2 sulfate · 1 hydrate | 5.0 g | 15.7 g |
| Potassium carbonate | 26.3 g | 26.3 g |
| Water to make | 1000 ml | 1000 ml |
| PH (25° C./adjusted using potassium hydroxide and sulfuric acid) | 10.15 | 12.50 |
| (Bleach-fixing solution) | | |
| Water | 800 ml | 800 ml |
| Ammonium iron (III) ethylenediaminetetraacetate | 47.0 g | 94.0 g |
| Ethylenediamine tetraacetic acid | 1.4 g | 2.8 g |
| m-Carboxymethylbenzenesulfinic acid | 8.3 g | 16.5 g |
| Nitric acid (67%) | 16.5 g | 33.0 g |
| Imidazole | 14.6 g | 29.2 g |
| Ammonium thiosulfate (750 g/l) | 107 ml | 214 ml |
| Ammonium sulfite | 16.0 g | 32.0 g |
| Potassium metabisulfite | 23.1 g | 46.2 g |
| Water to make | 1000 ml | 1000 ml |
| pH (25° C./adjusted using acetic acid and ammonia) | 6.0 | 6.0 |
| (Rinse solution) | | |
| Sodium chlorinated-isocyanurate | 0.02 g | 0.02 g |
| Deionized water (conductivity: 5 μS/cm or less) | 1000 ml | 1000 ml |
| PH | 6.5 | 6.5 |

Then, each of the samples was subjected to gradation exposure using a sensitometer (Model FWH, produced by Fuji Photo Film Co., Ltd., whose light source had a color temperature of 3,200° K.) through three-color separation optical wedges for sensitometry. The exposure was carried out under the condition such that the exposure time was 0.1 seconds and the exposure amount was 250 lx·sec.

Separately, the respective light-sensitive materials were subjected to the following scanning exposure.

For the scanning exposure, a scanning exposure equipment shown in FIG. 1 in JP-A-9-197312 was used. About light sources, a semiconductor laser was used to obtain a 688-nm light source (R light). The semiconductor laser was combined with SHG to obtain a 532-nm light source (G light) and a 473-nm light source (B light). An external modulator was used to modulate the light quantity of the R light. The modulated light was caused to be reflected on a rotary polyhedron. Using the reflected light, each sample was subjected to scanning exposure while the sample was moved perpendicularly to the scanning direction. The scanning exposure was carried out at 400 dpi. The average exposure time was $8 \times 10^{-8}$ seconds per pixel. To suppress fluctuation in light quantity from the semiconductor laser, due to change in temperature, a Peltier element was used to make the temperature constant.

Each of the exposed samples was processed with the foregoing running solution, and then evaluated in the same manner as the light-sensitive materials in Comparative Examples 2 to 3 and Example 2.

From the results obtained, it was confirmed that each of the dye-forming couplers of the present invention exhibited a high color-forming property and each of the dyes formed from said couplers was excellent in both hue and fastness.

Example 4

A light-sensitive material was made in the same manner as Sample 101 in JP-A-11-305396, except that ExY-2 and ExY-3 in the 13th layer and the 14th layer of Sample 101 described in JP-A-11-305396 were replaced with the dye-forming coupler (3) of the present invention in an equivalent molar amount; a light-sensitive material was made in the same manner as Sample 101 in JP-A-11-305396, except that ExY-2 and ExY-3 in the 13th layer and the 14th layer of Sample 101 described in JP-A-11-305396 were replaced with the dye-forming coupler (53) of the present invention in an equivalent molar amount; and a light-sensitive material was made in the same manner as Sample 101 in JP-A-11-305396, except that ExY-2 and ExY-3 in the 13th layer and the 14th layer of Sample 101 described in JP-A-11-305396 were replaced with the dye-forming coupler (103) of the present invention in an equivalent molar amount. The light-sensitive materials thus obtained were exposed to light and subjected to development in the same manner as described in Example 1 of JP-A-11-305396, and it was confirmed that the processed light-sensitive materials were excellent in both color-forming property and hue. Further, the processed light-sensitive materials were evaluated under the fading conditions described in the foregoing Examples in the present specification, and excellent fastness to humidity and heat were confirmed. Especially, the color-forming coupler (103) was quite excellent in color-forming property.

Example 5

A light-sensitive material was produced in the same manner as Sample 107 in Example 1 in JP-A-11-84601, except that couplers C-5, C-6 and C-10, which were contained in the 13th layer and 14th layer of Sample 107, and C-6 and C-10, which were contained in the 15th layer of Sample 107, were replaced by an equimole amount of the dye-forming coupler (3) of the present invention, respectively. A light-sensitive material was produced in the same manner as Sample 107 in Example 1 in JP-A-11-84601, except that couplers C-5, C-6 and C-10, which were contained in the 13th layer and 14th layer of Sample 107, and C-6 and C-10, which were contained in the 15th layer of Sample 107, were replaced by an equimole amount of the dye-forming coupler (53) of the present invention, respectively. A light-sensitive material was produced in the same manner as Sample 107 in Example 1 in JP-A-11-84601, except that couplers C-5, C-6 and C-10, which were contained in the 13th layer and 14th layer of Sample 107, and C-6 and C-10, which were contained in the 15th layer of Sample 107, were replaced by an equimole amount of the dye-forming coupler (103) of the present invention, respectively. The thus-prepared light-sensitive materials were exposed to light, and subjected to development, in the same manner as described in the Example 1 of JP-A-11-84601, and it was confirmed that these light-sensitive materials were excellent in color-forming property and hue. Further, the processed light-sensitive material was evaluated under the fading conditions as described in the above Examples in the present specification, and excellent fastness to humidity and heat were confirmed. Especially, the color-forming coupler (103) was quite excellent in color-forming property.

Example 6
(Preparation of Blue-Sensitive Layer Emulsion A)

To 1.06 liter of deionized distilled water containing 5.7 mass % of deionized gelatin, 46.3 ml of 10% aqueous solution of NaCl was added. Further, 46.4 ml of $H_2SO_4$ (1N) and Compound (X) (0.012 g) were added successively, and then the temperature was adjusted to 60° C. Immediately after that, to the mixture in a reaction vessel, silver nitrate (0.1 mole) and NaCl (0.1 mole) were added while stirring with high speed, over 10 minutes. Successively an aqueous solution of silver nitrate (1.5 mole) and an aqueous solution of NaCl (1.5 mole) were added over 60 minutes according to the flow rate-accelerating method such that the final addition rate became 4 times the initial addition rate. Therefore, a 0.2 mole % aqueous solution of silver nitrate and a 0.2 mole % aqueous solution of NaCl were added over 6 minutes at the constant addition rate. At this time, $K_3IrCl_5$ ($H_2O$) was added to the aqueous solution of NaCl in the amount so as to give a concentration of $5 \times 10^{-7}$ mole based on the total silver amount, so that the aquo-iridium compound was doped to the silver chloride grains.

Further, an aqueous solution of silver nitrate (0.2 mole) and an aqueous solution of NaCl (0.18 mole) and an aqueous solution of KBr (0.02 mole) were added over 6 minutes. At this time, $K_4Ru(CN)_6$ and $K_4Fe(CN)_6$ were dissolved in these halogen solution so as to give a concentration of $5 \times 10^{-5}$ mole based on the total silver amount, respectively. In this way, these metal compounds were incorporated in the silver halide grains.

Besides, during growth of the grain at the final stage, an aqueous solution of KI corresponding to 0.001 mole based on the total silver amount was added to a reaction vessel over 1 minute. The addition started from the time when 93% of the grain formation was completed.

Thereafter, Compound (Y) as a flocculant was added at 40° C., and pH was adjusted to about 3.5, followed by desalting and washing.

Compound X

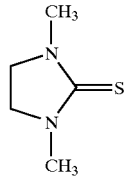

Compound Y

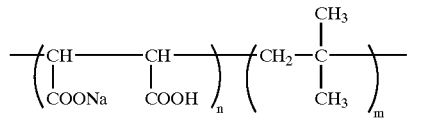

n and m each are an integer.

To the desalted and washed emulsion, deionized gelatin and an aqueous solution of NaCl, and an aqueous solution of NaOH were added. Then, the temperature of the emulsion was elevated to 50° C., and the pAg and pH of the emulsion were adjusted to 7.6 and 5.6, respectively.

The resulting emulsion was a gelatin composition comprising cubic silver halide grains having a halogen composition of silver chloride (98.9 mole %), silver bromide (1 mole %) and silver iodide (0.1 mole %), average side length of 0.70 μm and coefficient of variation of the side length of 8%.

The temperature of the above-mentioned emulsion grains was kept to 60° C. Then, $2.5 \times 10^{-4}$ mole/Ag mole of spectral sensitizing dye-1 and $2.0 \times 10^{-4}$ mole/Ag mole of spectral sensitizing dye-2 were added. Further, $1 \times 10^{-5}$ mole/Ag mole of thiosulfonic acid compound-1 was added. Then, a fine grain emulsion containing a doped iridium hexachloride, and having a halogen composition of silver bromide (90 mole %) and silver chloride (10 mole %), and an average grain size of 0.05 μm, was added and ripened for 10 minutes. Further, a fine grain emulsion containing having a halogen composition of silver bromide (40 mole %) and silver chloride (60 mole %), and an average grain size of 0.05 μm, was added and ripened for 10 minutes. Thus, the fine grains were dissolved, so that the silver bromide content of the cubic host grains increased up to 1.3 mole, and iridium hexachloride was doped in an amount of $1 \times 10^{-7}$ mole/Ag mole.

Successively, $1 \times 10^{-5}$ mole/Ag mole of sodium thiosulfate and $2 \times 10^{-5}$ mole/Ag mole of gold sensitizer-1 were added. Immediately after that, the temperature of the emulsion was elevated to 60° C. and the emulsion was ripened at the same temperature for 40 minutes, and then cooled to 50° C. Immediately after cooling, mercapto compounds −1 and −2 were added so as to give a concentration of $6 \times 10^{-4}$ mole per mole of Ag, respectively. Then, after ripening for 10 minutes, an aqueous solution of KBr was added so as to give a concentration of 0.008 mole based on silver, and ripened for 10 minutes. Thereafter, the temperature of the emulsion was lowered to room temperature to leave to stand it.

Thus, high-speed emulsion A-1 was prepared.

Cubic grains having an average side length of 0.55 μm and coefficient of variation of the side length of 9% were prepared by the same preparation method as with emulsion A-1, except that the temperature during grain formation was changed to 55° C.

Spectral sensitization and chemical sensitization were performed in the same manner as above, except for correcting the sensitization amounts so as to meet the specific surface area (according to the ratio of the side lengths 0.7/0.55=1.27 times). Thus, the low-speed Special sensitizing dye-1

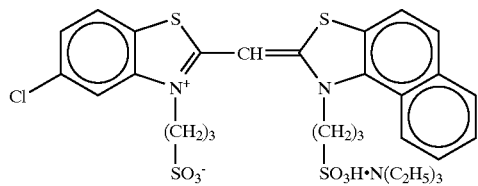

Special sensitizing dye-2

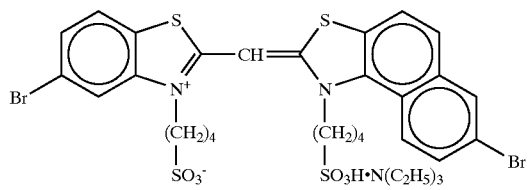

-continued

Thiosulfonic acid compound-1

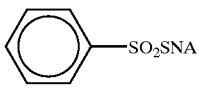

Mercapto-compound-1

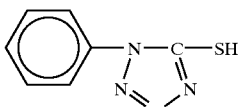

Mercapto compound-2

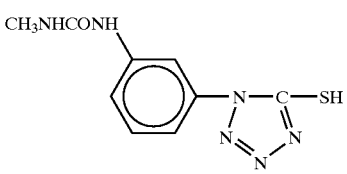

Gold sensitizing dye-1

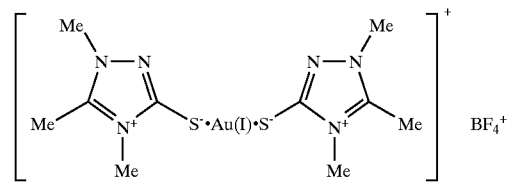

(Preparation of Green-Sensitive Layer Emulsion C)

Green-sensitive high-speed emulsion C-1 and Green-sensitive low-speed emulsion C-2 were prepared by the same preparation conditions as with the above-mentioned emulsions A-1 and A-2, except that the temperature during grain formation was lowered and sensitizing dyes were changed as described below.

(Sensitizing dye D)

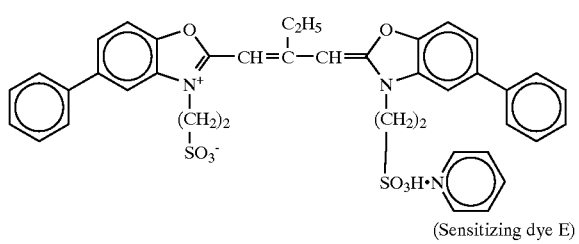

(Sensitizing dye E)

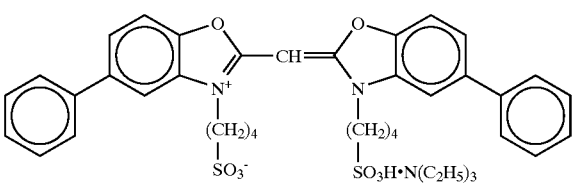

As to the grain size, average side length of the high-speed emulsion and average side length of the low-speed emulsion were 0.40 μm and 0.30 μm, respectively. The coefficient of variation of the side length of these emulsions was 8%, respectively.

Sensitizing dye D was added to the large grain size emulsion and the small grain size emulsion in an amount of $3.0 \times 10^{-4}$ mole and of $3.6 \times 10^{-4}$ mole, per mole of silver halide, respectively. Beside, Sensitizing dye E was added to the large grain size emulsion and the small grain size emulsion in an amount of $4.0 \times 10^{-5}$ mole and of $7.0 \times 10^{-5}$ mole, per mole of silver halide, respectively.

(Preparation of Red-Sensitive Layer Emulsion E)

Red-sensitive high-speed emulsion E-1 and Green-sensitive low-speed emulsion E-2 were prepared by the same preparation conditions as with the above-mentioned emulsions A-1 and A-2, except that the temperature during grain formation was lowered and sensitizing dyes were changed as described below.

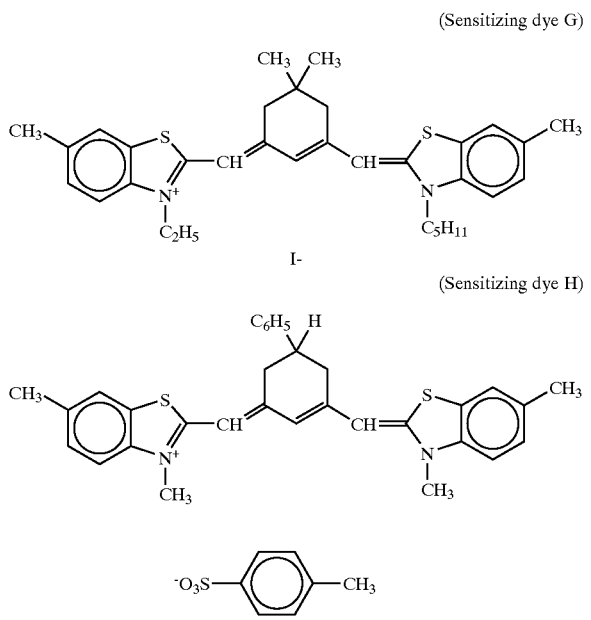

(Sensitizing dye G)

(Sensitizing dye H)

As to the grain size, average side length of the high-speed emulsion and average side length of the low-speed emulsion were 0.38 μm and 0.32 μm, respectively. The coefficient of variation of the side length of these emulsions was 9% and 10%, respectively.

Each of sensitizing dye G and H was added to the large grain size emulsion in an amount of $8.0 \times 10^{-5}$ mole, and to the small grain size emulsion in an amount of $10.7 \times 10^{-5}$ mole, per mole of silver halide, respectively.

Further, $3.0 \times 10^{-3}$ mole of the following compound (I) was added to the red sensitive layer per mole of silver halide, respectively.

(Compound I)

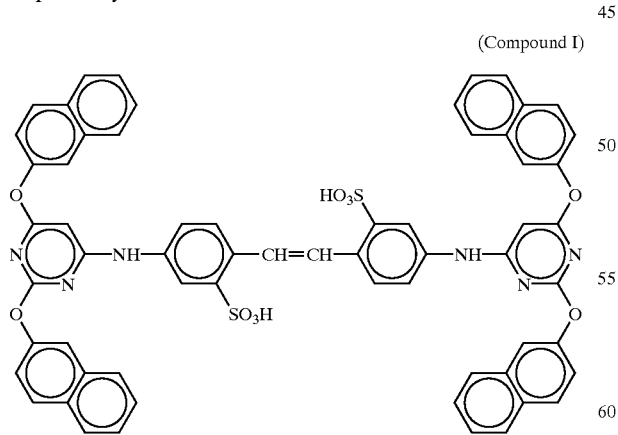

Preparation of Coating Solution for First Layer 57 g of a yellow coupler (ExY), 7 g of a dye image stabilizer (Cpd-1), 4 g of a dye image stabilizer (Cpd-2), 7 g of a dye image stabilizer (Cpd-3) and 2 g of a dye image stabilizer (Cpd-8) were dissolved in 21 g of a solvent (Solv-1) and 80 ml of ethyl acetate, and the resultant solution was added to 220 g of an aqueous 23.5% by mass gelatin solution containing 4 g of sodium dodecylbenzenesulfonate. The resultant mixture was emulsified and dispersed by a high speed stirring emulsifier (DISOLVER), followed by addition of water to prepare 900 g of emulsified dispersion A.

The emulsified dispersion A described above and the emulsions A-1 and A-2 were mixed and dissolved to prepare a coating solution of the first layer having the following composition. The coating amount of each emulsion is represented by the coating amount of silver.

The coating solutions for the second to seventh layers were prepared following the same procedures as for the coating solution of the first layer. 1-oxy-3,5-dichloro-s-triazine sodium salt (H-1), (H-2), and (H-3) were used as gelatin hardeners in each layer. In addition, Ab-1, Ab-2, Ab-3 and Ab-4 were added to each layer such that their total amounts were 15.0 mg/m$^2$, 60.0 mg/m$^2$, 5.0 mg/m$^2$ and 10.0 mg/m$^2$, respectively.

Hardener (H-1)

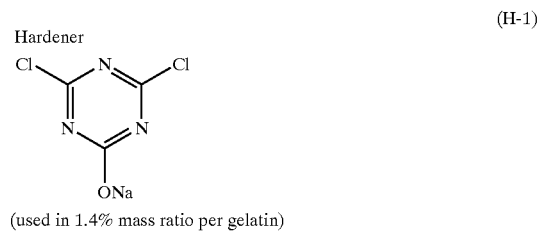

(used in 1.4% mass ratio per gelatin)

Hardener (H-2)

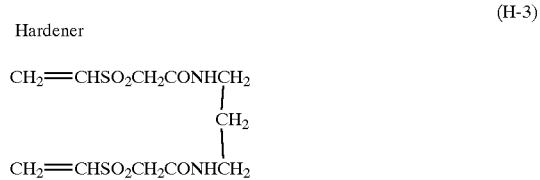

Hardener (H-3)

Antiseptic (Ab-1)

Antiseptic (Ab-2)

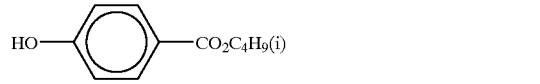

Antiseptic (Ab-3)

Antiseptic (Ab-4)

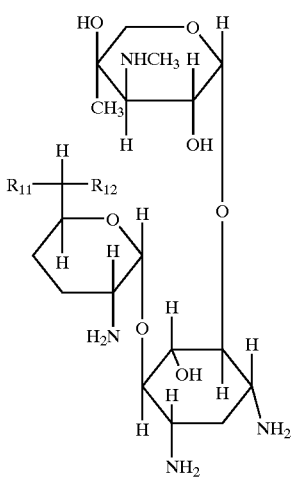

A mixture in 1:1:1:1 (molar ratio) of a, b, c, and d

Further, 1-(3-methylureidophenyl)-5-mercaptotetrazole was added to the second layer, the forth layer, the sixth layer and the seventh layer in amounts of 0.2 mg/m$^2$, 0.2 mg/m$^2$, 0.6 mg/m$^2$ and 0.1 mg/m$^2$, respectively.

Also, 4-hydroxy-6-methyl-1,3,3a,7-tetrazaindene was added to the blue-, and green-sensitive emulsion layers in amounts of $1\times10^{-4}$ mole and $2\times10^{-4}$ mole, respectively, per mole of silver halide.

Further, a copolymer latex of methacrylic acid and butyl acrylate (ratio by mass, 1:1; average molecular weight, 200,000 to 400,000) was added to the red-sensitive emulsion layer in an amount of 0.05 g/m$^2$.

Further, disodium catechol-3,5-disulfonate was added to the second layer, the fourth layer and the sixth layer in an amount of 6 mg/m$^2$, 6 mg/m$^2$ and 18 mg/m$^2$, respectively.

Furthermore, to prevent irradiation, the following dyes (the number given in parenthesis represents the coating amount) were added.

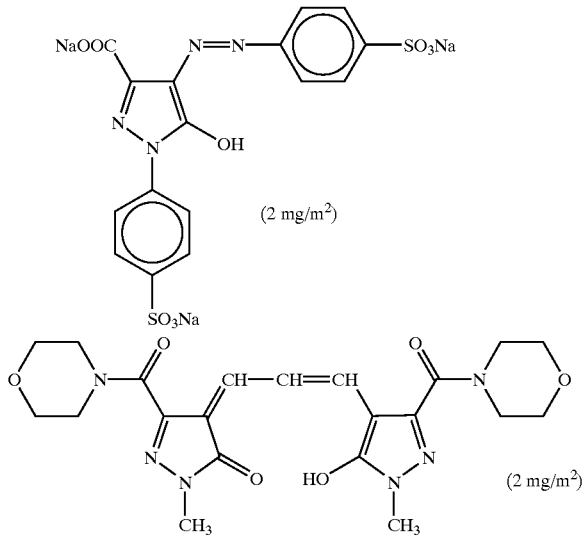

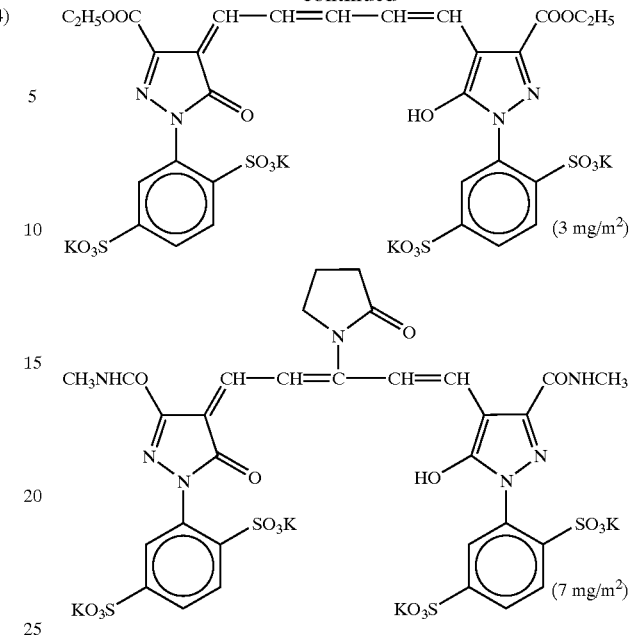

(Layer Constitution)

The composition of each layer is shown below. The numbers show coating amounts (g/m 2). In the case of the silver halide emulsion, the coating amount is in terms of silver.

Support

Polyethylene Resin Laminated Paper

{The polyethylene resin on the first layer side contained a white pigment (TiO$_2$; content of 16 mass %, ZnO; content of 4 mass %), a fluorescent whitening agent (4,4'-bis(5-methylbenzoxazolyl)stilbene; content of 0.03 mass %) and a bluish dye (ultramarine; content of 0.33 mass %), an amount of polyethylene resin is 29.2 g/m}

| First Layer (Blue-Sensitive Emulsion Layer) | |
|---|---|
| A silver chlorobromide emulsion A (gold and sulfur sensitized, cubic, a 3:7 mixture of a large-size emulsion A-1 and a small-size emulsion A-2 (in terms of mol of silver)) | 0.24 |
| Gelatin | 1.25 |
| Yellow coupler (ExY) | 0.57 |
| Color-image stabilizer (Cpd-1) | 0.07 |
| Color-image stabilizer (Cpd-2) | 0.04 |
| Color-image stabilizer (Cpd-3) | 0.07 |
| Color-image stabilizer (Cpd-8) | 0.02 |
| Solvent (Solv-1) | 0.21 |
| Second Layer (Color-Mixing Inhibiting Layer) | |
| Gelatin | 1.15 |
| Color-mixing inhibitor (Cpd-4) | 0.10 |
| Color-image stabilizer (Cpd-5) | 0.018 |
| Color-image stabilizer (Cpd-6) | 0.13 |
| Color-image stabilizer (Cpd-7) | 0.07 |
| Solvent (Solv-1) | 0.04 |
| Solvent (Solv-2) | 0.12 |
| Solvent (Solv-5) | 0.11 |
| Third Layer (Green-Sensitive Emulsion Layer) | |
| A silver chlorobromide emulsion C (gold and sulfur sensitized, cubic, a 1:3 mixture of a large-size emulsion C-1 and a small-size emulsion C-2 (in terms of mol of silver)) | 0.14 |
| Gelatin | 0.46 |

-continued

| | |
|---|---|
| Magenta coupler (ExM) | 0.15 |
| Ultraviolet absorbing agent (UV-A) | 0.14 |
| Color-image stabilizer (Cpd-2) | 0.003 |
| Color-mixing inhibitor (Cpd-4) | 0.002 |
| Color-image stabilizer (Cpd-6) | 0.09 |
| Color-image stabilizer (Cpd-8) | 0.02 |
| Color-image stabilizer (Cpd-9) | 0.01 |
| Color-image stabilizer (Cpd-10) | 0.01 |
| Color-image stabilizer (Cpd-11) | 0.0001 |
| Solvent (Solv-3) | 0.09 |
| Solvent (Solv-4) | 0.18 |
| Solvent (Solv-5) | 0.17 |
| Fourth Layer (Color-Mixing Inhibiting Layer) | |
| Gelatin | 0.68 |
| Color-mixing inhibitor (Cpd-4) | 0.06 |
| Color-image stabilizer (Cpd-5) | 0.011 |
| Color-image stabilizer (Cpd-6) | 0.08 |
| Color-image stabilizer (Cpd-7) | 0.04 |
| Solvent (Solv-1) | 0.02 |
| Solvent (Solv-2) | 0.07 |
| Solvent (Solv-5) | 0.065 |
| Fifth Layer (Red-Sensitive Emulsion Layer) | |
| A silver chlorobromide emulsion E (gold and sulfur sensitized, cubic, a 5:5 mixture of a large-size emulsion E-1 and a small-size emulsion E-2 (in terms of mol of silver)) | 0.16 |
| Gelatin | 0.95 |
| Cyan coupler (ExC-1) | 0.023 |
| Cyan coupler (ExC-2) | 0.05 |
| Cyan coupler (ExC-3) | 0.17 |
| Ultraviolet absorbing agent (UV-A) | 0.055 |
| Color-image stabilizer (Cpd-1) | 0.22 |
| Color-image stabilizer (Cpd-7) | 0.003 |
| Color-image stabilizer (Cpd-9) | 0.01 |
| Color-image stabilizer (Cpd-12) | 0.01 |
| Solvent (Solv-8) | 0.05 |
| Sixth Layer (Ultraviolet Absorbing Layer) | |
| Gelatin | 0.46 |
| Ultraviolet absorbing agent (UV-B) | 0.35 |
| Compound (S1-4) | 0.0015 |
| Solvent (Solv-7) | 0.18 |
| Seventh Layer (Protective Layer) | |
| Gelatin | 1.00 |
| Acryl-modified copolymer of polyvinyl alcohol (modification degree: 17%) | 0.4 |
| Liquid paraffin | 0.02 |
| Surface-active agent (Cpd-13) | 0.02 |

Yellow coupler

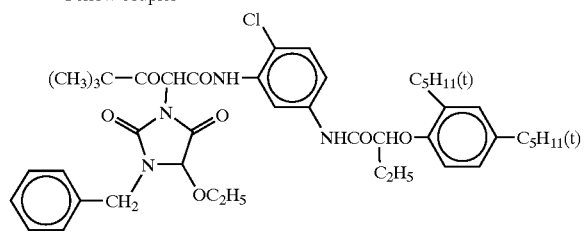

(ExY)

Magenta coupler

A mixture in 40:40:20 (molar ratio) of

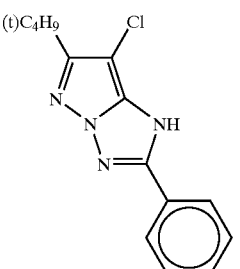

(ExM)

Cyan coupler

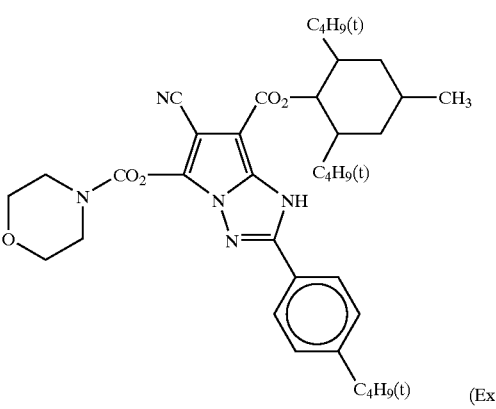

(ExC-1)

(ExC-2)

Cyan coupler

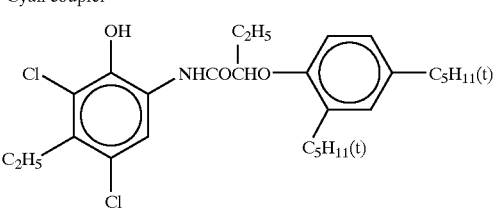

Cyan coupler (ExC-3)

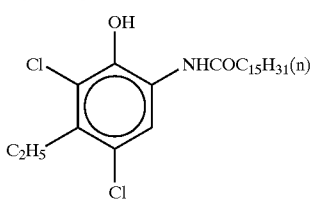

Cyan coupler (ExC-4)

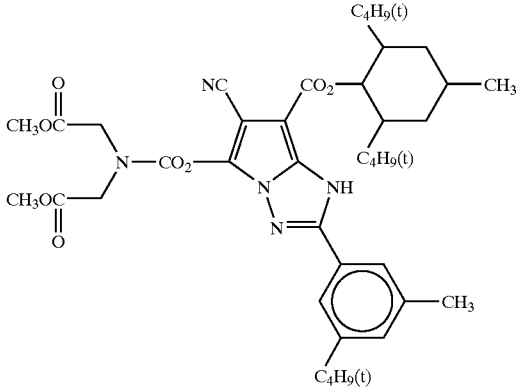

Cyan coupler (ExC-5)

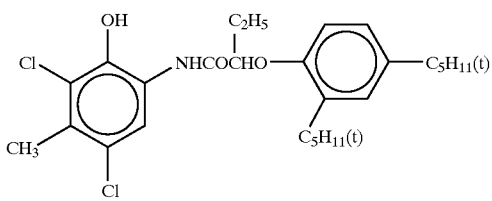

Color-image stabilizer (Cpd-1)

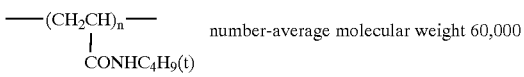

number-average molecular weight 60,000

Color-image stabilizer (Cpd-2)

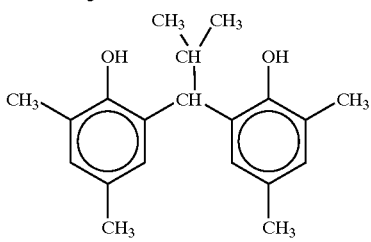

Color-image stabilizer (Cpd-3)

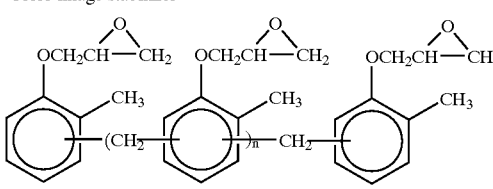

n = 7~8 (average value)

Color-image inhibitor (Cpd-4)

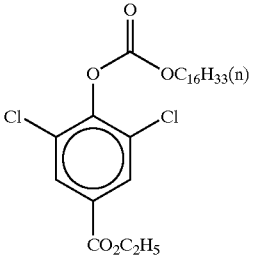

Color-image stabilizer (Cpd-5)

HO—⟨C₆H₄⟩—CO₂C₁₆H₃₃(n)

Color-image stabilizer (Cpd-6)

—(CH₂CH)ₘ—(CH₂C(CH₃))ₙ—
   |                |
   Ph              Ph number-average molecular weight 600
m/n = 10/90

Color-image stabilizer (Cpd-7)

[pyrazolidinone with C₁₆H₃₃(n) substituent and N-phenyl]

Color-image stabilizer (Cpd-8)

[spirobiindane with OC₃H₇ and C₃H₇O substituents and CH₃ groups]

Color-image stabilizer (Cpd-9)

[2,6-dichloro-4-(ethoxycarbonyl)phenyl hexadecyl carbonate]

Color-image stabilizer
(Cpd-10)
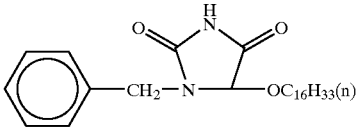
(Cpd-17)
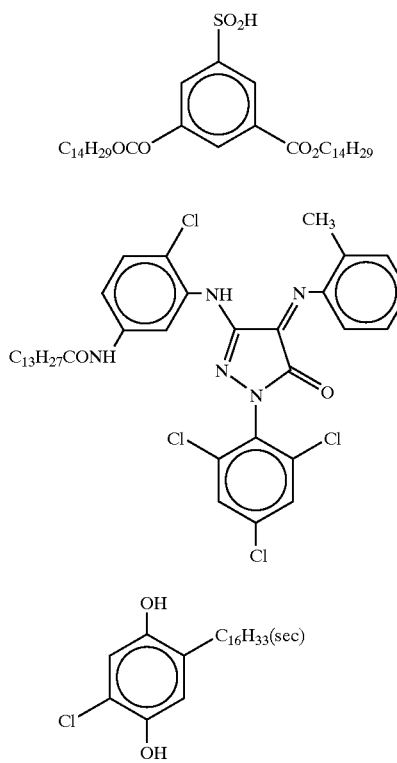
(Cpd-11)
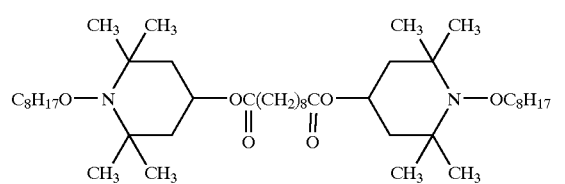
(Cpd-18)
Color-mixing inhibitor
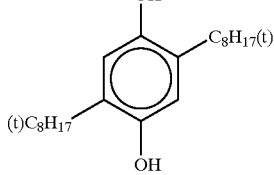
(Cpd-19)
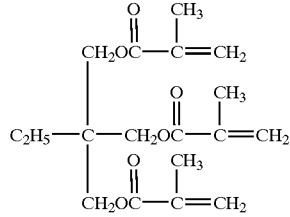
(Cpd-20)
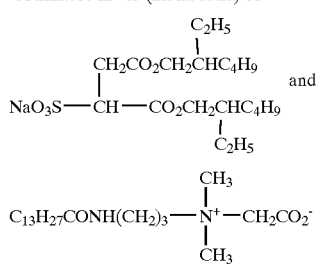
(Cpd-12)
$C_8H_{17}CH\text{—}CH(CH_2)_7CO_2C_8H_{17}$ (Solv-1)
$\phantom{C_8H_{17}CH}\diagdown O \diagup$
(Solv-2)
Surfactant
A mixture in 7:3 (molar ratio) of
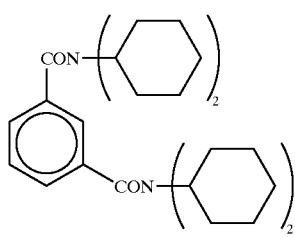
and
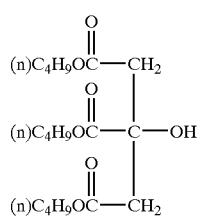
(Cpd-13)
$C_4H_9OC(CH_2)_8COC_4H_9$ (Solv-3)
$\phantom{C_4H_9}\overset{O}{\|}\phantom{(CH_2)_8}\overset{O}{\|}$
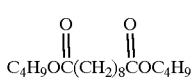
$O{=}P(OC_8H_{13}(n))_3$ (Solv-4)
(Cpd-14)
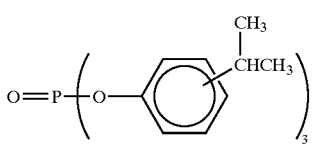
(Solv-5)
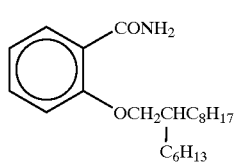
(Cpd-15)
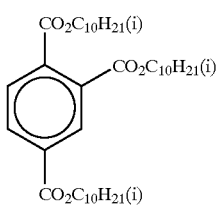
(Solv-7)
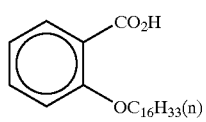
(Cpd-16)

(Solv-8)

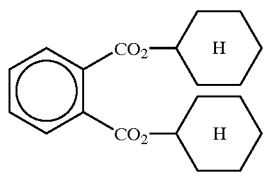

(S1-4)

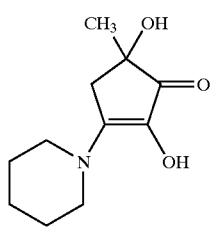

Ultraviolet absorbing agent (UV-1)

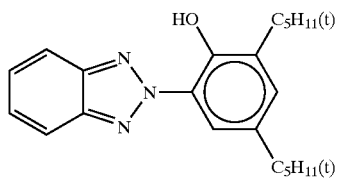

Ultraviolet absorbing agent (UV-2)

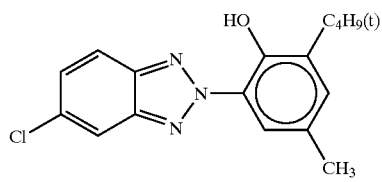

Ultraviolet absorbing agent (UV-3)

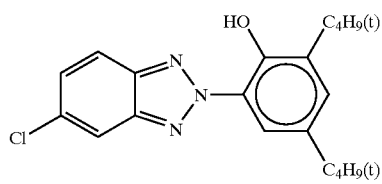

Ultraviolet absorbing agent (UV-5)

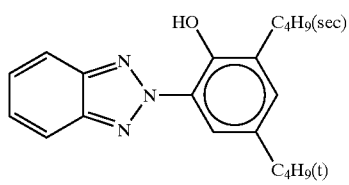

Ultraviolet absorbing agent (UV-6)

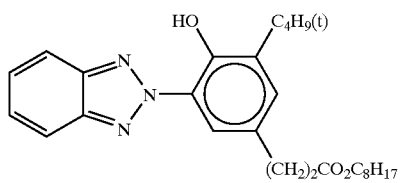

Ultraviolet absorbing agent (UV-7)

[Structure showing triazine UV absorber with $OC_4H_9(n)$ groups and $HO$/$(n)C_4H_9O$ substituents]

UV-A: A mixture of UV-1/UV-2/UV-3 = 7/2/2 (mass ratio)
UV-B: A mixture of UV-1/UV-2/UV-3/UV-5/UV-6 = 13/3/3/5/3 (mass ratio)
UV-C: A mixture of UV-1/UV-3 = 9/1 (mass ratio)

Processing method used in this example is presented below.

Processing A

The above-described light-sensitive material sample was processed to a 127 mm width roll-like form. Mini-lab printer processor PP350 (trade name) manufactured by Fuji Photo Film Co., Ltd. was used to subject the light-sensitive material sample to image-wise exposure through a negative film having an average density. A continuous processing (running test) was performed until an accumulated replenisher amount of color developer in the processing steps presented below reached two times the tank volume of a color developer. The processing with the resulting running processing solution was named processing A.

| Processing step | Temperature | Time | Replenisher amount* |
|---|---|---|---|
| Color development | 38.5° C. | 45 sec | 45 ml |
| Bleach-fixing | 38.0° C. | 45 sec | 35 ml |
| Rinse (1) | 38.0° C. | 20 sec | — |
| Rinse (2) | 38.0° C. | 20 sec | — |
| Rinse (3)** | 38.0° C. | 20 sec | — |
| Rinse (4)** | 38.0° C. | 20 sec | 121 ml |
| Drying | 80° C. | | |

(Note)
*Replenisher amount per $m^2$ of the light-sensitive material to be processed.
**A rinse cleaning system RC50D (trade name), manufactured by Fuji Photo Film Co., Ltd., was installed in the rinse (3), and the rinse solution was taken out from the rinse (3) and sent to a reverse osmosis membrane module (RC50D) by using a pump. The permeated water obtained in that tank was supplied to the rinse (4), and the concentrated water was returned to the rinse (3). Pump pressure was controlled such that the water to be permeated in the reverse osmosis module would be maintained in an amount of 50 to 300 ml/min, and the rinse solution was circulated under controlled temperature for 10 hours a day. The rinse was made in a tank counter-current system from (1) to (4).

The composition of each processing solution was as follows.

| | (Tank solution) | (Replenisher) |
|---|---|---|
| (Color developer) | | |
| Water | 800 ml | 800 ml |
| Fluorescent whitening agent (FL-1) | 2.2 g | 5.1 g |

-continued

| | (Tank solution) | (Replenisher) |
|---|---|---|
| Fluorescent whitening agent (FL-2) | 0.35 g | 1.75 g |
| Triisopropanolamine | 8.8 g | 8.8 g |
| Polyethylenegrycol (average molecular weight: 300) | 10.0 g | 10.0 g |
| Ethylenediamine tetraacetic acid | 4.0 g | 4.0 g |
| Sodium sulfite | 0.10 g | 0.20 g |
| Potassium chloride | 10.0 g | — |
| Sodium 4,5-dihydroxybenzene-1,3-disulfonate | 0.50 g | 0.50 g |
| Disodium-N,N-bis(sulfonatoethyl) hydroxylamine | 8.5 g | 14.0 g |
| 4-amino-3-methyl-N-ethyl-N-(β-methanesulfonamidoethyl) aniline · 3/2 sulfate · mono hydrate | 4.8 g | 14.0 g |
| Potassium carbonate | 26.3 g | 26.3 g |
| Water to make | 1000 ml | 1000 ml |
| pH (25° C./adjusted using sulfuric acid and potassium hydroxide) | 10.15 | 12.50 |

-continued

| | (Tank solution) | (Replenisher) |
|---|---|---|
| (Bleach-fixing solution) | | |
| Water | 800 ml | 800 ml |
| Ammonium thiosulfate (750 g/l) | 107 ml | 214 ml |
| m-Carboxymethylbenzenesulfinic acid | 8.3 g | 16.5 g |
| Ammonium iron (III) ethylenediaminetetraacetate | 47.0 g | 94.0 g |
| Ethylenediamine tetraacetic acid | 1.4 g | 2.8 g |
| Nitric acid (67%) | 16.5 g | 33.0 g |
| Imidazole | 14.6 g | 29.2 g |
| Ammonium sulfite | 16.0 g | 32.0 g |
| Potassium metabisulfite | 23.1 g | 46.2 g |
| Water to make | 1000 ml | 1000 ml |
| pH (25° C./adjusted using nitric acid and aqua ammonia) | 6.5 | 6.5 |
| (Rinse solution) | | |
| Sodium chlorinated-isocyanurate | 0.02 g | 0.02 g |
| Deionized water (conductivity: 5 μS/cm or less) | 1000 ml | 1000 ml |
| PH (25° C.) | 6.5 | 6.5 |

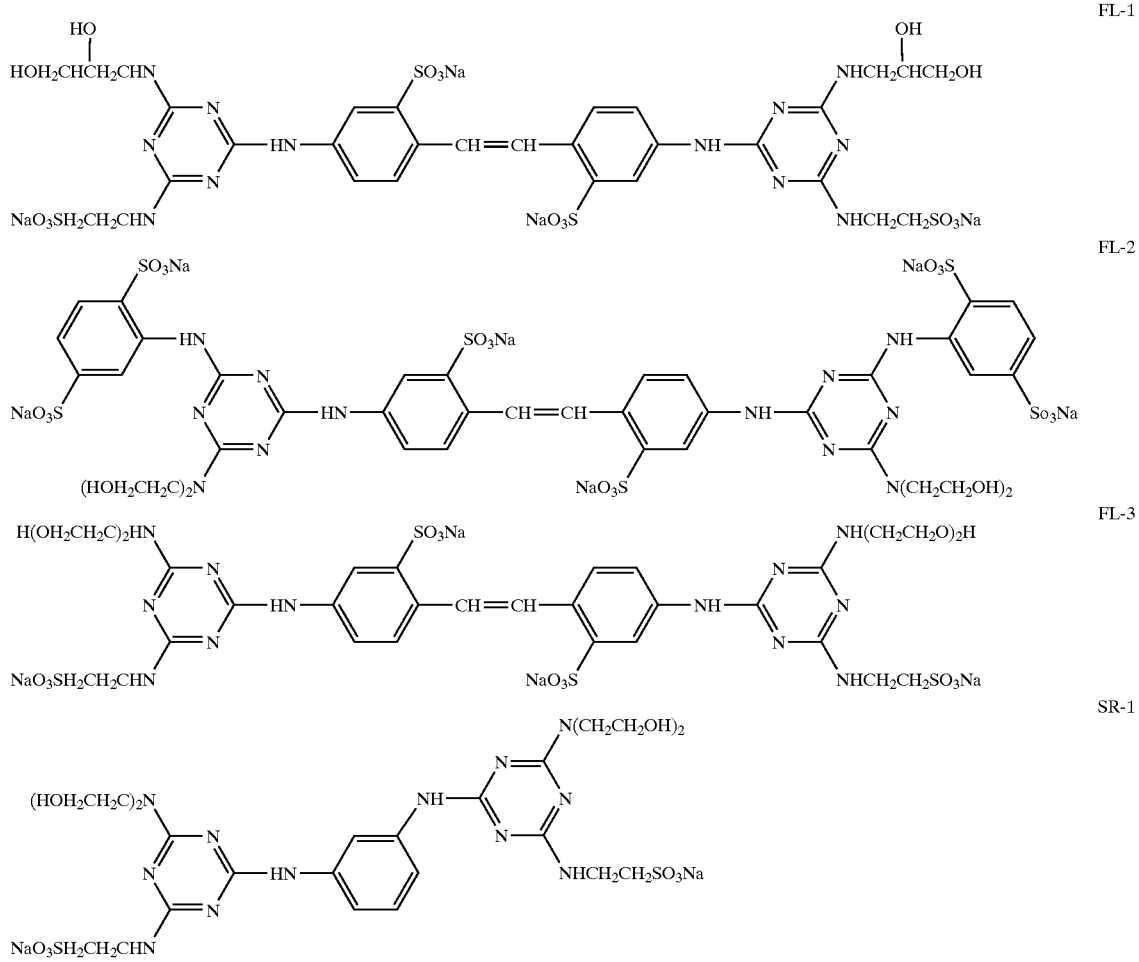

Next, samples 502 and 503 were prepared by the same preparation method as with the above-mentioned sample 501, except that the yellow coupler in the first layer was replaced with couplers for comparison (C-2) and (C-3), respectively.

Further, samples 504 to 516 were prepared by the same preparation method as with sample 501, except that both amounts of the silver halide emulsion and the yellow coupler in the first layer were reduced to 70 mole % to the originals and in addition, the yellow coupler was replaced with the compounds of the present invention.

(C-2)

Coupler for comparison

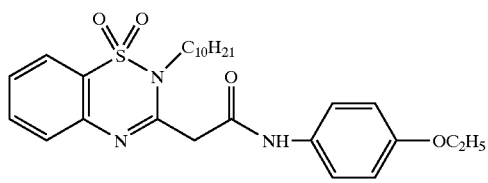

(Compound (XV) described in U.S. Pat. No. 3841880)

(C-3)

Coupler for comparison

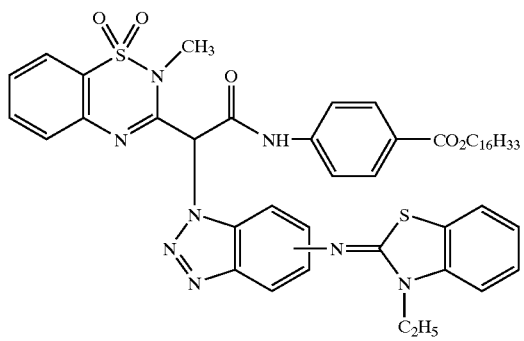

(Compound (17) described in JP-A-52-82423)

Yellow couplers that were used in the samples 501 to 516 in this example and relative coating molar ratios thereof are shown in Table 5.

The prepared samples were left to stand under the conditions of 25° C. and 55% RH for 10 days after coating, and they were exposed and processed. A running processing was performed using sample 501 in accordance with the above-described processing A. Thereafter, each sample was exposed and processed, to obtain a color print with using the thus-obtained running solution.

(Evaluation of Color-Forming Property and Color Reproducibility)

A sensorial evaluation with the naked eye revealed that the samples containing the yellow coupler of the present invention attained a hue having high saturation with reduced magenta or cyan contamination in the yellow color.

The maximum color densities (Dmax) of the samples in this example are shown in Table 5.

(Evaluation of Fastness to Light)

The above-described samples having developed yellow dye image were exposed to xenon light (100,000 lux xenon light irradiation apparatus) through a ultraviolet cut filter whose transmittance at 370 nm was 50%, and a heat-cut filter. Densities of the samples after irradiation for 28 days in the area exhibited the yellow density of 2.0 before irradiation, were measured. Fastness to light was evaluated by the remaining rate of density (%). The thus-obtained results are shown in Table 5.

(Evaluation of Fastness to Heat and Humidity Under Darkness)

The above-described samples having developed yellow dye image were left to stand under the conditions of 80° C. and 70% RH. Densities of the samples after reservation for 28 days in the area exhibited the yellow density of 2.0 before reservation, were measured. Fastness to heat and humidity under darkness was evaluated by the remaining rate of density (%). The thus-obtained results are shown in Table 5.

TABLE 5

| Sample No. | Yellow coupler Compound No. | Relative coating amount of yellow coupler (mole) | Maximum color density ($D_{max}$) | Fastness to light (Remaining rate of density %) | Fastness to heat and humidity under darkness (Remaining rate of density %) | Remarks |
| --- | --- | --- | --- | --- | --- | --- |
| 501 | ExY | 1 | 2.1 | 78 | 82 | Comparative example |
| 502 | (C-2) | 1 | 1.4 | 73 | 93 | Comparative example |
| 503 | (C-3) | 1 | 1.3 | 75 | 91 | Comparative example |
| 504 | Coupler (42) | 0.7 | 2.4 | 77 | 99 | This invention |
| 505 | Coupler (46) | 0.7 | 2.3 | 78 | 99 | This invention |
| 506 | Coupler (47) | 0.7 | 2.1 | 86 | 99 | This invention |
| 507 | Coupler (161) | 0.7 | 2.3 | 89 | 99 | This invention |
| 508 | Coupler (162) | 0.7 | 2.1 | 87 | 99 | This invention |
| 509 | Coupler (163) | 0.7 | 2.2 | 85 | 98 | This invention |
| 510 | Coupler (164) | 0.7 | 2.3 | 86 | 98 | This invention |
| 511 | Coupler (165) | 0.7 | 2.1 | 87 | 99 | This invention |
| 512 | Coupler (166) | 0.7 | 2.3 | 88 | 99 | This invention |
| 513 | Coupler (167) | 0.7 | 2.4 | 90 | 98 | This invention |
| 514 | Coupler (168) | 0.7 | 2.4 | 87 | 98 | This invention |
| 515 | Coupler (169) | 0.7 | 2.2 | 88 | 99 | This invention |
| 516 | Coupler (170) | 0.7 | 2.3 | 87 | 99 | This invention |

The above-described test results are summarized below.

The light-sensitive materials of the present invention provided sufficient color density, even though both amounts of the coupler and the silver halide emulsion were respectively reduced to 70 mole % of those in the comparative samples. Consequently the light-sensitive materials of the present invention are useful to save resources such as a coupler and silver halide. Further, Table 5 shows that the samples according to the present invention were excellent in fastness to heat and humidity under darkness as well as fastness to light. Particularly, the results demonstrated that any of the yellow couplers of the present invention were extremely excellent in fastness to heat and humidity under darkness. Beside, the results of fastness to light shown in Table 5 demonstrated that, among couplers represented by formulae (I) and (II) according to the present invention, those having an anilido moiety that had, at the 2-position of the anilido moiety, a long-chain alkoxy group, a branched alkoxy group, an aryloxy group (with a structure having a substituent at the ortho-position of the aryl group), an alkylthio group, or an arylthio group (with a structure having a substituent at the ortho-position of the aryl group), and those having an anilido moiety that had, at the position other than 2-position of the anilido moiety, a methoxy group or a t-alkyl group, were also excellent in fastness to light. Therefore, these couplers are especially preferred of the yellow couplers of the present invention.

Example 7

The Numbers of Compounds are the Same as Those in Example 6

Similarly, samples were prepared following the same procedures as for the samples 504 to 516 in Example 6, except that the fifth layer (red-sensitive emulsion layer) was replaced with the fifth layer (2) having the composition shown below. Evaluation was performed in the same manner as in Example 6, and results (effects of the present invention) similar to those in Example 6 were also obtained in the light-sensitive materials in this example according to the present invention.

| Fifth Layer (2) | |
|---|---|
| A silver chlorobromide emulsion E (gold and sulfur sensitized, cubic, a 5:5 mixture of a large-size emulsion E-1 and a small-size emulsion E-2 (in terms of mol of silver)) | 0.10 |
| Gelatin | 1.11 |
| Cyan coupler (ExC-1) | 0.02 |
| Cyan coupler (ExC-3) | 0.01 |
| Cyan coupler (ExC-4) | 0.11 |
| Cyan coupler (ExC-5) | 0.01 |
| Color-image stabilizer (Cpd-1) | 0.01 |
| Color-image stabilizer (Cpd-6) | 0.06 |
| Color-image stabilizer (Cpd-7) | 0.02 |
| Color-image stabilizer (Cpd-9) | 0.04 |
| Color-image stabilizer (Cpd-10) | 0.01 |
| Color-image stabilizer (Cpd-14) | 0.01 |
| Color-image stabilizer (Cpd-15) | 0.12 |
| Color-image stabilizer (Cpd-16) | 0.01 |
| Color-image stabilizer (Cpd-17) | 0.01 |
| Color-image stabilizer (Cpd-18) | 0.07 |
| Color-image stabilizer (Cpd-20) | 0.01 |
| Ultraviolet absorbing agent (UV-7) | 0.01 |
| Solvent (Solv-5) | 0.15 |

Example 8

The Numbers of Compounds are the Same as Those in Example 7

Samples of color print were obtained following the same procedures as for the samples in Example 7, except that the samples used in Example 7 were used and the processing A was replaced with the processing B shown below. Evaluation was performed in the same manner as in Example 6, and results (effects of the present invention) similar to those in Example 6 were also obtained in the samples and processing of this example according to the present invention.

Processing B

The above-described light-sensitive material samples were processed to a 127 mm width roll-like form. They were image-wise exposed to light through a negative film having an average density using a test processor made by remodeling a mini-lab printer processor PP350 (trade name), manufactured by Fuji Photo Film Co., Ltd., so that a processing time and temperature could be changed. A continuous processing (running test) was performed until an accumulated replenisher amount of color developer used in the following processing steps became two times the tank volume of a color developer tank. Then, a processing using the resulting running processing solution was named processing B.

| Processing step | Temperature | Time | Replenishment rate* |
|---|---|---|---|
| Color development | 45.0° C. | 20 sec | 45 ml |
| Bleach-fixing | 40.0° C. | 20 sec | 35 ml |
| Rinse (1) | 40.0° C. | 8 sec | — |
| Rinse (2) | 40.0° C. | 8 sec | — |
| Rinse (3)** | 40.0° C. | 8 sec | — |
| Rinse (4)** | 38.0° C. | 8 sec | 121 ml |
| Drying | 80° C. | 15 sec | |

*Replenishment rate per $m^2$ of the light-sensitive material to be processed.
**A rinse cleaning system RC50D (trade name), manufactured by Fuji Photo Film Co., Ltd., was installed in the rinse (3), and the rinse solution was taken out from the rinse (3) and sent to a reverse osmosis membrane module (RC50D) by using a pump. The permeated water obtained in that tank was supplied to the rinse (4), and the concentrated water was returned to the rinse (3). Pump pressure was controlled such that the water to be permeated in the reverse osmosis module would be maintained in an amount of 50 to 300 ml/min, and the rinse solution was circulated under controlled temperature for 10 hours a day. The rinse was made in a tank counter-current system from (1) to (4).

The composition of each processing solution was as follows.

| | (Tank solution) | (Replenisher) |
|---|---|---|
| (Color developer) | | |
| Water | 800 ml | 800 ml |
| Fluorescent whitening agent (FL-3) | 4.0 g | 8.0 g |
| Residual color reducing agent (SR-1) | 3.0 g | 5.5 g |
| Triisopropanolamine | 8.8 g | 8.8 g |
| Sodium p-toluenesulfonate | 10.0 g | 10.0 g |
| Ethylenediamine tetraacetic acid | 4.0 g | 4.0 g |
| Sodium sulfite | 0.10 g | 0.10 g |
| Potassium chloride | 10.0 g | — |
| Sodium 4,5-dihydroxybenzene-1,3-disulfonate | 0.50 g | 0.50 g |
| Disodium-N,N-bis(sulfonatoethyl) hydroxylamine | 8.5 g | 14.0 g |
| 4-amino-3-methyl-N-ethyl-N-(β-methanesulfonamidoethyl) aniline · 3/2 sulfate · mono hydrate | 7.0 g | 19.0 g |
| Potassium carbonate | 26.3 g | 26.3 g |
| Water to make | 1000 ml | 1000 ml |

-continued

|  | (Tank solution) | (Replenisher) |
|---|---|---|
| pH (25° C./adjusted using sulfuric acid and potassium hydroxide) | 10.25 | 12.6 |

(Bleach-fixing solution)

|  | (Tank solution) | (Replenisher) |
|---|---|---|
| Water | 800 ml | 800 ml |
| Ammonium thiosulfate (750 g/l) | 107 ml | 214 ml |
| Succinic acid | 29.5 g | 59.0 g |
| Ammonium iron (III) ethylenediaminetetraacetate | 47.0 g | 94.0 g |
| Ethylenediamine tetraacetic acid | 1.4 g | 2.8 g |
| Nitric acid (67%) | 17.5 g | 35.0 g |
| Imidazole | 14.6 g | 29.2 g |
| Ammonium sulfite | 16.0 g | 32.0 g |
| Potassium metabisulfite | 23.1 g | 46.2 g |
| Water to make | 1000 ml | 1000 ml |
| pH (25° C./adjusted using nitric acid and ammonia) | 6.00 | 6.00 |

(Rinse solution)

|  | (Tank solution) | (Replenisher) |
|---|---|---|
| Sodium chlorinated-isocyanurate | 0.02 g | 0.02 g |
| Deionized water (conductivity: 5 μS/cm or less) | 1000 ml | 1000 ml |
| pH (25° C.) | 6.5 | 6.5 |

Example 9

Support

A support used in the present example was prepared with the below shown method.

1) First Layer and Undercoat Layer

The two surfaces of the 90 μm thick polyethylenenaphthlate support were subjected to glow discharge treatment under the conditions of processing atmospheric pressure: 2.66×10 Pa; $H_2O$ partial pressure in the atmospheric vapor: 75%; discharge frequency: 30 kHz; output: 2500W; and processing intensity: 0.5·kV·A minute/$m^2$. After that, one surface of the support was coated with a coating solution having the following composition for the first layer so as to give a coating amount of 5 ml/$m^2$, by a bar coat method described in JP-B-58-4589.

| A dispersion liquid of conductive fine particles (10% aqueous dispersion of $SnO_2/Sb_2O_5$ particles. Secondary aggregate, whose average particle diameter was 0.05 μm, composed of particles whose primary particle diameter was 0.005 μm.) | 50 mass parts |
|---|---|
| Gelatin | 0.5 mass part |
| Water | 49 mass parts |
| Polyglycerolpolyglycidyl ether | 0.16 mass part |
| Poly(polymerization degree 20)oxyethylene sorbitan mono-laurate | 0.1 mass part |

Further, after coating the first layer, the polyethylenenaphthlate (PEN) support was wound around a stainless steel core of 20 cm in diameter and given a thermal history by heating at 110° C. (Tg of PEN support: 119° C.) for 48 hours. Thus, an annealing treatment was completed. The other surface of the support opposite to the first layer was coated with a coating solution having the following composition as an undercoat layer for an emulsion, so as to give a coating amount of 10 ml/$m^2$, by using a bar coat method.

| Gelatin | 1.01 mass part |
|---|---|
| Salicylic acid | 0.30 mass part |
| Resorcine | 0.40 mass part |
| Poly(polymerization degree 10)oxyethylene nonylphenylether | 0.11 mass part |
| Water | 3.53 mass parts |
| Methanol | 84.57 mass parts |
| n-Propanol | 10.08 mass parts |

Further, the second layer and the third layer described later were coated on the first layer in this order. At last, the color negative light-sensitive material having the composition described later was multi-coated on the opposite side, so that a transparent magnetic recording medium with a silver halide emulsion was prepared.

2) Second Layer (Transparent Magnetic Recording Layer)
(i) Dispersion of Magnetic Substance 1100 mass parts of Co-coated γ-$Fe_2O_3$ magnetic substance (average major axis length: 0.25 μm, $S_{BET}$: 39 $m^2$/g, Hc: 6.56×$10^4$ A/m, $\sigma_S$: 77.1 A$m^2$/kg, σr: 37.4 A$m^2$/kg), 220 mass parts of water, 165 mass parts of silane coupling agent [3-(poly(polymerization degree 10)oxyethynyl)oxypropyl trimethoxysilane] were added and well mixed by means of an open kneader for 3 hours. The resulting roughly dispersed viscous liquid was dried at 70° C. for a day to remove water. Thereafter, a heat treatment was performed at 110° C. for 1 hour to prepare surface-treated magnetic particles.

Further, a mixture having the following formulation was kneaded again by means of an open kneader for 4 hours.

| The above-mentioned surface-treated magnetic particles | 855 g |
|---|---|
| Diacethylcellulose | 25.3 g |
| Methylethylketone | 136.3 g |
| Cyclohexanone | 136.3 g |

Further, a mixture having the following formulation was finely dispersed at 2,000 rpm by means of a sand mill (¼ G sand mill), for 4 hours. 1 mm φ-glass beads were used as a media.

| The above kneaded solution | 45 g |
|---|---|
| Diacethylcellulose | 23.7 g |
| Methylethylketone | 127.7 g |
| Cyclohexanone | 127.7 g |

Further, an intermediate solution containing a magnetic substance was prepared according to the following formulation.

(ii) Preparation of Intermediate Solution Containing a Magnetic Substance

| The above-described magnetic substance finely dispersed solution | 674 g |
|---|---|
| Diacethyl cellulose solution (Solid content: 4.34%, Solvent: methylethylketone/cyclehexanone = 1/1) | 24280 g |
| Cyclohexanone | 46 g |

These were mixed and stirred by a dispersing means (Disper) to prepare an "intermediate solution containing a magnetic substance".

A dispersion solution of α-alumina abrasive having the following formulation for use in the present invention was prepared.
[a]Sumicorundum AA-1.5 (average primary particle diameter of 1.5 μm, specific surface area of 1.3 m²/g, trade name, manufactured by Sumitomo Chemical Co., Ltd.)
Preparation of Particle Dispersion Solution

| | |
|---|---|
| Sumicorundum AA-1.5 (trade name, manufactured by Sumitomo Chemical Co., Ltd.) | 152 g |
| Silane coupling agent KBM 903 (trade name, manufactured by Shinetsu silicone Co.) | 0.48 g |
| Diacetyl cellulose solution (solid content 4.5%, solvent: methyl ethylketone/cyclohexanone = 1/1) | 227.52 g |

The mixture having the above formulation was finely dispersed by means of a sand mill (¼ G), at the rate of 800 rpm, for 4 hours. As a media, zirconia beads having a diameter of 1 mmϕ were used.
[b] Colloidal Silica Particle-Dispersed Solution (Fine Particles)
"MEK-ST" (trade name) manufactured by Nissan Chemical Industries Ltd. was used.
This was a dispersed solution of colloidal silica having average primary particle diameter of 0.015 μm in methyl ethyl ketone as a dispersion medium, and the solid content of the colloidal silica was 30%.
(iii) Preparation of Second Layer Coating Solution

| | |
|---|---|
| The above-described magnetic substance-containing intermediate solution | 19053 g |
| Diacetyl cellulose solution (solid content 4.5%, solvent: methyl ethylketone/cyclohexanone = 1/1) | 264 g |
| Colloidal silica dispersion solution [MEK-ST] [dispersion solution b] (solid content 30%) | 128 g |
| Sumicorundum AA-1.5 dispersed solution [dispersion solution a] | 12 g |
| Millionate MR-400 (trade name, manufactured by Nippon Polyurethane Co., Ltd.) diluted solution (solid content 20%, diluting solvent: methyl ethylketone/cyclohexanone = 1/1) | 203 g |
| Methyl ethyl ketone | 170 g |
| Cyclohexanone | 170 g |

The coating solution, which was obtained by mixing and stirring the above, was coated in a coating amount of 29.3 ml/m by means of a wire bar. Drying of the coated layer was performed at 110° C. The thickness of the dried magnetic layer was 1.0 μm.
3) Third Layer (a Layer Containing a Higher Fatty Acid Ester Lubricant)
(i) Preparation of Undiluted Dispersion Solution Containing a Lubricant
Solution A presented below was dissolved by heating at 100° C. The resultant solution was added to Solution B, and then the resultant mixture was dispersed by means of a high pressure homogenizer to prepare an undiluted dispersion solution containing a lubricant.

Solution A

| | |
|---|---|
| The compound shown below $C_6H_{13}CH(OH)(CH_2)_{10}COOC_{50}H_{101}$ | 399 mass parts |
| The compound shown below n-$C_{50}H_{101}O(CH_2CH_2O)_{16}H$ | 171 mass parts |
| Cyclohexanone | 830 mass parts |

Solution B

| | |
|---|---|
| Cyclohexanone | 8600 mass parts |

(ii) Preparation of Spherical Inorganic Particle Dispersion Solution

Spherical inorganic particle dispersion solution [c1] was prepared according to the following formulation.

| | |
|---|---|
| Isopropyl alcohol | 93.54 mass parts |
| Silane coupling agent KBM 903 (trade name, manufactured by Shinetsu silicone Co.) compound 1-1.: $(CH_3O)_3Si-(CH_2)_3-NH_2$) | 5.53 mass parts |
| Compound 1 | 2.93 mass parts |

Compound 1

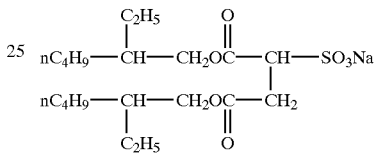

| | |
|---|---|
| SEA HOSTER KEP 50 (amorphous spherical silica having an average grain diameter of 0.5 μm; trade name, manufactured by NIPPON SHOKUBAI CO., LTD.) | 88.00 mass parts |

The mixture having the above-mentioned formulation was stirred for 10 minutes. Then, the following was further added.

| | |
|---|---|
| Diacetone alcohol | 252.93 mass parts |

An ultrasonic homogenizer SONIFIER 450 (trade name, manufactured by BRANSON Co., Ltd.) was used to disperse the resultant mixture solution for 3 hours with stirring while cooling on ice. Thus, a dispersion solution cl of spherical inorganic particles was completed.
(iii) Preparation of a Dispersion Solution Containing Spherical Organic High Molecular Particles
A dispersion solution [c2] containing spherical organic high molecular particles was prepared according to the following formulation.

| | |
|---|---|
| XC99-A8808 (trade name, manufactured by Toshiba Silicone Co., Ltd.; spherical cross-linking polysiloxane particles having an average grain size of 0.9 μm) | 60 mass parts |
| Methylethylketone | 120 mass parts |
| Cyclohexanone | 120 mass parts |
| (Solid content 20%, Solvent: methylethylketone/cyclohexane = 1/1) | |

An ultrasonic homogenizer SONIFIER 450 (trade name, manufactured by BRANSON Co., Ltd.) was used to disperse the resultant mixture solution for 2 hours with stirring while cooling on ice. Thus, a dispersion solution c2 of spherical organic high-molecular particles was completed.
(iv) Preparation of Third Layer Coating Solution
The following compositions were added to 542 g of the aforementioned undiluted dispersion solution containing a lubricant, so that the third layer coating solution was formed.

| | | |
|---|---|---|
| Diacetone alcohol | | 5950 g |
| Cyclohexanone | | 176 g |
| Ethyl acetate | | 1700 g |
| The aforementioned dispersion solution [c1] of SEA HOSTER KEP 50 | | 53.1 g |
| The aforementioned dispersion solution of [c2] of spherical organic high molecular particles | | 300 g |
| FC431 (trade name, manufactured by 3M Co., Ltd., solid content 50%, Solvent: Ethyl acetate) | | 2.65 g |
| BYK310 (trade name, manufactured by BYK Chem Japan Co., Ltd, Solid content: 25%) | | 5.3 g |

The above third layer coating solution was coated on the second layer in a coating amount of 10.35 ml/m², followed by drying at 110° C., and further dried at 97° C. for 3 minutes.

4) A Coating of Light Sensitive Layers

Then, each layer as following composition were multi-coated opposite to the obtained backing layer to prepare a color negative film.

(Composition of Light Sensitive Layers)

A number corresponding to each component represents a coated amount showed by g/m², and an amount of silver halide emulsion is shown with a coated amount in terms of silver. Additionally, Em shows an emulsion.

| | | |
|---|---|---|
| First layer (First halation preventing layer) | | |
| Black colloidal silver | Silver | 0.122 |
| Silver iodobromide emulsion (0.07 μm) | Silver | 0.01 |
| Gelatin | | 0.919 |
| ExM-1 | | 0.066 |
| ExC-1 | | 0.002 |
| ExC-3 | | 0.002 |
| Cpd-2 | | 0.001 |
| F-8 | | 0.001 |
| HBS-1 | | 0.050 |
| HBS-2 | | 0.002 |
| Second layer (Second halation preventing layer) | | |
| Black colloidal silver | Silver | 0.055 |
| Gelatin | | 0.425 |
| ExF-1 | | 0.002 |
| F-8 | | 0.001 |
| Solid dispersion dye ExF-7 | | 0.120 |
| HBS-1 | | 0.074 |
| Third layer (intermediate layer) | | |
| ExC-2 | | 0.050 |
| Cpd-1 | | 0.090 |
| Polyethyl acrylate latex | | 0.200 |
| HBS-1 | | 0.100 |
| Gelatin | | 0.700 |
| Fourth layer (low-speed red light-sensitive emulsion layer) | | |
| Em-D | Silver | 0.577 |
| Em-C | Silver | 0.347 |
| ExC-1 | | 0.188 |
| ExC-2 | | 0.011 |
| ExC-3 | | 0.075 |
| ExC-4 | | 0.121 |
| ExC-5 | | 0.010 |
| ExC-6 | | 0.007 |
| ExC-8 | | 0.050 |
| ExC-9 | | 0.020 |
| Cpd-2 | | 0.025 |
| Cpd-4 | | 0.025 |
| UV-2 | | 0.047 |
| UV-3 | | 0.086 |
| UV-4 | | 0.018 |
| HBS-1 | | 0.245 |
| HBS-5 | | 0.038 |
| Gelatin | | 0.994 |
| Fifth layer (medium-speed red light-sensitive emulsion layer) | | |
| Em-B | Silver | 0.431 |
| Em-C | Silver | 0.432 |
| ExC-1 | | 0.154 |
| ExC-2 | | 0.068 |
| ExC-3 | | 0.018 |
| ExC-4 | | 0.103 |
| ExC-5 | | 0.023 |
| ExC-6 | | 0.010 |
| ExC-8 | | 0.016 |
| ExC-9 | | 0.005 |
| Cpd-2 | | 0.036 |
| Cpd-4 | | 0.028 |
| HBS-1 | | 0.129 |
| Gelatin | | 0.882 |
| Sixth layer (high-speed red light-sensitive emulsion layer) | | |
| Em-A | Silver | 1.108 |
| ExC-1 | | 0.180 |
| ExC-3 | | 0.035 |
| ExC-6 | | 0.029 |
| ExC-8 | | 0.110 |
| ExC-9 | | 0.020 |
| Cpd-2 | | 0.064 |
| Cpd-4 | | 0.077 |
| HBS-1 | | 0.329 |
| HBS-2 | | 0.120 |
| Gelatin | | 1.245 |
| Seventh layer (intermediate layer) | | |
| Cpd-1 | | 0.094 |
| Cpd-6 | | 0.369 |
| Solid dispersion dye ExF-4 | | 0.030 |
| HBS-1 | | 0.049 |
| Polyethyl acrylate latex | | 0.088 |
| Gelatin | | 0.886 |
| Eighth layer (layer which gives an interlayer effect to red light sensitive layer) | | |
| Em-J | Silver | 0.153 |
| Em-K | Silver | 0.153 |
| Cpd-4 | | 0.030 |
| ExM-2 | | 0.120 |
| ExM-3 | | 0.016 |
| ExM-4 | | 0.026 |
| ExY-1 | | 0.016 |
| ExY-4 | | 0.036 |
| ExC-7 | | 0.026 |
| HBS-1 | | 0.218 |
| HBS-3 | | 0.003 |
| HBS-5 | | 0.030 |
| Gelatin | | 0.610 |
| Ninth layer (low-speed green light-sensitive emulsion layer) | | |
| Em-H | Silver | 0.329 |
| Em-G | Silver | 0.333 |
| Em-I | Silver | 0.088 |
| ExM-2 | | 0.378 |
| ExM-3 | | 0.047 |
| ExY-1 | | 0.017 |
| ExC-7 | | 0.007 |
| HBS-1 | | 0.098 |
| HBS-3 | | 0.010 |
| HBS-4 | | 0.077 |
| HBS-5 | | 0.548 |
| Cpd-5 | | 0.010 |
| Gelatin | | 1.470 |
| Tenth layer (medium-speed green light-sensitive emulsion layer) | | |
| Em-F | Silver | 0.457 |
| ExM-2 | | 0.032 |
| ExM-3 | | 0.029 |

-continued

| | | |
|---|---|---|
| ExM-4 | | 0.029 |
| ExY-3 | | 0.007 |
| ExC-6 | | 0.010 |
| ExC-7 | | 0.012 |
| ExC-8 | | 0.010 |
| HBS-1 | | 0.065 |
| HBS-3 | | 0.002 |
| HBS-4 | | 0.020 |
| HBS-5 | | 0.020 |
| Cpd-5 | | 0.004 |
| Gelatin | | 0.446 |
| Eleventh layer (high-speed green light-sensitive emulsion layer) | | |
| Em-E | Silver | 0.794 |
| ExC-6 | | 0.002 |
| ExC-8 | | 0.010 |
| ExM-1 | | 0.013 |
| ExM-2 | | 0.011 |
| ExM-3 | | 0.030 |
| ExM-4 | | 0.017 |
| ExY-3 | | 0.003 |
| Cpd-3 | | 0.004 |
| Cpd-4 | | 0.007 |
| Cpd-5 | | 0.010 |
| HBS-1 | | 0.148 |
| HBS-3 | | 0.003 |
| HBS-4 | | 0.020 |
| HBS-5 | | 0.037 |
| Polyethyl acrylate latex | | 0.099 |
| Gelatin | | 0.939 |
| Twelfth layer (yellow filter layer) | | |
| Cpd-1 | | 0.094 |
| Solid dispersion dye ExF-2 | | 0.070 |
| Solid dispersion dye ExF-5 | | 0.010 |
| Oil-soluble dye ExF-6 | | 0.010 |
| HBS-1 | | 0.049 |
| Gelatin | | 0.630 |
| Thirteenth layer (low-speed blue light-sensitive emulsion layer) | | |
| Em-O | Silver | 0.112 |
| Em-M | Silver | 0.320 |
| Em-N | Silver | 0.240 |
| ExC-1 | | 0.027 |
| ExC-7 | | 0.013 |
| ExY-1 | | 0.002 |
| ExY-2 | | 0.890 |
| ExY-4 | | 0.058 |
| Cpd-2 | | 0.100 |
| Cpd-3 | | 0.004 |
| HBS-1 | | 0.222 |
| HBS-5 | | 0.074 |
| Gelatin | | 1.553 |
| Fourteenth layer (high-speed blue light-sensitive emulsion layer) | | |
| Em-L | Silver | 0.714 |
| ExY-2 | | 0.211 |
| ExY-4 | | 0.068 |
| Cpd-2 | | 0.075 |
| Cpd-3 | | 0.001 |
| HBS-1 | | 0.124 |
| Gelatin | | 0.678 |
| Fifteenth layer (first protective layer) | | |
| Silver iodobromide emulsion (0.07 μm) | Silver | 0.301 |
| UV-1 | | 0.211 |
| UV-2 | | 0.132 |
| UV-3 | | 0.198 |
| UV-4 | | 0.026 |
| F-11 | | 0.009 |
| S-1 | | 0.086 |
| HBS-1 | | 0.175 |
| HBS-4 | | 0.050 |
| Gelatin | | 1.984 |

-continued

| | |
|---|---|
| Sixteenth layer (second protective layer) | |
| H-1 | 0.400 |
| B-1 (diameter: 1.7 μm) | 0.050 |
| B-2 (diameter: 1.7 μm) | 0.150 |
| B-3 | 0.050 |
| S-1 | 0.200 |
| Gelatin | 0.750 |

In addition to the above ingredients, in order to improve storage stability, processing suitability, resistance to pressure, mildew-proofing property, bacteria-proofing property, antistatic property and coating property, the individual layer properly contained W-1 to W-6, B-4 to B-6, F-1 to F-18, lead salts, platinum salts, iridium salts and rhodium salts.

(Preparation of Dispersion of Organic Solid Dispersed Dye)

ExF-2 in the 12th layer was dispersed by the following method.

(Preparation of Dispersion of Organic Solid Dispersed Dye)

ExF-2 in the 12th layer was dispersed by the following method.

| | |
|---|---|
| Wet cake of Ex2-F (containing 17.6 mass % of water) | 2.800 kg |
| Sodium octylphenyldiethyoxymethane sulfonate (31 mass % aqueous solution) | 0.376 kg |
| F-15 (7% aqueous solution) | 0.011 kg |
| Water | 4.020 kg |
| Total | 7.210 kg |
| (The pH of the mixture is adjusted to 7.2 with NaOH) | |

The slurry having the above-described composition was roughly dispersed with stirring by a dissolver stirrer, and then dispersed by an agitator mill LMK-4 under the conditions of round speed: 10 m/s; discharge amount: 0.6 kg/min; filling rate of zirconia beads having a grain size of 0.3 μm: 80%, until specific absorbance of the dispersion solution became 0.29. Thus, a dispersion of solid fine particles was obtained. An average particle diameter of the dye fine particles was 0.29 μm.

Similarly, solid dispersions of ExF-4 and ExF-7 were obtained. The average particle diameter of these dye particles was 0.28 μm and 0.49 μm, respectively. ExF-5 was dispersed according to the micro precipitation dispersion method described in Example 1 of European Patent No. 549,489 A. An average particle diameter of the dye fine particles was 0.06 μm.

TABLE 6

| Name of Emulsion | Average amount of iodine (mole %) | Sphere-equivalent diameter* (μm) | Aspect ratio | Circle-equivalent diameter** (μm) | Thickness of particle (μm) | Shape |
|---|---|---|---|---|---|---|
| Em-A | 4 | 0.92 | 14 | 2 | 0.14 | Tabular |
| Em-B | 5 | 0.8 | 12 | 1.6 | 0.13 | Tabular |
| Em-C | 4.7 | 0.51 | 7 | 0.85 | 0.12 | Tabular |
| Em-D | 3.9 | 0.37 | 2.7 | 0.4 | 0.15 | Tabular |
| Em-E | 5 | 0.92 | 14 | 2 | 0.14 | Tabular |
| Em-F | 5.5 | 0.8 | 12 | 1.6 | 0.13 | Tabular |

TABLE 6-continued

| Name of Emulsion | Average amount of iodine (mole %) | Sphere-equivalent diameter* (μm) | Aspect ratio | Circle-equivalent diameter** (μm) | Thickness of particle (μm) | Shape |
|---|---|---|---|---|---|---|
| Em-G | 4.7 | 0.51 | 7 | 0.85 | 0.12 | Tabular |
| Em-H | 3.7 | 0.49 | 3.2 | 0.58 | 0.18 | Tabular |
| Em-I | 2.8 | 0.29 | 1.2 | 0.27 | 0.23 | Tabular |
| Em-J | 5 | 0.8 | 12 | 1.6 | 0.13 | Tabular |
| Em-K | 3.7 | 0.47 | 3 | 0.53 | 0.18 | Tabular |
| Em-L | 5.5 | 1.4 | 9.8 | 2.6 | 0.27 | Tabular |
| Em-M | 8.8 | 0.64 | 5.2 | 0.85 | 0.16 | Tabular |
| Em-N | 3.7 | 0.37 | 4.6 | 0.55 | 0.12 | Tabular |
| Em-O | 1.8 | 0.19 | — | — | — | Cubic |

Note:
*Sphere-equivalent diameter is a diameter of a sphere whose area is equivalent to that of an individual silver halide grain.
**Circle-equivalent diameter is a diameter of a circle whose area is equivalent to that of an individual silver halide grain.

In Table 6, emulsions A to C were spectrally sensitized by adding an optimal amount of each of spectrally sensitizing dyes 1 to 3, respectively, and they were also optimally gold-sensitized, sulfur-sensitized and selenium-sensitized. Emulsions E to G were spectrally sensitized adding an optimal amount of each of spectrally sensitizing dyes 4 to 6, respectively, and they were also optimally gold-sensitized, sulfur-sensitized and selenium-sensitized. Emulsion J was spectrally sensitized adding an optimal amount of each of spectrally sensitizing dyes 7 to 8, respectively, and further optimally gold-sensitized, sulfur-sensitized and selenium-sensitized. Emulsion L was spectrally sensitized adding an optimal amount of each of spectrally sensitizing dyes 9 to 11, respectively, and further optimally gold-sensitized, sulfur-sensitized and selenium-sensitized. Emulsion O was spectrally sensitized adding an optimal amount of each of spectrally sensitizing dyes 10 to 12, respectively, and further optimally gold-sensitized and sulfur-sensitized. Emulsions D, H, I, K, M, and N were spectrally sensitized adding an optimal amount of each of spectrally sensitizing dyes shown in Table 7, respectively, and they were also optimally gold-sensitized, sulfur-sensitized and selenium-sensitized.

TABLE 7

| Name of Emulsion | Sensitizing dye | Added amount (mol/mol Ag) |
|---|---|---|
| Em-D | Sensitizing dye 1 | $5.44 \times 10^{-4}$ |
|  | Sensitizing dye 2 | $2.35 \times 10^{-4}$ |
|  | Sensitizing dye 3 | $7.26 \times 10^{-6}$ |
| Em-H | Sensitizing dye 8 | $6.52 \times 10^{-4}$ |
|  | Sensitizing dye 13 | $1.35 \times 10^{-4}$ |
|  | Sensitizing dye 6 | $2.48 \times 10^{-5}$ |
| Em-I | Sensitizing dye 8 | $6.09 \times 10^{-4}$ |
|  | Sensitizing dye 13 | $1.26 \times 10^{-4}$ |
|  | Sensitizing dye 6 | $2.32 \times 10^{-5}$ |
| Em-K | Sensitizing dye 7 | $6.27 \times 10^{-4}$ |
|  | Sensitizing dye 8 | $2.24 \times 10^{-4}$ |
| Em-M | Sensitizing dye 9 | $2.43 \times 10^{-4}$ |
|  | Sensitizing dye 10 | $2.43 \times 10^{-4}$ |
|  | Sensitizing dye 11 | $2.43 \times 10^{-4}$ |
| Em-N | Sensitizing dye 9 | $3.28 \times 10^{-4}$ |
|  | Sensitizing dye 10 | $3.28 \times 10^{-4}$ |
|  | Sensitizing dye 11 | $3.28 \times 10^{-4}$ |

TABLE 7-continued

The sensitizers in Table 7 are shown below.

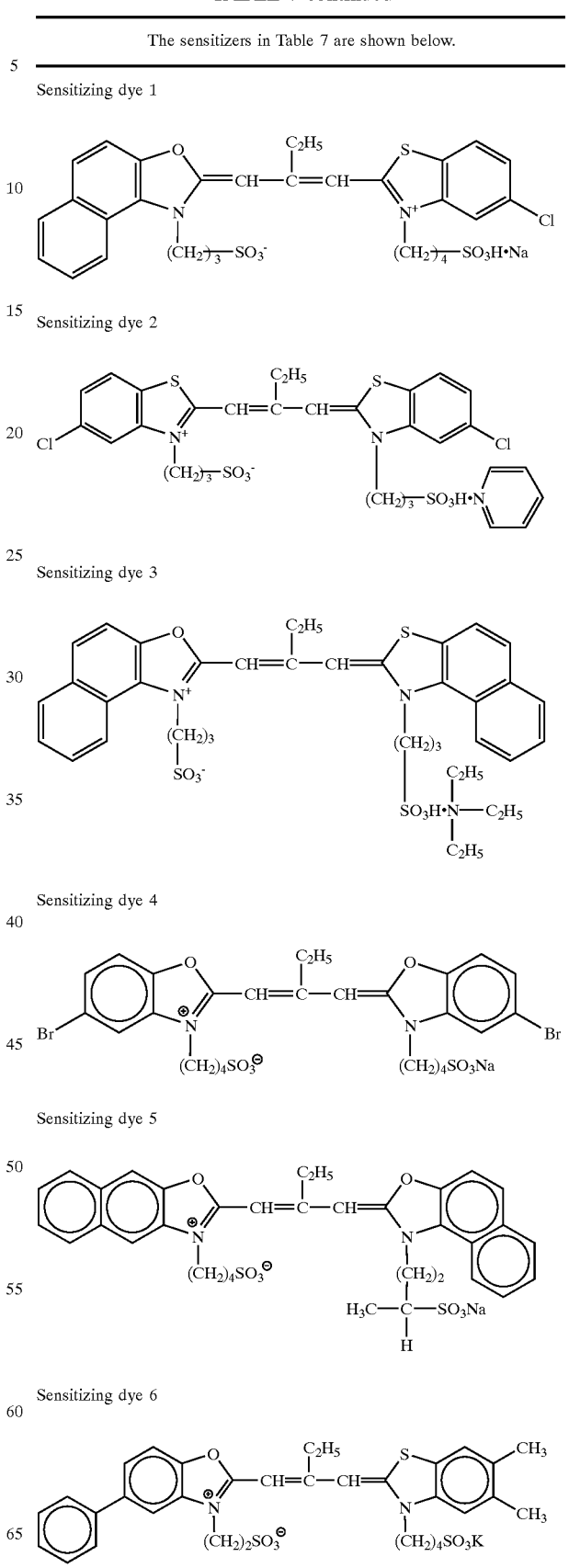

Sensitizing dye 1

Sensitizing dye 2

Sensitizing dye 3

Sensitizing dye 4

Sensitizing dye 5

Sensitizing dye 6

TABLE 7-continued

Sensitizing dye 7

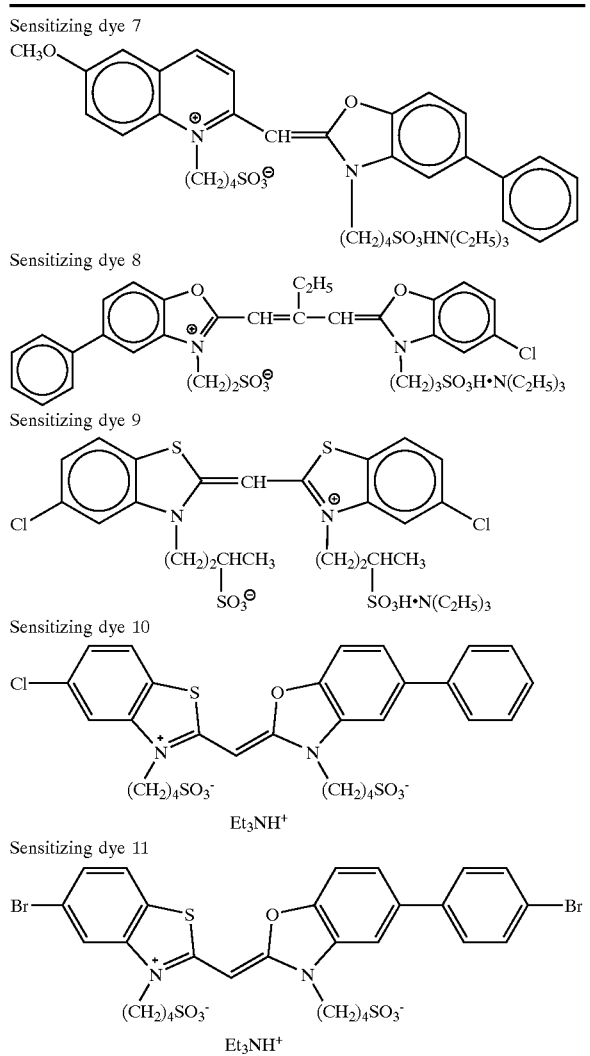

Sensitizing dye 8

Sensitizing dye 9

Sensitizing dye 10

Sensitizing dye 11

TABLE 7-continued

Sensitizing dye 12

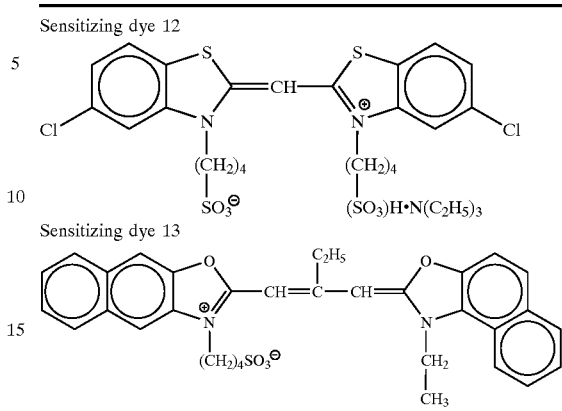

Sensitizing dye 13

In the preparation of tabular grains, low molecular gelatin was used according to the working examples in JP-A-1-158426.

Emulsions A to K each contained an optimal amount of each of Ir and Fe.

Emulsions L to O each were reduction-sensitized at the time of grain formation.

In the tabular grains, dislocation lines as described in JP-A-3-237450 were observed by means of high-pressure electron microscope.

In Emulsions A to C and J, an iodide ion-releasing agent was used to introduce the dislocation according to the working examples in JP-A-6-11782.

In Emulsion E, silver iodide fine grains that were prepared just before addition in a separate chamber installed with a magnetic coupling induction type stirrer described in JP-A-10-43570, were used to introduce the dislocation.

The compounds that were used in each layer, are shown below.

ExC-1

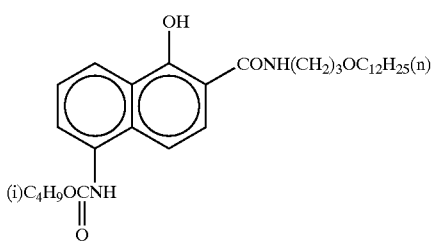

ExC-2

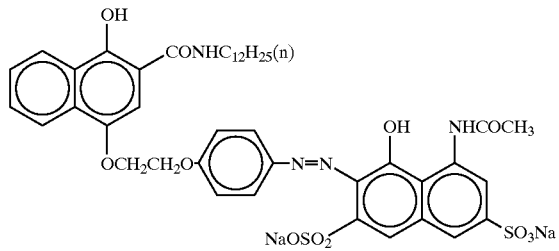

ExC-3

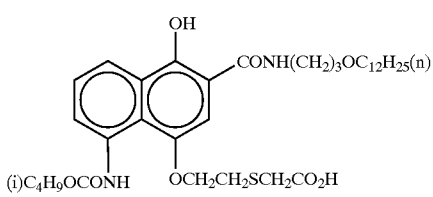

ExC-4

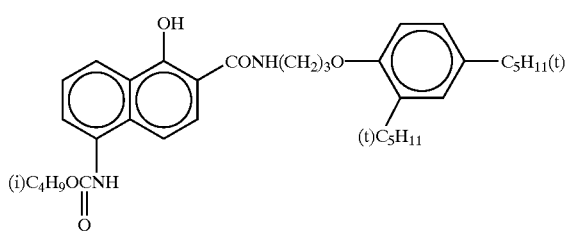

ExC-5
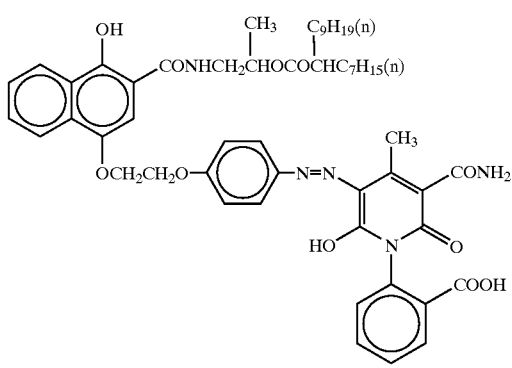
ExC-6
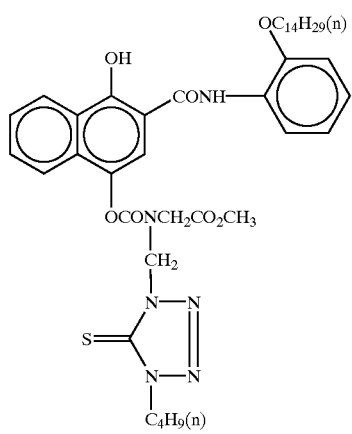
ExC-7
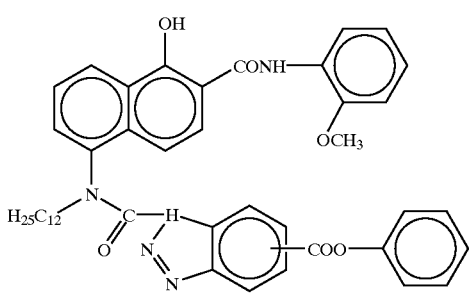
ExC-8
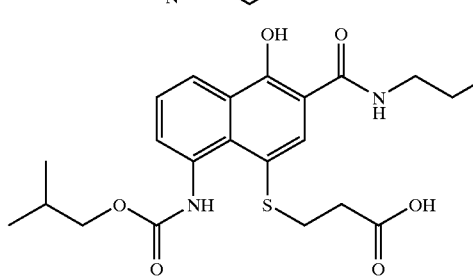
ExC-9
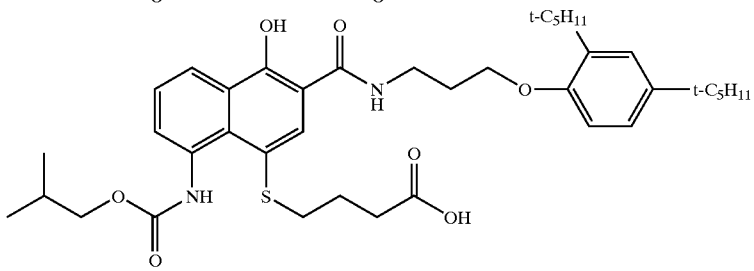
ExM-1
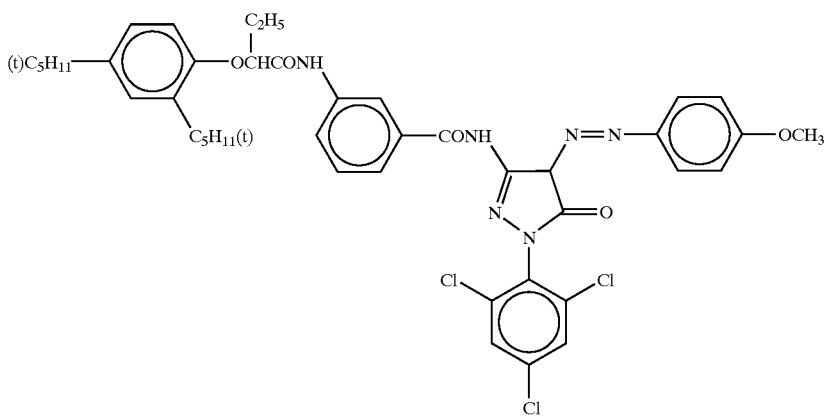

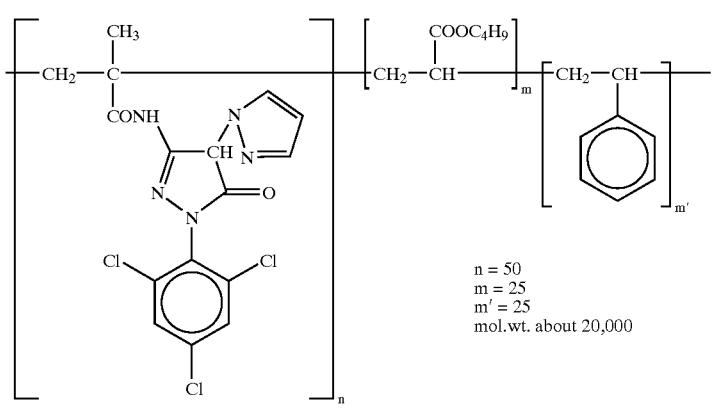
ExM-2
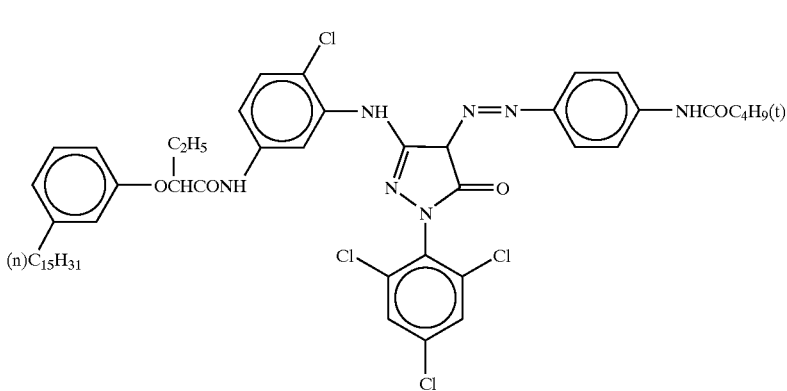
ExM-3
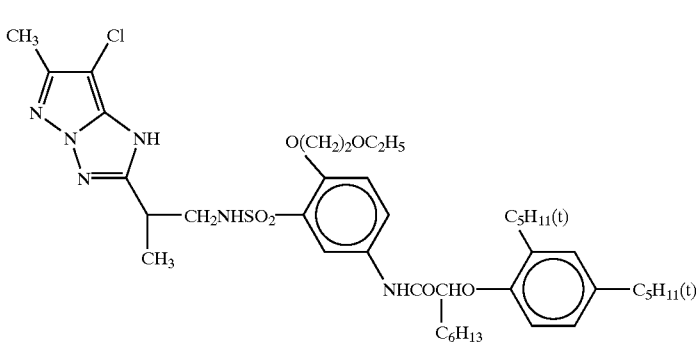
ExM-4
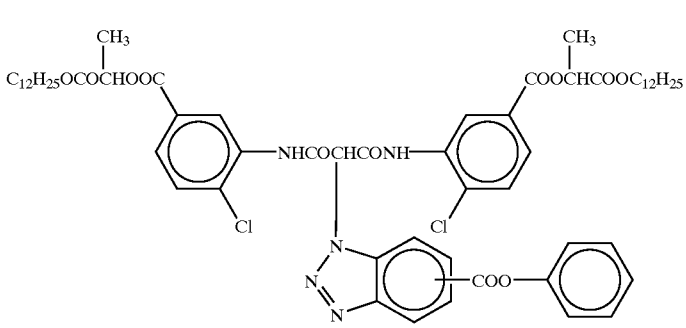
ExY-1

-continued
ExY-2
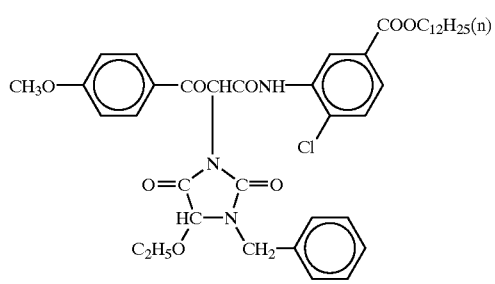
ExY-3
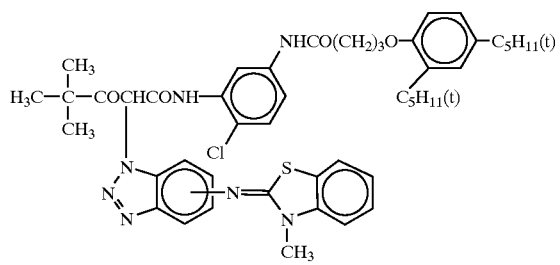
ExY-4
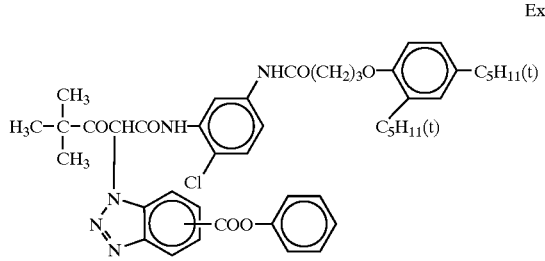
Cpd-1
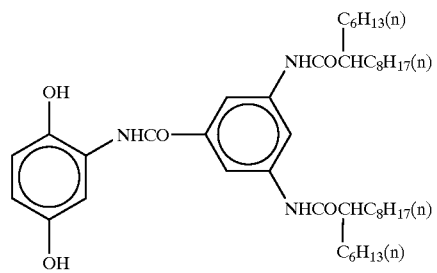
Cpd-2
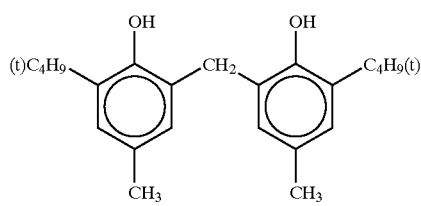
Cpd-3
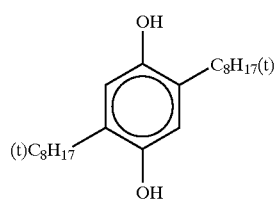
Cpd-4
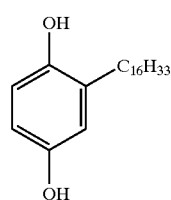
(n)C$_{14}$H$_{29}$OCOCH$_2$CH$_2$CONOH  Cpd-5
|
CH$_3$
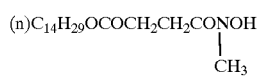
Cpd-6
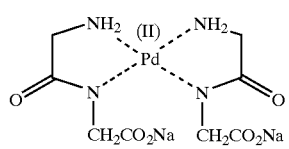
UV-1
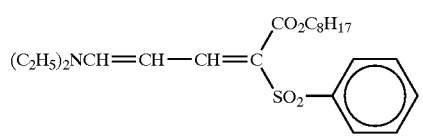
UV-2
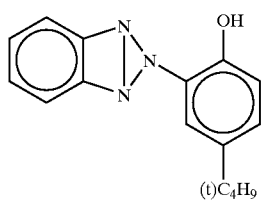
UV-3
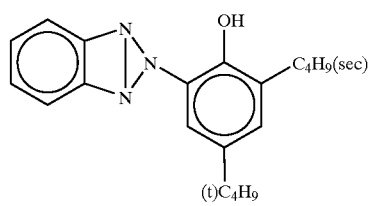
UV-4
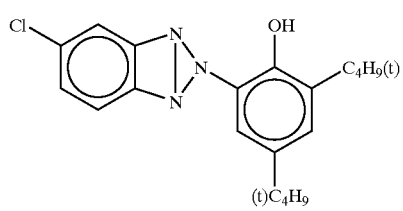
B-1
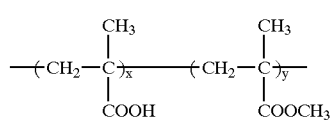
x/y = 10/90 (mass ratio)
average molecular weight: about 35,000

-continued
B-2
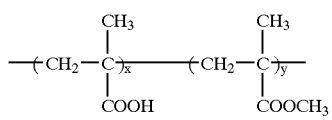
x/y = 40/60 (mass ratio)
average molecular weight: about 20,000
B-3
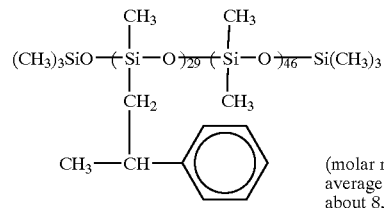
(molar ratio)
average molecular weight: about 8,000
HBS-1 Tricresyl phosphate
HBS-2 Di-n-butyl phthalate
HBS-3
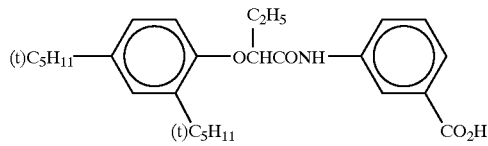
HBS-4 Tri(2-ethylhexyl) phosphate
HBS-5
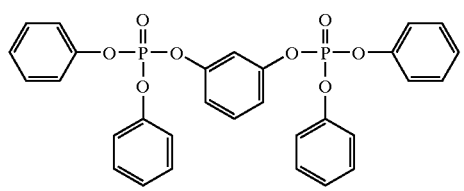
S-1
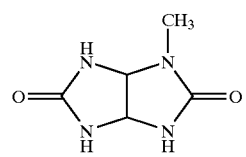
H-1
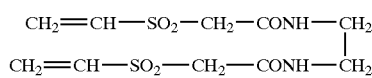
F-1
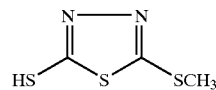
F-2
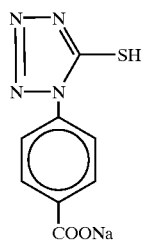
F-3
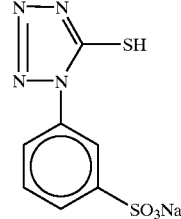
F-4
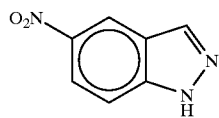
F-5
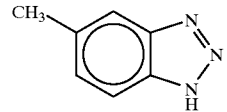
F-6
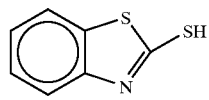
F-7
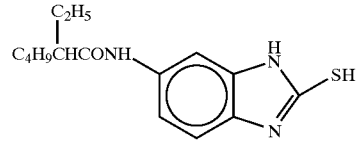
F-8
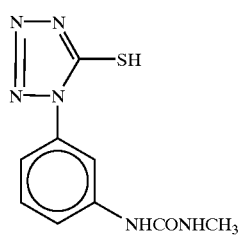
F-9
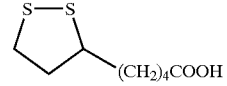
F-10
F-11
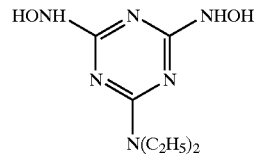

-continued

-continued

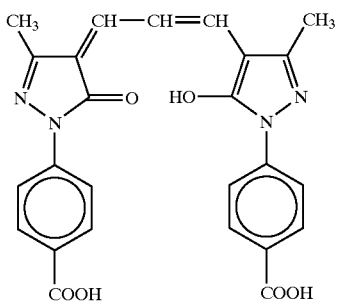
ExF-4

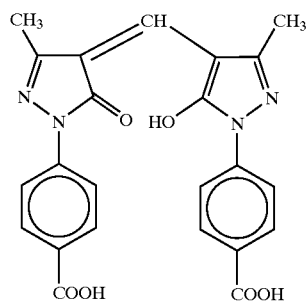
ExF-5

ExF-6

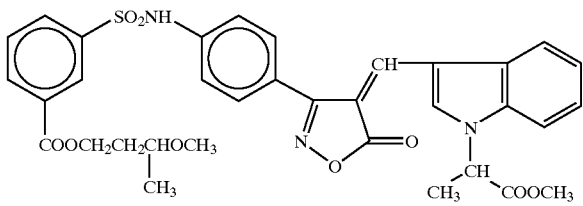

ExF-7

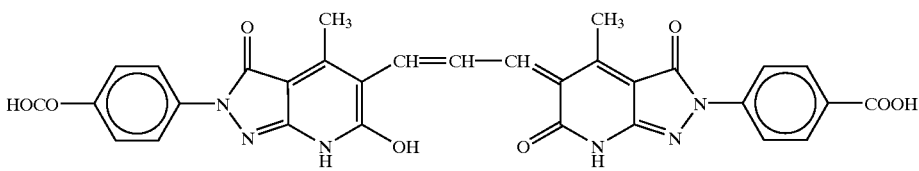

The above-described silver halide color photographic light-sensitive material was named sample 601.

The sample 601 was exposed to light through both a gelatin filter SC-39 (trade name) available from Fuji Photo Film Co., Ltd. and a continuous wedge for 1/100 second.

Processing was performed using an automatic processor FP-360 B (trade name) available from Fuji Photo Film Co., Ltd. according to the following steps. Note that the processor was remodeled so that the overflow from the bleaching bath was not introduced to the subsequent bath, but entirely discharged to a waste tank. Note that this FP-360 B was installed with an evaporation correction means described in JIII Technical Disclosure No. 94-4992 (published by Japan Institute of Invention & Innovation).

Processing steps and processing solution compositions are presented below.

(Processing Steps)

| Processing step | Processing time | Processing temperature | Replen-isher* | Tank Volume |
| --- | --- | --- | --- | --- |
| Color developing | 3 min 5 sec | 37.8° C. | 20 ml | 11.5 l |
| Bleaching | 50 sec | 38.0° C. | 5 ml | 5 l |
| Fixing (1) | 50 sec | 38.0° C. | — | 5 l |
| Fixing (2) | 50 sec | 38.0° C. | 8 ml | 5 l |
| Washing | 30 sec | 38.0° C. | 17 ml | 3 l |
| Stabilizing (1) | 20 sec | 38.0° C. | — | 3 l |
| Stabilizing (2) | 20 sec | 38.0° C. | 15 ml | 3 l |
| Drying | 1 min 30 sec | 60.0° C. | | |

*The replenishment rate is represented by a value per 1.1 m of a 35 mm wide light-sensitive material sample (equivalent to one 24-exposure film)

The stabilizer and fixer were made in a counter-flow system from (2) to (1), and the overflow of washing water was entirely introduced to the fixing bath (2). Note that the amount of the developer carried over to the bleaching step, the amount of the bleaching solution carried over to the fixing step, and the amount of the fixer carried over to the washing step were 2.5 ml, 2.0 ml, and 2.0 ml, respectively, per 1.1 m of a 35 mm wide light-sensitive material. Note also the preceding each crossover time was 6 sec, and this time was included in the processing time of the preceding processing step.

The aperture area of the processor was 100 cm$^2$ for the color developer, 120 cm$^2$ for the bleaching solution, and approximately 100 cm$^2$ for other solutions.

The composition of each processing solution was as follows, respectively:

| | Tank solution (g) | Replenisher (g) |
| --- | --- | --- |
| (Color-developer) | | |
| Diethylenetriaminepentaacetic acid | 3.0 | 3.0 |
| Disodium catechol-3,5-disulfonate | 0.3 | 0.3 |
| Sodium sulfite | 3.9 | 5.3 |
| Potassium carbonate | 39.0 | 39.0 |
| Disodium-N,N-bis(2-sulfonatoethyl) hydroxylamine | 1.5 | 2.0 |
| Potassium bromide | 1.3 | 0.3 |
| Potassium iodide | 1.3 mg | — |
| 4-Hydroxy-6-methyl-1,3,3a,7-tetrazaindene | 0.05 | — |
| Hydroxylamine sulfate | 2.4 | 3.3 |
| 2-Methyl-4-[N-ethyl-N-(β-hydroxyethyl)amino]-aniline sulfonate | 4.5 | 6.5 |
| Water to make | 1.0 liter | 1.0 liter |
| pH | 10.05 | 10.18 |
| (pH was adjusted by potassium hydroxide and sulfuric acid.) | | |
| (Bleaching solution) | | |
| 1,3-Diaminopropanetetraacetic acid iron (III) ammonium monohydrate | 113 | 170 |
| Ammonium bromide | 70 | 105 |

-continued

| | | |
|---|---|---|
| Ammonium nitrate | 14 | 21 |
| Succinic acid | 34 | 51 |
| Maleic acid | 28 | 42 |
| Water to make | 1.0 liter | 1.0 liter |
| pH | 4.6 | 4.0 |
| (pH was adjusted by aqueous ammonia.) | | |
| (Fixing (1) tank solution) | | |

A mixed solution of the above bleaching tank solution and the below shown fixing tank solution in the ratio of 5:95 (volume ratio).
(pH 6.8)
(Fixing (2))

| | | |
|---|---|---|
| Aqueous ammonium thiosulfate solution (750 g/liter) | 240 ml | 720 ml |
| Imidazole | 7 | 21 |
| Ammonium methanethiosulfonate | 5 | 15 |
| Ammonium methanesulfinate | 10 | 30 |
| Ethylenediaminetetraacetic acid | 13 | 39 |
| Water to make | 1.0 liter | 1.0 liter |
| pH | 7.4 | 7.45 |
| (pH was adjusted by aqueous ammonia and acetic acid) | | |
| (Washing water) | | |

Tap water was treated by passage through a mixed bed ion-exchange column filled with an H-type strong acidic cation exchange resin (Amberlite IR-120B, trade name, made by Rohm & Haas) and an OH-type strong basic anion exchange resin (Amberlite IR-400, the same as the above) so that the concentrations of Ca ions and Mg ions in water were both made to decrease to 3 mg/liter or below, followed by adding 20 mg/liter of sodium dichlorinated isocyanurate and 150 mg/liter of sodium sulfate. The pH of this water was in the range of 6.5 to 7.5.

| (Both tank solution and replenisher) | (g) |
|---|---|
| (Stabilizing solution) | |
| Sodium p-toluenesulfinate | 0.03 |
| Polyoxyethylene-p-monononylphenylether (av. polymerization degree: 10) | 0.2 |
| Sodium 1,2-benzoisothiazoline-3-one | 0.10 |
| Disodium ethylenediaminetetraacetate | 0.05 |
| 1,2,4-Triazole | 1.3 |
| 1,4-Bis(1,2,4-triazole-1-ylmethyl)pyperazine | 0.75 |
| Water to make | 1.0 liter |
| pH | 8.5 |

Samples 602 to 611 were prepared in the same manner as with sample 601, except that ExY-2 of the 13th layer and the 14th layer was replaced with the coupler of the present invention shown in Table 8 in an equivalent amount. The thus-obtained samples were left to stand for 7 days under the conditions of 25° C. and 65% RH. These samples were exposed to light through both a gelatin filter SC-39 (trade name) available from Fuji Photo Film Co., Ltd. and a continuous wedge for 1/100 second, and then processed according to the above-described processing steps. Each thus-processed sample was subjected to sensitometry. The maximum yellow color generation density (Dmax(Y)) was measured from the characteristic curve obtained in the sensitometry. A relative value of Dmax(Y) to that of sample 601 was calculated. Beside, these measured samples were stored for 14 days under the conditions of 50° C. and 80% RH. Thereafter, a remaining ratio of yellow density, which is indicated by a ratio of a yellow density of the reserved sample to that of the same sample but for measured just after processing, at the maximum yellow color generation density portion, was measured.

TABLE 8

| Sample No. | Coupler in the 13th and 14th layers | Relative value of Dmax (Y) to Sample 601 | Yellow density-remaining ratio after 14 days in 50° C. 80% RH | Remarks |
|---|---|---|---|---|
| 601 | ExY-2 | 1 | 70 | Comparative example |
| 602 | (171) | 1.15 | 99 | This invention |
| 603 | (172) | 1.16 | 98 | This invention |
| 604 | (173) | 1.25 | 99 | This invention |
| 605 | (174) | 1.28 | 99 | This invention |
| 606 | (175) | 1.29 | 99 | This invention |
| 607 | (176) | 1.24 | 99 | This invention |
| 608 | (177) | 1.22 | 98 | This invention |
| 609 | (178) | 1.27 | 98 | This invention |
| 610 | (179) | 1.25 | 99 | This invention |
| 611 | (180) | 1.25 | 99 | This invention |

As apparent from Table 8, when the compounds of the present invention were used, high Dmax of yellow density, which means an excellent color generation property, was attained, and a yellow image formed from the compounds of the present invention were excellent in fastness. Further, it is understood that, especially, yellow couplers having a pyrrol, pyrazole or imidazole moiety as a split-off group, and yellow couplers having a dissociation group or a hydroxyl group were excellent in color generation property.

Comparative Example 4

Preparation of Sample 701

(i) Preparation of Triacetyl Cellulose Film

A triacetyl cellulose film was prepared following a conventional solution casting method, including steps of dissolving triacetyl cellulose (13% by mass) in dichloromethane/methanol=92/8 (mass ratio), adding prasticizers of triphenyl phosphate and biphenyldiphenylphosphate (mass ratio 2:1) to the triacetyl cellulose solution so that the total content of the prasticizers became 14 mass % of triacetyl cellulose, and then forming a film from the resultant solution according to a band method. The dry thickness of the film (support) was 97 μm.

(ii) Composition of Undercoat Layer

The two surfaces of the above-described triacetyl cellulose film were coated with the following undercoat solution. The number corresponding to each ingredient indicates mass of the ingredient contained in 1 liter of the undercoat solution.

Note that the two surfaces of the film were subjected to a corona discharge treatment before coating the undercoat solution.

| | | |
|---|---|---|
| Gelatin | 10.0 | g |
| Salicylic acid | 0.5 | g |
| Glycerin | 4.0 | g |
| Acetone | 700 | ml |
| Methanol | 200 | ml |
| Dichloromethane | 80 | ml |
| Formaldehyde | 0.1 | mg |
| water to make | 1.0 | liter |

(iii) Coating of Backing Layers

The following backing layers were coated on one side of the support provided with undercoat.

| First Layer | |
|---|---|
| Binder: acid-processed gelatin (isoelectric point 9.0) | 1.00 g |
| Polymer latex P-2 (av. particle diameter 0.1 μm) | 0.13 g |
| Polymer latex P-3 (av. particle diameter 0.2 μm) | 0.23 g |
| Ultraviolet ray absorbent U-1 | 0.030 g |
| Ultraviolet ray absorbent U-3 | 0.010 g |
| Ultraviolet ray absorbent U-4 | 0.020 g |
| High-boiling organic solvent Oil-2 | 0.030 g |
| Surface active agent W-3 | 0.010 g |
| Surface active agent W-6 | 3.0 mg |
| Second Layer | |
| Binder: acid-processed gelatin (isoelectric point 9.0) | 3.10 g |
| Polymer latex: P-3 (av. particle diameter 0.2 μm) | 0.11 g |
| Ultraviolet ray absorbent U-1 | 0.030 g |
| Ultraviolet ray absorbent U-3 | 0.010 g |
| Ultraviolet ray absorbent U-4 | 0.020 g |
| High-boiling organic solvent Oil-2 | 0.030 g |
| Surface active agent W-3 | 0.010 g |
| Surface active agent W-6 | 3.0 mg |
| Dye D-2 | 0.10 g |
| Dye D-10 | 0.12 g |
| Potassium sulfate | 0.25 g |
| Calcium chloride | 0.5 mg |
| Sodium hydroxide | 0.03 g |
| Third Layer | |
| Binder: acid-processed gelatin (isoelectric point 9.0) | 3.30 g |
| Surface active agent W-3 | 0.020 g |
| Potassium sulfate | 0.30 g |
| Sodium hydroxide | 0.03 g |
| Fourth Layer | |
| Binder: lime-processed gelatin (isoelectric point 5.4) | 1.15 g |
| Copolymer of methacrylic acid and methyl methacrylate (1:9) (av. particle diameter, 2.0 μm) | 0.040 g |
| Copolymer of methacrylic acid and methyl methacrylate (6:4) (av. particle diameter, 2.0 μm) | 0.030 g |
| Surface active agent W-3 | 0.060 g |
| Surface active agent W-2 | 7.0 mg |
| Hardener H-1 | 0.23 g |

(iv) Coating of Light-sensitive Emulsion Layers (iv) Coating Solution of Light-sensitive Emulsion Layers The surface of the support on the side opposite to the backing layer, was coated with light-sensitive emulsion layers having the following compositions to produce a sample 701. The number corresponding to each ingredient indicates the addition amount per m². Note that the effect of the compound added is not limited to the use of the compound described below.

| First layer: Anti-halation Layer | | |
|---|---|---|
| Black colloidal silver | | 0.25 g |
| Gelatin | | 2.40 g |
| Ultraviolet absorber U-1 | | 0.15 g |
| Ultraviolet absorber U-3 | | 0.15 g |
| Ultraviolet absorber U-4 | | 0.10 g |
| Ultraviolet absorber U-5 | | 0.10 g |
| High boiling organic solvent Oil-1 | | 0.10 g |
| High boiling organic solvent Oil-2 | | 0.10 g |
| High boiling organic solvent Oil-5 | | 0.010 g |
| Dye D-4 | | 1.0 mg |
| Dye D-8 | | 2.5 mg |
| Fine crystal solid dispersion of Dye E-1 | | 0.05 g |
| Second layer: Intermediate layer | | |
| Gelatin | | 0.30 g |
| Compound Cpd-K | | 3.0 mg |
| Ultraviolet absorber U-6 | | 6.0 mg |
| High boiling organic solvent Oil-3 | | 0.010 g |
| High boiling organic solvent Oil-4 | | 0.010 g |
| High boiling organic solvent Oil-7 | | 2.0 mg |
| Dye D-7 | | 4.0 mg |
| Third layer: Light-sensitive emulsion layer | | |
| Emulsion R | Silver | 0.4 g |
| Fine grain silver iodide emulsion (cubic, av. sphere-equivalent diameter 0.05 μm) | Silver | 0.020 g |
| Gelatin | | 0.5 g |
| Compound Cpd-M | | 0.10 g |
| Compound Cpd-F | | 0.20 g |
| High boiling organic solvent Oil-6 | | 0.15 g |
| High boiling organic solvent Oil-8 | | 0.030 g |
| Fourth layer: Intermediate layer | | |
| Gelatin | | 1.0 g |
| Compound Cpd-M | | 0.30 g |
| High boiling organic solvent Oil-6 | | 0.20 g |
| Fifth layer: Intermediate layer | | |
| Yellow colloidal silver | | 0.010 g |
| Gelatin | | 0.40 g |
| Compound Cpd-D | | 0.020 g |
| High boiling organic solvent Oil-3 | | 0.010 g |
| Sixth layer: Low-sensitivity red-sensitive emulsion layer | | |
| Emulsion A | Silver | 0.10 g |
| Emulsion B | Silver | 0.15 g |
| Emulsion C | Silver | 0.15 g |
| Gelatin | | 0.80 g |
| Coupler C-1 | | 0.15 g |
| Coupler C-2 | | 7.0 mg |
| Coupler C-9 | | 3.0 mg |
| Coupler C-10 | | 2.0 mg |
| Ultraviolet absorber U-3 | | 0.010 g |
| Compound Cpd-I | | 0.020 g |
| Compound Cpd-D | | 3.0 mg |
| Compound Cpd-J | | 2.0 mg |
| High boiling organic solvent Oil-10 | | 0.030 g |
| Additive P-1 | | 5.0 mg |
| Seventh layer: Middle-sensitivity red-sensitive emulsion layer | | |
| Emulsion C | Silver | 0.15 g |
| Emulsion D | Silver | 0.15 g |
| Gelatin | | 0.70 g |
| Coupler C-1 | | 0.15 g |
| Coupler C-2 | | 7.0 mg |
| Coupler C-9 | | 3.0 mg |
| Compound Cpd-D | | 3.0 mg |
| Ultraviolet absorber U-3 | | 0.010 g |
| High boiling organic solvent Oil-10 | | 0.030 g |
| Additive P-1 | | 7.0 mg |
| Eighth layer: High-sensitivity red-sensitive emulsion layer | | |
| Emulsion E | Silver | 0.15 g |
| Emulsion F | Silver | 0.20 g |
| Gelatin | | 1.50 g |
| Coupler C-1 | | 0.60 g |
| Coupler C-2 | | 0.015 g |
| Coupler C-3 | | 0.030 g |
| Coupler C-9 | | 5.0 mg |
| Ultraviolet absorber U-1 | | 0.010 g |
| Ultraviolet absorber U-2 | | 0.010 g |
| High boiling organic solvent Oil-6 | | 0.030 g |
| High boiling organic solvent Oil-9 | | 0.020 g |
| High boiling organic solvent Oil-10 | | 0.050 g |
| Compound Cpd-D | | 5.0 mg |

-continued

| | | |
|---|---|---|
| Compound Cpd-K | | 1.0 mg |
| Compound Cpd-F | | 0.030 g |
| Compound Cpd-L | | 1.0 mg |
| Additive P-1 | | 0.010 g |
| Additive P-4 | | 0.030 g |
| Ninth layer: Intermediate layer | | |
| Gelatin | | 0.50 g |
| Additive P-2 | | 0.10 g |
| Dye D-5 | | 0.020 g |
| Dye D-9 | | 6.0 mg |
| Compound Cpd-I | | 0.010 g |
| Compound Cpd-M | | 0.040 g |
| Compound Cpd-O | | 3.0 mg |
| Compound Cpd-P | | 5.0 mg |
| High boiling organic solvent Oil-6 | | 0.050 g |
| Tenth layer: Intermediate layer | | |
| Yellow colloidal silver | Silver | 0.020 g |
| Gelatin | | 0.70 g |
| Additive P-2 | | 0.05 g |
| Ultraviolet absorber U-1 | | 0.010 g |
| Ultraviolet absorber U-3 | | 0.010 g |
| Compound Cpd-A | | 0.050 g |
| Compound Cpd-D | | 0.030 g |
| Compound Cpd-M | | 0.050 g |
| High boiling organic solvent Oil-3 | | 0.010 g |
| High boiling organic solvent Oil-6 | | 0.050 g |
| Eleventh layer: Low-sensitivity green-sensitive emulsion layer | | |
| Emulsion G | Silver | 0.25 g |
| Emulsion H | Silver | 0.30 g |
| Emulsion I | Silver | 0.25 g |
| Gelatin | | 0.90 g |
| Coupler C-4 | | 0.20 g |
| Coupler C-5 | | 0.050 g |
| Coupler C-6 | | 0.020 g |
| Compound Cpd-B | | 0.030 g |
| Compound Cpd-D | | 5.0 mg |
| Compound Cpd-G | | 2.5 mg |
| Compound Cpd-F | | 0.010 g |
| Compound Cpd-K | | 2.0 mg |
| Ultraviolet absorber U-6 | | 5.0 mg |
| High boiling organic solvent Oil-2 | | 0.25 g |
| Additive P-1 | | 5.0 mg |
| Twelfth layer: Middle-sensitivity green-sensitive emulsion layer | | |
| Emulsion I | Silver | 0.30 g |
| Emulsion J | Silver | 0.30 g |
| Silver bromide emulsion, with inner part of which was fogged (cube, av. sphere-equivalent diameter of 0.11 μm) | Silver | 3.0 mg |
| Gelatin | | 0.60 g |
| Coupler C-4 | | 0.25 g |
| Coupler C-5 | | 0.050 g |
| Coupler C-6 | | 0.020 g |
| Compound Cpd-A | | 5.0 mg |
| Compound Cpd-B | | 0.030 g |
| Compound Cpd-F | | 0.010 g |
| Compound Cpd-G | | 2.0 mg |
| High boiling organic solvent Oil-2 | | 0.20 g |
| High boiling organic solvent Oil-9 | | 0.050 g |
| Thirteenth layer: High-sensitivity green-sensitive emulsion layer | | |
| Emulsion K | Silver | 0.40 g |
| Gelatin | | 0.60 g |
| Coupler C-4 | | 0.30 g |
| Coupler C-5 | | 0.080 g |
| Coupler C-7 | | 0.050 g |
| Compound Cpd-A | | 5.0 mg |
| Compound Cpd-B | | 0.030 g |
| Compound Cpd-F | | 0.010 g |
| High boiling organic solvent Oil-2 | | 0.20 g |
| High boiling organic solvent Oil-9 | | 0.050 g |

-continued

| | | |
|---|---|---|
| Fourteenth layer: Yellow filter layer | | |
| Yellow colloidal silver | Silver | 0.010 g |
| Gelatin | | 0.6 g |
| Compound Cpd-C | | 0.010 g |
| Compound Cpd-M | | 0.10 g |
| High boiling organic solvent Oil-1 | | 0.020 g |
| High boiling organic solvent Oil-6 | | 0.10 g |
| Fine crystal solid dispersion of Dye E-2 | | 0.20 g |
| Fifteenth layer: Light-sensitive emulsion layer | | |
| Emulsion S | Silver | 0.20 g |
| Gelatin | | 0.40 g |
| Sixteenth layer: Intermediate layer | | |
| Gelatin | | 0.40 g |
| Compound Cpd-Q | | 0.20 g |
| Dye D-6 | | 3.0 mg |
| Seventeenth layer: Low-sensitivity blue-sensitive emulsion layer | | |
| Emulsion L | Silver | 0.15 g |
| Emulsion M | Silver | 0.20 g |
| Emulsion N | Silver | 0.10 g |
| Gelatin | | 0.60 g |
| Coupler C-8 | | 0.22 g |
| Compound Cpd-B | | 0.10 g |
| Compound Cpd-I | | 8.0 mg |
| Compound Cpd-K | | 1.0 mg |
| Compound Cpd-M | | 0.010 g |
| Ultraviolet absorber U-6 | | 0.010 g |
| High boiling organic solvent Oil-2 | | 0.010 g |
| Eighteenth layer: Middle-sensitivity blue-sensitive emulsion layer | | |
| Emulsion N | Silver | 0.20 g |
| Emulsion O | Silver | 0.20 g |
| Silver bromide emulsion, with inner part of which was fogged (cube, av. sphere-equivalent diameter of 0.11 μm) | Silver | 3.0 mg |
| Gelatin | | 0.60 g |
| Coupler C-8 | | 0.20 g |
| Compound Cpd-B | | 0.10 g |
| Compound Cpd-E | | 0.030 g |
| Compound Cpd-N | | 2.0 mg |
| High boiling organic solvent Oil-2 | | 0.010 g |
| Nineteenth layer: High-sensitivity blue-sensitive emulsion layer | | |
| Emulsion P | Silver | 0.20 g |
| Emulsion Q | Silver | 0.25 g |
| Gelatin | | 1.50 g |
| Coupler C-3 | | 5.0 mg |
| Coupler C-8 | | 0.77 g |
| High boiling organic solvent Oil-2 | | 0.10 g |
| High boiling organic solvent Oil-3 | | 0.020 g |
| Ultraviolet absorber U-6 | | 0.10 g |
| Compound Cpd-B | | 0.20 g |
| Compound Cpd-E | | 0.060 g |
| Compound Cpd-N | | 5.0 mg |
| Twentieth layer: First protective layer | | |
| Gelatin | | 0.70 g |
| Ultraviolet absorber U-1 | | 0.15 g |
| Ultraviolet absorber U-2 | | 0.050 g |
| Ultraviolet absorber U-5 | | 0.20 g |
| Compound Cpd-O | | 5.0 mg |
| Compound Cpd-A | | 0.030 g |
| Compound Cpd-H | | 0.20 g |
| Dye D-1 | | 8.0 mg |
| Dye D-2 | | 0.010 g |
| Dye D-3 | | 0.010 g |
| High boiling organic solvent Oil-3 | | 0.10 g |

-continued

Twenty-first layer: Second protective layer

| | | |
|---|---|---|
| Colloidal silver | Silver | 2.5 mg |
| Fine grain silver iodobromide emulsion (av. grain diameter of 0.06 μm, AgI content of 1 mol %) | Silver | 0.10 g |
| Gelatin | | 0.80 g |
| Ultraviolet absorber U-1 | | 0.030 g |
| Ultraviolet absorber U-6 | | 0.030 g |
| High boiling organic solvent Oil-3 | | 0.010 g |

Twenty-second layer: Third protective layer

| | |
|---|---|
| Gelatin | 1.00 g |
| Polymethyl methacrylate (av. particle diameter of 1.5 μm) | 0.10 g |
| Copolymer of methyl methacrylate and methacrylic acid (6:4) (av. particle diameter, 1.5 μm) | 0.15 g |
| Silicone oil SO-1 | 0.20 g |
| Surface active agent W-1 | 3.0 mg |

-continued

| | |
|---|---|
| Surface active agent W-2 | 8.0 mg |
| Surface active agent W-3 | 0.040 g |
| Surface active agent W-7 | 0.015 g |

Further, to all emulsion layers, in addition to the above-described components, additives F-1 to F-9 were added. Further, to each layer, in addition to the above-described components, a gelatin hardener H-1 and surface active agents W-3, W-4, W-5, and W-6 for coating and emulsifying, were added.

Further, as antifungal and antibacterial agents, phenol, 1, 2-benzisothiazoline-3-one, 2-phenoxyethanol, phenetylalcohol, and p-hydroxybenzoic acid butyl ester were added.

TABLE 9

Silver iodobromide emulsions used in Sample 701

| Emulsion | Characteristics | Average sphere-equivalent diameter (μm) | Variation coefficient (%) | Average AgI content (%) | Halogen composition structure of silver halide grains | AgI content at grain surface (%) | Other characteristics (1) | (2) | (3) | (4) | (5) |
|---|---|---|---|---|---|---|---|---|---|---|---|
| A | Monodisperse tetradecahedral grains | 0.24 | 9 | 3.5 | Threefold structure | 1.5 | | ○ | | | |
| B | Monodisperse (111) tabular grains Average aspect ratio 2.0 | 0.25 | 10 | 3.5 | Fourfold structure | 1.5 | ○ | | ○ | ○ | ○ |
| C | Monodisperse (111) tabular grains Average aspect ratio 2.0 | 0.30 | 19 | 3.0 | Threefold structure | 0.1 | ○ | ○ | | ○ | ○ |
| D | Monodisperse (111) tabular grains Average aspect ratio 3.0 | 0.35 | 21 | 4.8 | Threefold structure | 2.0 | ○ | ○ | | ○ | ○ |
| E | Monodisperse (111) tabular grains Average aspect ratio 3.0 | 0.40 | 10 | 2.0 | Fourfold structure | 1.5 | | ○ | | | |
| F | Monodisperse (111) tabular grains Average aspect ratio 4.5 | 0.55 | 12 | 1.6 | Threefold structure | 0.6 | ○ | ○ | | | ○ |
| G | Monodisperse cubic grains | 0.15 | 9 | 3.5 | Fourfold structure | 2.0 | | | ○ | | |
| H | Monodisperse cubic grains | 0.24 | 12 | 4.9 | Fourfold structure | 0.1 | ○ | ○ | | ○ | |
| I | Monodisperse (111) tabular grains Average aspect ratio 4.0 | 0.30 | 12 | 3.5 | Fivefold structure | 4.5 | ○ | ○ | | ○ | ○ |
| J | Monodisperse (111) tabular grains Average aspect ratio 5.0 | 0.45 | 21 | 3.0 | Fourfold structure | 0.2 | ○ | ○ | | ○ | ○ |
| K | Monodisperse (111) tabular grains Average aspect ratio 5.5 | 0.60 | 13 | 2.7 | Threefold structure | 1.3 | ○ | ○ | | | ○ |
| L | Monodisperse tetradecahedral gains | 0.31 | 9 | 7.5 | Threefold structure | 7.0 | | | ○ | | ○ |

TABLE 9-continued

Silver iodobromide emulsions used in Sample 701

| Emulsion | Characteristics | Average sphere-equivalent diameter (μm) | Variation coefficient (%) | Average AgI content (%) | Halogen composition structure of silver halide grains | AgI content at grain surface (%) | Other characteristics (1) | (2) | (3) | (4) | (5) |
|---|---|---|---|---|---|---|---|---|---|---|---|
| M | Monodisperse tetradecahedral grains | 0.31 | 9 | 7.5 | Threefold structure | 5.0 | ○ | ○ | | ○ | ○ |
| N | Monodisperse (111) tabular grains Average aspect ratio 3.0 | 0.33 | 13 | 2.1 | Fourfold structure | 4.0 | ○ | ○ | ○ | | |
| O | Monodisperse (111) tabular grains Average aspect ratio 3.0 | 0.43 | 9 | 2.5 | Fourfold structure | 1.0 | ○ | ○ | | ○ | ○ |
| P | Monodisperse (111) tabular grains Average aspect ratio 6.0 | 0.75 | 21 | 2.8 | Threefold structure | 0.5 | ○ | ○ | | | ○ |
| Q | Monodisperse (111) tabular grains Average aspect ratio 6.0 | 0.90 | 8 | 1.0 | Fourfold structure | 0.5 | ○ | ○ | | | ○ |
| R | Monodisperse (111) tabular grains Average aspect ratio 7.0 | 0.70 | 18 | 6.0 | Threefold structure | 0.5 | ○ | ○ | | | ○ |
| S | Monodisperse (111) tabular grains Average aspect ratio 4.0 | 0.30 | 12 | 4.5 | Threefold structure | 1.0 | ○ | ○ | ○ | | ○ |

(Other characteristics)
(1): A reduction sensitizer was added during formation of grains.
(2): A selenium sensitizer was used as an after-ripening chemical.
(3): A rhodium salt was added during formation of grains.
(4): After completion of after-ripening, silver nitrate in an amount of 10% in terms of the silver molar ratio relative to the emulsion grains at the time, and potassium bromide in an equimolar amount to the silver nitrate, were added to form shells.
(5): The presence of 10 or more dislocation lines/grain on average was observed under a transmission electron microscope.
All the photosensitive emulsions were after-ripened using sodium thiosulfate, potassium thiocyanate and sodium chloroaurate. Further, an iridium salt was added as necessary during formation of grains.
Chemically modified gelatin whose amino groups had been partially converted into phthalic amide was added to the emulsions B, C, E, H, J, N and Q when the emulsions were prepared.

TABLE 10

Spectral sensitization of Emulsions A to P

| Emulsion | Added sensitizing dye | Added amount per 1 mol of silver halide (g) | Stage when a sensitizing dye was added |
|---|---|---|---|
| A | S-1 | 0.01 | After afterripening |
| | S-2 | 0.35 | Before afterripening |
| | S-3 | 0.02 | Before afterripening |
| | S-8 | 0.03 | Before afterripening |
| | S-13 | 0.015 | Before afterripening |
| | S-14 | 0.01 | Before afterripening |
| B | S-2 | 0.35 | Before afterripening |
| | S-3 | 0.02 | Before afterripening |
| | S-8 | 0.03 | Before afterripening |
| | S-13 | 0.015 | Before afterripening |
| | S-14 | 0.01 | Before afterripening |
| C | S-2 | 0.45 | Before afterripening |
| | S-8 | 0.04 | Before afterripening |
| | S-13 | 0.02 | Before afterripening |
| D | S-2 | 0.5 | After afterripening |
| | S-3 | 0.05 | After afterripening |
| | S-8 | 0.05 | Before afterripening |
| | S-13 | 0.015 | Before afterripening |
| E | S-1 | 0.01 | Before afterripening |
| | S-2 | 0.45 | Before afterripening |
| | S-8 | 0.05 | Before afterripening |
| | S-13 | 0.01 | After afterripening |
| F | S-2 | 0.4 | Before afterripening |
| | S-3 | 0.04 | Before afterripening |
| | S-8 | 0.04 | Before afterripening |
| G | S-4 | 0.3 | After afterripening |
| | S-5 | 0.05 | After afterripening |
| | S-12 | 0.1 | After afterripening |
| H | S-4 | 0.2 | Before afterripening |
| | S-5 | 0.05 | After afterripening |
| | S-9 | 0.15 | Before afterripening |
| | S-14 | 0.02 | After afterripening |
| I | S-4 | 0.3 | Before afterripening |
| | S-9 | 0.2 | Before afterripening |
| | S-12 | 0.1 | Before afterripening |
| J | S-4 | 0.35 | Before afterripening |
| | S-5 | 0.05 | After afterripening |
| | S-12 | 0.1 | Before afterripening |

TABLE 10-continued

Spectral sensitization of Emulsions A to P

| Emulsion | Added sensitizing dye | Added amount per 1 mol of silver halide (g) | Stage when a sensitizing dye was added |
|---|---|---|---|
| K | S-4 | 0.3 | Before afterripening |
|   | S-9 | 0.05 | Before afterripening |
|   | S-12 | 0.1 | Before afterripening |
|   | S-14 | 0.02 | Before afterripening |
| L, M | S-6 | 0.1 | After afterripening |
|   | S-10 | 0.2 | After afterripening |
|   | S-11 | 0.05 | After afterripening |
| N | S-6 | 0.05 | After afterripening |
|   | S-7 | 0.05 | After afterripening |
|   | S-10 | 0.25 | After afterripening |
|   | S-11 | 0.05 | After afterripening |
| O | S-10 | 0.4 | After afterripening |
|   | S-11 | 0.15 | After afterripening |
| P | S-6 | 0.05 | After afterripening |
|   | S-7 | 0.05 | After afterripening |
|   | S-10 | 0.3 | Before afterripening |
|   | S-11 | 0.1 | Before afterripening |
| Q | S-6 | 0.05 | Before afterripening |
|   | S-7 | 0.05 | Before afterripening |
|   | S-10 | 0.2 | Before afterripening |
|   | S-11 | 0.25 | Before afterripening |
| R | S-15 | 0.35 | Before afterripening |
|   | S-9 | 0.05 | Before afterripening |
| S | S-7 | 0.30 | Before afterripening |

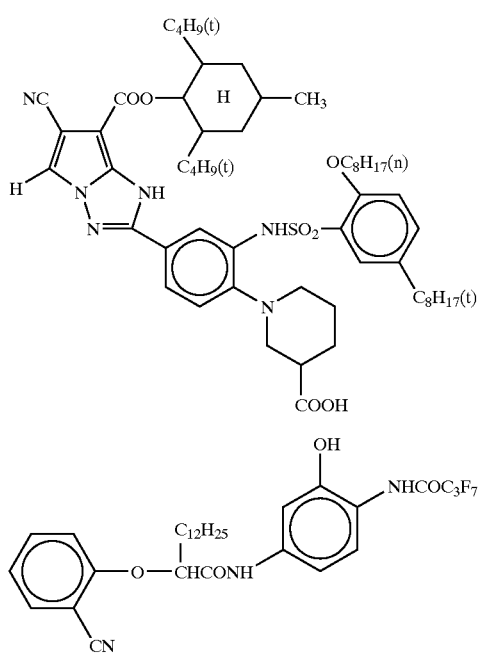

C-1

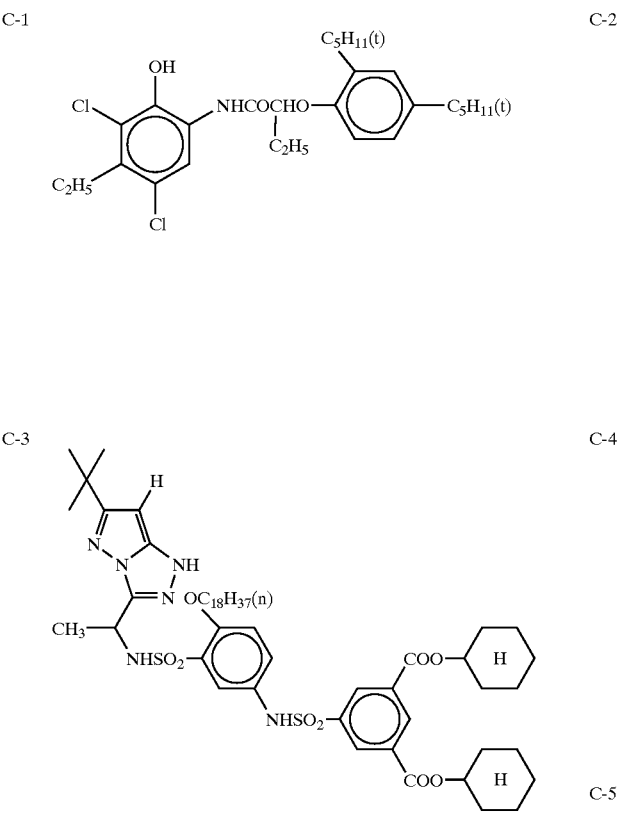

C-2

C-3

C-4

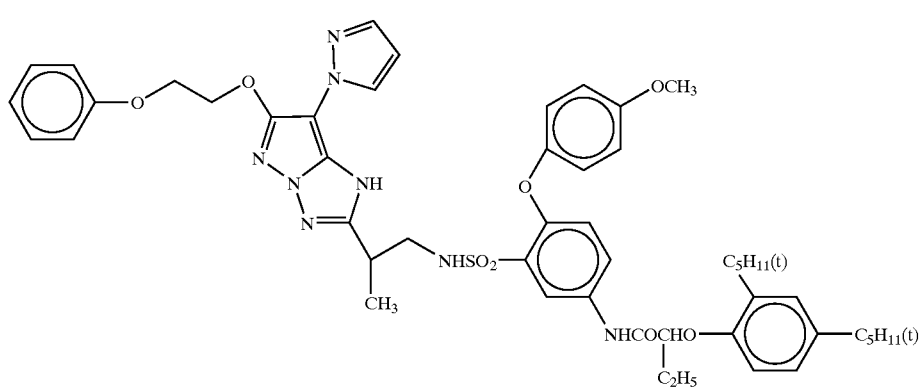

C-5

-continued
C-6
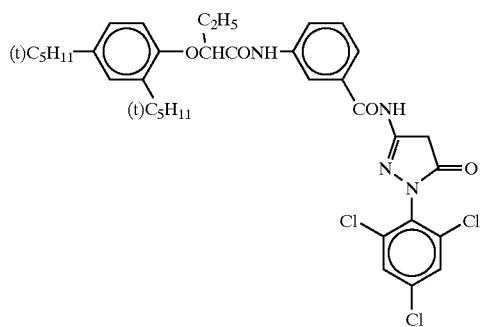
C-7
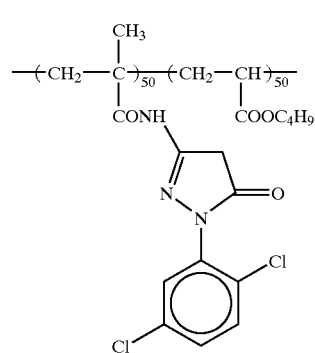
Number means mass %
Average moecular weight: about 25,000
C-8
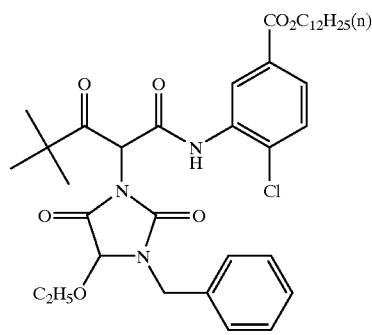
C-9
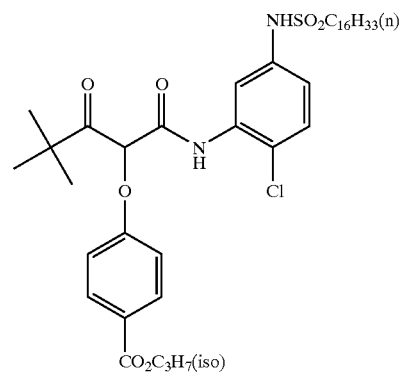
C-10
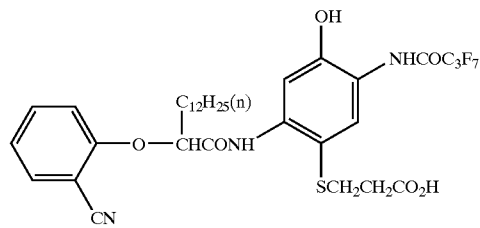
Oil-1
Tri-n-hexyl phosphate
Oil-2
Tricresyl phosphate
Oil-3
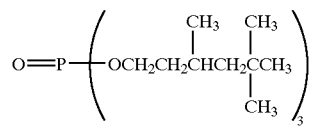
Oil-4
Tricyclohexyl phosphate
Oil-5
Bis(2-ethylhexyl) succinate
Oil-6
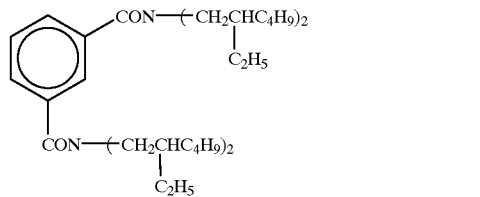
Oil-7
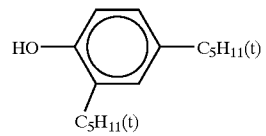
Oil-8
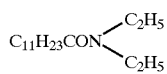
Oil-9
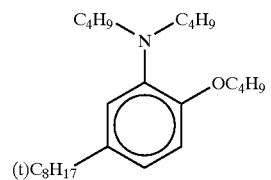

-continued
Oil-10
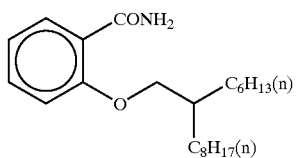
Cpd-A
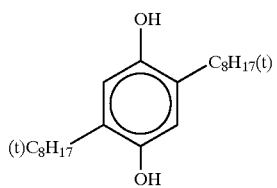
Cpd-B
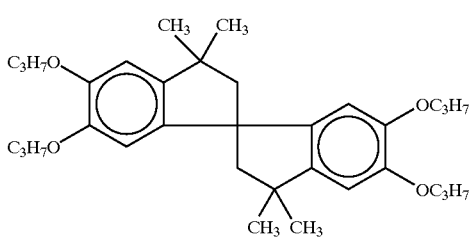
Cpd-C
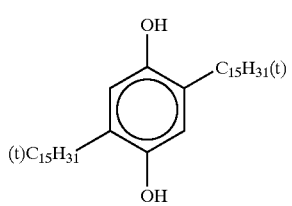
Cpd-D
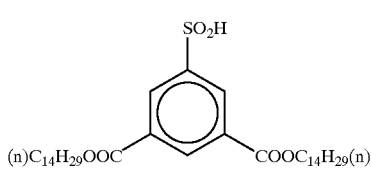
Cpd-E
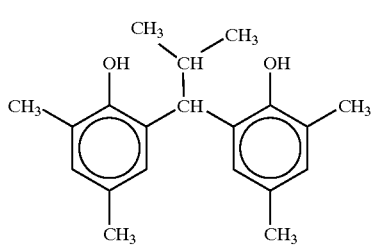
Cpd-F
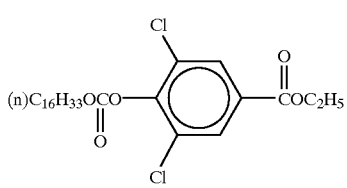
Cpd-G
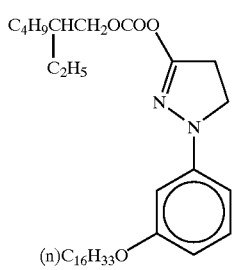
Cpd-H
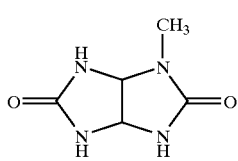
Cpd-I
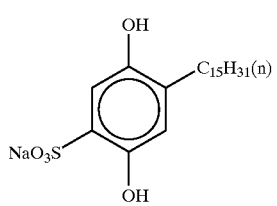
Cpd-J
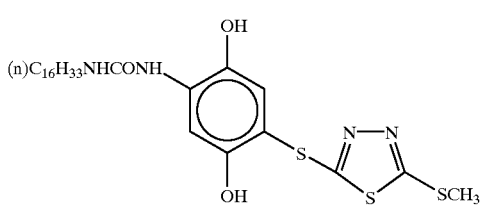
Cpd-K
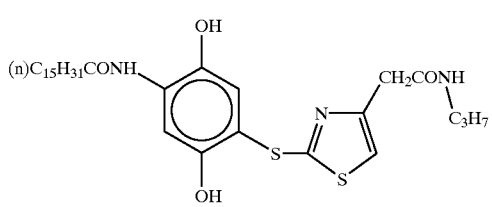
Cpd-L
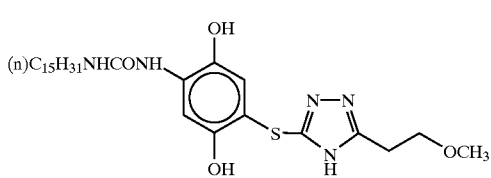
Cpd-M
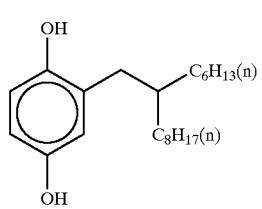

-continued
Cpd-N 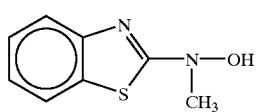 Cpd-O
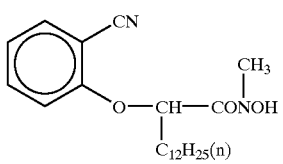
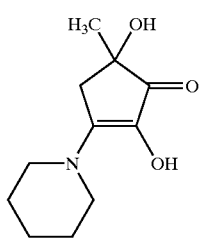
Cpd-P CH₂—NH  Cpd-Q
      |      \
      CH₂—NH  C=O
U-1 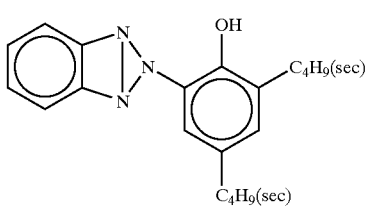 U-2 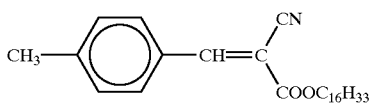
U-3 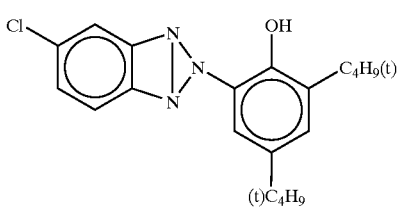 U-4 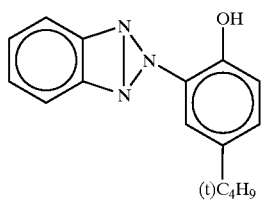
U-5 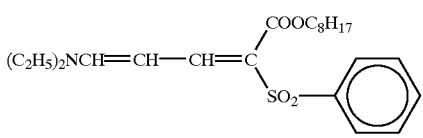 U-6 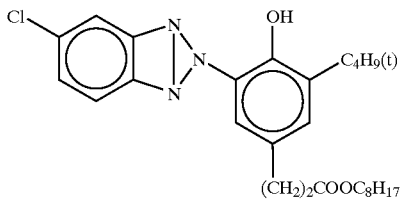
S-1 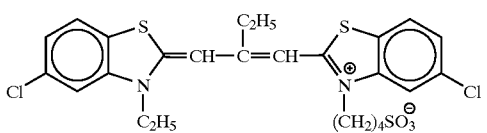 S-2 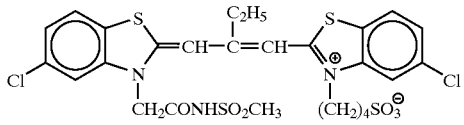
S-3 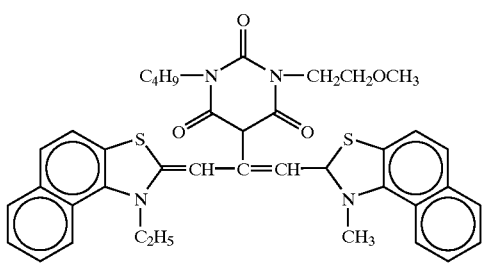 S-4 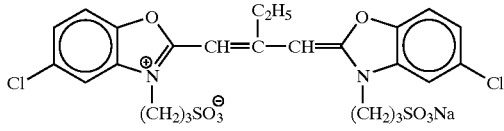
S-5 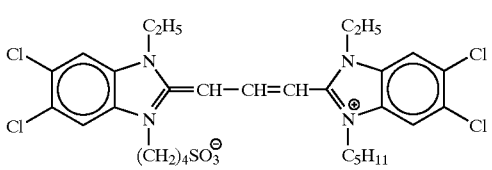 S-6 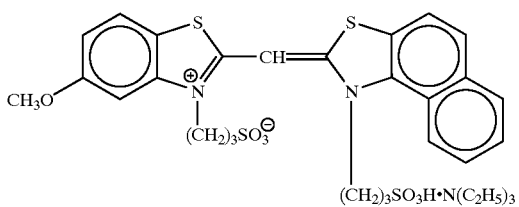

-continued
S-7
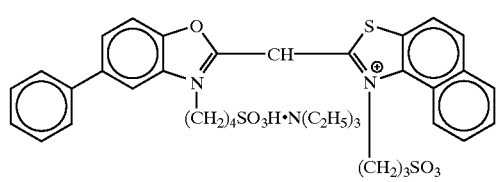
S-8
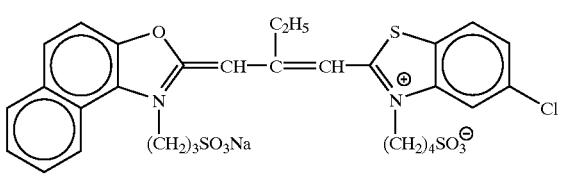
S-9
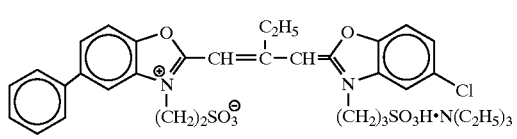
S-10
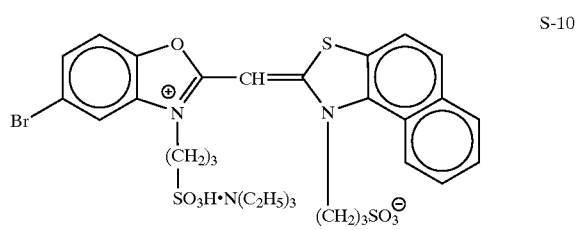
S-11
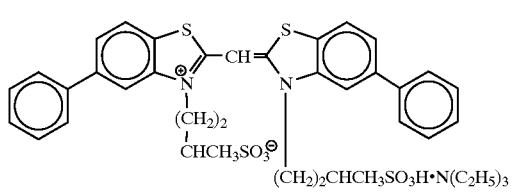
S-12
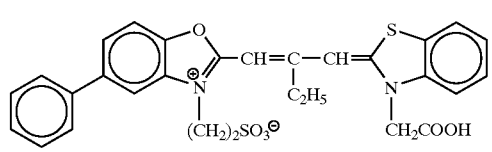
S-13
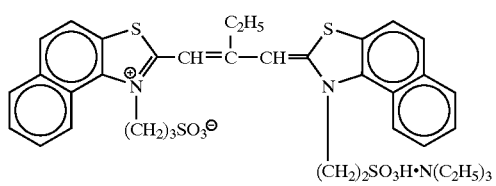
S-14
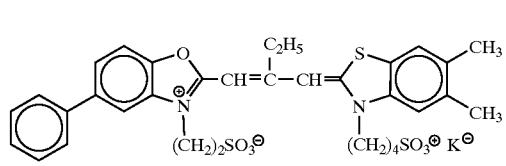
S-15
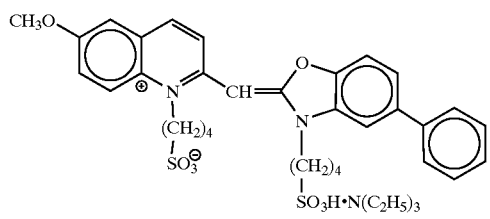
D-1
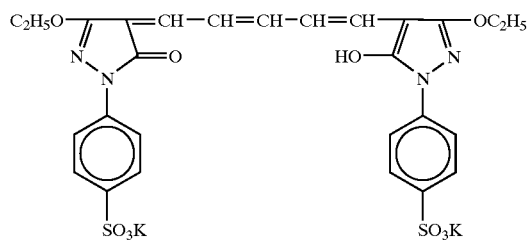
D-2
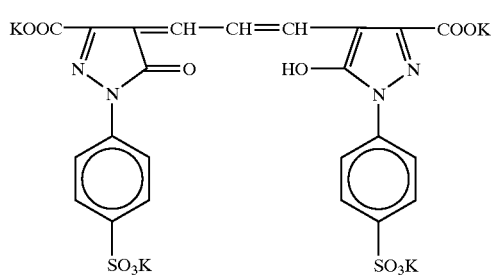
D-3
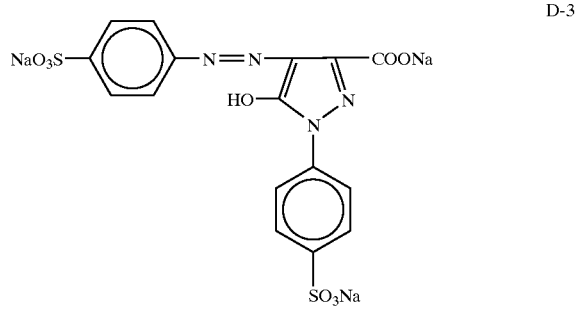

-continued
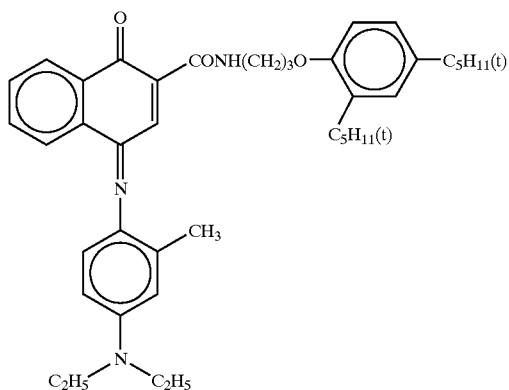
D-4
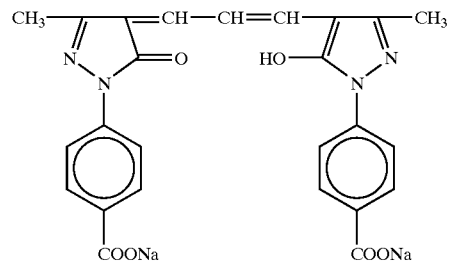
D-5
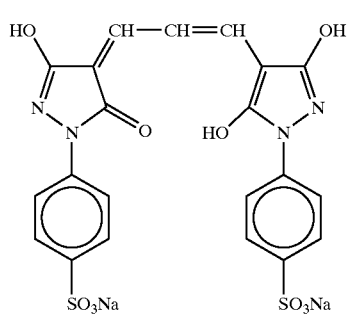
D-6
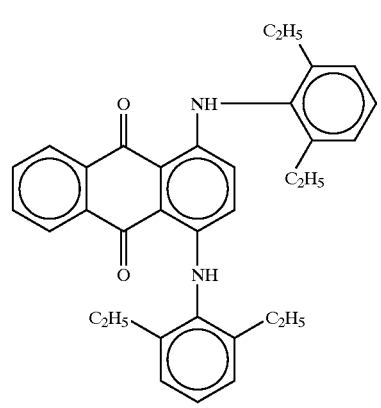
D-7
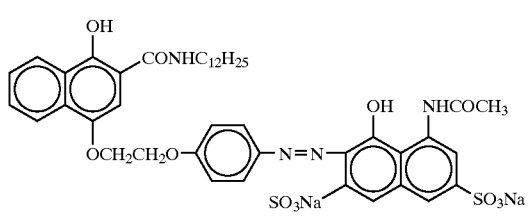
D-8
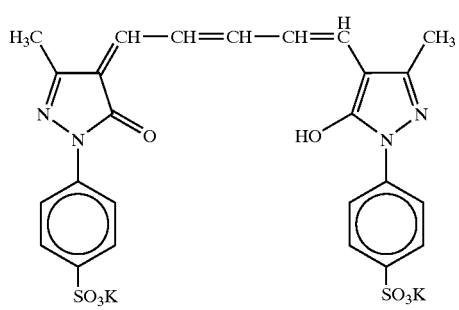
D-9
D-10
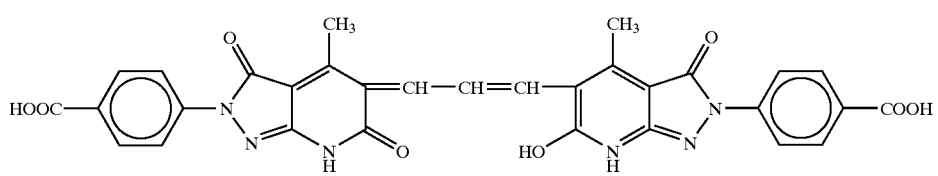
E-1

-continued
E-2
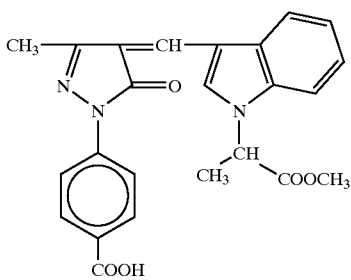
H-1
CH₂=CH—SO₂—CH₂—CONH—CH₂
CH₂=CH—SO₂—CH₂—CONH—CH₂
W-1
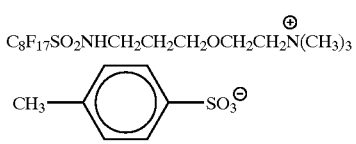
W-2
C₈F₁₇SO₂NCH₂COOK
|
C₃H₇
W-3
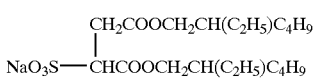
W-4
C₈H₁₇—⌬—(OCH₂CH₂)₃—SO₃Na
W-5
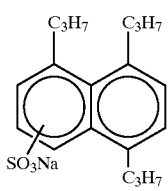
W-6
C₁₂H₂₅—⌬—SO₃Na
C₈F₁₇SO₃Li
W-7
$-\text{(CH}_2-\text{CH)}_n-$
|
CONHC₄H₉(t)   (n = 100 ~ 1000)
P-1
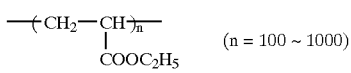
(n = 100 ~ 1000)
P-2
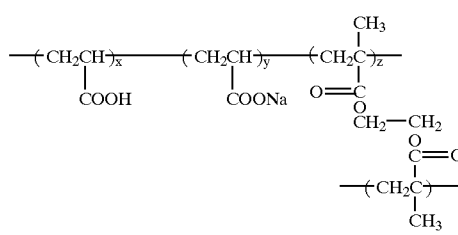
x:y:z = 42.5:7.5:50
P-3
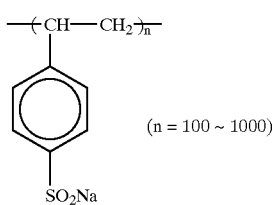
(n = 100 ~ 1000)
P-4
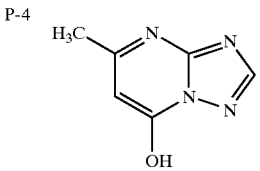
F-1
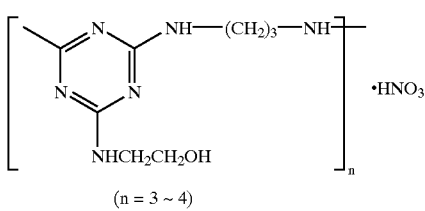
(n = 3 ~ 4)
F-2
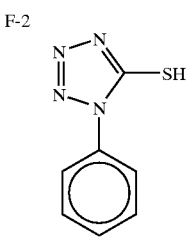
F-3

-continued

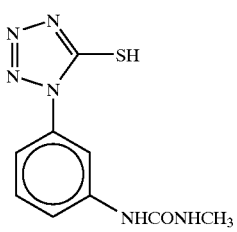 F-4

 F-5

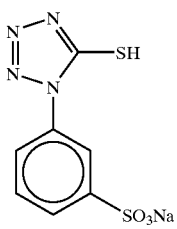 F-6

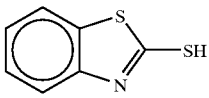 F-7

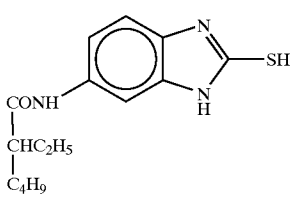 F-8

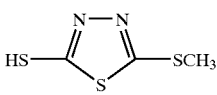 F-9

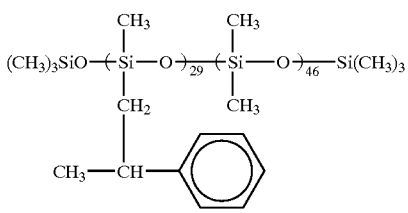

SO-1

Preparation of Dispersion of Organic Solid Dispersed Dye
(Preparation of Dispersion of Dye E-1)

To a wet cake of Dye E-1 (the net amount of E-1: 270 g), 100 g of Pluronic F88 (trade name, block copolymer of ethyleneoxide/propyleneoxide) manufactured by BASF and water were added and stirred. Water was added so as to give a total amount of 4000 g. Next, to the ulutravisco mill (UVM-2 (trade name), manufactured by AIMEX Co., Ltd.) filled with 1700 ml of zirconia beads having an average grain diameter of 0.5 mm, the resultant slurry was added and ground for 2 hours under the conditions of about 10 m/sec of round speed and 0.5 liter/min of discharge amount. The beads were filtered away to obtain a dispersion of the dye. Water was added to the dispersion so that the dye density was diluted to 3%. Then, for the purpose of stabilization, the dispersion was heated at 90° C. for 10 hours. An average particle diameter of these dye fine particles was 0.30 μm. The range of the distribution of the particle diameter (standard deviation of particle diameter×100/average particle diameter) was 20%.

(Preparation of Solid Dispersion of Dye E-2)

To 1400 g of a wet cake of Dye E-2 containing 30 mass % of water, water and 270 g of W-4 were added and stirred. Water was added so that a slurry containing 40 mass % of E-2 was obtained. Next, to the ulutravisco mill (UVM-2 (trade name), manufactured by AIMEX Co., Ltd.) filled with 1700 ml of zirconia beads having an average grain size of 0.5 mm, the resultant slurry was added and ground for 8 hours under the conditions of about 10 m/sec of round speed and 0.5 liter/min of discharge amount. Thus, a solid fine particle dispersion of Dye E-2 was obtained. This dispersion was diluted with an ion exchanged water to 20 mass %, to obtain solid fine particle dispersion. Note that the average particle size of each of yellow coupler-containing oleophilic fine particle dispersion ranged from 0.10 to 0.20 μm.

Comparative Example 5

Preparation of Sample 702

Sample 702 was prepared in the same as in Comparative Example 4, except that coupler for comparison (C-8) in Comparative Example 4 was replaced with coupler for comparison (Cp-1) in an equi-molar amount. Note that the average particle size of the yellow coupler-containing oleophilic fine particle dispersion ranged from 0.10 to 0.20 μm.

Dye for Comparison (Cp-1)

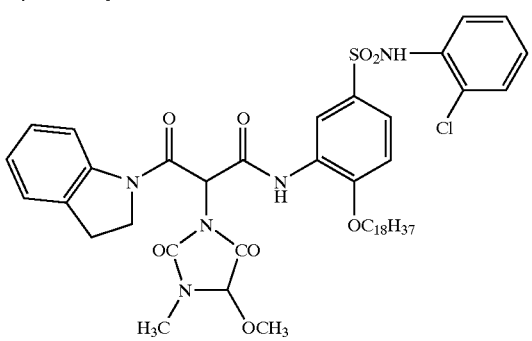

Example 10

Preparation of Samples 703, 704, 705, 706, 707, 708, 709, and 710

Light-sensitive materials 703 to 710 were prepared in the same manner as in Comparative Example 4, except that, instead of coupler for comparison (C-8), the above exemplified coupler (96), coupler (97), coupler (98), coupler (103), coupler (112), coupler (129), coupler (191), and coupler (194) were added, respectively, in an equivalent amount. The thus-obtained inventive samples were: Sample 703 (one wherein coupler (96) was used), Sample 704 (one wherein coupler (97) was used), Sample 705 (one wherein coupler (98) was used), Sample 706 (one wherein coupler (103) was used), Sample 707 (one wherein coupler (112) was used), Sample 708 (one wherein coupler (129) was used), Sample 709 (one wherein coupler (191) was used), and Sample 710 (one wherein coupler (194) was used). The average particle sizes of the thus-prepared yellow-coupler-containing oleophilic fine-particle dispersions each were in the range of 0.10 to 0.20 μm.

<Color-Forming Property Test>

Samples 701 to 710 obtained in the above Comparative examples 4 and 5, and Example 10 were subjected to the following processing steps (Processing-A).

In processing of each sample, a running processing was performed by processing an unexposed one and an entirely exposed one in proportion of 1:1, until an accumulated replenisher amount was four times the tank volume. After running equilibrium, a processing for evaluation was performed.

| Processing step | Time | Temperature | Tank volume | Replenisher amount |
|---|---|---|---|---|
| 1st development | 6 min | 38° C. | 37 liters | 2,200 ml/m² |
| 1st water-washing | 2 min | 38° C. | 16 liters | 4,000 ml/m² |
| Reversal | 2 min | 38° C. | 17 liters | 1,100 ml/m² |
| Color-development | 6 min | 38° C. | 30 liters | 2,200 ml/m² |
| Pre-bleaching | 2 min | 38° C. | 19 liters | 1,100 ml/m² |
| Bleaching | 6 min | 38° C. | 30 liters | 220 ml/m² |
| Fixing | 4 min | 38° C. | 29 liters | 1,100 ml/m² |
| 2nd water-washing | 4 min | 38° C. | 35 liters | 4,000 ml/m² |
| Final-rinsing | 1 min | 25° C. | 19 liters | 1,100 ml/m² |

Compositions of each processing solution used were as follows:

| | Tank solution | Replenisher |
|---|---|---|
| [1st developer] | | |
| Pentasodium nitrilo-N,N,N-trimethylenephosphonate | 1.5 g | 1.5 g |
| Pentasodium diethylenetriamine-pentaacetate | 2.0 g | 2.0 g |
| Sodium sulfite | 30 g | 30 g |
| Hydroquinone/potassium monosulfonate | 20 g | 20 g |
| Potassium carbonate | 15 g | 20 g |
| Sodium bicarbonate | 12 g | 15 g |
| 1-Phenyl-4-methyl-4-hydroxymethyl-3-pyrazolydone | 2.5 g | 3.0 g |
| Potassium bromide | 2.5 g | 1.4 g |
| Potassium thiocyanate | 1.2 g | 1.2 g |
| Potassium iodide | 2.0 mg | — |
| Diethylene glycol | 13 g | 15 g |
| Water to make | 1,000 ml | 1,000 ml |
| pH | 9.60 | 9.60 |
| (pH was adjusted by using sulfuric acid or potassium hydroxide) | | |
| [Reversal solution] (Both tank solution and replenisher) | | |
| Pentasodium nitrilo-N,N,N-trimethylenephosphonate | 3.0 g | |
| Stannous chloride dihydrate | 1.0 g | |
| p-Aminophenol | 0.1 g | |
| Sodium hydroxide | 8 g | |
| Glacial acetic acid | 15 ml | |
| Water to make | 1,000 ml | |
| pH | 6.00 | |
| (pH was adjusted by using acetic acid or sodium hydroxide) | | |
| [Color-developer] | | |
| Pentasodium nitrilo-N,N,N-trimethylenephosphonate | 2.0 g | 2.0 g |
| Sodium sulfite | 7.0 g | 7.0 g |
| Trisodium phosphate 12-hydrate | 36 g | 36 g |
| Potassium bromide | 1.0 g | — |
| Potassium iodide | 90 mg | — |
| Sodium hydroxide | 12.0 g | 12.0 g |
| Cytrazinic acid | 0.5 g | 0.5 g |
| N-Ethyl-N-(β-methanesulfonamidoethyl)-3-methyl-4-aminoaniline-3/2 sulfate-monohydrate | 10 g | 10 g |
| 3,6-Dithiaoctane-1,8-diol | 1.0 g | 1.0 g |
| Water to make | 1,000 ml | 1,000 ml |
| pH | 11.80 | 12.00 |
| (pH was adjusted by using sulfuric acid or potassium hydroxide) | | |
| [Pre-bleaching solution] | | |
| Disodium ethylenediaminetetraacetate dihydrate | 8.0 g | 8.0 g |
| Sodium sulfite | 6.0 g | 8.0 g |
| 1-Thioglycerol | 0.4 g | 0.4 g |
| Formaldehyde-sodium bisulfite adduct | 30 g | 35 g |
| Water to make | 1,000 ml | 1,000 ml |
| pH | 6.30 | 6.10 |
| (pH was adjusted by using acetic acid or sodium hydroxide) | | |
| [Bleaching solution] | | |
| Disodium ethylenediaminetetraacetate dihydrate | 2.0 g | 4.0 g |

-continued

|  | Tank solution | Replenisher |
|---|---|---|
| Iron (III) ammonium ethylenediamine-tetraacetate dihydrate | 120 g | 240 g |
| Potassium bromide | 100 g | 200 g |
| Ammonium nitrate | 10 g | 20 g |
| Water to make | 1,000 ml | 1,000 ml |
| pH | 5.70 | 5.50 |
| (pH was adjusted by using nitric acid or sodium hydroxide) | | |
| [Fixing solution] (Both tank solution and replenisher) | | |
| Ammonium thiosulfate | 80 g | |
| Sodium sulfite | 5.0 g | |
| Sodium bisulfite | 5.0 g | |
| Water to make | 1,000 ml | |
| pH | 6.60 | |
| (pH was adjusted by using acetic acid or aqueous ammonia) | | |
| [Stabilizing solution] | | |
| 1,2-Benzoisothiazolin-3-one | 0.02 g | 0.03 g |
| Polyoxyethylene-p-mononoyl phenyl ether (av. polymerization degree: 10) | 0.3 g | 0.3 g |
| Polymaleic acid (av. molecular weight 2,000) | 0.1 g | 0.15 g |
| Water to make | 1,000 ml | 1,000 ml |
| pH | 7.0 | 7.0 |

In the above-described processing steps, a processing solution was stirred with a continuous circulation in each bath. The lower part of each tank was installed with a bubble-releasing tube having tiny holes (diameter 0.3 mm) made at intervals of 1 cm. The processing solution was stirred while continuously releasing a nitrogen gas (bubbles) from this bubble-releasing tube. However, such stirring while releasing bubbles was not carried out in the pre-bleaching bath and the second washing bath.

<Evaluation of Fastness>

The exposed and processed samples 701 to 710 were left to stand for 6 weeks under the conditions of 80° C. and 70% RH. Then, fading of the yellow dye was evaluated by a degree of reduction in yellow density of the point that gave the yellow density of 2.5 just after completion of the processing.

Each of the processed samples generated a yellow color. Table 11 shows that light-sensitive material samples 703 to 710 according to the present invention exhibited excellent fastness to heat and humidity, compared to light-sensitive material samples 701 and 702 for comparison. Particularly the sample which had a split-off group carrying thereon a dissociation group, and sample which had an imidazole split-off group, exhibited high color generation property.

TABLE 11

| Sample No. | Kind of Coupler | Maximum yellow density (Dmax) | Fastness of a dye (fading of color from the initial density 2.5) | Remarks |
|---|---|---|---|---|
| 701 | C-8 | 1.80 | 0.52 | Comparative example |
| 702 | Coupler for comparison (Cp-1) | 2.48 | 0.18 | Comparative example |
| 703 | Coupler (96) | 1.77 | 0.04 | This invention |
| 704 | Coupler (97) | 1.75 | 0.03 | This invention |
| 705 | Coupler (98) | 1.65 | 0.02 | This invention |
| 706 | Coupler (103) | 2.95 | 0.04 | This invention |
| 707 | Coupler (112) | 2.89 | 0.03 | This invention |
| 708 | Coupler (129) | 2.83 | 0.04 | This invention |
| 709 | Coupler (191) | 2.87 | 0.02 | This invention |
| 710 | Coupler (194) | 2.74 | 0.02 | This invention |

Example 11

The Numbers of Compounds are the Same as Those in Example 10

Preparation of Silver Halide Color Photographic Light-Sensitive Material Sample 801

(i) Coating of Backing Layers

One surface of the 205 μm thick triacetyl cellulose support whose both surfaces had been undercoated, was coated with the same backing layers as in Example 10, except that the amount of Surfactant W-2 in the fourth layer of the backing layer was changed to 0.010 g.

(ii) Coating of Light-Sensitive Emulsion Layer

The surface of the support on the side opposite to the backing layers was coated with light-sensitive layers having the following compositions to produce a sample 801. The number corresponding to each ingredient indicates the addition amount per m$^2$. Note that the effect of the compound added is not limited to the use of the compound described below.

First layer: Anti-halation Layer

| | |
|---|---|
| Black colloidal silver | 0.10 g |
| Gelatin | 2.50 g |
| Compound Cpd-B | 0.050 g |
| Ultraviolet absorber U-1 | 0.050 g |
| Ultraviolet absorber U-3 | 0.10 g |
| Ultraviolet absorber U-5 | 0.050 g |
| Ultraviolet absorber U-7 | 0.10 g |
| Compound Cpd-F | 0.20 g |
| High boiling organic solvent Oil-1 | 0.10 g |
| High boiling organic solvent Oil-2 | 0.15 g |
| High boiling organic solvent Oil-5 | 0.010 g |
| Dye D-4 | 1.0 mg |
| Dye D-8 | 2.5 mg |
| Fine crystal solid dispersion of Dye E-1 | 0.10 g |

Second layer: Intermediate layer

| | |
|---|---|
| Gelatin | 1.8 g |
| Compound Cpd-M | 0.20 g |
| Compound Cpd-F | 0.050 g |
| Compound Cpd-K | 3.0 mg |
| Ultraviolet absorber U-6 | 6.0 mg |
| High boiling organic solvent Oil-3 | 0.010 g |
| High boiling organic solvent Oil-4 | 0.010 g |
| High boiling organic solvent Oil-6 | 0.10 g |
| High boiling organic solvent Oil-7 | 2.0 mg |
| Dye D-7 | 4.0 mg |

Third layer: Intermediate layer

| | | |
|---|---|---|
| Yellow colloidal silver | Silver | 7.0 mg |
| Gelatin | | 0.40 g |
| Compound Cpd-D | | 0.020 g |

-continued

| | | |
|---|---|---|
| High boiling organic solvent Oil-3 | | 0.010 g |
| High boiling organic solvent Oil-8 | | 0.010 g |
| Fourth layer: Low-sensitivity red-sensitive emulsion layer | | |
| Emulsion A | Silver | 0.15 g |
| Emulsion B | Silver | 0.15 g |
| Emulsion C | Silver | 0.10 g |
| Gelatin | | 0.80 g |
| Coupler C-11 | | 0.08 g |
| Coupler C-12 | | 7.0 mg |
| Coupler C-10 | | 2.0 mg |
| Ultraviolet absorber U-3 | | 0.010 g |
| Compound Cpd-I | | 5.0 mg |
| Compound Cpd-D | | 3.0 mg |
| Compound Cpd-J | | 2.0 mg |
| High boiling organic solvent Oil-10 | | 0.030 g |
| Additive P-1 | | 5.0 mg |
| Fifth layer: Middle-sensitivity red-sensitive emulsion layer | | |
| Emulsion C | Silver | 0.15 g |
| Emulsion D | Silver | 0.15 g |
| Silver bromide emulsion, with inner part of which was fogged (cube, av. sphere-equivalent grain diameter of 0.11 μm) | Silver | 3.0 mg |
| Gelatin | | 0.70 g |
| Coupler C-11 | | 0.12 g |
| Coupler C-12 | | 7.0 mg |
| Compound Cpd-D | | 3.0 mg |
| Ultraviolet absorber U-3 | | 0.010 g |
| High boiling organic solvent Oil-10 | | 0.030 g |
| Additive P-1 | | 7.0 mg |
| Sixth layer: High-sensitivity red-sensitive emulsion layer | | |
| Emulsion E | Silver | 0.20 g |
| Emulsion F | Silver | 0.25 g |
| Gelatin | | 1.50 g |
| Coupler C-11 | | 0.70 g |
| Coupler C-12 | | 0.025 g |
| Coupler C-3 | | 0.020 g |
| Coupler C-9 | | 5.0 mg |
| Ultraviolet absorber U-1 | | 0.010 g |
| Ultraviolet absorber U-2 | | 0.010 g |
| High boiling organic solvent Oil-6 | | 0.030 g |
| High boiling organic solvent Oil-9 | | 0.020 g |
| High boiling organic solvent Oil-10 | | 0.20 g |
| Compound Cpd-D | | 5.0 mg |
| Compound Cpd-K | | 1.0 mg |
| Compound Cpd-F | | 0.030 g |
| Compound Cpd-L | | 1.0 mg |
| Compound Cpd-R | | 0.030 g |
| Additive P-1 | | 0.010 g |
| Additive P-4 | | 0.030 g |
| Seventh layer: Intermediate layer | | |
| Gelatin | | 0.60 g |
| Dye D-5 | | 0.020 g |
| Dye D-9 | | 6.0 mg |
| Compound Cpd-I | | 0.010 g |
| Compound Cpd-O | | 3.0 mg |
| Compound Cpd-P | | 5.0 mg |
| High boiling organic solvent Oil-6 | | 0.050 g |
| Eighth layer: Intermediate layer | | |
| Yellow colloidal silver | Silver | 0.010 g |
| Gelatin | | 1.30 g |
| Additive P-2 | | 0.05 g |
| Ultraviolet absorber U-1 | | 0.010 g |
| Ultraviolet absorber U-2 | | 0.030 g |
| Compound Cpd-A | | 0.050 g |
| Compound Cpd-D | | 0.030 g |
| Compound Cpd-M | | 0.10 g |
| High boiling organic solvent Oil-3 | | 0.010 g |
| High boiling organic solvent Oil-6 | | 0.10 g |
| Ninth layer: Low-sensitivity green-sensitive emulsion layer | | |
| Emulsion G | Silver | 0.15 g |

-continued

| | | |
|---|---|---|
| Emulsion H | Silver | 0.30 g |
| Emulsion I | Silver | 0.20 g |
| Gelatin | | 1.60 g |
| Coupler C-14 | | 0.080 g |
| Coupler C-15 | | 0.020 g |
| Compound Cpd-A | | 5.0 mg |
| Compound Cpd-B | | 0.020 g |
| Compound Cpd-G | | 2.5 mg |
| Compound Cpd-F | | 0.010 g |
| High boiling organic solvent Oil-2 | | 0.040 g |
| Additive P-1 | | 5.0 mg |
| Tenth layer: Middle-sensitivity green-sensitive emulsion layer | | |
| Emulsion I | Silver | 0.20 g |
| Emulsion J | Silver | 0.20 g |
| Silver bromide emulsion, with inner part of which was fogged (cube, av. sphere-equivalent grain diameter of 0.11 μm) | Silver | 3.0 mg |
| Gelatin | | 0.50 g |
| Coupler C-14 | | 0.15 g |
| Coupler C-15 | | 0.050 g |
| Coupler C-6 | | 0.010 g |
| Compound Cpd-A | | 5.0 mg |
| Compound Cpd-B | | 0.020 g |
| High boiling organic solvent Oil-2 | | 0.020 g |
| Eleventh layer: High-sensitivity green-sensitive emulsion layer | | |
| Emulsion K | Silver | 0.50 g |
| Gelatin | | 1.20 g |
| Coupler C-14 | | 0.60 g |
| Coupler C-15 | | 0.22 g |
| Coupler C-7 | | 0.050 g |
| Compound Cpd-B | | 0.030 g |
| Compound Cpd-F | | 0.010 g |
| High boiling organic solvent Oil-2 | | 0.050 g |
| High boiling organic solvent Oil-9 | | 0.020 g |
| Twelfth layer: Yellow filter layer | | |
| Yellow colloidal silver | Silver | 5.0 mg |
| Gelatin | | 1.0 g |
| Compound Cpd-C | | 0.010 g |
| Compound Cpd-M | | 0.030 g |
| High boiling organic solvent Oil-1 | | 0.020 g |
| High boiling organic solvent Oil-6 | | 0.040 g |
| Fine crystal solid dispersion of Dye E-2 | | 0.20 g |
| Thirteenth layer: Intermediate layer | | |
| Gelatin | | 0.40 g |
| Compound Cpd-Q | | 0.20 g |
| Dye D-6 | | 4.0 mg |
| Fourteenth layer: Low-sensitivity blue-sensitive emulsion layer | | |
| Emulsion L | Silver | 0.15 g |
| Emulsion M | Silver | 0.20 g |
| Emulsion N | Silver | 0.10 g |
| Gelatin | | 0.80 g |
| Coupler C-8 | | 0.30 g |
| Compound Cpd-B | | 0.10 g |
| Compound Cpd-I | | 8.0 mg |
| Compound Cpd-K | | 1.0 mg |
| Ultraviolet absorber U-6 | | 0.010 g |
| High boiling organic solvent Oil-2 | | 0.10 g |
| Fifteenth layer: Middle-sensitivity blue-sensitive emulsion layer | | |
| Emulsion N | Silver | 0.10 g |
| Emulsion O | Silver | 0.20 g |
| Gelatin | | 0.80 g |
| Coupler C-8 | | 0.30 g |
| Compound Cpd-B | | 0.10 g |
| Compound Cpd-E | | 0.030 g |
| Compound Cpd-N | | 2.0 mg |
| High boiling organic solvent Oil-2 | | 0.10 g |

-continued

Sixteenth layer: High-sensitivity blue-sensitive emulsion layer

| | | |
|---|---|---|
| Emulsion P | Silver | 0.20 g |
| Emulsion Q | Silver | 0.20 g |
| Gelatin | | 2.00 g |
| Coupler C-8 | | 1.40 g |
| Coupler C-12 | | 0.010 g |
| High boiling organic solvent Oil-2 | | 0.50 g |
| Ultraviolet absorber U-6 | | 0.10 g |
| Compound Cpd-E | | 0.20 g |
| Compound Cpd-N | | 5.0 mg |

Seventeenth layer: First protective layer

| | |
|---|---|
| Gelatin | 1.00 g |
| Ultraviolet absorber U-1 | 0.10 g |
| Ultraviolet absorber U-2 | 0.050 g |
| Ultraviolet absorber U-5 | 0.10 g |
| Ultraviolet absorber U-7 | 0.10 g |
| Compound Cpd-B | 0.020 g |
| Compound Cpd-O | 5.0 mg |
| Compound Cpd-A | 0.030 g |
| Compound Cpd-H | 0.20 g |
| Dye D-1 | 8.0 mg |
| Dye D-2 | 0.010 g |
| Dye D-3 | 0.010 g |
| High boiling organic solvent Oil-3 | 0.10 g |

Eighteenth layer: Second protective layer

| | | |
|---|---|---|
| Colloidal silver | Silver | 2.5 mg |
| Fine grain silver iodobromide emulsion (av. grain diameter of 0.06 μm, AgI content of 1 mol %) | Silver | 0.10 g |
| Gelatin | | 0.80 g |
| Ultraviolet absorber U-1 | | 0.030 g |
| Ultraviolet absorber U-6 | | 0.030 g |
| High boiling organic solvent Oil-3 | | 0.010 g |

Nineteenth layer: Third protective layer

| | |
|---|---|
| Gelatin | 1.00 g |
| Polymethyl methacrylate (average particle diameter of 1.5 μm) | 0.10 g |
| Copolymer of methyl methacrylate and methacrylic acid (6:4) (av. particle diameter, 1.5 μm) | 0.15 g |
| Silicone oil SO-1 | 0.20 g |
| Surface active agent W-1 | 3.0 mg |
| Surface active agent W-2 | 8.0 mg |
| Surface active agent W-3 | 0.040 g |
| Surface active agent W-7 | 0.015 g |

Further, to all emulsion layers, in addition to the above-described components, additives F-1 to F-9 were added. Further, to each layer, in addition to the above-described components, a gelatin hardener H-1 and surface active agents W-3, W-4, W-5, and W-6 for coating and emulsifying, were added.

Further, as antifungal and antibacterial agents, phenol, 1,2-benzisothiazoline-3-one, 2-phenoxyethanol, phenetylalcohol, and p-benzoic acid butyl ester were added.

TABLE 12

Silver iodobromide emulsions used in Sample 801

| Emulsion | Characteristics | Average sphere-equivalent diameter (μm) | Variation coefficient (%) | Average AgI content (%) | Halogen composition structure of silver halide grains | AgI content at grain surface (%) | Other characteristics (1) | (2) | (3) | (4) | (5) |
|---|---|---|---|---|---|---|---|---|---|---|---|
| A | Monodisperse tetradecahedral grains | 0.20 | 10 | 2.5 | Threefold structure | 1.5 | ○ | | | | |
| B | Monodisperse (111) tabular grains Average aspect ratio 3.0 | 0.22 | 10 | 2.5 | Fourfold structure | 1.5 | | | ○ | ○ | ○ |
| C | Monodisperse (111) tabular grains Average aspect ratio 4.5 | 0.32 | 19 | 3.0 | Threefold structure | 0.1 | ○ | | | ○ | ○ |
| D | Monodisperse (111) tabular grains Average aspect ratio 6.0 | 0.32 | 21 | 4.8 | Threefold structure | 2.0 | ○ | | | ○ | ○ |
| E | Monodisperse (111) tabular grains Average aspect ratio 6.0 | 0.43 | 10 | 2.0 | Fourfold structure | 1.5 | ○ | | | | |
| F | Monodisperse (111) tabular grains Average aspect ratio 8.0 | 0.65 | 12 | 1.6 | Threefold structure | 0.6 | ○ | | | | ○ |
| G | Monodisperse cubic grains | 0.14 | 9 | 3.5 | Fourfold structure | 2.0 | | ○ | | | |
| H | Monodisperse cubic grains | 0.22 | 12 | 4.9 | Fourfold structure | 0.1 | ○ | ○ | | ○ | |
| I | Monodisperse (111) tabular grains Average aspect ratio 4.0 | 0.32 | 12 | 3.5 | Fivefold structure | 4.5 | ○ | ○ | | ○ | ○ |

TABLE 12-continued

Silver iodobromide emulsions used in Sample 801

| Emulsion | Characteristics | Average sphere-equivalent diameter (μm) | Variation coefficient (%) | Average AgI content (%) | Halogen composition structure of silver halide grains | AgI content at grain surface (%) | Other characteristics (1) | (2) | (3) | (4) | (5) |
|---|---|---|---|---|---|---|---|---|---|---|---|
| J | Monodisperse (111) tabular grains Average aspect ratio 7.0 | 0.40 | 21 | 2.0 | Fourfold structure | 0.2 | ○ | ○ | | ○ | ○ |
| K | Monodisperse (111) tabular grains Average aspect ratio 8.5 | 0.65 | 13 | 1.7 | Threefold structure | 1.3 | ○ | ○ | | | ○ |
| L | Monodisperse tetradecahedral grains | 0.30 | 9 | 7.5 | Threefold structure | 7.0 | | | ○ | | ○ |
| M | Monodisperse tetradecahedral grains | 0.30 | 9 | 7.5 | Threefold structure | 5.0 | | ○ | | ○ | ○ |
| N | Monodisperse (111) tabular grains Average aspect ratio 3.0 | 0.35 | 13 | 2.1 | Fourfold structure | 4.0 | ○ | ○ | ○ | | |
| O | Monodisperse (111) tabular grains Average aspect ratio 5.0 | 0.45 | 9 | 2.5 | Fourfold structure | 1.0 | | ○ | | ○ | ○ |
| P | Monodisperse (111) tabular grains Average aspect ratio 9.0 | 0.70 | 21 | 2.8 | Threefold structure | 0.5 | ○ | ○ | | | ○ |
| Q | Monodisperse (111) tabular grains Average aspect ratio 9.0 | 0.90 | 8 | 1.0 | Fourfold structure | 0.5 | ○ | ○ | | | ○ |

(Other characteristics)
(1): A reduction sensitizer was added during formation of grains.
(2): A selenium sensitizer was used as an after-ripening chemical.
(3): A rhodium salt was added during formation of grains.
(4): After completion of after-ripening, silver nitrate in an amount of 10% in terms of the silver molar ratio relative to the emulsion grains at the time, and potassium bromide in an equimolar amount to the silver nitrate, were added to form shells.
(5): The presence of 10 or more dislocation lines/grain on average was observed under a transmission electron microscope.
All the photosensitive emulsions were after-ripened using sodium photosulfate, potassium thiocyanate and sodium chloroaurate. Further, an iridium salt was added as necessary during formation of grains.
Chemically modified gelatin whose amino groups had been partially converted into phthalic amide was added to the emulsions B, C, E, H, J, N and Q when the emulsions were prepared.

TABLE 13

Spectral sensitization of Emulsions A to Q

| Emulsion | Added sensitizing dye | Added amount per 1 mol of silver halide (g) | Stage when a sensitizing dye was added |
|---|---|---|---|
| A | S-1 | 0.01 | After afterripening |
| | S-2 | 0.15 | Before afterripening |
| | S-3 | 0.02 | Before afterripening |
| | S-8 | 0.03 | Before afterripening |
| | S-13 | 0.25 | Before afterripening |
| B | S-2 | 0.15 | Before afterripening |
| | S-3 | 0.02 | Before afterripening |
| | S-8 | 0.03 | Before afterripening |
| | S-13 | 0.25 | Before afterripening |
| | S-14 | 0.01 | Before afterripening |
| C | S-2 | 0.25 | Before afterripening |
| | S-8 | 0.04 | Before afterripening |
| | S-13 | 0.02 | Before afterripening |
| D | S-2 | 0.2 | After afterripening |
| | S-3 | 0.05 | After afterripening |
| | S-8 | 0.05 | Before afterripening |
| | S-13 | 0.25 | Before afterripening |
| E | S-1 | 0.01 | Before afterripening |
| | S-2 | 0.25 | Before afterripening |
| | S-8 | 0.05 | Before afterripening |
| | S-13 | 0.25 | After afterripening |
| F | S-2 | 0.2 | Before afterripening |
| | S-3 | 0.04 | Before afterripening |
| | S-8 | 0.20 | Before afterripening |
| G | S-4 | 0.3 | After afterripening |
| | S-5 | 0.05 | After afterripening |
| | S-12 | 0.1 | After afterripening |
| H | S-4 | 0.2 | Before afterripening |
| | S-5 | 0.05 | After afterripening |
| | S-9 | 0.15 | Before afterripening |
| | S-14 | 0.02 | After afterripening |
| I | S-4 | 0.3 | Before afterripening |
| | S-9 | 0.2 | Before afterripening |
| | S-12 | 0.1 | Before afterripening |

TABLE 13-continued

Spectral sensitization of Emulsions A to Q

| Emulsion | Added sensitizing dye | Added amount per 1 mol of silver halide (g) | Stage when a sensitizing dye was added |
|---|---|---|---|
| J | S-4 | 0.35 | Before afterripening |
|  | S-5 | 0.05 | After afterripening |
|  | S-12 | 0.1 | Before afterripening |
| K | S-4 | 0.3 | Before afterripening |
|  | S-9 | 0.05 | Before afterripening |
|  | S-12 | 0.1 | Before afterripening |
|  | S-14 | 0.02 | Before afterripening |
| L, M | S-6 | 0.1 | After afterripening |
|  | S-10 | 0.2 | After afterripening |
|  | S-11 | 0.05 | After afterripening |
| N | S-6 | 0.05 | After afterripening |
|  | S-7 | 0.05 | After afterripening |
|  | S-10 | 0.25 | After afterripening |
|  | S-11 | 0.05 | After afterripening |
| O | S-10 | 0.4 | After afterripening |
|  | S-11 | 0.15 | After afterripening |
| P | S-6 | 0.05 | After afterripening |
|  | S-7 | 0.05 | After afterripening |
|  | S-10 | 0.3 | Before afterripening |
|  | S-11 | 0.1 | Before afterripening |
| Q | S-6 | 0.05 | Before afterripening |
|  | S-7 | 0.05 | Before afterripening |
|  | S-10 | 0.2 | Before afterripening |
|  | S-11 | 0.25 | Before afterripening |

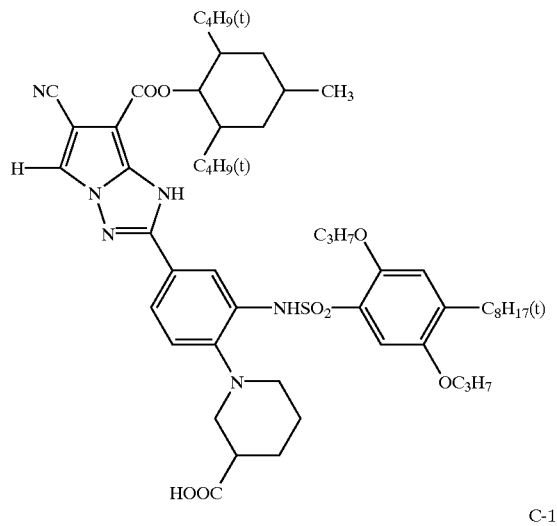

C-11

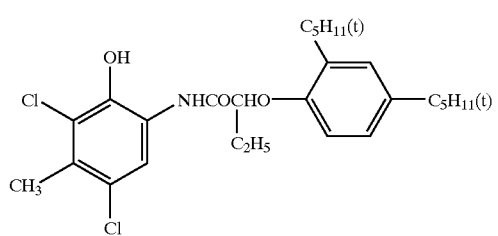

C-12

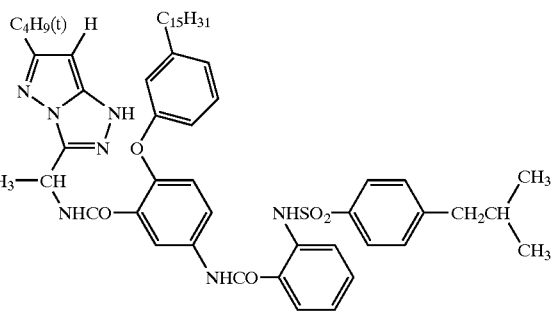

C-14

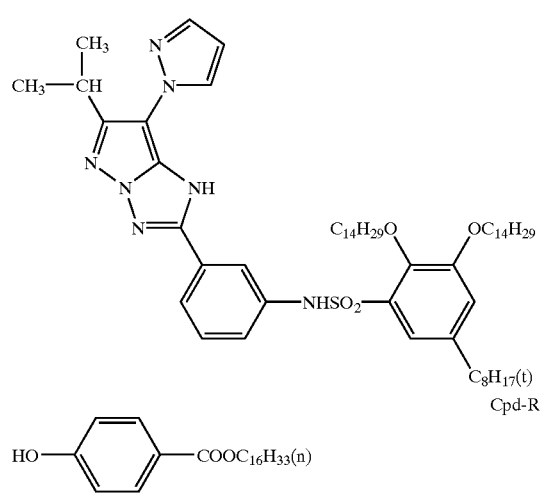

C-15

Next, samples 802 to 807 were prepared in the same manner as sample 801, except for replacing coupler C-8 in each of the 14th, 15th and 16th layers of sample 801 with the couplers presented in Table 14.

Each of these couplers was replaced in a molar amount equivalent to the coupler C-8 of each layer of the sample 801. Besides, additives other than particularly mentioned were not changed from those in Sample 801.

(Evaluation of Samples)

(i) Evaluation of Color-Formation Property

Samples 801 to 807 were exposed to white light through an optical wedge having a continuously changing density, and then they were processed following the processing B presented below.

Then, the maximum yellow density was measured. The higher the value is, the more color-forming property is improved and preferable.

(ii) Evaluation of Fastness

Samples 801 to 807 exposed and processed in the same manner as in the above (i) were stored for 6 weeks under the conditions of 80° C. and 70% RH, and then the fading of yellow dye was evaluated. The fading was evaluated by a degree of reduction in yellow density of the point that gave the yellow density of 2.5 just after completion of the processing.

TABLE 14

| Sample | Kind of coupler | Maximum yellow density (Dmax) | Fastness of a dye (fading of color from the initial density 2.5) | Remarks |
| --- | --- | --- | --- | --- |
| 801 | C-8 | 2.24 | 0.50 | Comparative example |
| 802 | Coupler for comparison (Cp-1) | 3.00 | 0.15 | Comparative example |
| 803 | Coupler (181) | 3.33 | 0.10 | This invention |
| 804 | Coupler (183) | 3.34 | 0.04 | This invention |
| 805 | Coupler (184) | 3.40 | 0.03 | This invention |
| 806 | Coupler (185) | 3.30 | 0.03 | This invention |
| 807 | Coupler (188) | 3.25 | 0.03 | This invention |

Table 14 shows that the couplers of the present invention exhibited high color-forming property and were excellent in dye image fastness. Particularly, it is understood that couplers having a dissociation group or an imidazole split-off group exhibited high color-forming property.

(Processing-B)

In this example, samples were subjected to the following processing steps (Processing-B).

Processing-B was different from Processing A in Example 10 in the points shown below (only the points changed are shown).

| | | |
| --- | --- | --- |
| Replenisher amount in the 1st development | 1,100 ml/m² | |
| Replenisher amount in color-development | 1,100 ml/m² | |

The compositions of each processing solution in Processing-B were different from those in Processing-A in the following points (only the points changed are shown).

| | Tank solution | Replenisher |
| --- | --- | --- |
| [1st developer] | | |
| 1-Phenyl-4-methyl-4-hydroxymethyl-3-pyrazolydone | 1.5 g | 2.0 g |
| [Reversal solution] | | |
| pH | 5.80 | — |
| [Color-developer] | | |
| Sodium sulfite | 6.0 g | 6.0 g |
| Trisodium phosphate 12-hydrate | 22 g | 22 g |
| Potassium iodide | 30 mg | — |
| 3,6-Dithiaoctane-1,8-diol | 0.7 g | 0.7 g |
| pH | 11.90 | 12.00 |
| [Pre-bleaching solution] | | |
| pH | 6.50 | 6.50 |

Example 12

A light-sensitive material was prepared in the same manner as sample 116 in Example 1 of JP-A-11-7109, except that the yellow coupler ExY used in the 1st layer of the sample 116 was replaced with the dye-forming coupler (103) of the present invention in an equi-molar amount. The resultant light-sensitive material was exposed and processed following the method in Example 1 of JP-A-11-7109, and it was confirmed that both excellent color-forming property and hue were attained.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A silver halide photographic light-sensitive material, which comprises at least one dye-forming coupler selected from the group consisting of a dye-forming coupler represented by formula (I), a dye-forming coupler represented by formula (II), and a dye-forming coupler represented by formula (I-2)

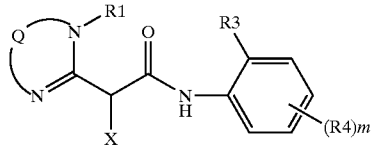

formula (I)

wherein Q represents a group represented by —C(—R$_{11}$)=C(—R$_{12}$)—SO$_2$—; R$_{11}$ and R$_{12}$ bond with each other to form, together with the —C=C— moiety, a 5- to 7-membered ring, or R$_{11}$ and R$_{12}$ each independently represent a hydrogen atom or a substituent; R1 represents a substituent; R3 represents a substituent; R4 represents a substituent; m represents an integer of 0 to 4; when m is 2 or more, R4s may be the same or different, or R4s may bond each other to form a ring; and X represents a hydrogen atom, or a group capable of being split-off upon a coupling reaction with an oxidized product of a developing agent;

formula (II)

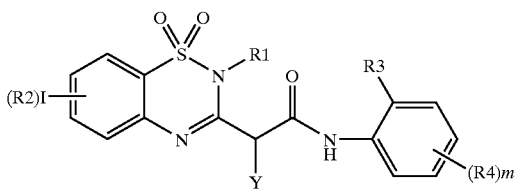

wherein R1 represents a substituent; R2 represents a substituent; l represents an integer of 0 to 4; when l is 2 or more, R2s may be the same or different, or R2s may bond with each other to form a ring; R3 represents a substituent; R4 represents a substituent; m represents an integer of 0 to 4; when m is 2 or more, R4s may be the same or different, or R4s may bond with each other to form a ring; and Y represents a group capable of being split-off upon a coupling reaction with an oxidized product of a developing agent;

formula (I-2)

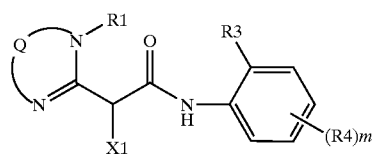

wherein Q1 represents a group represented by —C(—$R_{11}$)=C(—$R_{12}$)—Z—; Z represents —$SO_2$— or —CO—; $R_{11}$ and $R_{12}$ bond with each other to form, together with the —C=C— moiety, a 5- to 7-membered ring, or $R_{11}$ and $R_{12}$ each independently represent a hydrogen atom or a substituent; R1 represents a substituent; R3 represents a substituent; R4 represents a substituent; m represents an integer of 0 to 4; when m is 2 or more, R4s may be the same or different, or R4s may bond with each other to form a ring; and X1 represents a group that has thereon a dissociation group whose pKa is 1 to 12, and that is capable of being split-off upon a coupling reaction with an oxidized product of a developing agent;

with the proviso that the following compound (I-A) is excluded from the dye-forming coupler represented by formula (I) or (II)

(I-A)

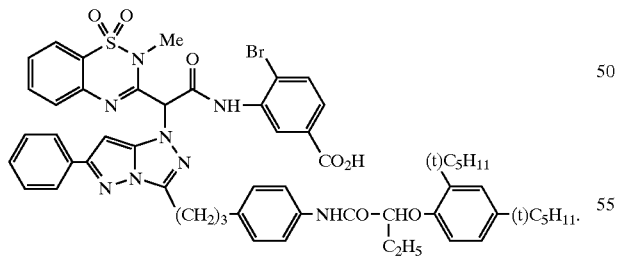

2. The silver halide photographic light-sensitive material as claimed in claim 1, wherein, in the formula (I), (II), or (I-2), R1 is a substituted or unsubstituted alkyl group, and R3 is a halogen atom, an alkoxy group, an aryloxy group, an alkyl group, an alkylthio group, or an arylthio group.

3. The silver halide photographic light-sensitive material as claimed in claim 1, wherein X, Y, or X1 in the above-mentioned formula (I), (II), or (I-2) is an imidazole-1-yl group which may have a substituent, a pyrazole-1-yl group which may have a substituent, or a pyrrole-1-yl group which may have a substituent.

4. A silver halide photographic light-sensitive material comprising a coupler capable of forming a dye upon a coupling reaction with an oxidized product of an aromatic primary amine, wherein at least one of said dye formed by coupling reaction is one selected from the group consisting of an azomethine dye compound represented by formula (D) and an azomethine dye compound represented by formula (IV):

formula (D)

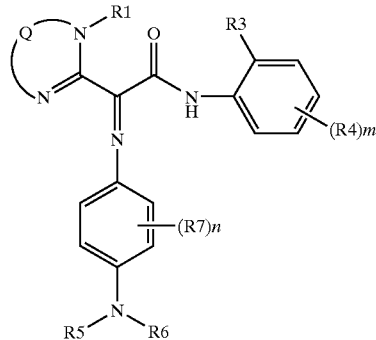

wherein, in formula (D), Q represents a group represented by —C(—$R_{11}$)=C(—$R_{12}$)—$SO_2$—; $R_{11}$ and $R_{12}$ bond with each other to form, together with the —C=C— moiety, a 5- to 7-membered ring, or $R_{11}$ and $R_{12}$ each independently represent a hydrogen atom or a substituent; R1 represents a substituent; R3 represents a substituent; R4 represents a substituent; m represents an integer of 0 to 4; when m is 2 or more, R4s may be the same or different, or R4s may bond with each other to form a ring; R5 and R6 each independently represent a hydrogen atom or a substituent, or R5 and R6 may bond with each other to form a ring; R7 represents a substituent; n represents an integer of 0 to 4; when n is 2 or more, R7s may be the same or different, or R7s may bond with each other to form a fused ring; or when n is 1 or more, R7 may bond with R5 or R6 to form a fused ring;

with the proviso that at least one group selected from the group consisting of R1, R3, R4, the substituent represented by $R_{11}$, the substituent represented by $R_{12}$, and at least one substituent on the ring that is formed by a combination of $R_{11}$ and $R_{12}$, is a group having 10 or more carbon atoms in total; and formula (IV)

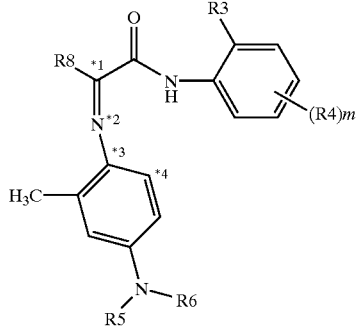

wherein, in formula-(IV), an angle that is defined by a dihedral angle C*1 N*2 C*3 C*4 and that is the most stabilized stereochemical structure in terms of energy, which is measured by quantum chemistry calculations, is within the range between −280 and 28°; and *1, *2, *3 and *4 each express a number labeled on the atom and define the angle represented by the dihedral angle C*1 N*2 C*3 C*4; R3 and R4 each independently represent a substituent; m represents an integer of 0 to 4; when m is 2 or more, R4s may be the same or different, or R4s may bond with each other to form a ring; R5 and R6 each independently represent a hydrogen atom or a substituent, or R5 and R6 may bond with each other to form a ring; R8 represents an aryl group or a heterocyclic group, with the proviso that at least one group selected from the group consisting of R3, R4, and at least one substituent on the aryl ring or heterocycle represented by R8, is a group having 10 or more carbon atoms in total; and that the calculation based on quantum chemistry, which is used to measure the dihedral angle C*1 N*2 C*3 C*4 is carried out using the basis function of 6–31 G** or more according to a widely used B3LYP method (density-functional method).

* * * * *